US008575317B2

(12) United States Patent
Kuramochi et al.

(10) Patent No.: US 8,575,317 B2
(45) Date of Patent: Nov. 5, 2013

(54) ANTI-NR10 ANTIBODY AND USE THEREOF

(75) Inventors: Taichi Kuramochi, Shizuoka (JP); Keiko Kasutani, Shizuoka (JP); Souhei Ohyama, Shizuoka (JP); Hiroyuki Tsunoda, Shizuoka (JP); Tomoyuki Igawa, Shizuoka (JP); Tatsuhiko Tachibana, Shizuoka (JP); Hirotake Shiraiwa, Shizuoka (JP); Keiko Esaki, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/809,138

(22) PCT Filed: Dec. 4, 2009

(86) PCT No.: PCT/JP2009/070376
§ 371 (c)(1),
(2), (4) Date: Mar. 1, 2011

(87) PCT Pub. No.: WO2010/064697
PCT Pub. Date: Jun. 10, 2010

(65) Prior Publication Data

US 2011/0229459 A1 Sep. 22, 2011

(30) Foreign Application Priority Data

Dec. 5, 2008 (WO) .................. PCT/JP2008/072152
Mar. 13, 2009 (WO) .................. PCT/JP2009/054941

(51) Int. Cl.
*C07K 16/28* (2006.01)
*A61K 39/00* (2006.01)

(52) U.S. Cl.
USPC .................................. 530/388.22; 424/144.1

(58) Field of Classification Search
None
See application file for complete search history.

(56) References Cited

U.S. PATENT DOCUMENTS

| | | | |
|---|---|---|---|
| 5,322,678 | A | 6/1994 | Morgan et al. |
| 5,670,373 | A | 9/1997 | Kishimoto |
| 5,795,965 | A | 8/1998 | Tsuchiya et al. |
| 5,945,311 | A | 8/1999 | Lindhofer et al. |
| 6,018,032 | A | 1/2000 | Koike et al. |
| 6,329,511 | B1 | 12/2001 | Vasquez et al. |
| 6,723,319 | B1 | 4/2004 | Ito et al. |
| 7,052,873 | B2 | 5/2006 | Tsuchiya |
| 7,276,585 | B2 | 10/2007 | Lazar et al. |
| 7,482,440 | B2 | 1/2009 | Maeda et al. |
| 8,431,127 | B2 | 4/2013 | Higuchi et al. |
| 2001/0001663 | A1 | 5/2001 | Kishimoto et al. |
| 2002/0142374 | A1 | 10/2002 | Gallo et al. |
| 2002/0187150 | A1 | 12/2002 | Mihara et al. |
| 2003/0125520 | A1 | 7/2003 | Maeda et al. |
| 2003/0215838 | A1 | 11/2003 | Sprecher et al. |
| 2003/0224487 | A1 | 12/2003 | Sprecher et al. |
| 2004/0071706 | A1 | 4/2004 | Ito et al. |
| 2004/0081651 | A1 | 4/2004 | Karpusas et al. |
| 2004/0223970 | A1 | 11/2004 | Afar et al. |
| 2004/0236080 | A1 | 11/2004 | Aburatani et al. |
| 2005/0130224 | A1 | 6/2005 | Saito et al. |
| 2005/0142133 | A1 | 6/2005 | Lazar et al. |
| 2005/0142635 | A1 | 6/2005 | Tsuchiya et al. |
| 2005/0261229 | A1 | 11/2005 | Gillies |
| 2006/0019342 | A1 | 1/2006 | Dall Acqua et al. |
| 2006/0134709 | A1 | 6/2006 | Stavenhagen et al. |
| 2006/0141456 | A1 | 6/2006 | Edwards et al. |
| 2006/0182743 | A1 | 8/2006 | Bilsborough |
| 2006/0194280 | A1 | 8/2006 | Dillon et al. |
| 2006/0275282 | A1 | 12/2006 | Moore et al. |
| 2006/0292147 | A1 | 12/2006 | Yoshizaki et al. |
| 2007/0036785 | A1 | 2/2007 | Kishimoto et al. |
| 2007/0041978 | A1 | 2/2007 | Hattori et al. |
| 2007/0059312 | A1 | 3/2007 | Baca et al. |
| 2007/0160611 | A1 | 7/2007 | Yao et al. |
| 2008/0075712 | A1 | 3/2008 | Hattori et al. |
| 2008/0125579 | A1 | 5/2008 | Owens et al. |
| 2008/0166756 | A1 | 7/2008 | Tsuchiya et al. |
| 2008/0219971 | A1 | 9/2008 | Smith et al. |
| 2009/0263392 | A1 | 10/2009 | Igawa et al. |
| 2009/0324589 | A1 | 12/2009 | Igawa et al. |
| 2010/0003254 | A1 | 1/2010 | Hattori et al. |
| 2010/0004429 | A1 | 1/2010 | Kai et al. |
| 2010/0008907 | A1 | 1/2010 | Nishimoto et al. |
| 2010/0015133 | A1 | 1/2010 | Igawa et al. |
| 2010/0055092 | A1 | 3/2010 | Hasegawa et al. |
| 2010/0239577 | A1 | 9/2010 | Igawa et al. |
| 2010/0240096 | A1 | 9/2010 | Maeda et al. |
| 2010/0240145 | A1 | 9/2010 | Maeda et al. |
| 2010/0297697 | A1 | 11/2010 | Ambrosius et al. |

(Continued)

FOREIGN PATENT DOCUMENTS

| | | |
|---|---|---|
| AU | 2006/214404 | 8/2006 |
| AU | 2007/249713 | 11/2007 |

(Continued)

OTHER PUBLICATIONS

Igawa et al., "Antibody recycling by engineered pH-dependent antigen binding improves the duration of antigen neutralization," *Nat. Biotechnol.*, 28(11):1203-7 (2010).

(Continued)

*Primary Examiner* — Robert Landsman
*Assistant Examiner* — Bruce D Hissong
(74) *Attorney, Agent, or Firm* — Fish & Richardson P.C.

(57) ABSTRACT

The present inventors successfully obtained anti-NR10 antibodies having an effective neutralizing activity against NR10. The anti-NR10 antibodies provided by the present invention are useful as, for example, pharmaceuticals for treating or preventing inflammatory diseases.

14 Claims, 33 Drawing Sheets

(56) References Cited

U.S. PATENT DOCUMENTS

| | | | |
|---|---|---|---|
| 2010/0298542 A1 | 11/2010 | Igawa et al. |
| 2010/0310556 A1 | 12/2010 | Higuchi et al. |
| 2011/0076275 A1 | 3/2011 | Igawa et al. |
| 2011/0111406 A1 | 5/2011 | Igawa et al. |
| 2011/0129459 A1 | 6/2011 | Kuramochi et al. |
| 2011/0245473 A1 | 10/2011 | Igawa et al. |
| 2012/0065379 A1 | 3/2012 | Igawa et al. |
| 2012/0071634 A1 | 3/2012 | Igawa et al. |
| 2013/0011866 A1 | 1/2013 | Igawa et al. |

FOREIGN PATENT DOCUMENTS

| | | |
|---|---|---|
| AU | 2007/255753 | 12/2007 |
| AU | 2008332271 | 6/2009 |
| AU | 2009290162 | 4/2010 |
| CA | 2 203 182 | 5/1996 |
| CA | 2 443 294 | 10/2002 |
| CA | 2 523 577 | 11/2004 |
| CA | 2 549 467 | 7/2005 |
| CA | 2 560 953 | 9/2005 |
| CA | 2 625 773 | 4/2007 |
| CA | 2 626 688 | 4/2007 |
| CA | 2 708 065 | 6/2009 |
| CA | 2 708 532 | 6/2009 |
| EA | 009026 | 10/2007 |
| EP | 0 783 893 | 7/1997 |
| EP | 1 188 830 | 3/2002 |
| EP | 1 510 943 | 3/2005 |
| EP | 1 870 459 | 12/2007 |
| EP | 2 006 381 | 12/2008 |
| EP | 2 031 064 | 3/2009 |
| EP | 2 047 863 | 4/2009 |
| EP | 2 236 604 | 10/2010 |
| EP | 2 241 332 | 10/2010 |
| EP | 2 275 443 | 1/2011 |
| JP | 2-028200 | 1/1990 |
| JP | 09-506001 | 6/1997 |
| JP | 2004-511426 | 4/2004 |
| TW | 200810778 | 3/2008 |
| TW | 200932266 | 8/2009 |
| WO | WO 92/19759 | 11/1992 |
| WO | WO 94/10354 | 5/1994 |
| WO | WO 94/12215 | 6/1994 |
| WO | WO 95/14710 | 6/1995 |
| WO | WO 95/33844 | 12/1995 |
| WO | WO 96/11020 | 4/1996 |
| WO | WO 96/12503 | 5/1996 |
| WO | WO 96/23071 | 8/1996 |
| WO | WO 96/27011 | 9/1996 |
| WO | WO 97/10354 | 3/1997 |
| WO | WO 98/03546 | 1/1998 |
| WO | WO 99/18212 | 4/1999 |
| WO | WO 99/58572 | 11/1999 |
| WO | WO 00/34317 | 6/2000 |
| WO | WO 00/75314 | 12/2000 |
| WO | WO 01/23556 | 4/2001 |
| WO | WO 01/82899 | 11/2001 |
| WO | WO 02/072605 | 9/2002 |
| WO | WO 03/000883 | 1/2003 |
| WO | WO 03/060090 | 7/2003 |
| WO | WO 03/105757 | 12/2003 |
| WO | WO 2004/085476 | 10/2004 |
| WO | WO 2004/091543 | 10/2004 |
| WO | WO 2004/096273 | 11/2004 |
| WO | WO 2004/113387 | 12/2004 |
| WO | WO 2005/035753 | 4/2005 |
| WO | WO 2005/035754 | 4/2005 |
| WO | WO 2005/035756 | 4/2005 |
| WO | WO 2005/056606 | 6/2005 |
| WO | WO 2006/004663 | 1/2006 |
| WO | WO 2006/067913 | 6/2006 |
| WO | WO 2006/070286 | 7/2006 |
| WO | WO 2006/088855 | 8/2006 |
| WO | WO 2006/106905 | 10/2006 |
| WO | WO 2006/109592 | 10/2006 |
| WO | WO 2006/118959 | 11/2006 |
| WO | WO 2006/119062 | 11/2006 |
| WO | WO 2007/108559 | 9/2007 |
| WO | WO 2007/114319 | 10/2007 |
| WO | WO 2007/114325 | 10/2007 |
| WO | WO2007133816 A2 | 11/2007 |
| WO | WO 2007/142325 | 12/2007 |
| WO | WO 2008/043822 | 4/2008 |
| WO | WO 2008/103432 | 8/2008 |
| WO | WO 2008/132453 | 11/2008 |
| WO | WO 2008/145141 | 12/2008 |
| WO | WO 2009/041613 | 4/2009 |
| WO | WO 2009/041621 | 4/2009 |
| WO | WO 2009/041643 | 4/2009 |
| WO | WO 2009/072598 | 6/2009 |
| WO | WO 2009/072604 | 6/2009 |
| WO | WO 2009/125825 | 10/2009 |
| WO | WO 2009/139822 | 11/2009 |
| WO | WO 2010/035769 | 4/2010 |
| WO | WO 2011/111007 | 9/2011 |

OTHER PUBLICATIONS

R&D Systems (R&D Systems, Anti-human IL-31 RA Antibody, Catalog #AF2769, Oct. 2008), 1 page.

USPTO Restriction Requirement in U.S. Appl. No. 12/745,781, dated Jul. 30, 2012, 9 pages.

Fish & Richardson P.C. Response to Restriction Requirement dated Jun. 25, 2012 in U.S. Appl. No. 12/746,229, filed Jul. 24, 2012, 2 pages.

Fish & Richardson P.C., Response to Species Election Requirement dated Jun. 25, 2012 in U.S. Appl. No. 12/936,587, filed Jul. 25, 2012, 1 page.

Fish & Richardson P.C., Fourth Preliminary Amendment and Response to Restriction Requirement dated Jun. 6, 2012 in U.S. Appl. No. 12/680,082, filed Jun. 29, 2012, 13 pages.

Fish & Richardson P.C., Amendment in Reply to Non-Final Office Action dated Feb. 14, 2013 in U.S. Appl. No. 12/680,082, filed Aug. 12, 2013, 17 pages.

USPTO Final Office Action in U.S. Appl. No. 12/679,922, dated Aug. 2, 2013, 12 pages.

Grimstad et al., "Anti-interleukin-31-antibodies ameliorate scratching behaviour in NC/Nga mice: a model of atopic dermatitis," Exp. Dermatol., 18(1):35-43 (2009).

European Search Report for App. Ser. No. EP 11 169 972, dated Aug. 29, 2011, 11 pages.

Burgess et al., "Possible dissociation of the heparin-binding and mitogenic activities of heparin-binding (acidic fibroblast) growth factor-1 from its receptor-binding activities by site-directed mutagenesis of a single lysine residue," *J. Cell. Biol.*, 111:2129-2138 (1990).

Kobayashi et al., "A monoclonal antibody specific for a distinct region of hen egg-white lysozyme," *Mol. Immunol.*, 19:619-30 (1982).

Lazar et al., "Transforming growth factor alpha: mutation of aspartic acid 47 and leucine 48 results in different biological activities," *Mol. Cell. Biol.*, 8:1247-1252 (1988).

Ozhegov et al., Tolkovyi Slovar Russkogo iazyka: 2004, p. 292 (with an English translation of the relevant passage defining "control").

Padlan et al., "Identification of specificity-determining residues in antibodies," *FASEB J.*, 9:133-139 (1995).

R&D Systems (R&D Systems, Biotinylated Anti-human IL-31 RA Antibody, Catalog #BAF2769, Nov. 2005), 1 page.

Rudikoff et al., "Single amino acid substitution altering antigen-binding specificity," *Proc. Natl. Acad. Sci. U.S.A.*, 79(6):1979-83 (1982).

USPTO Restriction Requirement in U.S. Appl. No. 12/745,781, dated Sep. 4, 2012, 10 pages.

Fish & Richardson P.C., Response to Restriction Requirement dated Sep. 4, 2012 in U.S. Appl. No. 12/745,781, filed Sep. 21, 2012, 176 pages.

USPTO Non-Final Office Action in U.S. Appl. No. 12/745,781, dated Oct. 18, 2012, 21 pages.

(56) References Cited

OTHER PUBLICATIONS

Fish & Richardson P.C., Amendment in Reply to Action dated Apr. 12, 2012 in U.S. App. No. 12/295,039, filed Sep. 11, 2012, 12 pages.
USPTO Notice of Allowance in U.S. Appl. No. 12/746,229, dated Aug. 23, 2012, 9 pages.
USPTO Non-Final Office Action in U.S. Appl. No. 12/936,587, dated Nov. 7, 2012, 13 pages.
USPTO Restriction Requirement in U.S. Appl. No. 12/680,082, dated Sep. 14, 2012, 6 pages.
Fish & Richardson P.C., Amendment and Response to Election Requirement dated Sep. 14, 2012 in U.S. Appl. No. 12/680,082, filed Nov. 8, 2012, 14 pages.
USPTO Restriction Requirement in U.S. Appl. No. 12/679,922, dated Oct. 2, 2012, 9 pages.
Fish & Richardson P.C., Response to Restriction Requirement dated Oct. 2, 2012 in U.S. Appl. No. 12/679,922, filed Nov. 1, 2012, 2 pages.
Bayry et al, "Immuno affinity purification of foot and mouth disease virus type specific antibodies using recombinant protein adsorbed to polystyrene wells," *J. Virol. Methods*, 81:21-30 (1999).
USPTO Non-Final Office Action in U.S. App. No. 13/595,139, dated Nov. 14, 2012, 10 pages.
USPTO Restriction Requirement in U.S. Appl. No. 12/936,587, dated Dec. 6, 2011, 7 pages.
U.S. Appl. No. 13/595,139, filed Aug. 27, 2012, Igawa et al.
Brown et al., "Tolerance of single, but not multiple, amino acid replacements in antibody $V_H$ CDR 2: a means of minimizing B cell wastage from somatic hypermutation?," *J. Immunol.*, 156(9):3285-91 (1996).
Deng et al., "An Agonist Murine Monoclonal Antibody to the Human c-Mpl Receptor Stimulates Megakaryocytopoiesis," *Blood*, 92:1981-88 (1998).
MacCallum et al., "Antibody-antigen interactions: contact analysis and binding site topography," *J. Mol. Biol.*, 262:732-45 (1996).
Sun et al., "Coexpression of Gas6/Axl in human ovarian cancers," *Oncology*, 66(6):450-7 (2004).
USPTO Non-Final Office Action in U.S. Appl. No. 12/679,922, dated Dec. 10, 2012, 22 pages.
International Search Report App. Ser. No. PCT/JP2007/057058, mailed May 7, 2001, 2 pages.
USPTO Notice of Allowance in U.S. Appl. No. 12/746,229, dated Dec. 17, 2012, 7 pages.
Dall'Acqua et al., "Antibody humanization by framework shuffling," *Methods*, 36(1):43-60 (2005).
Fish & Richardson P.C., Amendment in Reply to Action dated Jun. 28, 2011 in U.S. Appl. No. 12/295,039, filed Dec. 27, 2011, 14 pages.
Fish & Richardson P.C. Amendment in Reply to Non-Final Office Action dated Jun. 16, 2011 in U.S. Appl. No. 12/746,229, filed Dec. 13, 2011, 7 pages.
Tsuchiya, Credit Suisse Seminar, "Therapeutic Antibody," at Fuji-Gotemba Laboratories, p. 21 (2006).
Adams et al., "Humanization of a recombinant monoclonal antibody to produce a therapeutic HER dimerization inhibitor, pertuzumab," Cancer Immunol. Immunother., 55:717-727 (2006).
Binz et al., "Engineering novel binding proteins from nonimmunoglobulin domains," Nat. Biotechnol., 23:1257-68 (2005).
Bilsborough, "IL-31 is associated with cutaneous lymphocyte antigen-positive skin homing T cells in patients with atopic dermatitis," J. Allergy Clin. Immunol., 117:418-25 (2006).
Branden and Tooze, "Recognition of Foreign Molecules by the Immune System," Introduction to Protein Structure, 2d Ed., Garland Publishing, pp. 299-323 (1999).
Carter, "Bispecific human IgG by design," J. Immunol. Methods, 248:7-15 (2001).
Comper and Glasgow, "Charge selectivity in kidney ultrafiltration," Kidney Int., 47:1242-51 (1995).
Couto et al., "Anti-BA46 Monoclonal Antibody Mc3: Humanization Using a Novel Positional Consensus and in Vivo and in Vitro Characterization," Cancer Res., 55:1717-1722 (1995).
Deen et al., "Structural determinants of glomerular permeability," Am. J. Physiol. Renal. Physiol., 281:F579-F596 (2001).
Del Rio et al., "An Engineered Penicillin Acylase with Altered Surface Charge Is More Stable in Alkaline pH," Ann. NY Acad. Sci., 799:61-64 (1996).
Dillon et al., "Structural and functional characterization of disulfide isoforms of the human IgG2 subclass," J. Biol. Chem., 283:16206-15 (2008).
Ewert et al., "Stability improvement of antibodies for extracellular and intracellular applications: CDR grafting to stable frameworks and structure-based framework engineering," Methods, 34:184-199 (2004).
Ghetie and Ward, "FcRn: the MHC class I-related receptor that is more than an IgG transporter," Immunol. Today, 18:592-598 (1997).
Ghetie et al., "Increasing the serum persistence of an IgG fragment by random mutagenesis," Nat. Biotechnol., 15:637-640 (1997).
Ghetie et al., "Multiple roles for the major histocompatibility complex class I-related receptor FcRn," Annu. Rev. Immunol., 18:739-766 (2000).
Gobburu et al., "Pharmacokinetics/dynamics of 5c8, a monoclonal antibody to CD154 (CD40 ligand) suppression of an immune response in monkeys," J. Pharmacol. Exp. Ther., 286:925-930 (1998).
Goode et al., "The glomerular basement membrane charge-selectivity barrier: an oversimplified concept?" Nephrol. Dial. Transplant., 11:1714-16 (1996).
Graves et al., "Molecular modeling and preclinical evaluation of the humanized NR-LU-13 antibody," Clin. Cancer Res., 5:899-908 (1999).
Gupta et al., "Affinity chromatography and co-chromatography of bispecific monoclonal antibody immunoconjugates," J. Biochem. Biophys. Methods, 51:203-216 (2002).
Hanson et al., "Catalytic antibodies and their applications," Curr. Opin. Biotechnol., 16:631-636 (2005).
He et al., "Humanization and pharmacokinetics of a monoclonal antibody with specificity for both E- and P-selectin," J. Immunol., 160:1029-35 (1998).
Hinton et al., "An engineered human IgG1 antibody with longer serum half-life," J. Immunol., 176:346-356 (2006).
Ito et al., "The His-probe method: effects of histidine residues introduced into the complementarity-determining regions of antibodies on antigen-antibody interactions at different pH values," FEBS Lett., 309:85-88 (1992).
Kashmiri et al., "Generation, characterization, and in vivo studies of humanized anticarcinoma antibody CC49," Hybridoma, 14:461-473 (1995).
Khawli et al., "Improved tumor localization and radioimaging with chemically modified monoclonal antibodies," Cancer Biother. Radiopharm., 11:203-215 (1996).
Kim et al., "Antibody Engineering for the Development of Therapeutic Antibodies," Mol. Cells, 20:17-29 (2005).
Kim et al., "Chemical modification to reduce renal uptake of disulfide-bonded variable region fragment of anti-tac monoclonal antibody labeled with $^{99m}$Tc," Bioconjugate Chem., 10:447-453 (1999).
Kim et al., "Lowering of pI by acylation improves the renal uptake of 99mTc-labeled anti-Tac dsFv: effect of different acylating reagents," Nucl. Med. Biol., 29:795-801 (2002).
Kobayashi et al., "The pharmacokinetic characteristics of glycolated humanized anti-Tac Fabs are determined by their isoelectric points," Cancer Res., 59:422-430 (1999).
Kreutz et al., "Efficient bispecific monoclonal antibody purification using gradient thiophilic affinity chromatography," J. Chromatogr. B, 714:161-170 (1998).
Lindhofer et al., "Preferential species-restricted heavy/light chain pairing in rat/mouse quadromas," J. Immunol., 155:219-225 (1995).
Lobo et al., "Antibody pharmacokinetics and pharmacodynamics," J. Pharm. Sci., 93:2645-68 (2004).
Lund et al., "Expression and characterization of truncated forms of humanized L243 IgG1. Architectural features can influence synthesis of its oligosaccharide chains and affect superoxide production triggered through human Fcgamma receptor I," Eur. J. Biochem., 267:7246-57 (2000).

(56) References Cited

OTHER PUBLICATIONS

Manzke et al., "Single-step purification of bispecific monoclonal antibodies for immunotherapeutic use by hydrophobic interaction chromatography," J. Immunol. Methods, 208:65-73 (1997).
Martin et al., "Crystal structure at 2.8 A of an FcRn/heterodimeric Fc complex: mechanism of pH-dependent binding," Mol. Cell, 7:867-877 (2001).
Marvin et al., "Recombinant approaches to IgG-like bispecific antibodies," Acta. Pharmacol. Sin., 26:649-658 (2005).
Marvin et al., "Redesigning an antibody fragment for faster association with its antigen," Biochemistry, 42:7077-83 (2003).
Merchant et al., "An efficient route to human bispecific IgG," Nat. Biotechnol., 16:677-681 (1998).
Onda et al., "Lowering the Isoelectric Point of the Fv Portion of Recombinant Immunotoxins Leads to Decreased Nonspecific Animal Toxicity without Affecting Antitumor Activity," Cancer Res., 61:5070-77 (2001).
Pavlinkova et al., "Charge-modified single chain antibody constructs of monoclonal antibody CC49: Generation, characterization, pharmacokinetics, and biodistribution analysis," Nucl. Med. Biol., 26:27-34 (1999).
Pavlou et al., "The therapeutic antibodies market to 2008," Eur. J. Pharm. Biopharm., 59:389-396 (2005).
Poduslo et al., "Polyamine modification increases the permeability of proteins at the blood—nerve and blood-brain barriers," J. Neurochem., 66:1599-1609 (1996).
Rajpal et al., A general method for greatly improving the affinity of antibodies by using combinatorial libraries, Proc. Natl. Acad. Sci. USA, 102:8466-71 (2005).
Rathanaswami et al., "Demonstration of an in vivo generated sub-picomolar affinity fully human monoclonal antibody to interleukin-8," Biochem. Biophys. Res. Commun., 334:1004-13 (2005).
Reichert et al., "Monoclonal antibody successes in the clinic," Nat. Biotechnol., 23:1073-78 (2005).
Sal-Man et al., "Arginine mutations within a transmembrane domain of Tar, an *Escherichia coli* aspartate receptor, can drive homodimer dissociation and heterodimer association in vivo," Biochem. J., 385:29-36 (2005).
Schaeffer et al., "The Rat Glomerular Filtration Barrier Does Not Show Negative Charge Selectivity," Microcirculation, 9:329-342 (2002).
Segal et al., "Bispecific antibodies in cancer therapy," Curr. Opin. Immunol., 11:558-562 (1999).
Shaul, "Exploring the charge space of protein-protein association: a proteomic study," Proteins, 60:341-352 (2005).
Shields et al., "High resolution mapping of the binding site on human IgG1 for Fc gamma RI, Fc gamma RII, Fc gamma RIII, and FcRn and design of IgG1 variants with improved binding to the Fc gamma R," J. Biol. Chem., 276:6591-6604 (2001) (Epub Nov. 28, 2000).
Tarditi et al., "Selective high-performance liquid chromatographic purification of bispecific monoclonal antibodies," J. Chromatogr., 599:13-20 (1992).
Ten Kate et al., "Effect of isoelectric point on biodistribution and inflammation: imaging with indium-111-labelled IgG," Eur. J. Nucl. Med., 17:305-309 (1990).
Tsurushita et al., "Design of humanized antibodies: From anti-Tac to Zenapax," Methods, 36:69-83 (2005).
Wu et al., "Development of motavizumab, an ultra-potent antibody for the prevention of respiratory syncytial virus infection in the upper and lower respiratory tract," J. Mol. Biol., 368:652-65 (2007).
Yamasaki et al., "Pharmacokinetic analysis of in vivo disposition of succinylated proteins targeted to liver nonparenchymal cells via scavenger receptors: importance of molecular size and negative charge density for in vivo recognition by receptors," J. Pharmacol. Exp. Ther., 301:467-477 (2002).
Yang et al., "Tailoring structure-function and pharmacokinetic properties of single-chain Fv proteins by site-specific PEGylation," Protein Eng., 16:761-770 (2003).
Zuckier et al., "Chimeric human-mouse IgG antibodies with shuffled constant region exons demonstrate that multiple domains contribute to in vivo half-life," Cancer Res., 58:3905-08 (1998).
International Preliminary Report on Patentability for App. Ser. No. PCT/JP2008/072152, dated Aug. 10, 2010, 7 pages.
International Search Report for App. Ser. No. PCT/JP2008/072152, mailed Mar. 10, 2009, 4 pages.
International Search Report for App. Ser. No. PCT/JP2008/067534, mailed Oct. 21, 2008, 4 pages.
International Preliminary Report on Patentability for App. Ser. No. PCT/JP2008/067534, dated Apr. 7, 2010, 7 pages.
International Search Report for App. Ser. No. PCT/JP2009/057309, mailed Jul. 7, 2009, 8 pages.
Inteational Preliminary Report on Patentability for App. Ser. No. PCT/JP2009/057309, mailed Nov. 30, 2010, 7 pages.
USPTO Restriction Requirement in U.S. Appl. No. 12/295,039, dated Oct. 12, 2010, 9 pages.
International Preliminary Report on Patentability for App. Ser. No. PCT/JP2007/057036, dated Oct. 21, 2008, 6 pages.
International Search Report for App. Ser. No. PCT/JP2007/057036, dated May 1, 2007, 2 pages.
European Search Report for App. Ser. No. 07 74 0494, dated Sep. 3, 2009, 3 pages.
International Search Report for App. Ser. No. PCT/JP2009/070376, mailed Dec. 28, 2009, 6 pages.
International Search Report for App. Ser. No. PCT/JP2008/072142, mailed Jan. 6, 2009, 2 pages.
International Preliminary Report on Patentability for App. Ser. No. PCT/JP2008/072142, dated Aug. 10, 2010, 5 pages.
Benjamini et al., Immunology: A Short Course, 2nd Edition, p. 40 only (1991).
USPTO Final Office Action in U.S. Appl. No. 12/303,684, mailed Oct. 14, 2011, 17 pages.
Algonomics—Tripole® applications [online] Retrieved from the Internet on Feb. 29, 2012: http://web.archive.org/web20090221052902/http://www.algonomics.com/proteinengineering/tripole_applications.php, 2 pages (Feb. 21, 2009).
Almagro et al., "Humanization of antibodies," *Front Biosci.*, 13:1619-33 (2008).
Armour et al., "Recombinant human IgG molecules lacking Fcgamma receptor I binding and monocyte triggering activities," *Eur. J. Immunol.*, 29(8):2613-24 (1999).
Bartelds et al., "Clinical response to adalimumab: relationship to anti-adalimumab antibodies and serum adalimumab concentrations in rheumatoid arthritis," *Ann Rheum. Dis.*, 66:921-926 (2007).
Bender et al., "Immunogenicity, efficacy and adverse events of adalimumab in RA patients," *Rheumatol. Int.*, 27:269-274 (2007).
Chau et al., "HuM291(Nuvion), a humanized Fc receptor-nonbinding antibody against CD3, anergizes peripheral blood T cells as partial agonist of the T cell receptor," *Transplantation.*, 71(7):941-50 (2001).
Chen et al., "Generation and analysis of random point mutations in an antibody CDR2 sequence: many mutated antibodies lose their ability to bind antigen," *J. Exp. Med.*, 176(3):855-66 (1992).
Chen et al., "Defective secretion of an immunoglobulin caused by mutations in the heavy chain complementarity determining region 2," *J. Exp. Med.*, 180(2):577-86 (1994).
Chu et al., "Accumulation of succinimide in a recombinant monoclonal antibody in mildly acidic buffers under elevated temperatures," *Pharm. Res.*, 24(6):1145-56 (2007).
Cole et al., "Human IgG2 variants of chimeric anti-CD3 are nonmitogenic to T cells," *J. Immunol.*, 159(7):3613-21 (1997).
Cordoba et al., "Non-enzymatic hinge region fragmentation of antibodies in solution," *J. Chromatogr. B. Analyt. Technol. Biomed. Life Sci.*, 818(2):115-21 (2005).
Damschroder et al., "Framework shuffling of antibodies to reduce immunogenicity and manipulate functional and biophysical properties," *Mol. Immunol.*, 44(11):3049-60 (2007).
De Groot et al., "De-immunization of therapeutic proteins by T-cell epitope modification," *Dev. Biol. (Basel)*, 122:171-94 (2005).
Fujii, "Antibody affinity maturation by random mutagenesis," *Methods Mol. Biol.*, 248:345-59 (2004).

(56) References Cited

OTHER PUBLICATIONS

Gerstner et al., "Sequence plasticity in the antigen-binding site of a therapeutic anti-HER2 antibody," *J. Mol. Biol.*, 321(5):851-62 (2002).
Gessner et al., "The IgG Fc receptor family," *Ann. Hematol.*, 76:231-248 (1998).
Guyre et al., "Increased potency of Fc-receptor-targeted antigens," *Cancer Immunol. Immunother.*, 45(3-4):146-8 (1997).
Hinton et al., "Engineered human IgG antibodies with longer serum half-lives in primates," *J. Biol. Chem.*, 279(8):6213-6 (2004).
Hwang et al., "Use of human germline genes in a CDR homology-based approach to antibody humanization," Methods, 36:35-42 (2005).
Johnson et al., "Cation exchange-HPLC and mass spectrometry reveal C-terminal amidation of an IgG1 heavy chain," *Anal. Biochem.*, 360:75-83 (2007).
Jones et al., "Identification and removal of a promiscuous CD4+ T cell epitope from the C1 domain of factor VIII," *Thromb. Haemost.*, 3:991-1000 (2005).
Katayose et al., "MUC1-specific targeting immunotherapy with bispecific antibodies: inhibition of xenografted human bile duct carcinoma growth," *Cancer Res.*, 56(18):4205-12 (1996).
Komissarov et al., "Site-specific mutagenesis of a recombinant anti-single-stranded DNA Fab. Role of heavy chain complementarity-determining region 3 residues in antigen interaction," *J. Biol. Chem.*, 272(43):26864-70 (1997).
Leong et al., "Adapting pharmacokinetic properties of a humanized anti-interleukin-8 antibody for therapeutic applications using site-specific pegylation," *Cytokine*, 16(3):106-19 (2001).
Liu et al., "Heterogeneity of monoclonal antibodies," *J. Pharm. Sci.*, 97(7):2426-47 (2008).
Maini et al., "Double-blind randomized controlled clinical trial of the interleukin-6 receptor antagonist, tocilizumab, in European patients with rheumatoid arthritis who had an incomplete response to methotrexate," Arthritis Rheum., 54:2817-29 (2006).
Nesterova et al., "Glypican-3 as a novel target for an antibody-drug conjugate," AACR Abstract No. 656, Los Angeles, CA (Apr. 4-18, 2007).
Nishimoto et al., "Humanized anti-interleukin-6 receptor antibody treatment of multicentric Castleman disease," *Blood*, 106:2627-32 (2005).
Nishimoto et al., "Interleukin 6: from bench to bedside," *Nat. Clin. Pract. Rheumatol.*, 2:619-626 (2006).
Ono et al., "The humanized anti-HM1.24 antibody effectively kills multiple myeloma cells by human effector cell-mediated cytotoxicity," *Mol. Immunol.*, 36(6):387-95 (1999).
Pardridge et al., "Enhanced endocytosis in cultured human breast carcinoma cells and in vivo biodistribution in rats of a humanized monoclonal antibody after cationization of the protein," *J. Pharmacol. Exp. Ther.*, 286(1):548-54 (1998).
Pons et al., "Energetic analysis of an antigen/antibody interface: alanine scanning mutagenesis and double mutant cycles on the HyHEL-10/lysozyme interaction," *Protein Sci.*, 8(5):958-68 (1999).
Presta, "Engineering of therapeutic antibodies to minimize immunogenicity and optimize function," *Adv. Drug Deliv. Rev.*, 58(5-6):640-56 (2006).
Reddy et al., "Elimination of Fc receptor-dependent effector functions of a modified IgG4 monoclonal antibody to human CD4," *J. Immunol.*, 164(4):1925-33 (2000).
Reichert et al., "Development trends for monoclonal antibody cancer therapeutics," *Nat. Rev. Drug Discov.*, 6(5):349-56 (2007).
Rothe et al., "Ribosome display for improved biotherapeutic molecules," *Expert Opin. Biol. Ther.*, 6:177-187 (2006).
Salfeld et al., "Isotype selection in antibody engineering," *Nat. Biotechnol.*, 25:1369-72 (2007).
Sato et al., "Reshaping a human antibody to inhibit the interleukin 6-dependent tumor cell growth," *Cancer Res.*, 53:851-856 (1993).
Schmitz et al., "Phage display: a molecular tool for the generation of antibodies—a review," *Placenta.*, 21 Suppl A:S106-12 (2000).
Shire et al., "Challenges in the development of high protein concentration formulations," *J. Pharm. Sci.*, 93:1390-1402 (2004).
Strand et al., "Biologic therapies in rheumatology: lessons learned, future directions," *Nat. Rev. Drug Discov.*, 6:75-92 (2007).
Teeling et al., "The biological activity of human CD20 monoclonal antibodies is linked to unique epitopes on CD20," *J Immunol.*, 177(1):362-71 (2006).
Vaisitti et al., "Cationization of monoclonal antibodies: another step towards the "magic bullet"?," *J. Biol. Regul. Homeost. Agents.*, 19(3-4):105-12 (2005).
Vajdos et al., "Comprehensive functional maps of the antigen-binding site of an anti-ErbB2 antibody obtained with shotgun scanning mutagenesis," *J. Mol. Biol.*, 320(2):415-28 (2002).
Van Walle et al., "Immunogenicity screening in protein drug development," *Expert Opin. Biol. Ther.*, 7(3):405-18 (2007).
Wiens et al., "Somatic mutation in VH complementarity-determining region 2 and framework region 2: differential effects on antigen binding and Ig secretion," *J. Immunol.*, 159(3):1293-302 (1997).
Wiens et al., "Mutation of a single conserved residue in VH complementarity-determining region 2 results in a severe Ig secretion defect," *J. Immunol.*, 167(4):2179-86 (2001).
Xiang et al., "Study of B72.3 combining sites by molecular modeling and site-directed mutagenesis," *Protein Eng.*, 13(5):339-44 (2000).
Zwick et al., "The long third complementarity-determining region of the heavy chain is important in the activity of the broadly neutralizing anti-human immunodeficiency virus type 1 antibody 2F5," *J. Virol.*, 78(6):3155-61 (2004).
Amersham Biosciences, "Affinity Chromatography: Principles and Methods," Edition AD, pp. 16-18, 137 (2002).
Krauss et al., "Impact of antibody framework residue VH-71 on the stability of a humanised anti-MUC1 scFv and derived immunoenzyme," *Br. J. Cancer*, 90:1863-70 (2004).
Marks et al., "By-passing immunization: building high affinity human antibodies by chain shuffling," *Biotechnology (N.Y.)*, 10(7):779-83 (1992).
Ohno et al., "Antigen-binding specificities of antibodies are primarily determined by seven residues of VH," *Proc. Natl. Acad. Sci. U.S.A.*, 82(9):2945-9 (1985).
Presta et al., "Molecular engineering and design of therapeutic antibodies," *Curr. Opin. Immunol.*, 20(4):460-70. doi: 10.1016/j.coi. 2008.06.012 (2008).
Roitt et al., *Immunology, M., Mir*, (2000), pp. 110, 150, and 537-9 (in Russian, with what is believed to be a published English equivalent of those pages).
Singer et al., Genes & Genomes 1:63 (1998) (in Russian, with English translation).
Yang et al., "CDR walking mutagenesis for the affinity maturation of a potent human anti-HIV-1 antibody into the picomolar range," *J. Mol. Bio.*, 254(3):392-403 (1995).
Zhu et al., "MHC class I-related neonatal Fc receptor for IgG is functionally expressed in monocytes, intestinal macrophages, and dendritic cells," *J. Immunol.*, 166(5):3266-76 (2001).
USPTO Notice of Allowance in U.S. Appl. No. 12/746,229, dated Feb. 12, 2013, 7 pages.
USPTO Notice of Allowance in U.S. Appl. No. 12/746,229, dated Mar. 27, 2013, 8 pages.
USPTO Non-Final Office Action U.S. Appl. No. 12/680,082, dated Feb. 14, 2013, 12 pages.
USPTO Non-Final Office Action in U.S. Appl. No. 12/679,922, dated Jan. 3, 2013, 25 pages.
USPTO Restriction Requirement in U.S. Appl. No. 13/257,145, dated Mar. 20, 2013, 11 pages.
Castellani et al., "Interleukin-31: A New Cytokine Involved in Inflammation of the Skin," *Int. J. Immunopathol. Pharmacol.*, 19:1-4 (2006).
Sonkoly et al., "IL-31: a new link between T cells and pruritus in atopic skin inflammation," *J. Allergy Clin. Immunol.*, 117:411-417 (2006).
Calbiochem® Buffers, "A guide for the preparation and use of buffers in biological systems," by Chandra Mohan, Ph.D., Copyright © 2003 EMD Biosciences, Inc., an Affiliate of Merck KGaA, Darmstadt, Germany, 37 pages.

(56) References Cited

OTHER PUBLICATIONS

Fish & Richardson P.C., Response to Restriction Requirement dated Oct. 12, 2010 in U.S. Appl. No. 12/295,039, filed Apr. 11, 2011, 9 pages.
USPTO Restriction Requirement in U.S. Appl. No. 12/303,684, mailed Aug. 23, 2010, 7 pages.
Fish & Richardson P.C., Amendment and Response to Restriction Requirement dated Aug. 23, 2010 in U.S. Appl. No. 12/303,684, filed Sep. 15, 2010, 3 pages.
USPTO Non-Final Office Action in U.S. Appl. No. 12/303,684, mailed Oct. 14, 2010, 18 pages.
Fish & Richardson P.C., Amendment in Reply to Office Action dated Oct. 14, 2010 in U.S. Appl. No. 12/303,684, filed Apr. 12, 2011, 11 pages.
Martinez et al., "Disulfide connectivity of human immunoglobulin G2 structural isoforms," *Biochemistry*, 47(28):7496-7508 (2008).
Wypych et al., "Human IgG2 antibodies display disulfide-mediated structural isoforms," *J. Biol. Chem.*, 283(23):16194-16205 (2008).
USPTO Final Office Action in U.S. Appl. No. 12/295,039, dated Apr. 12, 2012, 8 pages.
USPTO Restriction Requirement in U.S. Appl. No. 12/746,229, dated Apr. 12, 2012, 5 pages.
Allen et al., "Interchain disulfide bonding in human IgG2 antibodies probed by site-directed mutagenesis," *Biochemistry*, 48(17):3755-66 (2009).
Fish & Richardson P.C., Amendment in Reply to Office Action dated Oct. 18, 2012 in U.S. Appl. No. 12/745,781, filed Apr. 17, 2013, 23 pages.
Fish & Richardson P.C., Preliminary Amendment and Response to Restriction Requirement dated Mar. 20, 2013 in U.S. Appl. No. 13/257,145, filed Apr. 22, 2013, 7 pages.
Igawa et al., "Engineering the variable region of therapeutic IgG antibodies," *MAbs*, 3(3):243-52 (2011).
Igawa et al., "Reduced elimination of IgG antibodies by engineering the variable region," *Protein Eng. Des. Sel.*, 23(5):385-92 (2010).
Maeda et al., "pH-dependent receptor/ligand dissociation as a determining factor for intracellular sorting of ligands for epidermal growth factor receptors in rat hepatocytes," *J. Control Release*, 82(1):71-82 (2002).
Maxfield et al., "Endocytic recycling," *Nat. Rev. Mol. Cell Biol.*, 5(2):121-32 (2004).
Murtaugh et al., "A combinatorial histidine scanning library approach to engineer highly pH-dependent protein switches," *Protein Sci.*, 20(9):1619-31 doi:10.1002/pro 696 (2011).
European Search Report for App. Ser. No. EP 09 72 9337, dated Nov. 3, 2011, 3 pages.
USPTO Final Office Action in U.S. Appl. No. 12/745,781, dated May 21, 2013, 16 pages.
Levin et al., "Optimizing the affinity and specificity of proteins with molecular display," *Mol. Biosyst.*, 2(1):49-57 (2006) (Epub Nov. 8, 2005).
Wang et al., "Polyethylene Glycol-modified Chimeric Toxin Composed of Transforming Growth Factor alpha and *Pseudomonas* Exotoxin," *Cancer. Res.*, 53:4588-4594 (1993).
Fish & Richardson P.C., Amendment in Reply to Final Office Action dated Oct. 14, 2011 in U.S. Appl. No. 12/303,686, filed Jun. 12, 2012, 20 pages.
USPTO Interview Summary in U.S. Appl. No. 12/303,684, mailed Jun. 14, 2012, 4 pages.
Fish & Richardson P.C., Third Preliminary Amendment and Response to Restriction Requirement dated Dec. 6, 2011 in U.S. Appl. No. 12/936,587, filed Jun. 5, 2012, 7 pages.
USPTO Restriction Requirement in U.S. Appl. No. 12/680,082, dated Jun. 6, 2012, 12 pages.
Fish & Richardson P.C. Amendment and Response to Restriction Requirement dated Apr. 12, 2012 in U.S. Appl. No. 12/746,229, filed May 10, 2012, 7 pages.
USPTO Restriction Requirement in U.S. Appl. No. 12/746,229, dated Jun. 25, 2012, 4 pages.
USPTO Restriction Requirement in U.S. Appl. No. 12/936,587, dated Jun. 25, 2012, 5 pages.
MacNeal, Robert J., "Itching (Pruritus)," Merck Manual, May 2009 [retrieved on Jun. 10, 2011]. Retrieved from the Internet: http://www.merckmanuals.com/professional/sec10/ch109/ch109d.html, 6 pages.
Phillips, "The challenge of gene therapy and DNA delivery," J. Pharm. Pharmacol., 53:1169-74 (2001).
Pirollo et al., "Targeted delivery of small interfering RNA: approaching effective cancer therapies," Cancer Res., 68:1247-50 (2008).
Vidal et al., "Making sense of antisense," Eur. J. Cancer, 41:2812-18 (2005).
Zhang et al., "Structures and biological functions of IL-31 and IL-31 receptors," Cytokine Growth Factor Rev., 19:347-356 (2008).
USPTO Restriction Requirement in U.S. Appl. No. 12/303,684, mailed Jun. 21, 2011, 5 pages.
USPTO Non-Final Office Action in U.S. Appl. No. 12/746,229, mailed Jun. 16, 2011, 16 pages.
USPTO Non-Final Office Action in U.S. Appl. No. 12/295,039, dated Jun. 28, 2011, 9 pages.
Cork et al., "Epidermal barrier dysfunction in atopic dermatitis," *J. Invest. Dermatol.*, 129:1892-1908 (2009).
Fish & Richardson P.C., Response to Restriction Requirement dated Jun. 21, 2011 in U.S. Appl. No. 12/303,684, filed Jul. 12, 2011, 2 pages.
Dall'Acqua et al., "Modulation of the effector functions of a human IgG1 through engineering of its hinge region," *J. Immunol.*, 177(2):1129-38 (2006).
Rose-John et al., "Interleukin-6 biology is coordinated by membrane-bound and soluble receptors: role in inflammation and cancer," *J. Leukoc. Biol.*, 80(2):227-36 (2006).
USPTO Non-Final Office Action in U.S. Appl. No. 13/257,145, dated Jul. 2, 2013, 20 pages.
Fish & Richardson P.C., Amendment in Reply to Action dated Jan. 3, 2013 in U.S. Appl. No. 12/679,922, filed Jul. 2, 2013, 18 pages.
Pakula et al., "Genetic Analysis of Protein Stability and Function," *Annu. Rev. Genet.*, (1989), 23:289-310.
Roitt et al., *Immunology, M., Mir*, (2000), pp. 110-111 (in Russian, with what is believed to be a published English equivalent of those pages taken from Roitt et al., "Antibody Structure and Function," Immunology, Fifth Ed., (1998), pp. 80-81).
International Preliminary Report on Patentability for App. Ser. No. PCT/JP2009/070376, dated Jul. 5, 2011, 11 pages.
Chirino et al., "Minimizing the immunogenicity of protein therapeutics," *Drug Discov. Today*, 9(2):82-90 (2004).
Dillon et al., "Interleukin 31, a cytokine produced by activated T cells, induces dermatitis in mice," *Nat. Immunol.*, 5(7):752-760 (2004).
Diveu et al., "GPL, a novel cytokine receptor related to GP130 and leukemia inhibitory factor receptor," *J. Biol. Chem.*, 278(50):49850-49859 (2003).
Hanes et al., "Picomolar affinity antibodies from a fully synthetic naive library selected and evolved by ribosome display," *Nat. Biotechnol.*, 18(12):1287-1292 (2000).
Neis et al., "Enhanced expression levels of IL-31 correlate with IL-4 and IL-13 in atopic and allergic contact dermatitis," *J. Allergy Clin. Immunol.*, 118(4):930-937 (2006).
Raap et al., "Correlation of IL-31 serum levels with severity of atopic dermatitis," *J. Allergy Clin. Immunol.*, 122(2):421-423 (2008).
Tan et al., "Engineering the isoelectric point of a renal cell carcinoma targeting antibody greatly enhances scFv solubility," *Immunotechnology*, 4(2):107-114 (1998).
Yagi et al., "Interleukin-31 stimulates production of inflammatory mediators from human colonic subepithelial myofibroblasts," *Int. J. Mol. Med.*, 19(6):941-946 (2007).

| | FR 1 | CDR 1 | FR 2 | CDR 2 |
|---|---|---|---|---|
| | 0 1 2 | 3 | | |
| | 1 2 3 4 5 6 7 8 9 0 1 2 3 4 5 6 7 8 9 0 1 2 3 | 4 5 6 7 a 8 9 0 1 2 3 4 | 5 6 7 8 9 0 1 2 3 4 5 6 7 8 9 | 0 1 2 3 4 5 6 |
| NS18 | D I Q M T Q S P A S L S A S V G E T V T I T C | R A S E   N I Y S F L A | W Y Q Q K Q G K S P H L L V Y | N A K T L A K |
| NS22 | - - - - - - - - - - - - - - - - - - - - - - - | - T - -   - - - - - - - | - - - - - - - - - - - - - - - | - - - - - - - |
| NS23 | - - - - - - - - - - - - - - - - - - - - F - - | - - N -   - - - - Y - - | - - - - - - - - - - Q - - - - | - - - - - - E |
| NS33 | E N V L - - - - - I M - - - P - - K - - M - - | - - - S S V S S - Y - H | - - - - - S - A - - K - W I - | S T S N - - S |

| | FR 3 | CDR 3 | FR 4 | |
|---|---|---|---|---|
| | 6 7 8 | 9 | 1 0 | |
| | 7 8 9 0 1 2 3 4 5 6 7 8 9 0 1 2 3 4 5 6 7 8 9 0 1 2 3 4 5 6 7 8 | 9 0 1 2 3 4 5 6 7 | 8 9 0 1 2 3 4 5 6 7 | |
| NS18 | G V P S R F S G S G S G T Q F S L K I N S L Q P E D F G S Y Y C | Q H H Y E S P L T | F G G G T K L E I K | SEQ ID NO: 8 |
| NS22 | - - - - - - - - - - - - - - - - - - - - - - - - - - - - - - F - | - - - - - - - - - | - - - - - - - - - - | SEQ ID NO: 16 |
| NS23 | - - - - - - - - - - - - - - - - - - - - - - - - - - - - - - - - | - - - - G T - P - | - - - - - - - - - - | SEQ ID NO: 24 |
| NS33 | - - - A - - - - - - - - - S Y Y F T I S - V E A - - A A T - - - | - Q Y S G Y - - - | - - - - - - - - - - | SEQ ID NO: 32 |

FIG. 2

Humanized

| | FR1 | CDR1 | FR2 | CDR2 | FR3 | CDR3 | FR4 | |
|---|---|---|---|---|---|---|---|---|
| | 0 1 2 3 | | 4 | 5 6 | 6 7 8 9 | 10 | 11 | |
| | 123456789012345678901234567890 | 12345 | 67890123456789 | 012ab4567890123 45 | 6789012345678901 2abc34567890123 4 | 567890abcd12 | 34567890123 | |
| H0 | QVQLVQSGAEVKKPGASVKVSCKASGYTFT | GYIMN | WVRQAPGQGLEWMG | LINPYNGGTSYNQKFKG | RVTITADESTSTAYMELSSLRSEDTAVYYCAR | DGYDDGPYTMDY | WGQGTLVTVSS | SEQ ID NO:50 |
| Hp5 | ------------------------------ | ----- | --Q-S--------- | ----------------- | -------------------------------- | ------------ | ----------- | |
| Hp7 | ------------------------------ | ----- | -------------- | E---------------- | -------------------------------- | ------------ | ----------- | |
| Hp8 | ------------------------------ | ----- | -------------- | --D-------------- | -------------------------------- | ------------ | ----------- | |
| Hp6 | ------------------------------ | ----- | -------------- | ------------D---- | -------------------------------- | ------------ | ----------- | |
| Hp9 | ------------------------------ | ----- | -------------- | -------------Q--- | -------------------------------- | ------------ | ----------- | |
| Hp1 | ------------------------------ | ----- | -------------- | ---------------Q- | -------------------------------- | ------------ | ----------- | |
| Hp13 | ------------------------------ | ----- | -------------- | ---------------QD | -------------------------------- | ------------ | ----------- | |
| Hp3 | ------------------------------ | ----- | -------------- | -------------Q-QD | -------------------------------- | ------------ | ----------- | |

FIG. 28-1

| | FR1 | CDR1 | FR2 | CDR2 | FR3 | CDR3 | FR4 | |
|---|---|---|---|---|---|---|---|---|
| | 0 1 2 3 | | 4 | 5 6 | 6 7 8 9 | 10 | 11 | |
| | 123456789012345678901234567890 | 12345 | 67890123456789 | 012ab4567890123 45 | 67890123456789012abc345678901234 | 567890abcd12 | 34567890123 | |
| H0 | QVQLVQSGAEVKKPGASVKVSCKASGYTFT | GYIMN | WVRQAPGQGLEWMG | LINPYNGGTSYNQKFKG | RVTITADESTSTAYMELSSLRSEDTAVYYCAR | DGYDDGPYTMDY | WGQGTLVTVSS | SEQ ID NO:50 |
| Ha355 | ------------------------------ | ----- | -------------- | ----------------- | -------------------------------- | ---------LET | ----------- | |
| Ha356 | ------------------------------ | ----- | -------------- | ----------------- | -------------------------------- | ----------ET | ----------- | |
| Ha360 | ------------------------------ | ----- | -------------- | ----------------- | -------------------------------- | --L-------ET | ----------- | |
| Ha362 | ------------------------------ | ----- | -------------- | ----------------- | -------------------------------- | --L-------ES | ----------- | |
| Ha101 | ------------------------------ | --V-- | -------------- | ----------------- | -------------------------------- | ------------ | ----------- | |
| Ha103 | ------------------------------ | ---I- | -------------- | ----------------- | -------------------------------- | ------------ | ----------- | |
| Ha111 | ------------------------------ | ---L- | -------------- | ----------------- | -------------------------------- | ------------ | ----------- | |
| Ha204 | ------------------------------ | ----- | -------------- | ---------D------- | -------------------------------- | ------------ | ----------- | |
| Ha219 | ------------------------------ | ----- | -------------- | ------------P---- | -------------------------------- | ------------ | ----------- | |
| Ha401 | ------------------------------ | --VI- | -------------- | ---------D------- | -------------------------------- | ------------ | ----------- | |
| H17 | ------------------------------ | --VL- | -------------- | ---------D--PQ-QD | -------------------------------- | ------------ | ----------- | |
| H19 | ------------------------------ | --A-- | -------------- | ---------D--PQ-QD | -------------------------------- | ------------ | ----------- | |

FIG. 28-2

| | FR1 | CDR1 | FR2 | CDR2 | FR3 | CDR3 | FR4 | |
|---|---|---|---|---|---|---|---|---|
| | 0 1 2 3<br>123456789012345678901234567890 | 12345 | 4<br>67890123456789 | 5 6<br>012ab456789012345 | 6 7 8 9<br>67890123456789012abc345678901234 | 10<br>567890abcd12 | 11<br>34567890123 | |
| H0 | QVQLVQSGAEVKKPGASVKVSCKASGYTFT | GYIMN | WVRQAPGQGLEWMG | LINPYNGGTSYNQKFKG | RVTITADESTSTAYMELSSLRSEDTAVYYCAR | DGYDDGPYTMDY | WGQGTLVTVSS | SEQ ID NO:50 |
| H28 | ------------------------------ | --VL- | -------------- | ---------D--PQ-QD | -------------------------------- | ---------LET | ----------- | |
| H30 | ------------------------------ | ----- | -------------- | ---------D--PQ-QD | -------------------------------- | ---------LET | ----------- | |
| H34 | ------------------------------ | --A-- | -------------- | ---------D--PQ-QD | -------------------------------- | ---------LET | ----------- | |
| H42 | ------------------------------ | --VL- | -------------- | ---------D--PQ-QD | -------K------------------------ | ---------LET | ----------- | |
| H44 | ------------------------------ | ----- | -------------- | ---------D--PQ-QD | -------K------------------------ | ---------LET | ----------- | |
| H46 | ------------------------------ | --A-- | -------------- | ---------D--PQ-QD | -------K------------------------ | ---------LET | ----------- | |
| H57 | ------------------------------ | ----- | -------------- | ---------D--PQ-Q- | -------------------------------- | ---------LET | ----------- | |
| H71 | ------------------------------ | --A-- | -------------- | ---------D--PQ-Q- | -------------------------------- | ---------LET | ----------- | |
| H78 | ------------------------------ | ----- | -------------- | ---------D--PQ-Q- | -------K------------------------ | ---------LET | ----------- | |
| H92 | ------------------------------ | --A-- | -------------- | ---------D--PQ-Q- | -------K------------------------ | ---------LET | ----------- | |
| H97 | ------------------------------ | ----- | -------------- | -------------Q-QD | -------------------------------- | ---------LET | ----------- | |
| H98 | ------------------------------ | ----- | -------------- | -------------Q-QD | -------K------------------------ | ---------LET | ----------- | |

FIG. 28-3

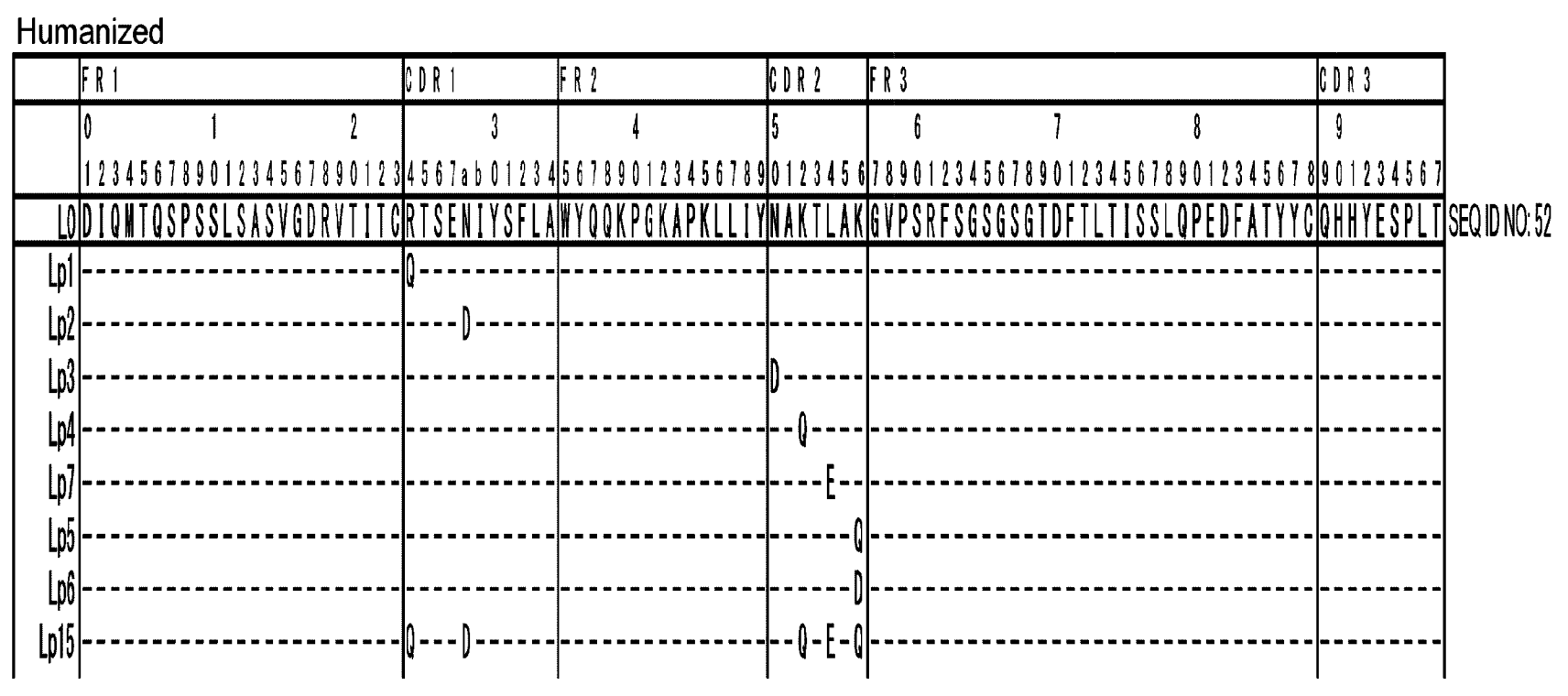

Humanized

| | FR1 | CDR1 | FR2 | CDR2 | FR3 | CDR3 | |
|---|---|---|---|---|---|---|---|
| | 0 1 2 | 3 | 4 | 5 | 6 7 8 | 9 | |
| | 12345678901234567890123 | 4567ab01234 | 567890123456789 | 0123456 | 78901234567890123456789012345678 | 901234567 | |
| L0 | DIQMTQSPSSLSASVGDRVTITC | RTSENIYSFLA | WYQQKPGKAPKLLIY | NAKTLAK | GVPSRFSGSGSGTDFTLTISSLQPEDFATYYC | QHHYESPLT | SEQ ID NO: 52 |
| Lp1 | ----------------------- | Q---------- | --------------- | ------- | -------------------------------- | --------- | |
| Lp2 | ----------------------- | ----D------ | --------------- | ------- | -------------------------------- | --------- | |
| Lp3 | ----------------------- | ----------- | --------------- | D------ | -------------------------------- | --------- | |
| Lp4 | ----------------------- | ----------- | --------------- | --Q---- | -------------------------------- | --------- | |
| Lp7 | ----------------------- | ----------- | --------------- | ----E-- | -------------------------------- | --------- | |
| Lp5 | ----------------------- | ----------- | --------------- | ------Q | -------------------------------- | --------- | |
| Lp6 | ----------------------- | ----------- | --------------- | ------D | -------------------------------- | --------- | |
| Lp15 | ----------------------- | Q---D------ | --------------- | --Q-E-Q | -------------------------------- | --------- | |

FIG. 29-1

| | FR1 | CDR1 | FR2 | CDR2 | FR3 | CDR3 | |
|---|---|---|---|---|---|---|---|
| | 0 1 2 | 3 | 4 | 5 | 6 7 8 | 9 | |
| | 12345678901234567890123 | 4567ab01234 | 567890123456789 | 0123456 | 78901234567890123456789012345678 | 901234567 | |
| L0 | DIQMTQSPSSLSASVGDRVTITC | RTSENIYSFLA | WYQQKPGKAPKLLIY | NAKTLAK | GVPSRFSGSGSGTDFTLTISSLQPEDFATYYC | QHHYESPLT | SEQ ID NO:52 |
| La134 | ----------------------- | -------R--- | --------------- | ------- | -------------------------------- | --------- | |
| La130 | ----------------------- | -------R-V- | --------------- | ------- | -------------------------------- | --------- | |
| La303 | ----------------------- | ----------- | --------------- | ------- | -------------------------------- | ----D---- | |
| La328 | ----------------------- | ----------- | --------------- | ------- | -------------------------------- | -----D--- | |
| La326 | ----------------------- | ----------- | --------------- | ------- | -------------------------------- | --------F | |
| La402 | ----------------------- | Q------R-V- | --------------- | ------- | -------------------------------- | ----D---- | |
| L11 | ----------------------- | Q---D--R-V- | --------------- | --Q-E-Q | -------------------------------- | ----D---- | |
| L12 | ----------------------- | Q---D----V- | --------------- | --Q-E-Q | -------------------------------- | ----D---- | |
| L17 | ----------------------- | QA--D----V- | --------------- | --Q-E-Q | -------------------------------- | ----D---- | |
| L50 | ----------------------- | QA--D------ | --------------- | --Q-E-Q | -------------------------------- | ----D---- | |

FIG. 29-2

ANTI-NR10 ANTIBODY AND USE THEREOF

CROSS-REFERENCE TO RELATED APPLICATIONS

This application is the National Stage of International Application Serial No. PCT/JP2009/070376, filed on Dec. 4, 2009, which claims the benefit of International Applications Serial Nos. PCT/JP2008/072152, filed on Dec. 5, 2008 and PCT/JP2009/054941, filed on Mar. 13, 2009. The contents of the foregoing applications are incorporated herein by reference.

TECHNICAL FIELD

The present invention relates to anti-NR10 antibodies, and pharmaceutical compositions comprising an anti-NR10 antibody.

BACKGROUND

Many cytokines are known as humoral factors involved in the growth and differentiation of various types of cells, or in the activation of differentiated mature cell functions. Cytokine-stimulated cells produce different types of cytokines, thereby forming networks of multiple cytokines in the body. Biological homeostasis is maintained by a delicate balance of the mutual regulation between cytokines in these networks. Many inflammatory diseases are thought to result from a failure of such cytokine networks. Thus, monoclonal antibody-based anti-cytokine therapy is drawing much attention. For example, anti-TNF antibodies and anti-IL-6 receptor antibodies have been demonstrated to be highly effective clinically. On the other hand, there are many examples of failure where no therapeutic effects were produced when a single cytokine, such as IL-4, was blocked alone, due to the activation of compensatory pathways in actual pathological conditions.

The present inventors succeeded in isolating a novel cytokine receptor NR10 that was highly homologous to gp130, a receptor for IL-6 signal transduction (Patent Document 1). NR10 forms a heterodimer with oncostatin M receptor (OSMR) and functions as an IL-31 receptor (Non-patent Document 1). Regarding IL-31, it has been reported that transgenic mice overexpressing IL-31 spontaneously develop pruritic dermatitis (Patent Document 2).

Antibodies that bind to NR10 and inhibit the binding between NR10 and IL-31 may be effective in treating inflammatory diseases. For clinical use, anti-NR10 antibodies are required to have low immunogenicity. Furthermore, in order to achieve high therapeutic effects, antibodies with strong NR10-binding or neutralizing activity are desired.

Prior art documents of the present invention are described below.

Patent Document 1: WO00/75314

Patent Document 2: WO03/060090

Non-patent Document 1: IL-31 is associated with cutaneous lymphocyte antigen-positive skin homing T cells in patients with atopic dermatitis, J Allergy Clin Immunol. 2006 February; 117(2): 418-25.

SUMMARY

Problems to be Solved by the Invention

The present invention was achieved in view of the circumstances described above. An objective of the present invention is to provide anti-NR10 antibodies, and pharmaceutical compositions comprising an anti-NR10 antibody.

Means for Solving the Problems

The present inventors conducted dedicated studies to achieve the objective described above. The present inventors succeeded in obtaining anti-NR10 antibodies having an effective neutralizing activity against NR10. Furthermore, the present inventors succeeded in humanizing the antibodies while maintaining their activity. The present inventors also successfully produced antibodies with improved pharmacokinetics, enhanced antigen-binding activity, improved stability, and/or reduced risk of immunogenicity. These antibodies are useful as therapeutic agents for inflammatory diseases.

The present invention relates to anti-NR10 antibodies, and pharmaceutical compositions comprising an anti-NR10 antibody. More specifically, the present invention includes:

[1] an antibody that recognizes domain 1 of NR10;

[2] the antibody of [1], which has a neutralizing activity;

[3] the antibody of [1] or [2], which is a humanized antibody;

[4] an anti-NR10 antibody which is any one of:

(1) an antibody comprising a heavy chain variable region which comprises CDR1 comprising the amino acid sequence of SEQ ID NO: 1, CDR2 comprising the amino acid sequence of SEQ ID NO: 2, and CDR3 comprising the amino acid sequence of SEQ ID NO: 3;

(2) an antibody comprising the heavy chain variable region of SEQ ID NO: 4;

(3) an antibody comprising a light chain variable region which comprises CDR1 comprising the amino acid sequence of SEQ ID NO: 5, CDR2 comprising the amino acid sequence of SEQ ID NO: 6, and CDR3 comprising the amino acid sequence of SEQ ID NO: 7;

(4) an antibody comprising the light chain variable region of SEQ ID NO: 8;

(5) an antibody comprising the heavy chain variable region of (1) and the light chain variable region of (3);

(6) an antibody comprising the heavy chain variable region of (2) and the light chain variable region of (4);

(7) an antibody in which one or more amino acids are substituted, deleted, added, and/or inserted in the antibody of any one of (1) to (6), which has an activity equivalent to that of the antibody of any one of (1) to (6); and (8) an antibody which binds to the same epitope as an epitope bound by the antibody of any one of (1) to (7);

[5] an anti-NR10 antibody which is any one of:

(1) an antibody comprising a heavy chain variable region which comprises CDR1 comprising the amino acid sequence of SEQ ID NO: 9, CDR2 comprising the amino acid sequence of SEQ ID NO: 10, and CDR3 comprising the amino acid sequence of SEQ ID NO: 11;

(2) an antibody comprising the heavy chain variable region of SEQ ID NO: 12;

(3) an antibody comprising a light chain variable region which comprises CDR1 comprising the amino acid sequence of SEQ ID NO: 13, CDR2 comprising the amino acid sequence of SEQ ID NO: 14, and CDR3 comprising the amino acid sequence of SEQ ID NO: 15;

(4) an antibody comprising the light chain variable region of SEQ ID NO: 16;

(5) an antibody comprising the heavy chain variable region of (1) and the light chain variable region of (3);

(6) an antibody comprising the heavy chain variable region of (2) and the light chain variable region of (4);

(7) an antibody in which one or more amino acids are substituted, deleted, added, and/or inserted in the antibody of any one of (1) to (6), which has an activity equivalent to that of the antibody of any one of (1) to (6); and (8) an antibody which binds to the same epitope as an epitope bound by the antibody of any one of (1) to (7);

[6] an anti-NR10 antibody which is any one of:

(1) an antibody comprising a heavy chain variable region which comprises CDR1 comprising the amino acid sequence of SEQ ID NO: 17, CDR2 comprising the amino acid sequence of SEQ ID NO: 18, and CDR3 comprising the amino acid sequence of SEQ ID NO: 19;

(2) an antibody comprising the heavy chain variable region of SEQ ID NO: 20;

(3) an antibody comprising a light chain variable region which comprises CDR1 comprising the amino acid sequence of SEQ ID NO: 21, CDR2 comprising the amino acid sequence of SEQ ID NO: 22, and CDR3 comprising the amino acid sequence of SEQ ID NO: 23;

(4) an antibody comprising the light chain variable region of SEQ ID NO: 24;

(5) an antibody comprising the heavy chain variable region of (1) and the light chain variable region of (3);

(6) an antibody comprising the heavy chain variable region of (2) and the light chain variable region of (4);

(7) an antibody in which one or more amino acids are substituted, deleted, added, and/or inserted in the antibody of any one of (1) to (6), which has an activity equivalent to that of the antibody of any one of (1) to (6); and (8) an antibody which binds to the same epitope as an epitope bound by the antibody of any one of (1) to (7);

[7] an anti-NR10 antibody which is any one of:

(1) an antibody comprising a heavy chain variable region which comprises CDR1 comprising the amino acid sequence of SEQ ID NO: 25, CDR2 comprising the amino acid sequence of SEQ ID NO: 26, and CDR3 comprising the amino acid sequence of SEQ ID NO: 27;

(2) an antibody comprising the heavy chain variable region of SEQ ID NO: 28;

(3) an antibody comprising a light chain variable region which comprises CDR1 comprising the amino acid sequence of SEQ ID NO: 29, CDR2 comprising the amino acid sequence of SEQ ID NO: 30, and CDR3 comprising the amino acid sequence of SEQ ID NO: 31;

(4) an antibody comprising the light chain variable region of SEQ ID NO: 32;

(5) an antibody comprising the heavy chain variable region of (1) and the light chain variable region of (3);

(6) an antibody comprising the heavy chain variable region of (2) and the light chain variable region of (4);

(7) an antibody in which one or more amino acids are substituted, deleted, added, and/or inserted in the antibody of any one of (1) to (6), which has an activity equivalent to that of the antibody of any one of (1) to (6); and (8) an antibody which binds to the same epitope as an epitope bound by the antibody of any one of (1) to (7);

[8] an antibody or antibody variable region which is any one of:

(1) a heavy chain variable region comprising CDR1 of SEQ ID NO: 196, CDR2 of SEQ ID NO: 197, and CDR3 of SEQ ID NO: 11 (H17);

(2) a heavy chain variable region comprising CDR1 of SEQ ID NO: 176, CDR2 of SEQ ID NO: 197, and CDR3 of SEQ ID NO: 11 (H19);

(3) a heavy chain variable region comprising CDR1 of SEQ ID NO: 196, CDR2 of SEQ ID NO: 197, and CDR3 of SEQ ID NO: 184 (H28, H42);

(4) a heavy chain variable region comprising CDR1 of SEQ ID NO: 9, CDR2 of SEQ ID NO: 197, and CDR3 of SEQ ID NO: 184 (H30, H44);

(5) a heavy chain variable region comprising CDR1 of SEQ ID NO: 176, CDR2 of SEQ ID NO: 197, CDR3 of SEQ ID NO: 184 (H34, H46);

(6) a heavy chain variable region comprising CDR1 of SEQ ID NO: 9, CDR2 of SEQ ID NO: 198, and CDR3 of SEQ ID NO: 184 (H57, H78);

(7) a heavy chain variable region comprising CDR1 of SEQ ID NO: 176, CDR2 of SEQ ID NO: 198, and CDR3 of SEQ ID NO: 184 (H71, H92);

(8) a heavy chain variable region comprising CDR1 of SEQ ID NO: 9, CDR2 of SEQ ID NO: 199, and CDR3 of SEQ ID NO: 184 (H97, H98);

(9) a light chain variable region comprising CDR1 of SEQ ID NO: 200, CDR2 of SEQ ID NO: 170, and CDR3 of SEQ ID NO: 193 (L11);

(10) a light chain variable region comprising CDR1 of SEQ ID NO: 201, CDR2 of SEQ ID NO: 170, and CDR3 of SEQ ID NO: 193 (L12);

(11) a light chain variable region comprising CDR1 of SEQ ID NO: 202, CDR2 of SEQ ID NO: 170, and CDR3 of SEQ ID NO: 193 (L17);

(12) a light chain variable region comprising CDR1 of SEQ ID NO: 203, CDR2 of SEQ ID NO: 170, and CDR3 of SEQ ID NO: 193 (L50);

(13) an antibody comprising the heavy chain variable region of (3) and the light chain variable region of (11);

(14) an antibody comprising the heavy chain variable region of (4) and the light chain variable region of (11);

(15) an antibody comprising the heavy chain variable region of (5) and the light chain variable region of (11);

(16) an antibody comprising the heavy chain variable region of (6) and the light chain variable region of (11);

(17) an antibody comprising the heavy chain variable region of (7) and the light chain variable region of (11);

(18) an antibody comprising the heavy chain variable region of (8) and the light chain variable region of (12);

(19) an antibody in which one or more amino acids are substituted, deleted, added, and/or inserted in the antibody of any one of (13) to (18), which has an activity equivalent to that of the antibody of any one of (13) to (18); and

(20) an antibody which binds to the same epitope as an epitope bound by the antibody of any one of (13) to (18);

[9] an antibody or antibody variable region which is any one of:

(1) a heavy chain variable region comprising the amino acid sequence of SEQ ID NO: 204 (H17);

(2) a heavy chain variable region comprising the amino acid sequence of SEQ ID NO: 205 (H19);

(3) a heavy chain variable region comprising the amino acid sequence of SEQ ID NO: 206 (H28);

(4) a heavy chain variable region comprising the amino acid sequence of SEQ ID NO: 207 (H30);

(5) a heavy chain variable region comprising the amino acid sequence of SEQ ID NO: 208 (H34), (6) a heavy chain variable region comprising the amino acid sequence of SEQ ID NO: 209 (H42);

(7) a heavy chain variable region comprising the amino acid sequence of SEQ ID NO: 210 (H44);

(8) a heavy chain variable region comprising the amino acid sequence of SEQ ID NO: 211 (H46);

(9) a heavy chain variable region comprising the amino acid sequence of SEQ ID NO: 212 (H57);

(10) a heavy chain variable region comprising the amino acid sequence of SEQ ID NO: 213 (H71);

(11) a heavy chain variable region comprising the amino acid sequence of SEQ ID NO: 214 (H78);

(12) a heavy chain variable region comprising the amino acid sequence of SEQ ID NO: 215 (H92);

(13) a heavy chain variable region comprising the amino acid sequence of SEQ ID NO: 216 (H97);

(14) a heavy chain variable region comprising the amino acid sequence of SEQ ID NO: 217 (H98);

(15) a light chain variable region comprising the amino acid sequence of SEQ ID NO: 218 (L11);

(16) a light chain variable region comprising the amino acid sequence of SEQ ID NO: 219 (L12);

(17) a light chain variable region comprising the amino acid sequence of SEQ ID NO: 220 (L17);

(18) a light chain variable region comprising the amino acid sequence of SEQ ID NO: 221 (L50);

(19) an antibody comprising the heavy chain variable region of (3) and the light chain variable region of (17) (H28L17);

(20) an antibody comprising the heavy chain variable region of (4) and the light chain variable region of (17) (H30L17);

(21) an antibody comprising the heavy chain variable region of (5) and the light chain variable region of (17) (H34L17);

(22) an antibody comprising the heavy chain variable region of (6) and the light chain variable region of (17) (H42L17);

(23) an antibody comprising the heavy chain variable region of (7) and the light chain variable region of (17) (H44L17);

(24) an antibody comprising the heavy chain variable region of (8) and the light chain variable region of (17) (H46L17);

(25) an antibody comprising the heavy chain variable region of (9) and the light chain variable region of (17) (H57L17);

(26) an antibody comprising the heavy chain variable region of (10) and the light chain variable region of (17) (H71L17);

(27) an antibody comprising the heavy chain variable region of (11) and the light chain variable region of (17) (H78L17);

(28) an antibody comprising the heavy chain variable region of (12) and the light chain variable region of (17) (H92L17);

(29) an antibody comprising the heavy chain variable region of (13) and the light chain variable region of (18) (H97L50);

(30) an antibody comprising the heavy chain variable region of (14) and the light chain variable region of (18) (H98L50),

(31) an antibody in which one or more amino acids are substituted, deleted, added, and/or inserted in the antibody of any one of (19) to (30), which has an activity equivalent to that of the antibody of any one of (19) to (30); and

(32) an antibody which binds to the same epitope as an epitope bound by the antibody of any one of (19) to (30);

[10] the anti-NR10 antibody of any one of [4] to [9], which is a humanized antibody;

[11] an antibody, antibody heavy chain, or antibody light chain, which is any one of:

(1) a heavy chain comprising the amino acid sequence of SEQ ID NO: 222 (H17);

(2) a heavy chain comprising the amino acid sequence of SEQ ID NO: 223 (H19);

(3) a heavy chain comprising the amino acid sequence of SEQ ID NO: 224 (H28);

(4) a heavy chain comprising the amino acid sequence of SEQ ID NO: 225 (H30);

(5) a heavy chain comprising the amino acid sequence of SEQ ID NO: 226 (H34);

(6) a heavy chain comprising the amino acid sequence of SEQ ID NO: 227 (H42);

(7) a heavy chain comprising the amino acid sequence of SEQ ID NO: 228 (H44);

(8) a heavy chain comprising the amino acid sequence of SEQ ID NO: 229 (H46);

(9) a heavy chain comprising the amino acid sequence of SEQ ID NO: 230 (H57);

(10) a heavy chain comprising the amino acid sequence of SEQ ID NO: 231 (H71);

(11) a heavy chain comprising the amino acid sequence of SEQ ID NO: 232 (H78);

(12) a heavy chain comprising the amino acid sequence of SEQ ID NO: 233 (H92);

(13) a heavy chain comprising the amino acid sequence of SEQ ID NO: 234 (H97);

(14) a heavy chain comprising the amino acid sequence of SEQ ID NO: 235 (H98);

(15) a light chain comprising the amino acid sequence of SEQ ID NO: 236 (L11);

(16) a light chain comprising the amino acid sequence of SEQ ID NO: 237 (L12);

(17) a light chain comprising the amino acid sequence of SEQ ID NO: 238 (L17);

(18) a light chain comprising the amino acid sequence of SEQ ID NO: 239 (L50);

(19) an antibody comprising the heavy chain of (3) and the light chain of (17) (H28L17);

(20) an antibody comprising the heavy chain of (4) and the light chain of (17) (H30L17);

(21) an antibody comprising the heavy chain of (5) and the light chain of (17) (H34L17);

(22) an antibody comprising the heavy chain of (6) and the light chain of (17) (H42L17);

(23) an antibody comprising the heavy chain of (7) and the light chain of (17) (H44L17);

(24) an antibody comprising the heavy chain of (8) and the light chain of (17) (H46L17);

(25) an antibody comprising the heavy chain of (9) and the light chain of (17) (H57L17);

(26) an antibody comprising the heavy chain of (10) and the light chain of (17) (H71L17);

(27) an antibody comprising the heavy chain of (11) and the light chain of (17) (H78L17);

(28) an antibody comprising the heavy chain of (12) and the light chain of (17) (H92L17);

(29) an antibody comprising the heavy chain of (13) and the light chain of (18) (H97L50);

(30) an antibody comprising the heavy chain of (14) and the light chain of (18) (H98L50);

(31) an antibody in which one or more amino acids are substituted, deleted, added, and/or inserted in the antibody of any one of (19) to (30), which has an activity equivalent to that of the antibody of any one of (19) to (30); and

(32) an antibody which binds to the same epitope as an epitope bound by the antibody of any one of (19) to (30);

[12] a pharmaceutical composition comprising the antibody of any one of [1] to [11];

[13] the pharmaceutical composition of [12], which is an agent for treating an inflammatory disease;

[14] a method for treating or preventing an inflammatory disease, which comprises the step of administering the antibody of any one of [1] to [11]; and

[15] use of the antibody of any one of [1] to [11] in the preparation of a therapeutic agent for an inflammatory disease.

BRIEF DESCRIPTION OF THE DRAWINGS

FIG. 2 shows the amino acid sequences of the light chain variable regions of mouse antibodies NS18, NS22, NS23, and NS33.

FIG. 25-1 is a set of graphs showing the assessment (BaF) of the activity of each variant.

FIG. 25-2 is a continuation of FIG. 25-1.

FIG. 28-1 shows the amino acid sequence of each variant of H0 (SEQ ID NO: 50).

FIG. 28-2 is a continuation of FIG. 28-1.

FIG. 28-3 is a continuation of FIG. 28-2.

FIG. 29-1 shows the amino acid sequence of each variant of L0 (SEQ ID NO: 52).

FIG. 29-2 is a continuation of FIG. 29-1.

DETAILED DESCRIPTION

NR10

Figure 1:
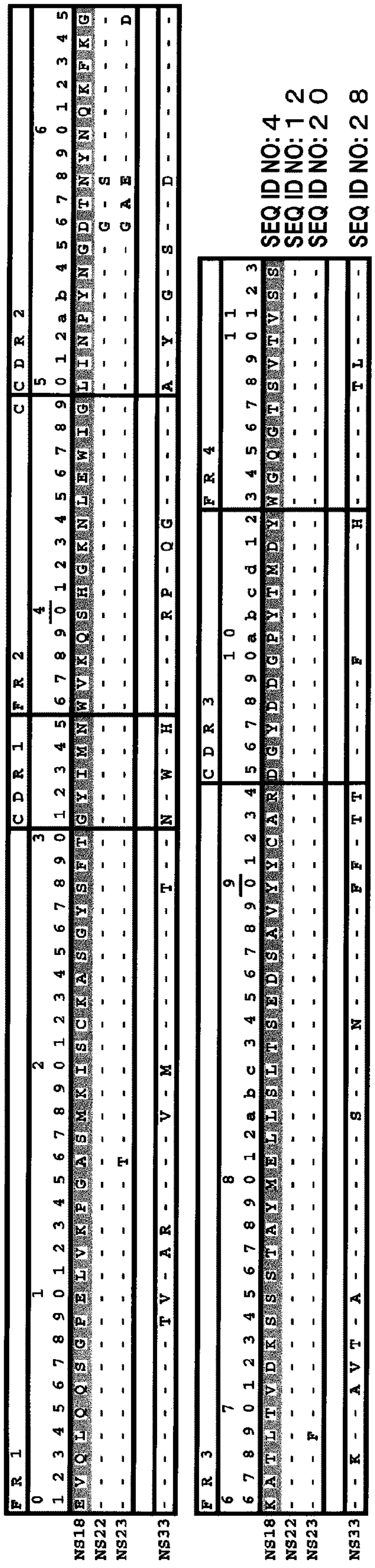
FIG. 1 shows the amino acid sequences of the heavy chain variable regions of mouse antibodies NS18, NS22, NS23, and NS33.

NR10 is a protein that forms a heterodimer with oncostatin M receptor (OSMR) and functions as an IL-31 receptor. NR10 is also known as glm-r (J Biol Chem 277, 16831-6, 2002), GPL (J Biol Chem 278, 49850-9, 2003), IL31RA (Nat Immunol 5, 752-60, 2004), and such. Thus, NR10 in the present invention also includes proteins called by such names.

In the present invention, NR10 (also referred to as IL31RA, GPL, or glm-r) is not particularly limited in terms of its origin, and includes those derived from humans, mice, monkeys, and other mammals. NR10 derived from humans, mice, and monkeys is preferred, and human-derived NR10 is particularly preferred.

There are multiple known splicing variants of human-derived NR10 (WO 00/075314). Of the above-described splicing variants, NR10.1 consists of 662 amino acids and contains a transmembrane domain. NR10.2 is a soluble receptor-like protein consisting of 252 amino acids without the transmembrane domain. Meanwhile, known NR10 splicing variants that function as transmembrane receptor proteins include NR10.3 and IL-31RAv3. The human NR10 of the present invention is not particularly limited, as long as it forms a heterodimer with oncostatin M receptor (OSMR) and functions as an IL-31 receptor. Preferred NR10 includes NR10.3 (also referred to as ILRAv4 (Nat Immunol 5, 752-60, 2004)) and IL-31RAv3. NR 10.3 (IL31RAv4) consists of 662 amino acids (WO 00/075314; Nat Immunol 5, 752-60, 2004) and IL31RAv3 consists of 732 amino acids (GenBank Accession No: NM_139017). The amino acid sequence of IL31RAv4 is shown in SEQ ID NO: 79, and the amino acid sequence of IL31RAv3 is shown in SEQ ID NO: 80. Meanwhile, mouse-derived NR10 includes proteins comprising the amino acid sequence of SEQ ID NO: 81. In addition, cynomolgus monkey-derived NR10 includes proteins comprising the amino acid sequence of SEQ ID NO: 66.

Antibodies (Sequences)

Preferred embodiments of the anti-NR10 antibody of the present invention include the anti-NR10 antibodies of any one of (1) to (8) in (A) to (D) below.

(A)NS18

(1) antibodies having a heavy chain variable region that comprises CDR1 having the amino acid sequence of SEQ ID NO: 1 (HCDR1), CDR2 having the amino acid sequence of SEQ ID NO: 2 (HCDR2), and CDR3 having the amino acid sequence of SEQ ID NO: 3 (HCDR3);

(2) antibodies having the heavy chain variable region of SEQ ID NO: 4 (VH);

(3) antibodies having a light chain variable region that comprises CDR1 having the amino acid sequence of SEQ ID NO: 5 (LCDR1), CDR2 having the amino acid sequence of SEQ ID NO: 6 (LCDR2), and CDR3 having the amino acid sequence of SEQ ID NO: 7 (LCDR3);
(4) antibodies having the light chain variable region of SEQ ID NO: 8 (VL);
(5) antibodies having the heavy chain variable region of (1) and the light chain variable region of (3);
(6) antibodies having the heavy chain variable region of (2) and the light chain variable region of (4);
(7) antibodies in which one or more amino acids are substituted, deleted, added, and/or inserted in the antibodies of any one of (1) to (6), which have an activity equivalent to that of the antibodies of any one of (1) to (6); and
(8) antibodies that bind to the same epitope as an epitope bound by the antibodies of any one of (1) to (7).

(B) NS22

(1) antibodies having a heavy chain variable region that comprises CDR1 having the amino acid sequence of SEQ ID NO: 9 (HCDR1), CDR2 having the amino acid sequence of SEQ ID NO: 10 (HCDR2), and CDR3 having the amino acid sequence of SEQ ID NO: 11 (HCDR3);
(2) antibodies having the heavy chain variable region of SEQ ID NO: 12 (VH);
(3) antibodies having a light chain variable region that comprises CDR1 having the amino acid sequence of SEQ ID NO: 13 (LCDR1), CDR2 having the amino acid sequence of SEQ ID NO: 14 (LCDR2), and CDR3 having the amino acid sequence of SEQ ID NO: 15 (LCDR3);
(4) antibodies having the light chain variable region of SEQ ID NO: 16 (VL);
(5) antibodies having the heavy chain variable region of (1) and the light chain variable region of (3);
(6) antibodies having the heavy chain variable region of (2) and the light chain variable region of (4);
(7) antibodies in which one or more amino acids are substituted, deleted, added, and/or inserted in the antibodies of any one of (1) to (6), which have an activity equivalent to that of the antibodies of any one of (1) to (6); and
(8) antibodies that bind to the same epitope as an epitope bound by the antibodies of any one of (1) to (7).

Specific examples of the above-described substitution, deletion, addition, and/or insertion of one or more amino acids are not particularly limited and include, for example, the following modifications.

Substitution of Ile at position 3 in the heavy chain CDR1 of SEQ ID NO: 9 with another amino acid. The amino acid after substitution is not particularly limited but preferred examples thereof include Val.

Substitution of Met at position 4 in the heavy chain CDR1 of SEQ ID NO: 9 with another amino acid. The amino acid after substitution is not particularly limited but preferred examples thereof include Ile.

Substitution of Met at position 4 in the heavy chain CDR1 of SEQ ID NO: 9 with another amino acid. The amino acid after substitution is not particularly limited but preferred examples thereof include Leu.

Substitution of Ile at position 3 in the heavy chain CDR1 of SEQ ID NO: 9 with another amino acid. The amino acid after substitution is not particularly limited but preferred examples thereof include Ala.

Substitution of Leu at position 1 in the heavy chain CDR2 of SEQ ID NO: 10 with another amino acid. The amino acid after substitution is not particularly limited but preferred examples thereof include Glu.

Substitution of Asn at position 3 in the heavy chain CDR2 of SEQ ID NO: 10 with another amino acid. The amino acid after substitution is not particularly limited but preferred examples thereof include Asp.

Substitution of Gln at position 13 in the heavy chain CDR2 of SEQ ID NO: 10 with another amino acid. The amino acid after substitution is not particularly limited but preferred examples thereof include Asp.

Substitution of Lys at position 14 in the heavy chain CDR2 of SEQ ID NO: 10 with another amino acid. The amino acid after substitution is not particularly limited but preferred examples thereof include Gln.

Substitution of Lys at position 16 in the heavy chain CDR2 of SEQ ID NO: 10 with another amino acid. The amino acid after substitution is not particularly limited but preferred examples thereof include Gln.

Substitution of Gly at position 17 in the heavy chain CDR2 of SEQ ID NO: 10 with another amino acid. The amino acid after substitution is not particularly limited but preferred examples thereof include Asp.

Substitution of Lys and Gly at positions 16 and 17, respectively, in the heavy chain CDR2 of SEQ ID NO: 10 with another amino acid. The amino acid after substitution is not particularly limited but preferred examples include substitution of Lys at position 16 with Gln, and Gly at position 17 with Asp.

Substitution of Lys, Lys, and Gly at positions 14, 16, and 17, respectively, in the heavy chain CDR2 of SEQ ID NO: 10 with another amino acid. The amino acid after substitution is not particularly limited but preferred examples include substitution of Lys at position 14 with Gln, Lys at position 16 with Gln, and Gly at position 17 with Asp.

Substitution of Gln, Lys, Lys, and Gly at positions 13, 14, 16, and 17, respectively, in the heavy chain CDR2 of SEQ ID NO: 10 with another amino acid. The amino acid after substitution is not particularly limited but preferred examples include substitution of Gln at position 13 with Asp, Lys at position 14 with Gln, Lys at position 16 with Gln, and Gly at position 17 with Asp.

Substitution of Ser at position 10 in the heavy chain CDR2 of SEQ ID NO: 10 with another amino acid. The amino acid after substitution is not particularly limited but preferred examples thereof include Asp.

Substitution of Gln at position 13 in the heavy chain CDR2 of SEQ ID NO: 10 with another amino acid. The amino acid after substitution is not particularly limited but preferred examples thereof include Pro.

Substitution of Tyr at position 3 in the heavy chain CDR3 of SEQ ID NO: 11 with another amino acid. The amino acid after substitution is not particularly limited but preferred examples thereof include Leu.

Substitution of Met at position 10 in the heavy chain CDR3 of SEQ ID NO: 11 with another amino acid. The amino acid after substitution is not particularly limited but preferred examples thereof include Leu.

Substitution of Asp at position 11 in the heavy chain CDR3 of SEQ ID NO: 11 with another amino acid. The amino acid after substitution is not particularly limited but preferred examples thereof include Glu.

Substitution of Tyr at position 12 in the heavy chain CDR3 of SEQ ID NO: 11 with another amino acid. The amino acid after substitution is not particularly limited but preferred examples thereof include Thr and Ser.

Substitution of Met, Asp, and Tyr at positions 10, 11, and 12, respectively, in the heavy chain CDR3 of SEQ ID NO: 11 with another amino acid. The amino acid after substitution is not particularly limited but preferred examples include substitution of Met at position 10 with Leu, Asp at position 11 with Glu, and Tyr at position 12 with Thr.

Substitution of Asp and Tyr at positions 11 and 12, respectively, in the heavy chain CDR3 of SEQ ID NO: 11 with another amino acid. The amino acid after substitution is not particularly limited but preferred examples include substitution of Asp at position 11 with Glu, and Tyr at position 12 with Thr.

Substitution of Tyr, Asp, and Tyr at positions 3, 11, and 12, respectively, in the heavy chain CDR3 of SEQ ID NO: 11 with another amino acid. The amino acid after substitution is not particularly limited but preferred examples include substitution of Tyr at position 3 with Leu, Asp at position 11 with Glu, and Tyr at position 12 with Thr or Ser.

Substitution of Arg at position 1 in the light chain CDR1 of SEQ ID NO: 13 with another amino acid. The amino acid after substitution is not particularly limited but preferred examples thereof include Gln.

Substitution of Asn at position 5 in the light chain CDR1 of SEQ ID NO: 13 with another amino acid. The amino acid after substitution is not particularly limited but preferred examples thereof include Asp.

Substitution of Arg and Asn at positions 1 and 5, respectively, in the light chain CDR1 of SEQ ID NO: 13 with another amino acid. The amino acid after substitution is not particularly limited but preferred examples include substitution of Arg at position 1 with Gln, and Asn at position 5 with Asp.

Substitution of Ser at position 8 in the light chain CDR1 of SEQ ID NO: 13 with another amino acid. The amino acid after substitution is not particularly limited but preferred examples thereof include Arg.

Substitution of Leu at position 10 in the light chain CDR1 of SEQ ID NO: 13 with another amino acid. The amino acid after substitution is not particularly limited but preferred examples thereof include Val.

Substitution of Ser and Leu at positions 8 and 10, respectively, in the light chain CDR1 of SEQ ID NO: 13 with another amino acid. The amino acid after substitution is not particularly limited but preferred examples include substitution of Ser at position 8 with Arg, and Leu at position 10 with Val.

Substitution of Thr at position 2 in the light chain CDR1 of SEQ ID NO: 13 with another amino acid. The amino acid after substitution is not particularly limited but preferred examples thereof include Ala and Ser.

Substitution of Asn at position 1 in the light chain CDR2 of SEQ ID NO: 14 with another amino acid. The amino acid after substitution is not particularly limited but preferred examples thereof include Asp.

Substitution of Lys at position 3 in the light chain CDR2 of SEQ ID NO: 14 with another amino acid. The amino acid after substitution is not particularly limited but preferred examples thereof include Gln.

Substitution of Leu at position 5 in the light chain CDR2 of SEQ ID NO: 14 with another amino acid. The amino acid after substitution is not particularly limited but preferred examples thereof include Glu.

Substitution of Lys at position 7 in the light chain CDR2 of SEQ ID NO: 14 with another amino acid. The amino acid after substitution is not particularly limited but preferred examples thereof include Gln and Asp.

Substitution of Lys, Leu, and Lys at positions 3, 5, and 7, respectively, in the light chain CDR2 of SEQ ID NO: 14 with another amino acid. The amino acid after substitution is not particularly limited but preferred examples include substitution of Lys at position 3 with Gln, Leu at position 5 with Glu, and Lys at position 7 with Gln.

Substitution of Glu at position 5 in the light chain CDR3 of SEQ ID NO: 15 with another amino acid. The amino acid after substitution is not particularly limited but preferred examples thereof include Asp.

Substitution of Ser at position 6 in the light chain CDR3 of SEQ ID NO: 15 with another amino acid. The amino acid after substitution is not particularly limited but preferred examples thereof include Asp.

Substitution of Thr at position 9 in the light chain CDR3 of SEQ ID NO: 15 with another amino acid. The amino acid after substitution is not particularly limited but preferred examples thereof include Phe.

Each of the above-described substitutions may be made alone, or multiple substitutions may be made in combination. Furthermore, the above substitutions may be combined with other substitutions. These substitutions can improve the antibody pharmacokinetics (retention in plasma), enhance the antigen-binding activity, improve the stability, and/or reduce the risk of immunogenicity.

In the present invention, specific examples of the variable regions having a combination of the above-described substitutions include, for example, heavy chain variable regions having the amino acid sequence of SEQ ID NO: 167 and light chain variable regions having the amino acid sequence of SEQ ID NO: 168. Moreover, examples of the antibodies having a combination of the above-described substitutions include, for example, antibodies that comprise a heavy chain variable region having the amino acid sequence of SEQ ID NO: 167 and a light chain variable region having the amino acid sequence of SEQ ID NO: 168.

Moreover, specific examples of the heavy chain or light chain variable regions having a combination of the above-described substitutions include, for example, the following variable regions:

(a) heavy chain variable regions that comprise CDR1 of SEQ ID NO: 196, CDR2 of SEQ ID NO: 197, and CDR3 of SEQ ID NO: 11 (H17);
(b) heavy chain variable regions that comprise CDR1 of SEQ ID NO: 176, CDR2 of SEQ ID NO: 197, and CDR3 of SEQ ID NO: 11 (H19);
(c) heavy chain variable regions that comprise CDR1 of SEQ ID NO: 196, CDR2 of SEQ ID NO: 197, and CDR3 of SEQ ID NO: 184 (H28, H42);
(d) heavy chain variable regions that comprises CDR1 of SEQ ID NO: 9, CDR2 of SEQ ID NO: 197, and CDR3 of SEQ ID NO: 184 (H30, H44);
(e) heavy chain variable regions that comprise CDR1 of SEQ ID NO: 176, CDR2 of SEQ ID NO: 197, and CDR3 of SEQ ID NO: 184 (H34, H46);
(f) heavy chain variable regions that comprise CDR1 of SEQ ID NO: 9, CDR2 of SEQ ID NO: 198, and CDR3 of SEQ ID NO: 184 (H57, H78);
(g) heavy chain variable regions that comprise CDR1 of SEQ ID NO: 176, CDR2 of SEQ ID NO: 198, and CDR3 of SEQ ID NO: 184 (H71, H92);
(h) heavy chain variable regions that comprise CDR1 of SEQ ID NO: 9, CDR2 of SEQ ID NO: 199, and CDR3 of SEQ ID NO: 184 (H97, H98);
(i) light chain variable regions that comprise CDR1 of SEQ ID NO: 200, CDR2 of SEQ ID NO: 170, and CDR3 of SEQ ID NO: 193 (L11);
(j) light chain variable regions that comprise CDR1 of SEQ ID NO: 201, CDR2 of SEQ ID NO: 170, and CDR3 of SEQ ID NO: 193 (L12);

(k) light chain variable regions that comprise CDR1 of SEQ ID NO: 202, CDR2 of SEQ ID NO: 170, and CDR3 of SEQ ID NO: 193 (L17); and (l) light chain variable regions that comprise CDR1 of SEQ ID NO: 203, CDR2 of SEQ ID NO: 170, and CDR3 of SEQ ID NO: 193 (L50).

Furthermore, specific examples of the antibodies having a combination of the above-described substitutions include, for example:

(i) antibodies that comprise the heavy chain variable region of (c) and the light chain variable region of (k);

(ii) antibodies that comprise the heavy chain variable region of (d) and the light chain variable region of (k);

(iii) antibodies that comprise the heavy chain variable region of (e) and the light chain variable region of (k);

(iv) antibodies that comprise the heavy chain variable region of (f) and the light chain variable region of (k);

(v) antibodies that comprise the heavy chain variable region of (g) and the light chain variable region of (k); and (vi) antibodies that comprise the heavy chain variable region of (h) and the light chain variable region of (l).

(C) NS23

(1) antibodies having a heavy chain variable region that comprises CDR1 having the amino acid sequence of SEQ ID NO: 17 (HCDR1), CDR2 having the amino acid sequence of SEQ ID NO: 18 (HCDR2), and CDR3 having the amino acid sequence of SEQ ID NO: 19 (HCDR3);

(2) antibodies having the heavy chain variable region of SEQ ID NO: 20 (VH);

(3) antibodies having a light chain variable region that comprises CDR1 having the amino acid sequence of SEQ ID NO: 21 (LCDR1), CDR2 having the amino acid sequence of SEQ ID NO: 22 (LCDR2), and CDR3 having the amino acid sequence of SEQ ID NO: 23 (LCDR3);

(4) antibodies having the light chain variable region of SEQ ID NO: 24 (VL);

(5) antibodies having the heavy chain variable region of (1) and the light chain variable region of (3);

(6) antibodies having the heavy chain variable region of (2) and the light chain variable region of (4);

(7) antibodies in which one or more amino acids are substituted, deleted, added, and/or inserted in the antibodies of any one of (1) to (6), which have an activity equivalent to that of the antibodies of any one of (1) to (6); and (8) antibodies that bind to the same epitope as an epitope bound by the antibodies of any one of (1) to (7).

(D) NS33

(1) antibodies having a heavy chain variable region that comprise CDR1 having the amino acid sequence of SEQ ID NO: 25 (HCDR1), CDR2 having the amino acid sequence of SEQ ID NO: 26 (HCDR2), and CDR3 having the amino acid sequence of SEQ ID NO: 27 (HCDR3);

(2) antibodies having the heavy chain variable region of SEQ ID NO: 28 (VH);

(3) antibodies having a light chain variable region that comprise CDR1 having the amino acid sequence of SEQ ID NO: 29 (LCDR1), CDR2 having the amino acid sequence of SEQ ID NO: (LCDR2), and CDR3 having the amino acid sequence of SEQ ID NO: 31 (LCDR3);

(4) antibodies having the light chain variable region of SEQ ID NO: 32 (VL);

(5) antibodies having the heavy chain variable region of (1) and the light chain variable region of (3);

(6) antibodies having the heavy chain variable region of (2) and the light chain variable region of (4);

(7) antibodies in which one or more amino acids are substituted, deleted, added, and/or inserted in the antibodies of any one of (1) to (6), which have an activity equivalent to that of the antibodies of any one of (1) to (6); and (8) antibodies that bind to the same epitope as an epitope bound by the antibodies of any one of (1) to (7).

Any framework regions (FR) may be used for the above-described antibodies of (1) or (3); however, FRs derived from human are preferably used. Furthermore, any constant regions may be used for the above-described antibodies of (1) to (8); however, constant regions derived from human are preferably used. For the antibodies of the present invention, the amino acid sequence of the original FR or constant region may be used without modification, or after being modified to a different amino acid sequence by substitution, deletion, addition, and/or insertion of one or more amino acids.

The amino acid sequence of the heavy chain of the above-described NS18 is shown in SEQ ID NO: 34 and the nucleotide sequence encoding this amino acid sequence is shown in SEQ ID NO: 33. Meanwhile, the amino acid sequence of the light chain is shown in SEQ ID NO: 36 and the nucleotide sequence encoding this amino acid sequence is shown in SEQ ID NO: 35.

The amino acid sequence of the heavy chain of NS22 is shown in SEQ ID NO: 38 and the nucleotide sequence encoding this amino acid sequence is shown in SEQ ID NO: 37. Meanwhile, the amino acid sequence of the light chain is shown in SEQ ID NO: 40 and the nucleotide sequence encoding this amino acid sequence is shown in SEQ ID NO: 39.

The amino acid sequence of the heavy chain of NS23 is shown in SEQ ID NO: 42 and the nucleotide sequence encoding this amino acid sequence is shown in SEQ ID NO: 41. Meanwhile, the amino acid sequence of the light chain is shown in SEQ ID NO: 44 and the nucleotide sequence encoding this amino acid sequence is shown in SEQ ID NO: 43.

The amino acid sequence of the heavy chain of NS33 is shown in SEQ ID NO: 46 and the nucleotide sequence encoding this amino acid sequence is shown in SEQ ID NO: 45. Meanwhile, the amino acid sequence of the light chain is shown in SEQ ID NO: 48 and the nucleotide sequence encoding this amino acid sequence is shown in SEQ ID NO: 47.

In the present invention, the "activity equivalent to that of the antibody of any one of (1) to (6)" means that the activity of binding and/or neutralizing NR10 (for example, human NR10) is equivalent. In the present invention, the term "equivalent" means that the activity is not necessarily the same but may be enhanced or reduced as long as the activity is retained. Antibodies with a reduced activity include, for example, antibodies having an activity that is 30% or more, preferably 50% or more, and more preferably 80% or more of that of the original antibody.

The antibodies of any one of (1) to (6) mentioned above may have a substitution, deletion, addition, and/or insertion of one or more amino acids in the amino acid sequence of the variable regions (CDR sequences and/or FR sequences), as long as the NR10-binding and/or neutralizing activity is retained. Methods well known to those skilled in the art to prepare the amino acid sequence of an antibody that has a substitution, deletion, addition, and/or insertion of one or more amino acids in the amino acid sequence and retains NR10-binding and/or neutralizing activity, include methods for introducing mutations into proteins. For example, those skilled in the art can prepare mutants functionally equivalent to the antibody having NR10-binding and/or neutralizing activity by introducing appropriate mutations into the amino acid sequence of the antibody having NR10-binding and/or neutralizing activity using site-directed mutagenesis (Hashimoto-Gotoh, T, Mizuno, T, Ogasahara, Y, and Nakagawa, M. (1995) An oligodeoxyribonucleotide-directed dual amber method for site-directed mutagenesis. Gene 152, 271-275, Zoller, M J, and Smith, M. (1983) Oligonucleotide-directed mutagenesis of DNA fragments cloned into M13 vectors. Methods Enzymol. 100, 468-500, Kramer, W, Drutsa, V, Jansen, H W, Kramer, B, Pflugfelder, M, and Fritz, H J (1984) The gapped duplex DNA approach to oligonucleotide-directed mutation construction. Nucleic Acids Res. 12, 9441-9456, Kramer W, and Fritz H J (1987) Oligonucleotide-directed construction of mutations via gapped duplex DNA Methods. Enzymol. 154, 350-367, Kunkel, TA (1985) Rapid and efficient site-specific mutagenesis without phenotypic selection. Proc Natl Acad Sci USA. 82, 488-492) or the like. Thus, antibodies that contain one or more amino acid mutations in the variable regions and have NR10-binding and/or neutralizing activity are also included in the antibody of the present invention.

When an amino acid residue is altered, the amino acid is preferably mutated for a different amino acid(s) that conserves the properties of the amino acid side-chain. Examples of amino acid side chain properties are: hydrophobic amino acids (A, I, L, M, F, P, W, Y, and V), hydrophilic amino acids (R, D, N, C, E, Q, G, H, K, S, and T), amino acids containing aliphatic side chains (G, A, V, L, I, and P), amino acids containing hydroxyl group-containing side chains (S, T, and Y), amino acids containing sulfur-containing side chains (C and M), amino acids containing carboxylic acid- and amide-containing side chains (D, N, E, and Q), amino acids containing basic side chains (R, K, and H), and amino acids containing aromatic side chains (H, F, Y, and W) (amino acids are represented by one-letter codes in parentheses). Amino acid substitutions within each group are called conservative substitutions. It is already known that a polypeptide containing a modified amino acid sequence in which one or more amino acid residues in a given amino acid sequence are deleted, added, and/or substituted with other amino acids can retain the original biological activity (Mark, D. F. et al., Proc. Natl. Acad. Sci. USA; (1984) 81:5662-6; Zoller, M. J. and Smith, M., Nucleic Acids Res. (1982) 10:6487-500; Wang, A. et al., Science (1984) 224:1431-3; Dalbadie-McFarland, G. et al., Proc. Natl. Acad. Sci. USA (1982) 79:6409-13). Such mutants have an amino acid identity of at least 70%, more preferably at least 75%, even more preferably at least 80%, still more preferably at least 85%, yet more preferably at least 90%, and most preferably at least 95%, with the variable regions (for example, CDR sequences, FR sequences, or whole variable regions) of the present invention. Herein, sequence identity is defined as the percentage of residues identical to those in the original amino acid sequence of the heavy chain variable region or light chain variable region, determined after the sequences are aligned and gaps are appropriately introduced to maximize the sequence identity as necessary. The identity of amino acid sequences can be determined by the method described below.

Alternatively, the amino acid sequences of variable regions that have a substitution, deletion, addition, and/or insertion of one or more amino acids in the amino acid sequence of the variable regions (CDR sequences and/or FR sequences) and retain NR10-binding and/or neutralizing activity can be obtained from nucleic acids that hybridize under stringent conditions to nucleic acid composed of the nucleotide sequence encoding the amino acid sequence of the variable regions. Stringent hybridization conditions to isolate a nucleic acid that hybridizes under stringent conditions to a nucleic acid that includes the nucleotide sequence encoding the amino acid sequence of the variable regions include, for example, the conditions of 6M urea, 0.4% SDS, 0.5×SSC, and 37° C., or hybridization conditions with stringencies equivalent thereto. With more stringent conditions, for example, the conditions of 6M urea, 0.4% SDS, 0.1×SSC, and 42° C., isolation of nucleic acids with a much higher homology can be expected. The sequences of the isolated nucleic acids can be determined by the known methods described below. The overall nucleotide sequence homology of the isolated nucleic acid is at least 50% or higher sequence identity, preferably 70% or higher, more preferably 90% or higher (for example, 95%, 96%, 97%, 98%, 99%, or higher).

Nucleic acids that hybridize under stringent conditions to a nucleic acid composed of the nucleotide sequence encoding the amino acid sequence of the variable regions can also be isolated using, instead of the above-described methods using hybridization techniques, gene amplification methods such as polymerase chain reaction (PCR) using primers synthesized based on the information of nucleotide sequence encoding the amino acid sequence of the variable regions.

Specifically, the identity of one nucleotide sequence or amino acid sequence to another can be determined using the algorithm BLAST, by Karlin and Altschul (Proc. Natl. Acad. Sci. USA (1993) 90, 5873-7). Programs such as BLASTN and BLASTX were developed based on this algorithm (Altschul et al., J. Mol. Biol. (1990) 215, 403-10). To analyze nucleotide sequences according to BLASTN based on BLAST, the parameters are set, for example, as score=100 and wordlength=12. On the other hand, parameters used for the analysis of amino acid sequences by BLASTX based on BLAST include, for example, score=50 and wordlength=3. Default parameters for each program are used when using the BLAST and Gapped BLAST programs. Specific techniques for such analyses are known in the art (see the website of the National Center for Biotechnology Information (NCBI), Basic Local Alignment Search Tool (BLAST); http://www.ncbi.nlm.nih.gov).

The present invention also provides antibodies that bind to the same epitope as an epitope bound by the antibodies of any one of (1) to (7).

Whether an antibody recognizes the same epitope as that recognized by another antibody can be confirmed by the competition between the two antibodies against the epitope. Competition between the antibodies can be evaluated by competitive binding assays using means such as ELISA, fluorescence energy transfer method (FRET), and fluorometric microvolume assay technology (FMAT(R)). The amount of antibodies bound to an antigen indirectly correlate with the binding ability of candidate competitor antibodies (test antibodies) that competitively bind to the same epitope. In other words, as the amount of or the affinity of test antibodies against the same epitope increases, the amount of antibodies bound to the antigen decreases, and the amount of test antibodies bound to the antigen increases. Specifically, appropriately labeled antibodies and antibodies to be evaluated are simultaneously added to the antigens, and the thus bound antibodies are detected using the label. The amount of antibodies bound to the antigen can be easily determined by labeling the antibodies beforehand. This label is not particularly limited, and the labeling method is selected according to the assay technique used. The labeling method includes fluorescent labeling, radiolabeling, enzymatic labeling, and such.

For example, fluorescently labeled antibodies and unlabeled antibodies or test antibodies are simultaneously added to animal cells expressing NR10, and the labeled antibodies are detected by fluorometric microvolume assay technology.

Herein, the "antibody that recognizes the same epitope" refers to an antibody that can reduce the binding of the labeled antibody by at least 50% at a concentration that is usually 100 times higher, preferably 80 times higher, more preferably 50 times higher, even more preferably 30 times higher, and still more preferably 10 times higher than a concentration at which the non-labeled antibody reduces the binding of the labeled antibody by 50% ($IC_{50}$).

Antibodies that bind to the epitope to which the antibodies set forth in any one of (1) to (7) above bind are useful because they have a particularly high neutralizing activity.

The antibodies set forth in any one of (1) to (8) above are preferably humanized antibodies, but are not particularly limited thereto.

Furthermore, the present invention provides genes encoding the anti-NR10 antibodies of any one of (1) to (8) of (A) to (D) above. The genes of the present invention may be any form of genes, for example, DNAs or RNAs.

Antibodies (Humanized)

Preferred embodiments of the antibodies of the present invention include humanized antibodies that bind to NR10. The humanized antibodies can be prepared by methods known to those skilled in the art.

The variable region of antibody is typically composed of three complementarity-determining regions (CDRs) sandwiched by four frames (FRs). The CDRs substantially determine the binding specificity of antibody. The amino acid sequences of CDRs are highly diverse. In contrast, the amino acid sequences of FRs often exhibit high homology between antibodies having different binding specificities. It is therefore said in general that the binding specificity of an antibody can be transplanted to a different antibody by grafting the CDRs.

Humanized antibodies are also referred to as reshaped human antibodies, and they are prepared by transferring the CDRs of an antibody derived from a non-human mammal such as a mouse, to the CDRs of a human antibody. General genetic recombination techniques for their preparation are also known (see European Patent Application Publication No. 125023 and WO 96/02576).

Specifically, for example, when the CDRs are derived from a mouse antibody, a DNA sequence designed such that the CDRs of the mouse antibody are linked with framework regions (FRs) of human antibody is synthesized by PCR using, as primers, several oligonucleotides that have portions overlapping the ends of both CDRs and FRs (see the method described in WO 98/13388). The resulting DNA is then ligated to a DNA encoding a human antibody constant region, inserted into an expression vector, and introduced into a host to produce the antibody (see European Patent Application Publication No. EP 239400 and International Patent Application Publication No. WO 96/02576).

Human antibody framework regions to be linked with CDRs are selected so that the CDRs form a favorable antigen-binding site. If needed, amino acid substitution, deletion, addition, and/or insertion may be introduced into the framework regions of antibody variable region so that the CDRs of the reshaped human antibody form a proper antigen-binding site. For example, mutations can be introduced into the amino acid sequence of FR by applying the PCR method which is used to graft mouse CDRs to human FRs. Specifically, mutations can be introduced into a portion of the nucleotide sequences of primers that anneal to the FRs. The mutations are introduced into FRs synthesized by such primers. The antigen-binding activity of mutant antibodies having amino acid substitutions can be determined and assessed by the method described above, and thereby mutant FR sequences having desired properties can be selected (Sato, K. et al., Cancer Res. (1993) 53, 851-856). Constant (C) regions from human antibodies are used for those of humanized antibodies.

For example, Cγ1, Cγ2, Cγ3, Cγ4, Cμ, Cδ, Cα1, Cα2, and Cϵ are used for H chains; and Cκ and Cλ are used for L chains. The amino acid sequence of Cκ is shown in SEQ ID NO: 58, and the nucleotide sequence encoding this amino acid sequence is shown in SEQ ID NO: 57. The amino acid sequence of Cγ1 is shown in SEQ ID NO: 60, and the nucleotide sequence encoding this amino acid sequence is shown in SEQ ID NO: 59. The amino acid sequence of Cγ2 is shown in SEQ ID NO: 62, and the nucleotide sequence encoding this amino acid sequence is shown in SEQ ID NO: 61. The amino acid sequence of Cγ4 is shown in SEQ ID NO: 64, and the nucleotide sequence encoding this amino acid sequence is shown in SEQ ID NO: 63. Furthermore, human antibody C regions may be modified to improve the stability of antibody or antibody production. Modified human antibody C regions include, for example, the C regions described herein below. Human antibodies used for humanization may be of any isotype such as IgG, IgM, IgA, IgE, or IgD; however, IgG is preferably used in the present invention. IgG that can be used includes IgG1, IgG2, IgG3, IgG4, and the like.

Moreover, after a humanized antibody is prepared, amino acids in the variable region (for example, CDR and FR) and constant region of the humanized antibody may be deleted, added, inserted, and/or substituted with other amino acids. The antibodies of the present invention also include such humanized antibodies with amino acid substitutions and the like.

The origin of CDRs of a humanized antibody is not particularly limited, and may be any animal. For example, it is possible to use the sequences of mouse antibodies, rat antibodies, rabbit antibodies, camel antibodies, and the like. CDR sequences of mouse antibodies are preferred.

In general, it is difficult to humanize antibodies while retaining the binding and neutralizing activities of the original antibodies. The present invention, however, succeeded in obtaining humanized antibodies having the binding and/or neutralizing activities equivalent to those of the original mouse antibodies. Humanized antibodies are useful when administered to humans for the therapeutic purposes, because they exhibit reduced immunogenicity in the human body.

Preferred examples of the humanized anti-NR10 antibodies of the present invention include, for example:

(a) humanized antibodies that comprise a heavy chain variable region having the amino acid sequence of SEQ ID NO: 50 (H0-VH);

(b) humanized antibodies that comprise a heavy chain variable region having the amino acid sequence of SEQ ID NO: 112 (H1-VH);

(c) humanized antibodies that comprise a light chain variable region having the amino acid sequence of SEQ ID NO: 52 (L0-VL);

(d) humanized antibodies that comprise a heavy chain variable region having the amino acid sequence of SEQ ID NO: 50 (H0-VH) and a light chain variable region having the amino acid sequence of SEQ ID NO: 52 (L0-VL); and (e) humanized antibodies that comprise a heavy chain variable region having the amino acid sequence of SEQ ID NO: 112 and a light chain variable region having the amino acid sequence of SEQ ID NO: 52.

The heavy chain variable region having the amino acid sequence of SEQ ID NO: 50 (H0-VH), heavy chain variable region having the amino acid sequence of SEQ ID NO: 112, and light chain variable region having the amino acid sequence of SEQ ID NO: 52 (L0-VL) may have a substitution, deletion, addition, and/or insertion of one or more amino acids. The substitution, deletion, addition, and/or insertion of amino acids may be made in either or both of the CDRs and FRs.

Thus, other preferred embodiments of the humanized anti-NR10 antibody of the present invention include, for example:

(f) antibodies that comprise a heavy chain variable region having an amino acid sequence in which one or more amino acids are substituted, deleted, added, and/or inserted in the amino acid sequence of SEQ ID NO: 50 (H0-VH);

(g) antibodies that comprise a heavy chain variable region having an amino acid sequence in which one or more amino acids are substituted, deleted, added, and/or inserted in the amino acid sequence of SEQ ID NO: 112 (H1-VH);

(h) antibodies that comprise a light chain variable region having an amino acid sequence in which one or more amino acids are substituted, deleted, added, and/or inserted in the amino acid sequence of SEQ ID NO: 52 (L0-VL);

(i) antibodies that comprise a heavy chain variable region having an amino acid sequence in which one or more amino acids are substituted, deleted, added, and/or inserted in the amino acid sequence of SEQ ID NO: 50 (H0-VH), and a light chain variable region having an amino acid sequence in which one or more amino acids are substituted, deleted, added, and/or inserted in the amino acid sequence of SEQ ID NO: 52 (L0-VL);

(j) antibodies that comprise a heavy chain variable region having an amino acid sequence in which one or more amino acids are substituted, deleted, added, and/or inserted in the amino acid sequence of SEQ ID NO: 112 (H1-VH), and a light chain variable region having an amino acid sequence in which one or more amino acids are substituted, deleted, added, and/or inserted in the amino acid sequence of SEQ ID NO: 52 (L0-VL);

Without particular limitation, the antibodies of any one of (f) to (j) preferably have an activity similar to that of the antibodies of any one of (a) to (e).

The substitution, deletion, addition, and/or insertion of amino acids are not particularly limited, but specific examples include, for example, the above-described amino acid substitutions.

More specifically, for example, the following amino acid substitutions may be included:

Substitution of Ile at position 3 of CDR1 (SEQ ID NO: 9) in the heavy chain variable region of SEQ ID NO: 50 or 112 with Val (SEQ ID NO: 173). Thus, the present invention provides heavy chain variable regions in which CDR1 having the amino acid sequence of SEQ ID NO: 9 is substituted with CDR1 having the amino acid sequence of SEQ ID NO: 173 in a heavy chain variable region having the amino acid sequence of SEQ ID NO: 50 or 112.

Substitution of Met at position 4 of CDR1 (SEQ ID NO: 9) in the heavy chain variable region of SEQ ID NO: 50 or 112 with Ile (SEQ ID NO: 174). Thus, the present invention provides heavy chain variable regions in which CDR1 having the amino acid sequence of SEQ ID NO: 9 is substituted with CDR1 having the amino acid sequence of SEQ ID NO: 174 in a heavy chain variable region having the amino acid sequence of SEQ ID NO: 50 or 112.

Substitution of Met at position 4 of CDR1 (SEQ ID NO: 9) in the heavy chain variable region of SEQ ID NO: 50 or 112 with Leu (SEQ ID NO: 175). Thus, the present invention provides heavy chain variable regions in which CDR1 having the amino acid sequence of SEQ ID NO: 9 is substituted with CDR1 having the amino acid sequence of SEQ ID NO: 175 in a heavy chain variable region having the amino acid sequence of SEQ ID NO: 50 or 112.

Substitution of Ile at position 3 of CDR1 (SEQ ID NO: 9) in the heavy chain variable region of SEQ ID NO: 50 or 112 with Ala (SEQ ID NO: 176). Thus, the present invention provides heavy chain variable regions in which CDR1 having the amino acid sequence of SEQ ID NO: 9 is substituted with CDR1 having the amino acid sequence of SEQ ID NO: 176 in a heavy chain variable region having the amino acid sequence of SEQ ID NO: 50 or 112.

Substitution of Leu at position 1 of CDR2 (SEQ ID NO: 10) in the heavy chain variable region of SEQ ID NO: 50 or 112 with Glu (SEQ ID NO: 113). Thus, the present invention provides heavy chain variable regions in which CDR2 having the amino acid sequence of SEQ ID NO: 10 is substituted with CDR2 having the amino acid sequence of SEQ ID NO: 113 in a heavy chain variable region having the amino acid sequence of SEQ ID NO: 50 or 112.

Substitution of Asn at position 3 of CDR2 (SEQ ID NO: 10) in the heavy chain variable region of SEQ ID NO: 50 or 112 with Asp (SEQ ID NO: 114). Thus, the present invention provides heavy chain variable regions in which CDR2 having the amino acid sequence of SEQ ID NO: 10 is substituted with CDR2 having the amino acid sequence of SEQ ID NO: 114 in a heavy chain variable region having the amino acid sequence of SEQ ID NO: 50 or 112.

Substitution of Gln at position 13 of CDR2 (SEQ ID NO: 10) in the heavy chain variable region of SEQ ID NO: 50 or 112 with Asp (SEQ ID NO: 115). Thus, the present invention provides heavy chain variable regions in which CDR2 having the amino acid sequence of SEQ ID NO: 10 is substituted with CDR2 having the amino acid sequence of SEQ ID NO: 115 in a heavy chain variable region having the amino acid sequence of SEQ ID NO: 50 or 112.

Substitution of Lys at position 14 of CDR2 (SEQ ID NO: 10) in the heavy chain variable region of SEQ ID NO: 50 or 112 with Gln (SEQ ID NO: 116). Thus, the present invention provides heavy chain variable regions in which CDR2 having the amino acid sequence of SEQ ID NO: 10 is substituted with CDR2 having the amino acid sequence of SEQ ID NO: 116 in a heavy chain variable region having the amino acid sequence of SEQ ID NO: 50 or 112.

Substitution of Lys at position 16 of CDR2 (SEQ ID NO: 10) in the heavy chain variable region of SEQ ID NO: 50 or 112 with Gln (SEQ ID NO: 117). Thus, the present invention provides heavy chain variable regions in which CDR2 having the amino acid sequence of SEQ ID NO: 10 is substituted with CDR2 having the amino acid sequence of SEQ ID NO: 117 in a heavy chain variable region having the amino acid sequence of SEQ ID NO: 50 or 112.

Substitution of Gly at position 17 of CDR2 (SEQ ID NO: 10) in the heavy chain variable region of SEQ ID NO: 50 or 112 with Asp (SEQ ID NO: 118). Thus, the present invention provides heavy chain variable regions in which CDR2 having the amino acid sequence of SEQ ID NO: 10 is substituted with CDR2 having the amino acid sequence of SEQ ID NO: 118 in a heavy chain variable region having the amino acid sequence of SEQ ID NO: 50 or 112.

Substitution of Lys at position 16 and Gly at position 17 of CDR2 (SEQ ID NO: 10) in the heavy chain variable region of SEQ ID NO: 50 or 112 with Gln and Asp, respectively (SEQ ID NO: 119). Thus, the present invention provides heavy chain variable regions in which CDR2 having the amino acid sequence of SEQ ID NO: 10 is substituted with CDR2 having the amino acid sequence of SEQ ID NO: 119 in a heavy chain variable region having the amino acid sequence of SEQ ID NO: 50 or 112.

Substitution of Lys at position 14, Lys at position 16, and Gly at position 17 of CDR2 (SEQ ID NO: 10) in the heavy chain variable region of SEQ ID NO: 50 or 112 with Gln, Gln, and Asp, respectively (SEQ ID NO: 167). Thus, the present invention provides heavy chain variable regions in which CDR2 having the amino acid sequence of SEQ ID NO: 10 is substituted with CDR2 having the amino acid sequence of SEQ ID NO: 167 in a heavy chain variable region having the amino acid sequence of SEQ ID NO: 50 or 112.

Substitution of Gln at position 13, Lys at position 14, Lys at position 16, and Gly at position 17 of CDR2 (SEQ ID NO: 10) in the heavy chain variable region of SEQ ID NO: 50 or 112 with Asp, Gln, Gln, and Asp, respectively (SEQ ID NO: 172). Thus, the present invention provides heavy chain variable regions in which CDR2 having the amino acid sequence of SEQ ID NO: 10 is substituted with CDR2 having the amino acid sequence of SEQ ID NO: 172 in a heavy chain variable region having the amino acid sequence of SEQ ID NO: 50 or 112.

Substitution of Ser at position 10 of CDR2 (SEQ ID NO: 10) in the heavy chain variable region of SEQ ID NO: 50 or 112 with Asp (SEQ ID NO: 177). Thus, the present invention provides heavy chain variable regions in which CDR2 having the amino acid sequence of SEQ ID NO: 10 is substituted with CDR2 having the amino acid sequence of SEQ ID NO: 177 in a heavy chain variable region having the amino acid sequence of SEQ ID NO: 50 or 112.

Substitution of Gln at position 13 of CDR2 (SEQ ID NO: 10) in the heavy chain variable region of SEQ ID NO: 50 or 112 with Pro (SEQ ID NO: 178). Thus, the present invention provides heavy chain variable regions in which CDR2 having the amino acid sequence of SEQ ID NO: 10 is substituted with CDR2 having the amino acid sequence of SEQ ID NO: 178 in a heavy chain variable region having the amino acid sequence of SEQ ID NO: 50 or 112.

Substitution of Tyr at position 3 of CDR3 (SEQ ID NO: 11) in the heavy chain variable region of SEQ ID NO: 50 or 112 with Leu (SEQ ID NO: 179). Thus, the present invention provides heavy chain variable regions in which CDR3 having the amino acid sequence of SEQ ID NO: 11 is substituted with CDR3 having the amino acid sequence of SEQ ID NO: 179 in a heavy chain variable region having the amino acid sequence of SEQ ID NO: 50 or 112.

Substitution of Met at position 10 of CDR3 (SEQ ID NO: 11) in the heavy chain variable region of SEQ ID NO: 50 or 112 with Leu (SEQ ID NO: 180). Thus, the present invention provides heavy chain variable regions in which CDR3 having the amino acid sequence of SEQ ID NO: 11 is substituted with CDR3 having the amino acid sequence of SEQ ID NO: 180 in a heavy chain variable region having the amino acid sequence of SEQ ID NO: 50 or 112.

Substitution of Asp at position 11 of CDR3 (SEQ ID NO: 11) in the heavy chain variable region of SEQ ID NO: 50 or 112 with Glu (SEQ ID NO: 181). Thus, the present invention provides heavy chain variable regions in which CDR3 having the amino acid sequence of SEQ ID NO: 11 is substituted with CDR3 having the amino acid sequence of SEQ ID NO: 181 in a heavy chain variable region having the amino acid sequence of SEQ ID NO: 50 or 112.

Substitution of Tyr at position 12 of CDR3 (SEQ ID NO: 11) in the heavy chain variable region of SEQ ID NO: 50 or 112 with Thr (SEQ ID NO: 182). Thus, the present invention provides heavy chain variable regions in which CDR3 having the amino acid sequence of SEQ ID NO: 11 is substituted with CDR3 having the amino acid sequence of SEQ ID NO: 182 in a heavy chain variable region having the amino acid sequence of SEQ ID NO: 50 or 112.

Substitution of Tyr at position 12 of CDR3 (SEQ ID NO: 11) in the heavy chain variable region of SEQ ID NO: 50 or 112 with Ser (SEQ ID NO: 183). Thus, the present invention provides heavy chain variable regions in which CDR3 having the amino acid sequence of SEQ ID NO: 11 is substituted with CDR3 having the amino acid sequence of SEQ ID NO: 183 in a heavy chain variable region having the amino acid sequence of SEQ ID NO: 50 or 112.

Substitution of Met at position 10, Asp at position 11, and Tyr at position 12 of CDR3 (SEQ ID NO: 11) in the heavy chain variable region of SEQ ID NO: 50 or 112 with Leu, Glu, Thr, respectively (SEQ ID NO: 184). Thus, the present invention provides heavy chain variable regions in which CDR3 having the amino acid sequence of SEQ ID NO: 11 is substituted with CDR3 having the amino acid sequence of SEQ ID NO: 184 in a heavy chain variable region having the amino acid sequence of SEQ ID NO: 50 or 112.

Substitution of Asp at position 11 and Tyr at position 12 of CDR3 (SEQ ID NO: 11) in the heavy chain variable region of SEQ ID NO: 50 or 112 with Glu and Thr, respectively (SEQ ID NO: 185). Thus, the present invention provides heavy chain variable regions in which CDR3 having the amino acid sequence of SEQ ID NO: 11 is substituted with CDR3 having the amino acid sequence of SEQ ID NO: 185 in a heavy chain variable region having the amino acid sequence of SEQ ID NO: 50 or 112.

Substitution of Tyr at position 3, Asp at position 11, and Tyr at position 12 of CDR3 (SEQ ID NO: 11) in the heavy chain variable region of SEQ ID NO: 50 or 112 with Leu, Glu, and Thr, respectively (SEQ ID NO: 186). Thus, the present invention provides heavy chain variable regions in which CDR3 having the amino acid sequence of SEQ ID NO: 11 is substituted with CDR3 having the amino acid sequence of SEQ ID NO: 186 in a heavy chain variable region having the amino acid sequence of SEQ ID NO: 50 or 112.

Substitution of Tyr at position 3, Asp at position 11, and Tyr at position 12 of CDR3 (SEQ ID NO: 11) in the heavy chain variable region of SEQ ID NO: 50 or 112 with Leu, Glu, and Ser, respectively (SEQ ID NO: 187). Thus, the present invention provides heavy chain variable regions in which CDR3 having the amino acid sequence of SEQ ID NO: 11 is substituted with CDR3 having the amino acid sequence of SEQ ID NO: 187 in a heavy chain variable region having the amino acid sequence of SEQ ID NO: 50 or 112.

Substitution of Arg at position 1 of CDR1 (SEQ ID NO: 13) in the light chain variable region of SEQ ID NO: 52 with Gln (SEQ ID NO: 121). Thus, the present invention provides light chain variable regions in which CDR1 having the amino acid sequence of SEQ ID NO: 13 is substituted with CDR1 having the amino acid sequence of SEQ ID NO: 121 in a light chain variable region having the amino acid sequence of SEQ ID NO: 52.

Substitution of Asn at position 5 of CDR1 (SEQ ID NO: 13) in the light chain variable region of SEQ ID NO: 52 with Asp (SEQ ID NO: 122). Thus, the present invention provides light chain variable regions in which CDR1 having the amino acid sequence of SEQ ID NO: 13 is substituted with CDR1 having the amino acid sequence of SEQ ID NO: 122 in a light chain variable region having the amino acid sequence of SEQ ID NO: 52.

Substitution of Ser at position 8 of CDR1 (SEQ ID NO: 13) in the light chain variable region of SEQ ID NO: 52 with Arg (SEQ ID NO: 188). Thus, the present invention provides light chain variable regions in which CDR1 having the amino acid sequence of SEQ ID NO: 13 is substituted with CDR1 having the amino acid sequence of SEQ ID NO: 188 in a light chain variable region having the amino acid sequence of SEQ ID NO: 52.

Substitution of Leu at position 10 of CDR1 (SEQ ID NO: 13) of the light chain variable region of SEQ ID NO: 52 with Val (SEQ ID NO: 189). Thus, the present invention provides light chain variable regions in which CDR1 having the amino acid sequence of SEQ ID NO: 13 is substituted with CDR1 having the amino acid sequence of SEQ ID NO: 189 in a light chain variable region having the amino acid sequence of SEQ ID NO: 52.

Substitution of Ser at position 8 and Leu at position 10 of CDR1 (SEQ ID NO: 13) of the light chain variable region of SEQ ID NO: 52 with Arg and Val, respectively (SEQ ID NO: 190). Thus, the present invention provides light chain variable regions in which CDR1 having the amino acid sequence of SEQ ID NO: 13 is substituted with CDR1 having the amino acid sequence of SEQ ID NO: 190 in a light chain variable region having the amino acid sequence of SEQ ID NO: 52.

Substitution of Thr at position 2 of CDR1 (SEQ ID NO: 13) in the light chain variable region of SEQ ID NO: 52 with Ala (SEQ ID NO: 191). Thus, the present invention provides light chain variable regions in which CDR1 having the amino acid sequence of SEQ ID NO: 13 is substituted with CDR1 having the amino acid sequence of SEQ ID NO: 191 in a light chain variable region having the amino acid sequence of SEQ ID NO: 52.

Substitution of Thr at position 2 of CDR1 (SEQ ID NO: 13) in the light chain variable region of SEQ ID NO: 52 with Ser (SEQ ID NO: 192). Thus, the present invention provides light chain variable regions in which CDR1 having the amino acid sequence of SEQ ID NO: 13 is substituted with CDR1 having the amino acid sequence of SEQ ID NO: 192 in a light chain variable region having the amino acid sequence of SEQ ID NO: 52.

Substitution of Asn at position 1 of CDR2 (SEQ ID NO: 14) in the light chain variable region of SEQ ID NO: 52 with Asp (SEQ ID NO: 123). Thus, the present invention provides light chain variable regions in which CDR2 having the amino acid sequence of SEQ ID NO: 14 is substituted with CDR2 having the amino acid sequence of SEQ ID NO: 123 in a light chain variable region having the amino acid sequence of SEQ ID NO: 52.

Substitution of Lys at position 3 of CDR2 (SEQ ID NO: 14) in the light chain variable region of SEQ ID NO: 52 with Gln (SEQ ID NO: 124). Thus, the present invention provides light chain variable regions in which CDR2 having the amino acid sequence of SEQ ID NO: 14 is substituted with CDR2 having the amino acid sequence of SEQ ID NO: 124 in a light chain variable region having the amino acid sequence of SEQ ID NO: 52.

Substitution of Leu at position 5 of CDR2 (SEQ ID NO: 14) in the light chain variable region of SEQ ID NO: 52 with Glu (SEQ ID NO: 125). Thus, the present invention provides light chain variable regions in which CDR2 having the amino acid sequence of SEQ ID NO: 14 is substituted with CDR2 having the amino acid sequence of SEQ ID NO: 125 in a light chain variable region having the amino acid sequence of SEQ ID NO: 52.

Substitution of Lys at position 7 of CDR2 (SEQ ID NO: 14) in the light chain variable region of SEQ ID NO: 52 with Gln (SEQ ID NO: 126). Thus, the present invention provides light chain variable regions in which CDR2 having the amino acid sequence of SEQ ID NO: 14 is substituted with CDR2 having the amino acid sequence of SEQ ID NO: 126 in a light chain variable region having the amino acid sequence of SEQ ID NO: 52.

Substitution of Lys at position 7 of CDR2 (SEQ ID NO: 14) in the light chain variable region of SEQ ID NO: 52 with Asp (SEQ ID NO: 127). Thus, the present invention provides light chain variable regions in which CDR2 having the amino acid sequence of SEQ ID NO: 14 is substituted with CDR2 having the amino acid sequence of SEQ ID NO: 127 in a light chain variable region having the amino acid sequence of SEQ ID NO: 52.

Substitution of Arg at position 1 and Asn at position 5 of CDR1 (SEQ ID NO: 13) in the light chain variable region of SEQ ID NO: 52 with Gln and Asp, respectively (SEQ ID NO: 169). Thus, the present invention provides light chain variable regions in which CDR1 having the amino acid sequence of SEQ ID NO: 13 is substituted with CDR1 having the amino acid sequence of SEQ ID NO: 169 in a light chain variable region having the amino acid sequence of SEQ ID NO: 52.

Substitution of Lys at position 3, Leu at position 5, and Lys at position 7 of CDR2 (SEQ ID NO: 14) in the light chain variable region of SEQ ID NO: 52 with Gln, Glu, and Gln, respectively (SEQ ID NO: 170). Thus, the present invention provides light chain variable regions in which CDR2 having the amino acid sequence of SEQ ID NO: 14 is substituted with CDR2 having the amino acid sequence of SEQ ID NO: 170 in a light chain variable region having the amino acid sequence of SEQ ID NO: 52.

Substitution of Glu at position 5 of CDR3 (SEQ ID NO: 15) in the light chain variable region of SEQ ID NO: 52 with Asp (SEQ ID NO: 193). Thus, the present invention provides light chain variable regions in which CDR3 having the amino acid sequence of SEQ ID NO: 15 is substituted with CDR3 having the amino acid sequence of SEQ ID NO: 193 in a light chain variable region having the amino acid sequence of SEQ ID NO: 52.

Substitution of Ser at position 6 of CDR3 (SEQ ID NO: 15) in the light chain variable region of SEQ ID NO: 52 with Asp (SEQ ID NO: 194). Thus, the present invention provides light chain variable regions in which CDR3 having the amino acid sequence of SEQ ID NO: 15 is substituted with CDR3 having the amino acid sequence of SEQ ID NO: 194 in a light chain variable region having the amino acid sequence of SEQ ID NO: 52.

Substitution of Thr at position 9 of CDR3 (SEQ ID NO: 15) in the light chain variable region of SEQ ID NO: 52 with Phe (SEQ ID NO: 195). Thus, the present invention provides light chain variable regions in which CDR3 having the amino acid sequence of SEQ ID NO: 15 is substituted with CDR3 having the amino acid sequence of SEQ ID NO: 195 in a light chain variable region having the amino acid sequence of SEQ ID NO: 52.

In addition, the substitutions other than those described above include a substitution of Arg at position 3 of heavy chain FR2 having the amino acid sequence of SEQ ID NO: 97 with another amino acid. The amino acid after substitution is not particularly limited; but preferred examples thereof include Gln. When Arg at position 3 in SEQ ID NO: 97 has been replaced with Gln, Ala at position 5 may be substituted with Ser to produce a human FR2 sequence. The amino acid sequence in which Arg and Ala at positions 3 and 5 in the amino acid sequence of SEQ ID NO: 97 have been replaced with Gln and Ser, respectively, is shown in SEQ ID NO: 120. Thus, the present invention provides heavy chain variable regions in which FR2 having the amino acid sequence of SEQ ID NO: 97 is substituted with FR2 having the amino acid sequence of SEQ ID NO: 120 in a heavy chain variable region having the amino acid sequence of SEQ ID NO: 50 or 112.

Each of the above-described amino acid substitutions may be used alone or in combination with other amino acid substitutions described above. They also may be combined with amino acid substitutions other than those described above.

Specific examples of the antibodies in which the above-described substitutions have been carried out include, for example, antibodies that comprise a heavy chain variable region having the amino acid sequence of SEQ ID NO: 167, antibodies that comprise a light chain variable region having the amino acid sequence of SEQ ID NO: 168, and antibodies that comprise a heavy chain variable region having the amino acid sequence of SEQ ID NO: 167 and a light chain variable region having the amino acid sequence of SEQ ID NO: 168. Furthermore, specific examples of the heavy chain variable regions in which the above-described substitutions have been carried out include, for example, the following heavy chain variable regions:

(1) heavy chain variable regions having the amino acid sequence of SEQ ID NO: 204 (H17);
(2) heavy chain variable regions having the amino acid sequence of SEQ ID NO: 205 (H19);
(3) heavy chain variable regions having the amino acid sequence of SEQ ID NO: 206 (H28);
(4) heavy chain variable regions having the amino acid sequence of SEQ ID NO: 207 (H30);
(5) heavy chain variable regions having the amino acid sequence of SEQ ID NO: 208 (H34);
(6) heavy chain variable regions having the amino acid sequence of SEQ ID NO: 209 (H42);
(7) heavy chain variable regions having the amino acid sequence of SEQ ID NO: 210 (H44);
(8) heavy chain variable regions having the amino acid sequence of SEQ ID NO: 211 (H46);
(9) heavy chain variable regions having the amino acid sequence of SEQ ID NO: 212 (H57);
(10) heavy chain variable regions having the amino acid sequence of SEQ ID NO: 213 (H71);
(11) heavy chain variable regions having the amino acid sequence of SEQ ID NO: 214 (H78);
(12) heavy chain variable regions having the amino acid sequence of SEQ ID NO: 215 (H92);
(13) heavy chain variable regions having the amino acid sequence of SEQ ID NO: 216 (H97); and
(14) heavy chain variable regions having the amino acid sequence of SEQ ID NO: 217 (H98).

Meanwhile, specific examples of the light chain variable regions in which the above-described substitutions carried out include, for example, the following light chain variable regions:

(15) light chain variable regions having the amino acid sequence of SEQ ID NO: 218 (L11);
(16) light chain variable regions having the amino acid sequence of SEQ ID NO: 219 (L12);
(17) light chain variable regions having the amino acid sequence of SEQ ID NO: 220 (L17); and
(18) light chain variable regions having the amino acid sequence of SEQ ID NO: 221 (L50).

Furthermore, specific examples of the antibodies comprising the above-described heavy chain and light chain variable regions include, for example, the following antibodies:

(19) antibodies that comprise the heavy chain variable region of (3) and the light chain variable region of (17) (H28L17);
(20) antibodies that comprise the heavy chain variable region of (4) and the light chain variable region of (17) (H30L17);
(21) antibodies that comprise the heavy chain variable region of (5) and the light chain variable region of (17) (H34L17);
(22) antibodies that comprise the heavy chain variable region of (6) and the light chain variable region of (17) (H42L17);
(23) antibodies that comprise the heavy chain variable region of (7) and the light chain variable region of (17) (H44L17);
(24) antibodies that comprise the heavy chain variable region of (8) and the light chain variable region of (17) (H46L17);
(25) antibodies that comprise the heavy chain variable region of (9) and the light chain variable region of (17) (H57L17);
(26) antibodies that comprise the heavy chain variable region of (10) and the light chain variable region of (17) (H71L17);
(27) antibodies that comprise the heavy chain variable region of (11) and the light chain variable region of (17) (H78L17);
(28) antibodies that comprise the heavy chain variable region of (12) and the light chain variable region of (17) (H92L17);
(29) antibodies that comprise the heavy chain variable region of (13) and the light chain variable region of (18) (H97L50); and
(30) antibodies that comprise the heavy chain variable region of (14) and the light chain variable region of (18) (H98L50).

The constant region used for the humanized antibodies of the present invention may be any constant region derived from a human antibody. Preferred examples of such constant regions derived from human antibodies include, for example, constant regions derived from IgG1 or IgG2. Moreover, constant regions in which one or more amino acids are substituted, deleted, added, and/or inserted in the constant region derived from a human antibody may also be used.

The constant regions in which one or more amino acids are substituted, deleted, added, and/or inserted in the constant region derived from a human antibody are not particularly limited, and include, for example, the following constant regions:

constant regions having the amino acid sequence of SEQ ID NO: 128 (M58);

constant regions having the amino acid sequence of SEQ ID NO: 129 (M14); and constant regions having the amino acid sequence of SEQ ID NO: 62 (SKSC).

Specific examples of the heavy chains or antibodies having the above-described constant regions include, for example:

(1) heavy chains that comprise a variable region having the amino acid sequence of SEQ ID NO: 167 and a constant region having the amino acid sequence of SEQ ID NO: 128;
(2) heavy chains in which CDR2 having the amino acid sequence of SEQ ID NO: 171 in the heavy chains of (1) is substituted with CDR2 having the amino acid sequence of SEQ ID NO: 172;
(3) antibodies that comprise the heavy chain of (1) and a light chain having the amino acid sequence of SEQ ID NO: 152; and
(4) antibodies that comprise the heavy chain of (2) and a light chain having the amino acid sequence of SEQ ID NO: 152.

More specific examples of the humanized anti-NR10 antibodies of the present invention include, for example, the following antibodies:

(k) antibodies that comprise a heavy chain having the amino acid sequence of SEQ ID NO: 54 (H0-VH+constant region);
(l) antibodies that comprise a heavy chain having the amino acid sequence of SEQ ID NO: 130 (H1-VH+constant region);
(m) antibodies that comprise a light chain having the amino acid sequence of SEQ ID NO: 56 (L0-VL+constant region);
(n) antibodies that comprise a heavy chain having the amino acid sequence of SEQ ID NO: 54 (H0-VH+constant region) and a light chain having the amino acid sequence of SEQ ID NO: 56 (L0-VL+constant region); and (o) antibodies that comprise a heavy chain having the amino acid sequence of SEQ ID NO: 130 (H1-VH+constant region) and a light chain having the amino acid sequence of SEQ ID NO: 56 (L0-VL+constant region).

The heavy chain having the amino acid sequence of SEQ ID NO: 54 (H0-VH+constant region) and the light chain having the amino acid sequence of SEQ ID NO: 56 (L0-VL+constant region) may have a substitution, deletion, addition, and/or insertion of one or more amino acids. The substitution, deletion, addition, and/or insertion of amino acids may be carried out in either or both of the variable and constant regions.

Thus, the present invention provides:

(p) antibodies that comprise a heavy chain having an amino acid sequence in which one or more amino acids are substituted, deleted, added, and/or inserted in the amino acid sequence of SEQ ID NO: 54 (H0-VH+constant region);

(q) antibodies that comprise a heavy chain having an amino acid sequence in which one or more amino acids are substituted, deleted, added, and/or inserted in the amino acid sequence of SEQ ID NO: 130 (H1-VH+constant region);

(r) antibodies that comprise a light chain having an amino acid sequence in which one or more amino acids are substituted, deleted, added, and/or inserted in the amino acid sequence of SEQ ID NO: 56 (L0-VL+constant region);

(s) antibodies that comprise a heavy chain having an amino acid sequence in which one or more amino acids are substituted, deleted, added, and/or inserted in the amino acid sequence of SEQ ID NO: 54 (H0-VH+constant region) and a light chain having an amino acid sequence in which one or more amino acids are substituted, deleted, added, and/or inserted in the amino acid sequence of SEQ ID NO: 56 (L0-VL+constant region); and (t) antibodies that comprise a heavy chain having an amino acid sequence in which one or more amino acids are substituted, deleted, added, and/or inserted in the amino acid sequence of SEQ ID NO: 130 (H1-VH+constant region) and a light chain having an amino acid sequence in which one or more amino acids are substituted, deleted, added, and/or inserted in the amino acid sequence of SEQ ID NO: 56 (L0-VL+constant region).

Without particular limitation, the antibodies of any one of (p) to (t) preferably have an activity similar to that of the antibodies of any one of (k) to (O).

The substitution, deletion, addition, and/or insertion of amino acids are not particularly limited, but specific examples thereof include, for example, the above-described amino acid substitutions.

Furthermore, the nucleotide sequence encoding the amino acid sequence of the above-described humanized heavy chain variable region (SEQ ID NO: 50) is shown in SEQ ID NO: 49. The nucleotide sequence encoding the amino acid sequence of the humanized light chain variable region (SEQ ID NO: 52) is shown in SEQ ID NO: 51. The nucleotide sequence encoding the amino acid sequence of the humanized heavy chain (SEQ ID NO: 54) is shown in SEQ ID NO: 53. The nucleotide sequence encoding the amino acid sequence of the humanized light chain (SEQ ID NO: 56) is shown in SEQ ID NO: 55.

Moreover, the present invention provides antibodies that recognize the same epitope as recognized by the antibodies of any one of (a) to (t) above. The binding to the same epitope is as already described above.

Furthermore, the present invention provides the following antibodies:

(u) antibodies that comprise a heavy chain having the amino acid sequence of SEQ ID NO: 151;

(v) antibodies that comprise a light chain comprising the amino acid sequence of SEQ ID NO: 152; and (w) antibodies that comprise the heavy chain of (u) and the light chain of (v).

Moreover, the present invention provides the following heavy and light chains and antibodies:

(1) heavy chains having the amino acid sequence of SEQ ID NO: 222 (H17);

(2) heavy chains having the amino acid sequence of SEQ ID NO: 223 (H19);

(3) heavy chains having the amino acid sequence of SEQ ID NO: 224 (H28);

(4) heavy chains having the amino acid sequence of SEQ ID NO: 225 (H30);

(5) heavy chains having the amino acid sequence of SEQ ID NO: 226 (H34);

(6) heavy chains having the amino acid sequence of SEQ ID NO: 227 (H42);

(7) heavy chains having the amino acid sequence of SEQ ID NO: 228 (H44);

(8) heavy chains having the amino acid sequence of SEQ ID NO: 229 (H46);

(9) heavy chains having the amino acid sequence of SEQ ID NO: 230 (H57);

(10) heavy chains having the amino acid sequence of SEQ ID NO: 231 (H71);

(11) heavy chains having the amino acid sequence of SEQ ID NO: 232 (H78);

(12) heavy chains having the amino acid sequence of SEQ ID NO: 233 (H92);

(13) heavy chains having the amino acid sequence of SEQ ID NO: 234 (H97);

(14) heavy chains having the amino acid sequence of SEQ ID NO: 235 (H98);

(15) light chains having the amino acid sequence of SEQ ID NO: 236 (L11)

(16) light chains having the amino acid sequence of SEQ ID NO: 237 (L12);

(17) light chains having the amino acid sequence of SEQ ID NO: 238 (L17);

(18) light chains having the amino acid sequence of SEQ ID NO: 239 (L50);

(19) antibodies that comprise the heavy chain of (3) and the light chain of (17) (H28L17);

(20) antibodies that comprise the heavy chain of (4) and the light chain of (17) (H30L17);

(21) antibodies that comprise the heavy chain of (5) and the light chain of (17) (H34L17);

(22) antibodies that comprise the heavy chain of (6) and the light chain of (17) (H42L17);

(23) antibodies that comprise the heavy chain of (7) and the light chain of (17) (H44L17);

(24) antibodies that comprise the heavy chain of (8) and the light chain of (17) (H46L17);

(25) antibodies that comprise the heavy chain of (9) and the light chain of (17) (H57L17);

(26) antibodies that comprise the heavy chain of (10) and the light chain of (17) (H71L17);

(27) antibodies that comprise the heavy chain of (11) and the light chain of (17) (H78L17);

(28) antibodies that comprise the heavy chain of (12) and the light chain of (17) (H92L17);

(29) antibodies that comprise the heavy chain of (13) and the light chain of (18) (H97L50);
(30) antibodies that comprise the heavy chain of (14) and the light chain of (18) (H98L50);
(31) heavy chains having an amino acid sequence in which one or more amino acids are substituted, deleted, added and/or inserted in the heavy chains of any one of (1) to (14);
(32) light chains having an amino acid sequence in which one or more amino acids are substituted, deleted, added and/or inserted in the light chains of any one of (15) to (18);
(33) antibodies having an amino acid sequence in which one or more amino acids are substituted, deleted, added and/or inserted in the antibodies of any one of (19) to (30); and
(34) antibodies that recognize the same epitope as recognized by the antibodies of any one of (19) to (33).

The substitution, deletion, addition, and/or insertion of amino acids are as described above. Antibodies that recognize the same epitope as recognized by an antibody are also described above.

The present invention also provides genes encoding the variable regions, heavy chains, light chains, or antibodies of the present invention.

The present invention also provides vectors carrying the above-described genes.

The present invention also provides host cells transformed with the above-described vectors.

The present invention also relates to methods for producing variable regions, heavy chains, light chains, or antibodies of the present invention, which comprise the step of culturing the above-described host cells.

The vectors, host cells, and culture of host cells are described herein below.

Antibodies that Recognize Domains

Preferred embodiments of the anti-NR10 antibody of the present invention include antibodies that recognize domain 1 or domain 2. In the present invention, domain 1 refers to the region of amino acids at positions 21 to 120 (LPAKP to LENIA) in the amino acid sequence of human NR10 of SEQ ID NO: 76, where the amino acid numbering is based on the sequence including the signal peptide. In addition, in the present invention, domain 2 refers to the region of amino acids at positions 121 to 227 (KTEPP to EEEAP) in the amino acid sequence of human NR10 of SEQ ID NO: 76, where the amino acid numbering is based on the sequence including the signal peptide.

Such antibodies are not particularly limited; however, in general, they have a neutralizing activity, and preferably are humanized antibodies.

Examples of the preferred antibodies in the present invention include antibodies that recognize domain 1. The antibodies that recognize domain 1 have a strong neutralizing activity, and thus are particularly useful as pharmaceuticals.

Antibodies (Neutralizing Activity)

The present invention also provides anti-NR10 antibodies having a neutralizing activity.

In the present invention, the neutralizing activity against NR10 refers to an activity of inhibiting the binding between NR10 and its ligand IL-31, and preferably an activity of suppressing a biological activity based on NR10.

Antibodies having a NR10-neutralizing activity can be selected, for example, by adding candidate antibodies to an IL-31-dependent cell line and observing their growth-suppressing effect on the cell line. In this method, antibodies that suppress the growth of the IL-31-dependent cell line are determined as antibodies having a neutralizing activity against NR10.

Antibodies (General)

The antibodies of the present invention are not limited in terms of their origin, and may be derived from any animals such as humans, mice, and rats. Moreover, the antibodies may be recombinant antibodies such as chimeric antibodies and humanized antibodies. As described above, the preferred antibodies of the present invention include humanized antibodies.

The chimeric antibodies contain, for example, the heavy and light chain constant regions of a human antibody, and the heavy and light chain variable regions of an antibody of a non-human mammal, such as mouse. The chimeric antibodies can be produced by known methods. For example, the antibodies can be produced by cloning an antibody gene from hybridomas, inserting it into an appropriate vector, and introducing the construct into hosts (see, for example, Carl, A. K. Borrebaeck, James, W. Larrick, THERAPEUTIC MONOCLONAL ANTIBODIES, Published in the United Kingdom by MACMILLAN PUBLISHERS LTD, 1990). Specifically, cDNAs of the antibody variable regions (V regions) are synthesized from mRNA of hybridomas using reverse transcriptase. Once DNAs encoding the V regions of an antibody of interest are obtained, these are linked with DNAs encoding the constant regions (C regions) of a desired human antibody. The resulting constructs are inserted into expression vectors. Alternatively, the DNAs encoding the antibody V regions may be inserted into expression vectors comprising DNAs encoding the C regions of a human antibody. The DNAs are inserted into expression vectors so that they are expressed under the regulation of the expression regulatory regions, for example, enhancers and promoters. In the next step, host cells can be transformed with the expression vectors to allow expression of chimeric antibodies.

Methods for obtaining human antibodies are also known. For example, desired human antibodies with antigen-binding activity can be obtained by (1) sensitizing human lymphocytes with antigens of interest or cells expressing antigens of interest in vitro; and (2) fusing the sensitized lymphocytes with human myeloma cells such as U266 (see Japanese Patent Application Kokoku Publication No. (JP-B) H01-59878 (examined, approved Japanese patent application published for opposition)). Alternatively, the desired human antibody can also be obtained by immunizing a transgenic animal having an entire repertoire of human antibody genes with a desired antigen (see International Patent Application Publication Nos. WO 93/12227, WO 92/03918, WO 94/02602, WO 94/25585, WO 96/34096, and WO 96/33735).

Furthermore, techniques to obtain human antibodies by panning with a human antibody phage library are known. For example, the variable region of a human antibody is expressed as a single chain antibody (scFv) on the surface of a phage, using a phage display method, and phages that bind to the antigen can be selected. By analyzing the genes of selected phages, the DNA sequences encoding the variable regions of human antibodies that bind to the antigen can be determined. If the DNA sequences of scFvs that bind to the antigen are identified, appropriate expression vectors comprising these sequences can be constructed to obtain human antibodies. Such methods are well known. Reference can be made to WO 92/01047, WO 92/20791, WO 93/06213, WO 93/11236, WO 93/19172, WO 95/01438, WO 95/15388, and such.

The antibodies of the present invention include not only divalent antibodies as represented by IgG, but also monovalent antibodies, multivalent antibodies as represented by IgM, and bispecific antibodies capable of binding to different antigens, as long as they have a NR10-binding activity and/or neutralizing activity. The multivalent antibodies of the present invention include multivalent antibodies in which the antigen-binding sites are all identical, and multivalent antibodies in which all or some of the antigen-binding sites are different. The antibodies of the present invention are not limited to full-length antibody molecules, but may also be low-molecular-weight antibodies or modified products thereof, as long as they bind to NR10 protein.

Alternatively, the antibodies of the present invention may be low-molecular-weight antibodies. Such low-molecular-weight antibodies are antibodies including antibody fragments lacking some portions of a whole antibody (for example, whole IgG), and are not particularly limited as long as they retain NR10-binding and/or neutralizing activity. In the present invention, the low-molecular-weight antibodies are not particularly limited, as long as they contain a portion of whole antibodies. The low-molecular-weight antibodies preferably contain a heavy chain variable region (VH) or light chain variable region (VL). Particularly preferred low-molecular-weight antibodies contain both VH and VL. In addition, preferred examples of the low-molecular-weight antibodies of the present invention include low-molecular-weight antibodies containing CDRs of an antibody. The CDRs contained in the low-molecular-weight antibodies may include some or all of the six CDRs of an antibody.

The low-molecular-weight antibodies of the present invention preferably have a smaller molecular weight than whole antibodies. However, the low-molecular-weight antibodies may form multimers, for example, dimers, trimers, or tetramers, and thus their molecular weights can be greater than those of whole antibodies.

Specific examples of the antibody fragments include, for example, Fab, Fab', F(ab')2, and Fv. Meanwhile, specific examples of the low-molecular-weight antibodies include, for example, Fab, Fab', F(ab')2, Fv, scFv (single chain Fv), diabodies, and sc(Fv)2 (single chain (Fv)2). Multimers (for example, dimers, trimers, tetramers, and polymers) of these antibodies are also included in the low-molecular-weight antibodies of the present invention.

Antibody fragments can be obtained, for example, by treating antibodies with enzymes to produce antibody fragments. Enzymes known to generate antibody fragments include, for example, papain, pepsin, and plasmin. Alternatively, a gene encoding such an antibody fragment can be constructed, introduced into an expression vector, and expressed in appropriate host cells (see, for example, Co, M. S. et al., J. Immunol. (1994)152, 2968-2976; Better, M. & Horwitz, A. H. Methods in Enzymology (1989)178, 476-496; Plueckthun, A. & Skerra, A. Methods in Enzymology (1989)178, 476-496; Lamoyi, E., Methods in Enzymology (1989)121, 652-663; Rousseaux, J. et al., Methods in Enzymology (1989)121, 663-669; Bird, R. E. et al., TIBTECH (1991) 9, 132-137).

Digestive enzymes cleave a specific site of an antibody fragment, yielding antibody fragments of specific structures shown below. Genetic engineering techniques can be applied to such enzymatically-obtained antibody fragments to delete an arbitrary portion of the antibody.

Antibody fragments obtained by using the above-described digestive enzymes are as follows:
Papain digestion: $F(ab)_2$ or Fab
Pepsin digestion: F(ab')2 or Fab'
Plasmin digestion: Facb The low-molecular-weight antibodies of the present invention include antibody fragments lacking an arbitrary region, as long as they have a NR10-binding activity and/or neutralizing activity.

"Diabody" refers to a bivalent antibody fragment constructed by gene fusion (Holliger P et al., Proc. Natl. Acad. Sci. USA 90: 6444-6448 (1993); EP 404,097; WO 93/11161, etc). Diabodies are dimers composed of two polypeptide chains. In each of the polypeptide chains forming a dimer, a VL and a VH are usually linked by a linker in the same chain. In general, the linker in a diabody is short enough such that the VL and VH cannot bind to each other. Specifically, the number of amino acid residues constituting the linker is, for example, about five residues. Thus, the VL and VH encoded on the same polypeptide cannot form a single-chain variable region fragment, and will form a dimer with another single-chain variable region fragment. As a result, the diabody has two antigen binding sites.

ScFv antibodies are single-chain polypeptides produced by linking a heavy chain variable region ([VH]) and a light chain variable region ([VL]) via a linker or such (Huston, J. S. et al., Proc. Natl. Acad. Sci. U.S.A. (1988) 85, 5879-5883; Pluckthun "The Pharmacology of Monoclonal Antibodies" Vol. 113, eds., Resenburg and Moore, Springer Verlag, New York, pp. 269-315, (1994)). The H-chain V region and L-chain V region of scFv may be derived from any antibody described herein. The peptide linker for linking the V regions is not particularly limited. For example, an arbitrary single-chain peptide containing about three to 25 residues can be used as the linker. Specifically, it is possible to use the peptide linkers or such described below.

The V regions of both chains can be linked, for example, by PCR as described above. First, among the following DNAs, a DNA encoding a complete or desired partial amino acid sequence is used as a template to link the V regions by PCR:

DNA sequence encoding an H chain or H-chain V region of an antibody, and

DNA sequence encoding an L chain or L-chain V region of an antibody.

DNAs encoding the V regions of H chain and L chain are amplified by PCR using a pair of primers having sequences corresponding to those at both ends of the DNA to be amplified. Then, a DNA encoding the peptide linker portion is prepared. The peptide linker-encoding DNA can also be synthesized by PCR. Here, nucleotide sequences that can be ligated to the amplification products of V regions synthesized separately are added to the 5' end of the primers to be used. Then, PCR is carried out using each DNA of the [H chain V region DNA]-[peptide linker DNA]-[L chain V region DNA], and assembly PCR primers.

The assembly PCR primers are composed of a combination of a primer that anneals to the 5' end of the [H chain V region DNA] and a primer that anneals to the 3' end of the [L chain V region DNA]. In other words, the assembly PCR primers are a set of primers that can be used to amplify DNA encoding the full-length sequence of scFv to be synthesized. Meanwhile, nucleotide sequences that can be ligated to the V-region DNAs have been added to the [peptide linker DNA]. Thus, these DNAs are linked together, and then the whole scFv is ultimately generated as an amplification product by the assembly PCR primers. Once the scFv-encoding DNAs are generated, expression vectors carrying these DNAs and recombinant cells transformed with these expression vectors can be obtained by conventional methods. Furthermore, the scFv can be obtained by culturing the resulting recombinant cells to express the scFv-encoding DNAs.

The order of the heavy chain and light chain variable regions to be linked together is not particularly limited, and they may be arranged in any order. Examples of the arrangement are listed below.

[VH] linker [VL]

[VL] linker [VH]

sc(Fv)2 is a single-chain low-molecular-weight antibody produced by linking two VHs and two VLs using linkers and such (Hudson et al., J. Immunol. Methods 1999; 231: 177-189). For example, sc(Fv)2 can be produced by linking scFvs via a linker.

Antibodies in which two VHs and two VLs are arranged in the order of VH-VL-VH-VL ([VH] linker [VL] linker [VH] linker [VL]) from the N terminus of the single-chain polypeptide are preferred. However, the order of the two VHs and two VLs is not limited to the above arrangement, and they may be arranged in any order. Examples of the arrangement are listed below:

[VL] linker [VH] linker [VH] linker [VL]

[VH] linker [VL] linker [VL] linker [VH]

[VH] linker [VH] linker [VL] linker [VL]

[VL] linker [VL] linker [VH] linker [VH]

[VL] linker [VH] linker [VL] linker [VH]

The amino acid sequence of the heavy chain variable region or light chain variable region in a low-molecular-weight antibody may contain a substitution, deletion, addition, and/or insertion. Furthermore, the heavy chain variable region and light chain variable region may also lack some portions or be added with other polypeptides, as long as they have antigen binding ability when linked together. Alternatively, the variable regions may be chimerized or humanized.

In the present invention, linkers which bind the variable regions of the antibody include arbitrary peptide linkers that can be introduced using genetic engineering, or synthetic linkers such as those disclosed in Protein Engineering, 9(3), 299-305, 1996.

The preferred linkers in the present invention are peptide linkers. The lengths of the peptide linkers are not particularly limited and those skilled in the art can appropriately select the lengths depending on the purpose. Typical lengths are one to 100 amino acids, preferably 3 to 50 amino acids, more preferably 5 to 30 amino acids, and particularly preferably 12 to 18 amino acids (for example, 15 amino acids).

Amino acid sequences of such peptide linkers include, for example:

```
Ser;

Gly-Ser;

Gly-Gly-Ser;

Ser-Gly-Gly;

Gly-Gly-Gly-Ser (SEQ ID NO: 82);

Ser-Gly-Gly-Gly (SEQ ID NO: 83);

Gly-Gly-Gly-Gly-Ser (SEQ ID NO: 84);

Ser-Gly-Gly-Gly-Gly (SEQ ID NO: 85);

Gly-Gly-Gly-Gly-Gly-Ser (SEQ ID NO: 86);

Ser-Gly-Gly-Gly-Gly-Gly (SEQ ID NO: 87);
```

-continued

```
Gly-Gly-Gly-Gly-Gly-Gly-Ser (SEQ ID NO: 88);

Ser-Gly-Gly-Gly-Gly-Gly-Gly (SEQ ID NO: 89);

(Gly-Gly-Gly-Gly-Ser (SEQ ID NO: 84))n;
and

(Ser-Gly-Gly-Gly-Gly (SEQ ID NO: 85))n,
```

where n is an integer of 1 or larger.

The amino acid sequence of peptide linker can be appropriately selected by those skilled in the art depending on the purpose. For example, the above-mentioned "n", which determines the length of the peptide linker, is usually 1 to 5, preferably 1 to 3, and more preferably 1 or 2.

Synthetic linkers (chemical crosslinking agents) include crosslinking agents that are routinely used to crosslink peptides, for example, N-hydroxy succinimide (NHS), disuccinimidyl suberate (DSS), bis(sulfosuccinimidyl) suberate ($BS^3$), dithiobis(succinimidyl propionate) (DSP), dithiobis (sulfosuccinimidyl propionate) (DTSSP), ethylene glycol bis (succinimidyl succinate) (EGS), ethylene glycol bis(sulfosuccinimidyl succinate) (sulfo-EGS), disuccinimidyl tartrate (DST), disulfosuccinimidyl tartrate (sulfo-DST), bis[2-(succinimidoxycarbonyloxy)ethyl]sulfone (BSOCOES), and bis [2-(sulfosuccinimidoxycarbonyloxy)ethyl]sulfone (sulfo-BSOCOES). These crosslinking agents are commercially available.

When four antibody variable regions are linked, three linkers are usually required. Such multiple linkers may be the same or different.

The antibodies of the present invention include antibodies in which one or more amino acid residues have been added to the amino acid sequence of an antibody of the present invention.

Further, fusion proteins which result from a fusion between one of the above antibodies and a second peptide or protein is included in the present invention. The fusion proteins can be prepared by ligating a polynucleotide encoding an antibody of the present invention and a polynucleotide encoding a second peptide or polypeptide in frame, inserting this into an expression vector, and expressing the fusion construct in a host. Some techniques known to those skilled in the art are available for this purpose. The partner peptide or polypeptide to be fused with an antibody of the present invention may be a known peptide, for example, FLAG (Hopp, T. P. et al., BioTechnology 6, 1204-1210 (1988)), 6×His consisting of six His (histidine) residues, 10×His, influenza hemagglutinin (HA), human c-myc fragment, VSV-GP fragment, p18HIV fragment, T7-tag, HSV-tag, E-tag, SV40 T antigen fragment, lck tag, α-tubulin fragment, B-tag, Protein C fragment. Other partner polypeptides to be fused with the antibodies of the present invention include, for example, GST (glutathione-S-transferase), HA (influenza hemagglutinin), immunoglobulin constant region, β-galactosidase, and MBP (maltose-binding protein). A polynucleotide encoding one of these commercially available peptides or polypeptides can be fused with a polynucleotide encoding an antibody of the present invention. The fusion polypeptide can be prepared by expressing the fusion construct.

Furthermore, the antibodies of the present invention may be conjugated antibodies which are linked to any of various molecules including polymeric substances such as polyethylene glycol (PEG) and hyaluronic acid, radioactive substances, fluorescent substances, luminescent substances, enzymes, and toxins. Such conjugated antibodies can be obtained by chemically modifying the obtained antibodies.

Methods for modifying antibodies have been established in this field (for example, U.S. Pat. Nos. 5,057,313 and 5,156,840). The "antibodies" of the present invention also include such conjugated antibodies.

Furthermore, the antibodies used in the present invention may be bispecific antibodies. The bispecific antibody refers to an antibody that has variable regions recognizing different epitopes in the same antibody molecule. In the present invention, the bispecific antibodies may recognize different epitopes on an NR10 molecule, or recognize NR10 with one antigen-binding site and a different substance with the other antigen-binding site.

Methods for producing bispecific antibodies are known. Bispecific antibodies can be prepared, for example, by linking two antibodies that recognize different antigens. Antibodies to be linked together may be half molecules each of which contains an H chain and an L chain, or quarter molecules that consist of only one H chain. Alternatively, hybridomas producing different monoclonal antibodies can be fused to produce a bispecific antibody-producing fused cell. Furthermore, bispecific antibodies can be produced by genetic engineering techniques.

The antibodies of the present invention may differ in amino acid sequence, molecular weight, isoelectric point, presence/absence of sugar chains, and conformation depending on the cell or host producing the antibody or the purification method as described below. However, a resulting antibody is included in the present invention, as long as it is functionally equivalent to an antibody of the present invention. For example, when an antibody of the present invention is expressed in prokaryotic cells, for example *E. coli*, a methionine residue is added to the N terminus of the original antibody amino acid sequence. Such antibodies are included in the present invention.

Antibody Production

The antibodies of the present invention may be polyclonal or monoclonal antibodies. Such monoclonal antibodies having NR10-binding and/or neutralizing activity can be obtained, for example, by the following procedure: anti-NR10 monoclonal antibodies are prepared by using as an antigen NR10 or a fragment thereof that is derived from a mammal such as human or mouse by known methods, and then antibodies having NR10-binding and/or neutralizing activity are selected from the thus obtained anti-NR10 monoclonal antibodies. Specifically, a desired antigen or cells expressing the desired antigen are used as a sensitizing antigen for immunization according to conventional immunization methods. Anti-NR10 monoclonal antibodies can be prepared by fusing the obtained immune cells with known parental cells using conventional cell fusion methods, and screening them for monoclonal antibody-producing cells (hybridomas) by conventional screening methods. Animals to be immunized include, for example, mammals such as mice, rats, rabbits, sheep, monkeys, goats, donkeys, cows, horses, and pigs. The antigen can be prepared using the known NR10 gene sequence according to known methods, for example, by methods using baculovirus (for example, WO 98/46777).

Hybridomas can be prepared, for example, according to the method of Milstein et al. (Kohler, G. and Milstein, C., Methods Enzymol. (1981) 73: 3-46) or such. When the immunogenicity of an antigen is low, immunization may be performed after linking the antigen with a macromolecule having immunogenicity, such as albumin.

Embodiments of the antibodies of the present invention that have a binding and/or neutralizing activity against NR10 include monoclonal antibodies that have a binding and/or neutralizing activity against human NR10. Antigens used to prepare monoclonal antibodies that have a binding and/or neutralizing activity against human NR10 are not particularly limited, as long as they enable preparation of antibodies that have a binding and/or neutralizing activity against human NR10. For example, it is known that there are a number of variants of human NR10, and any variant may be used as an immunogen as long as it enables preparation of antibodies that have a binding and/or neutralizing activity against human NR10. Alternatively, under the same condition, a peptide fragment of NR10 or a protein in which artificial mutations have been introduced into the natural NR10 sequence may be used as an immunogen. Human NR10.3 is one of preferred immunogens in preparing antibodies that have an activity of binding and/or neutralizing NR10 in the present invention.

Furthermore, the binding and/or neutralizing activity of antibody against NR10 can be measured, for example, by observing the effect of suppressing the growth of the IL-31-dependent cell line as described in the Examples.

Meanwhile, monoclonal antibodies can also be obtained by DNA immunization. DNA immunization is a method in which a vector DNA constructed such that the gene encoding an antigen protein can be expressed in an animal to be immunized is administered to the animal, and the immunogen is expressed within the body of the animal to provide immunostimulation. As compared to common immunization methods based on the administration of protein antigens, the DNA immunization is expected to be advantageous in that:

it enables immunostimulation while retaining the structure of a membrane protein; and the immunogen does not need to be purified.

On the other hand, it is difficult to combine DNA immunization with an immunostimulating means such as an adjuvant.

In order to obtain a monoclonal antibody by DNA immunization, first, DNA encoding NR10 is administered to an animal to be immunized. The DNA encoding NR10 can be synthesized by known methods such as PCR. The resulting DNA is inserted into an appropriate expression vector, and administered to the animal to be immunized. Expression vectors that can be used include commercially available expression vectors such as pcDNA3.1. The vector can be administered to the living body by conventional methods. For example, DNA immunization can be carried out by introducing gold particles coated with the expression vector into cells by gene gun. Booster using NR10-expressing cells after DNA immunization is a preferred method to yield a monoclonal antibody.

Once the mammal is immunized as described above and the serum level of a desired antibody is confirmed to be increased, immune cells are collected from the mammal and subjected to cell fusion. Preferred immune cells are spleen cells in particular.

Mammalian myeloma cells are used for fusion with the above immune cells. It is preferred that myeloma cells have appropriate selection markers for screening. The selection marker refers to a phenotype that allows (or does not allow) survival under particular culture conditions. Known selection markers include hypoxanthine-guanine phosphoribosyltransferase deficiency (hereinafter abbreviated as "HGPRT deficiency") and thymidine kinase deficiency (hereinafter abbreviated as "TK deficiency"). HGPRT- or TK-deficient cells exhibit hypoxanthine-aminopterin-thymidine sensitivity (hereinafter abbreviated as "HAT sensitivity"). In HAT selection medium, HAT-sensitive cells cannot synthesize DNA and thus will die. However, when fused with normal cells, they can continue to synthesize DNA via the salvage pathway of the normal cells and thus can grow even in HAT selection medium.

HGPRT- or TK-deficient cells can be selected using a medium containing 6-thioguanine, 8-azaguanine (hereinafter abbreviated as "8AG"), or 5'-bromodeoxyuridine. While normal cells are killed due to incorporation of these pyrimidine analogs into DNA, cells lacking these enzymes can survive in the selection medium because they cannot incorporate these pyrimidine analogs. Another selection marker called G418 resistance confers resistance to 2-deoxystreptamine antibiotics (gentamicin analogs) due to the neomycin resistance gene. Various myeloma cells suitable for cell fusion are known.

Cell fusion between immune cells and myeloma cells can be essentially carried out according to known methods, for example, the method by Kohler and Milstein (Kohler. G. and Milstein, C., Methods Enzymol. (1981) 73, 3-46).

More specifically, cell fusion can be carried out, for example, in a common culture medium in the presence of a cell fusion-promoting agent. The fusion-promoting agent includes, for example, polyethylene glycol (PEG) and Sendai virus (HVJ). If required, an auxiliary agent such as dimethyl sulfoxide may also be added to improve fusion efficiency.

The immune cells and myeloma cells may be used at an arbitrarily determined ratio. For example, the ratio of immune cells to myeloma cells is preferably from 1 to 10. Culture media to be used for cell fusion include, for example, media that are suitable for the cell growth of myeloma cell line, such as RPMI 1640 and MEM, and other common culture media used for this type of cell culture. In addition, the culture media may also be supplemented with serum supplement such as fetal calf serum (FCS).

Predetermined amounts of immune cells and myeloma cells are mixed well in the culture medium, and then mixed with a PEG solution pre-heated to 37° C. to produce fused cells (hybridomas). In the cell fusion method, for example, PEG with mean molecular weight of about 1,000-6,000 can be added to the cells typically at a concentration of 30% to 60% (w/v). Then, successive addition of the appropriate culture medium listed above and removal of supernatant by centrifugation are repeated to eliminate the cell fusion agent and such, which are unfavorable to the growth of hybridomas.

The resulting hybridomas can be screened using a selection medium according to the selection marker possessed by myeloma cells used in the cell fusion. For example, HGPRT- or TK-deficient cells can be screened by culturing them in a HAT medium (a medium containing hypoxanthine, aminopterin, and thymidine). Specifically, when HAT-sensitive myeloma cells are used in cell fusion, cells successfully fused with normal cells can be selectively grown in the HAT medium. The cell culture using the above HAT medium is continued for a sufficient period of time to allow all cells except the desired hybridomas (non-fused cells) to die. Specifically, in general, the desired hybridomas can be selected by culturing the cells for several days to several weeks. Then, screening and single cloning of hybridomas that produce an antibody of interest can be carried out by performing ordinary limiting dilution methods. Alternatively, antibodies that recognize NR10 can be prepared by the method described in WO 03/104453.

Screening and single cloning of an antibody of interest can be suitably carried out by known screening methods based on antigen-antibody reaction. For example, an antigen is bound to a carrier such as beads made of polystyrene or such and commercially available 96-well microtiter plates, and then reacted with the culture supernatant of hybridoma. Next, the carrier is washed and then reacted with an enzyme-labeled secondary antibody or such. When the culture supernatant contains an antibody of interest reactive to the sensitizing antigen, the secondary antibody binds to the carrier via this antibody. Finally, the secondary antibody bound to the carrier is detected to determine whether the culture supernatant contains the antibody of interest. Hybridomas producing a desired antibody capable of binding to the antigen can be cloned by the limiting dilution method or such. Not only the antigen used for immunization but also an NR10 protein substantially equivalent thereto can be preferably used as an antigen for this purpose. For example, a cell line expressing NR10, the extracellular domain of NR10, or an oligopeptide composed of a partial amino acid sequence constituting the domain may be used as the antigen.

In addition to the above-described method for preparing hybridomas through immunization of a nonhuman animal with an antigen, antibodies of interest can also be obtained by sensitizing human lymphocytes with an antigen. Specifically, first, human lymphocytes are sensitized with an NR10 protein in vitro. Then, the sensitized lymphocytes are fused with an appropriate fusion partner. For example, human-derived myeloma cells with the ability to divide permanently can be used as the fusion partner (see Japanese Patent Application Kokoku Publication No. (JP-B) H1-59878 (examined, approved Japanese patent application published for opposition). Antibodies obtained by this method are human antibodies having an activity of binding to the NR10 protein.

The nucleotide sequence encoding an anti-NR10 antibody obtained by the above-described method or such, and its amino acid sequence can be obtained by methods known to those skilled in the art. Amino acids contained in the amino acid sequences described in the present invention may undergo post-translational modification (for example, modification of N-terminal glutamine into pyroglutamic acid by pyroglutamylation is well-known to persons skilled in the art). Naturally, such sequences with post-translationally modified amino acids are also included in the amino acid sequences described in the present invention.

Based on the obtained sequence of the anti-NR10 antibody, the anti-NR10 antibody can be prepared, for example, by genetic recombination techniques known to those skilled in the art. Specifically, a polynucleotide encoding an antibody can be constructed based on the sequence of the NR10-recognizing antibody, inserted into an expression vector, and then expressed in appropriate host cells (see for example, Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; Bird, R. E. and Walker, B. W., Trends Biotechnol. (1991) 9, 132-137).

The vectors include M13 vectors, pUC vectors, pBR322, pBluescript, and pCR-Script. Alternatively, when aiming to subclone and excise cDNA, the vectors include, for example, pGEM-T, pDIRECT, and pT7, in addition to the vectors described above. Expression vectors are particularly useful when using vectors for producing the antibodies of the present invention. For example, when aiming for expression in *E. coli* such as JM109, DH5α, HB101, and XL1-Blue, the expression vectors not only have the above-described characteristics that allow vector amplification in *E. coli*, but must also carry a promoter that allows efficient expression in *E. coli*, for example, lacZ promoter (Ward et al., Nature (1989) 341, 544-546; FASEB J. (1992) 6, 2422-2427), araB promoter (Better et al., Science (1988) 240, 1041-1043), T7 promoter or such. Such vectors include pGEX-5X-1 (Pharmacia), "QIAexpress system" (Qiagen), pEGFP, or pET (in this case, the host is preferably BL21 that expresses T7 RNA polymerase) in addition to the vectors described above.

The vectors may contain signal sequences for antibody secretion. As a signal sequence for antibody secretion, a pelB signal sequence (Lei, S. P. et al J. Bacteriol. (1987) 169, 4379) may be used when a protein is secreted into the *E. coli* periplasm. The vector can be introduced into host cells by calcium chloride or electroporation methods, for example.

In addition to vectors for *E. coli*, the vectors for producing the antibodies of the present invention include mammalian expression vectors (for example, pcDNA3 (Invitrogen), pEF-BOS (Nucleic Acids. Res. 1990, 18(17), p5322), pEF, and pCDM8), insect cell-derived expression vectors (for example, the "Bac-to-BAC baculovirus expression system" (Gibco-BRL) and pBacPAK8), plant-derived expression vectors (for example, pMH1 and pMH2), animal virus-derived expression vectors (for example, pHSV, pMV, and pAdex-Lcw), retroviral expression vectors (for example, pZIPneo), yeast expression vectors (for example, "*Pichia* Expression Kit" (Invitrogen), pNV11, and SP-Q01), and *Bacillus subtilis* expression vectors (for example, pPL608 and pKTH50), for example.

When aiming for expression in animal cells such as CHO, COS, and NIH3T3 cells, the vectors must have a promoter essential for expression in cells, for example, SV40 promoter (Mulligan et al., Nature (1979) 277, 108), MMLV-LTR promoter, EF1α promoter (Mizushima et al., Nucleic Acids Res. (1990) 18, 5322), and CMV promoter, and more preferably they have a gene for selecting transformed cells (for example, a drug resistance gene that allows evaluation using an agent (neomycin, G418, or such). Vectors with such characteristics include pMAM, pDR2, pBK-RSV, pBK-CMV, pOPRSV, and pOP13, for example.

In addition, the following method can be used for stable gene expression and gene amplification in cells: CHO cells deficient in a nucleic acid synthesis pathway are introduced with a vector (for example, pSV2-dhfr (Molecular Cloning $2^{nd}$ edition, Cold Spring Harbor Laboratory Press, 1989)) that carries a DHFR gene which compensates for the deficiency, and the vector is amplified using methotrexate (MTX). Alternatively, the following method can be used for transient gene expression: COS cells with a gene expressing SV40 T antigen on their chromosome are transformed with a vector (pcD and such) with an SV40 replication origin. Replication origins derived from polyoma virus, adenovirus, bovine papilloma virus (BPV), and such can also be used. To amplify gene copy number in host cells, the expression vectors may further carry selection markers such as aminoglycoside transferase (APH) gene, thymidine kinase (TK) gene, *E. coli* xanthine-guanine phosphoribosyltransferase (Ecogpt) gene, and dihydrofolate reductase (dhfr) gene.

Thus, the present invention provides methods for producing the polypeptides of the present invention or polypeptides encoded by genes encoding the polypeptides of the present invention, which comprise the step of culturing host cells containing a vector into which a polynucleotide encoding the polypeptide of the present invention has been introduced.

More specifically, the present invention provides methods for producing the polypeptides of the present invention, comprising the steps of:

(a) culturing a host cell containing a vector into which a gene encoding the polypeptide of the present invention has been introduced; and (b) obtaining the polypeptide encoded by the gene.

The antibodies of the present invention obtained by the methods described above can be isolated from inside host cells or from outside the cells (the medium, or such), and purified to homogeneity. The antibodies can be isolated and purified by methods routinely used for isolating and purifying antibodies, and the type of method is not limited. For example, the antibodies can be isolated and purified by appropriately selecting and combining column chromatography, filtration, ultrafiltration, salting out, solvent precipitation, solvent extraction, distillation, immunoprecipitation, SDS-polyacrylamide gel electrophoresis, isoelectrofocusing, dialysis, recrystallization, and such.

The chromatographies include, for example, affinity chromatography, ion exchange chromatography, hydrophobic chromatography, gel filtration, reverse phase chromatography, and adsorption chromatography (Strategies for Protein Purification and Characterization: A Laboratory Course Manual. Ed Daniel R. Marshak et al., Cold Spring Harbor Laboratory Press, 1996). The chromatographic methods described above can be conducted using liquid chromatography, for example, HPLC and FPLC. Columns that can be used for affinity chromatography include protein A columns and protein G columns. Columns using protein A include, for example, Hyper D, POROS, and Sepharose FF (GE Amersham Biosciences). The present invention includes antibodies that are highly purified using these purification methods.

The NR10-binding activity of the obtained antibodies can be determined by methods known to those skilled in the art. Methods for determining the antigen-binding activity of an antibody include, for example, ELISA (enzyme-linked immunosorbent assay), EIA (enzyme immunoassay), RIA (radioimmunoassay), and fluorescent antibody method. For example, when enzyme immunoassay is used, antibody-containing samples, such as purified antibodies and culture supernatants of antibody-producing cells, are added to antigen-coated plates. A secondary antibody labeled with an enzyme, such as alkaline phosphatase, is added and the plates are incubated. After washing, an enzyme substrate, such as p-nitrophenyl phosphate, is added, and the absorbance is measured to evaluate the antigen-binding activity.

Pharmaceutical Compositions

The present invention also provides pharmaceutical compositions comprising the antibody mentioned above as an active ingredient. Moreover, the present invention provides therapeutic agents for inflammatory diseases which comprise the antibody mentioned above as an active ingredient.

In the present invention, inflammatory disease refers to diseases with pathological features involved in cytological and histological reactions that occur in affected blood vessels and adjacent tissues in response to an injury or abnormal stimulation caused by physical, chemical, or biological agents (Stedman's Medical Dictionary, 5th Ed., MEDICAL VIEW CO., 2005). Generally, inflammatory diseases include, dermatitis (atopic dermatitis, chronic dermatitis, and such), inflammatory bowel diseases (colitis and such), asthma, arthritis (rheumatoid arthritis, osteoarthritis, and such), bronchitis, Th2 autoimmune diseases, systemic lupus erythematosus, myasthenia gravis, chronic GVHD, Crohn's disease, spondylitis deformans, lumbar pain, gout, inflammation after surgery or injury, swelling, neuralgia, laryngopharyngitis, cystitis, hepatitis (non-alcoholic steatohepatitis, alcoholic hepatitis, and such), hepatitis B, hepatitis C, arteriosclerosis, and pruritus.

Preferred examples of inflammatory diseases that are subjects of the present invention include atopic dermatitis, chronic dermatitis, rheumatism, osteoarthritis, chronic asthma, and pruritus.

The phrase "comprise(s) an anti-NR10 antibody as an active ingredient" means comprising an anti-NR10 antibody as at least one of the active ingredients, and does not limit the proportion of the antibody. In addition, the therapeutic agents for inflammatory diseases in the present invention may also comprise, in combination with the anti-NR10 antibody mentioned above, other ingredients that enhance the treatment of inflammatory diseases.

The therapeutic agents of the present invention may also be used for preventive purposes.

The anti-NR10 antibody of the present invention may be prepared as formulations according to standard methods (see, for example, Remington's Pharmaceutical Science, latest edition, Mark Publishing Company, Easton, USA). Further, they may contain pharmaceutically acceptable carriers and/or additives if necessary. For example, they may contain surfactants (for example, PEG and Tween), excipients, antioxidants (for example, ascorbic acid), coloring agents, flavoring agents, preservatives, stabilizers, buffering agents (for example, phosphoric acid, citric acid, and other organic acids), chelating agents (for example, EDTA), suspending agents, isotonizing agents, binders, disintegrators, lubricants, fluidity promoters, and corrigents. However, without limitation to these, the agents for preventing or treating inflammatory diseases of the present invention may contain other commonly used carriers. Such carriers specifically include light anhydrous silicic acid, lactose, crystalline cellulose, mannitol, starch, carmelose calcium, carmelose sodium, hydroxypropylcellulose, hydroxypropylmethylcellulose, polyvinylacetaldiethylaminoacetate, polyvinylpyrrolidone, gelatin, medium chain fatty acid triglyceride, polyoxyethylene hydrogenated castor oil 60, sucrose, carboxymethylcellulose, corn starch, and inorganic salt. The agents may also contain other low-molecular-weight polypeptides, proteins such as serum albumin, gelatin, and immunoglobulin, and amino acids such as glycine, glutamine, asparagine, arginine, and lysine. When the anti-NR10 antibody is prepared as an aqueous solution for injection, the anti-NR10 antibody may be dissolved in an isotonic solution containing, for example, physiological saline, dextrose, or other adjuvants. The adjuvants may include, for example, D-sorbitol, D-mannose, D-mannitol, and sodium chloride. In addition, appropriate solubilizing agents, for example, alcohols (for example, ethanol), polyalcohols (for example, propylene glycols and PEGs), and non-ionic detergents (polysorbate 80 and HCO-50) may be used concomitantly.

If necessary, anti-NR10 antibodies may be encapsulated in microcapsules (microcapsules made of hydroxymethylcellulose, gelatin, polymethylmethacrylate, and the like), and made into components of colloidal drug delivery systems (liposomes, albumin microspheres, microemulsions, nanoparticles, and nano-capsules) (for example, see "Remington's Pharmaceutical Science 16th edition" &, Oslo Ed. (1980)). Moreover, methods for making sustained-release drugs are known, and these can be applied for anti-NR10 antibodies (Langer et al., J. Biomed. Mater. Res. (1981) 15, 167-277; Langer, Chem. Tech. (1982) 12, 98-105; U.S. Pat. No. 3,773,919; European Patent Application (EP) No. 58,481; Sidman et al., Biopolymers (1983) 22, 547-56; EP 133,988).

The pharmaceutical compositions of the present invention can be administered either orally or parenterally, but are preferably administered parenterally. Specifically, the agents are administered to patients by injection or percutaneous administration. Injections include, for example, intravenous injections, intramuscular injections, and subcutaneous injections, for systemic or local administration. The agents may be given to sites where inflammation is to be suppressed, or areas surrounding the sites by local infusion, intramuscular injection in particular. The administration methods can be properly selected according to the patient's age and condition. The single-administration dose can be selected, for example, from within the range of 0.0001 to 100 mg of the active ingredient per kg body weight. Alternatively, for example, when the agents are administered to human patients, the dose of the active ingredient can be selected from within the range of 0.001 to 1,000 mg/kg body weight. The single-administration dose preferably contains, for example, about 0.01 to 50 mg/kg body weight of the antibody of the present invention. However, the dose of an agent for preventing or treating inflammatory diseases of the present invention is not limited to these examples.

All prior-art documents cited in the present specification are herein incorporated by reference.

EXAMPLES

Herein below, the present invention will be specifically described with reference to Examples, but it is not to be construed as being limited thereto.

Example 1

Preparation of Hybridomas 1.1. Preparation of Human and Cynomolgus Monkey NR10 Plasmids for DNA Immunization 1.1.1. Preparation of Expression Vectors for hNR10 and cynNR10

Human NR10 (nucleotide sequence, SEQ ID NO: 75; amino acid sequence, SEQ ID NO: 76) was inserted into the expression vector pMacII, which expresses a protein under the control of mouse β-actin promoter (WO2005/054467), to prepare an expression vector for hNR10. In the same manner, an expression vector for cynNR10 was constructed from cynomolgus monkey NR10 (nucleotide sequence, SEQ ID NO: 65; amino acid sequence, SEQ ID NO: 66).

1.1.2. Preparation of DNA Cartridge

In order to use the hNR10 or cynNR10 expression vector prepared in 1.1.1 for DNA immunization of mice, the Helios Gene Gun Cartridge Kit (BIO-RAD) was used to produce a DNA cartridge for each DNA that allows immunization with 1 μg of DNA at one time.

1.2. Preparation of Hybridomas Producing Anti-Human NR10 Antibody 1.2.1. Preparation of Hybridomas Using Mice Immunized with Human or Cynomolgus Monkey NR10

Ten Balb/c mice (female; six weeks old at the beginning of immunization; Charles River Laboratories Japan) were immunized with human or cynomolgus monkey NR10 by the following procedure. For primary immunization, the mice were immunized with the DNA cartridge prepared with the hNR10 expression vector using the Helios Gene Gun System (BIO-RAD). One week later, secondary immunization was performed by the Helios Gene Gun System (BIO-RAD) using the DNA cartridge prepared with the cynNR10 expression vector. The third and subsequent immunizations were carried out at one-week intervals using the hNR10 and cynNR10 expression vectors alternately. After the titer of serum antibody against human NR10 was confirmed to be elevated, a human NR10 protein (extracellular domain) (Referential Example 4) diluted with PBS(−) was intravenously administered at 10 μg/head as the final immunization. Four days after the final immunization, mouse spleen cells were fused with mouse myeloma P3X63Ag8U.1 cells (abbreviated as P3U1; ATCC CRL-1597) by a conventional method using PEG1500 (Roche Diagnostics). The resulting fused cells, i.e., hybridomas, were cultured in RPMI1640 supplemented with 10% FBS (hereinafter abbreviated as 10% FBS/RPMI1640).

1.2.2. Selection of Hybridomas

On the next day of fusion, the fused cells were suspended in a semisolid medium (StemCells), and cultured for selection as well as colonization of hybridomas.

Figure 3:
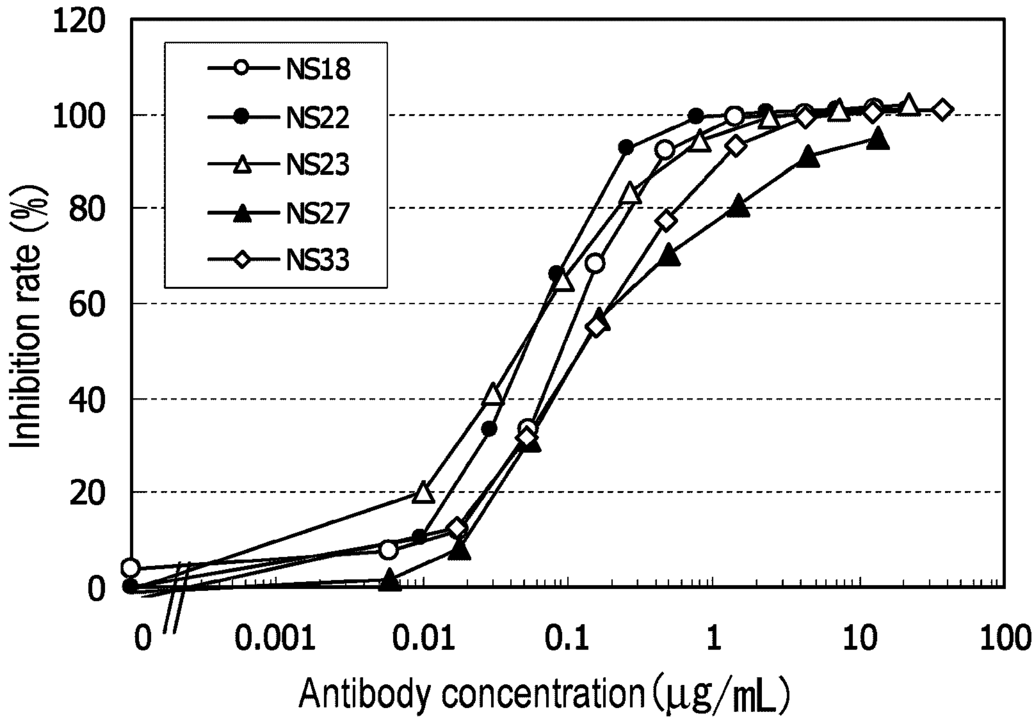
FIG. 3 is a graph showing the inhibition of hNR10/hOSMR/BaF3 cell growth by hybridoma culture supernatants.
Figure 4:
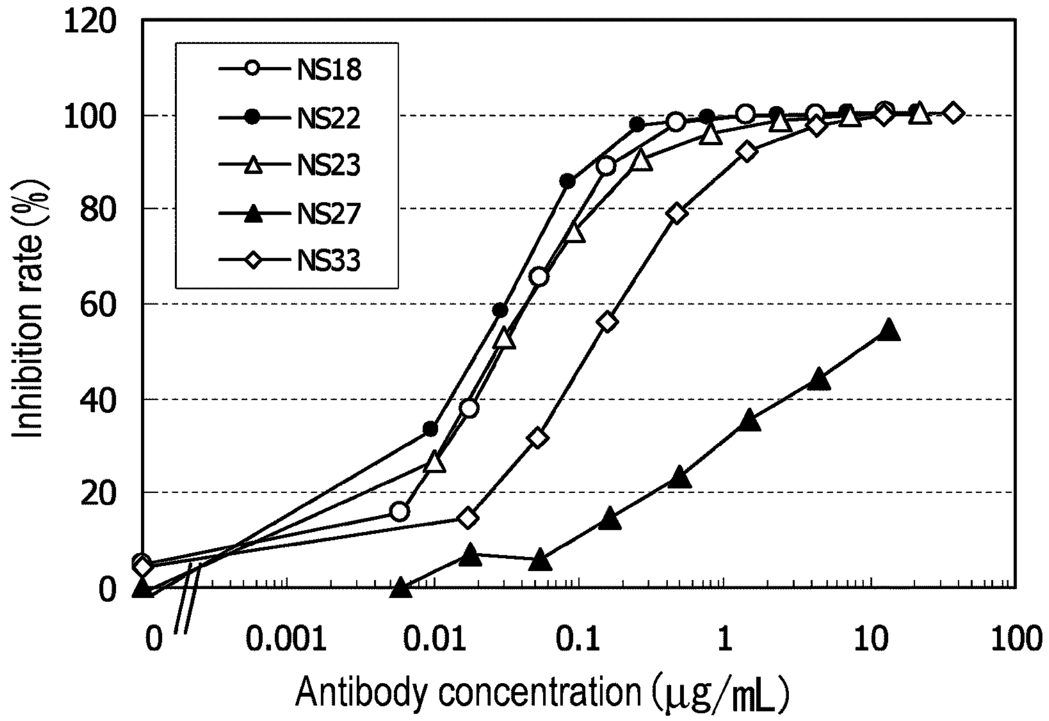
FIG. 4 is a graph showing the inhibition of cynNR10/cynOSMR/BaF3 cell growth by hybridoma culture supernatants.

After nine or ten days of fusion, hybridoma colonies were picked up and each colony was seeded into each well of 96-well plates containing the HAT selection medium (10% FBS/RPMI1640, 2 vol % of HAT 50× concentrate (Dainippon Pharmaceutical), and 5 vol % of BM-Condimed H1 (Roche Diagnostics)). After three to four days of culture, the culture supernatant was collected from each well to determine the concentration of mouse IgG in the supernatant. The culture supernatants in which mouse IgG was detected were assessed for a neutralizing activity using a human IL-31-dependent cell line (hNR10/hOSMR/BaF3 cells; Referential Example 2), and several clones having a strong NR10-neutralizing activity were obtained (FIG. 3). Clones that suppress the human IL-31-induced growth of cells in a concentration-dependent manner and suppress the cynomolgus monkey IL-31-induced growth of cells (cynNR10/cynOSMR/BaF3 cells; Referential Example 2) in a concentration-dependent manner were obtained (FIG. 4).

Example 2

Preparation of Chimeric Antibodies

Preparation of Expression Vectors for Chimeric Antibodies

Total RNAs were extracted from the hybridomas using RNeasy Mini Kits (QIAGEN), and cDNAs were synthesized from them using SMART RACE cDNA Amplification Kit (BD Biosciences). Antibody variable region genes were isolated by PCR using PrimeSTAR HS DNA polymerase (TaKaRa), 10× Universal Primer A Mix attached to SMART RACE cDNA Amplification Kit (BD Biosciences), and primers designed for each antibody constant region (H chain, mIgG1-mot; L chain, mIgK-mot). The nucleotide sequence of each isolated DNA fragment was determined with ABI PRISM 3730xL DNA Sequencer or ABI PRISM 3700 DNA Sequencer (Applied Biosystems), using BigDye Terminator Cycle Sequencing Kit (Applied Biosystems) according to the method described in the appended instruction manual. The determined amino acid sequences of H chain and L chain variable regions in the mouse antibodies NS18, NS22, NS23, and NS33 were shown in FIGS. 1 and 2, respectively.

Each of the resulting H and L chain fragments was subjected to PCR using PrimeSTAR HS DNA Polymerase (TaKaRa) and the primer sets shown in Table 1. The resulting amplified fragments were ligated with the constant region (human γ1 or γ2, and human κ, respectively), and then inserted into an animal cell expression vector. The nucleotide sequence of each DNA fragment was determined with ABI PRISM 3730xL DNA Sequencer or ABI PRISM 3700 DNA Sequencer (Applied Biosystems), using BigDye Terminator Cycle Sequencing Kit (Applied Biosystems) according to the method described in the appended instruction manual.

TABLE 1

| | Sequence (5' → 3') | SEQ ID NO: |
|---|---|---|
| mIgG1-rnot | TAATAGCGGCCGCTCATTATTTAC CAGGAGAGTGGGAGAG | 90 |
| mIgK-rnot | TAATAGCGGCCGCTCATTAACACT CATTCCTGTTGAAGCT | 91 |
| mNS18H-feco | GACGAATTCCACCATGGGATGGAG CTGGATCTT | 92 |
| mNS18L-feco | GACGAATTCCACCATGAGTGTGCC CACTCAGGT | 93 |
| mNS33H-feco | GACGAATTCCACCATGGAATGTAA CTGGATACT | 94 |
| mNS33L-feco | GACGAATTCCACCATGGATTTTCT GGTGCAGAT | 95 |

TABLE 1-continued

| | Forward primer | Reverse primer |
|---|---|---|
| NS18 H chain | mNS18H-feco | mIG1-rnot |
| NS18 L chain | mNS18L-feco | mIGK-rnot |
| NS22 H chain | Mns18H-feco | mIG1-rnot |
| NS22 L chain | mNS18L-feco | mIGK-rnot |
| NS23 H chain | mNS18H-feco | mIG1-rnot |
| NS23 L chain | mNS18L-feco | mIGK-rnot |
| NS33 H chain | mNS33H-feco | mIG1-rnot |
| NS33 L chain | mNS33L-feco | mIGK-rnot |

Preparation of Chimeric Antibodies

Human embryonic kidney cancer cell line HEK293H (Invitrogen) was suspended in DMEM (Invitrogen) supplemented with 10% fetal bovine serum (Invitrogen), and 10 ml of cells were seeded into dishes for adherent cells (10 cm in diameter; CORNING) at a cell density of $6\times10^5$ cells/ml. The cells were incubated in a $CO_2$ incubator (37° C., 5% $CO_2$) for one whole day and night. Then, the medium was removed by aspiration, and 6.9 ml of CHO-S-SFMII medium (Invitrogen) was added. CHO-S-SFMII medium was added to the prepared plasmid DNA mixture (13.8 μg in total) to a volume of 700 μl. This was mixed with 20.7 μl of 1 μg/ml polyethyleneimine (Polysciences Inc.), and allowed to stand at room temperature for 10 minutes. The solution was added to the cells in each dish. The cells were incubated in a $CO_2$ incubator (37° C., 5% $CO_2$) for four to five hours. Then, 6.9 ml of CHO-S-SFMII medium (Invitrogen) was added, and the cells were incubated in a $CO_2$ incubator for three to four days. The culture supernatants were collected and then centrifuged (approx. 2000 g, five minutes, room temperature) to remove the cells. The supernatants were filtered through 0.22-μm filter MILLEX®-GV (Millipore). Each sample was stored at 4° C. until use. Antibodies were purified from the supernatants using Protein G Sepharose (Amersham Biosciences). The purified antibodies were concentrated with Amicon Ultra 15 (Millipore), and then the solvent was replaced with PBS(−) containing 0.05% $NaN_3$ using PD-10 Desalting columns (Amersham Biosciences. The absorbance at 280 nm was measured with ND-1000 Spectrophotometer (NanoDrop), and the concentrations were determined by the method of Pace et al. (Protein Science (1995) 4: 2411-2423).

Assessment of the Activity of Chimeric NS22

Figure 5:
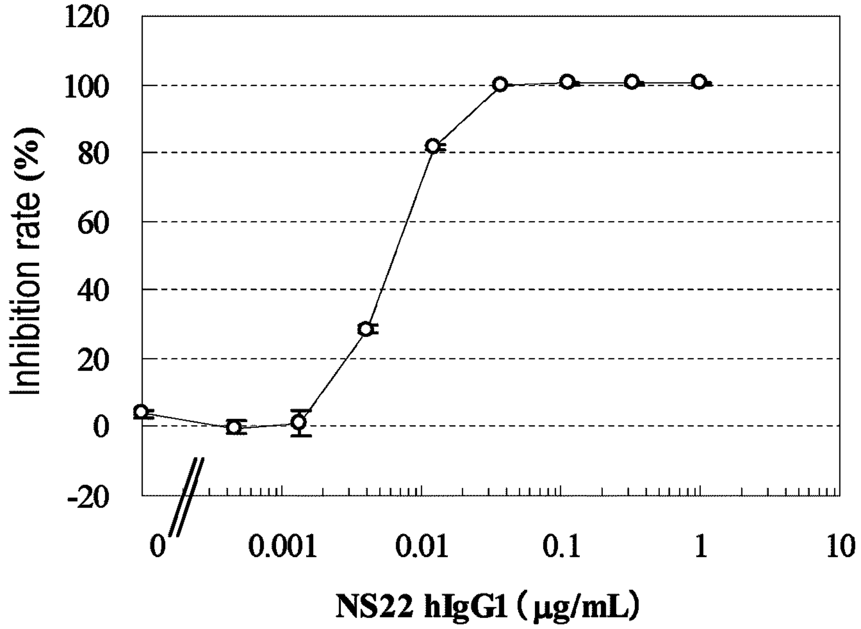
FIG. 5 is a graph showing the assessment of the activity of chimeric NS22 (BaF).

The activity of neutralizing hIL-31 was assessed using the hNR10/hOSMR/BaF3 cell line, which grows in an hIL-31 dose-dependent manner, as described below.

hNR10/hOSMR/BaF3 cells were prepared at $1.5\times10^5$ cells/ml using RPMI1640 medium (GIBCO) containing 10% FBS (MOREGATE) and 1% Penicillin-Streptomycin (Invitrogen). hIL-31 (R&D Systems) was added to an aliquot of the cells to a final concentration of 4 ng/ml (IL-31(+); final conc.: 2 ng/ml). The remaining cell suspension was used as IL-31 (−). The purified NS22 was adjusted to 2 μg/ml using the medium, and eight serial dilutions were prepared at a common dilution ratio of 3 (final conc.: 1 μg/ml or less). 50 μl each of the cell suspension and the dilution of chimeric NS22 (human γ1, κ) was added to each well of 96-well flat-bottom plates (CORNING), and the cells were cultured in a 5% $CO_2$ incubator at 37° C. for two days. After culture, 20 μl of a mixture of equal amounts of Cell Counting Kit-8 (Dojindo) and PBS was added to each well, and the absorbance (450 nm/620 nm) was measured (TECAN, SUNRISE CLASSIC). After the reaction was allowed to continue for two hours in a 5% $CO_2$ incubator at 37° C., the absorbance was measured again. The neutralizing activity of NS22 was presented as an inhibition rate using a value obtained by subtracting the O-hour value from the 2-hour value. The result showed that NS22 suppressed the IL-31-induced growth of the hNR10/hOSMR/BaF3 cell line in a concentration-dependent manner. This demonstrates that NS22 has a neutralizing activity against the human IL-31 signaling (FIG. 5).

The IL-31-neutralizing activity was assessed as described below using the DU145 cell line (human prostate cancer cell line), in which IL-6 production is induced upon IL-31 stimulation.

DU145 cells were prepared at $2.5\times10^5$ cells/ml in MEM (Invitrogen) containing 10% FBS (MOREGATE), 2 mmol/l L-glutamine (Invitrogen), and 1 mmol/l sodium pyruvate (SIGMA), and 200-μl aliquots were dispensed into each well of 48-well plates (CORNING). The cells were incubated at 37° C. under 5% $CO_2$ overnight. The purified chimeric NS22 (human γ1, κ) was diluted to 100 μg/ml with MEM containing 10% FBS, 2 mmol/l L-glutamine, and sodium pyruvate. Using this solution, six serial dilutions were prepared at a common dilution ratio of 5. Each dilution was combined with 100 ng/ml human interleukin-31 (R&D systems) at a ratio of 1:1, and a 50-μl aliquot was added to each well. After two days of culture at 37° C. under 5% $CO_2$, the concentration of IL-6 in the culture supernatant was determined using DuoSet ELISA Development kit (R&D systems). The neutralizing activity of NS22 was assessed by determining the inhibition rate (%). Specifically, assuming the IL-6 concentration in the absence of IL-31 (A) as the maximal inhibitory activity (100% inhibition) and the IL-6 concentration in the presence of IL-31 without NS22 (B) as no inhibitory activity (0% inhibition), the IL-6 concentration in the presence of IL-31 and NS22 (C) was determined according to the following formula:

$$\text{Inhibition rate (\%)}=(B-C)/(B-A)\times100$$

Figure 6:
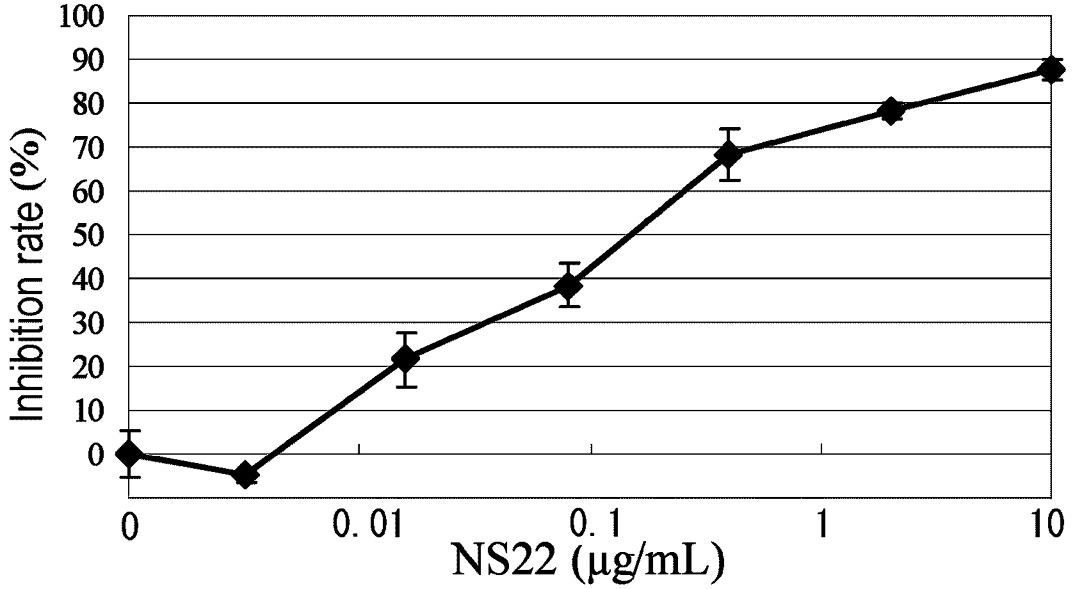
FIG. 6 is a graph showing the assessment of the activity of chimeric NS22 (DU-145).

The result showed that NS22 suppressed the IL-31-induced IL-6 production in the DU145 cell line in a concentration-dependent manner and thus demonstrated that NS22 had a neutralizing activity against the human IL-31 signaling (FIG. 6).

Assessment of Competition of Chimeric Anti-NR10 Antibody with IL-31

Human IL-31 (R&D Systems) was labeled with FMAT Blue Monofunctional Reactive Dye (Applied Biosystems). 100 μl of hIL-31 prepared at 0.5 mg/ml using 50 mM sodium phosphate buffer (pH 8.0) was mixed with 5.25 μl of 25 nmoles FMAT Blue dissolved in DMSO (Junsei). After vortexing, the mixture was allowed to stand at room temperature for 15 minutes. The FMAT Blue-conjugating reaction with hIL-31 was terminated by adding 5 μl of 1 M Tris-HCl (pH 7.4) and 1.1 μl of 10% Tween20, and then FMAT Blue-labeled hIL-31 and unreacted FMAT Blue were separated by gel filtration using Superdex 75 (GE Healthcare, 17-0771-01) column with 0.1% Tween20/PBS developing solution.

Antibodies were assessed for the activity of inhibiting the IL-31/NR10 binding by using hNR10-expressing CHO cells as described below.

Figure 7:
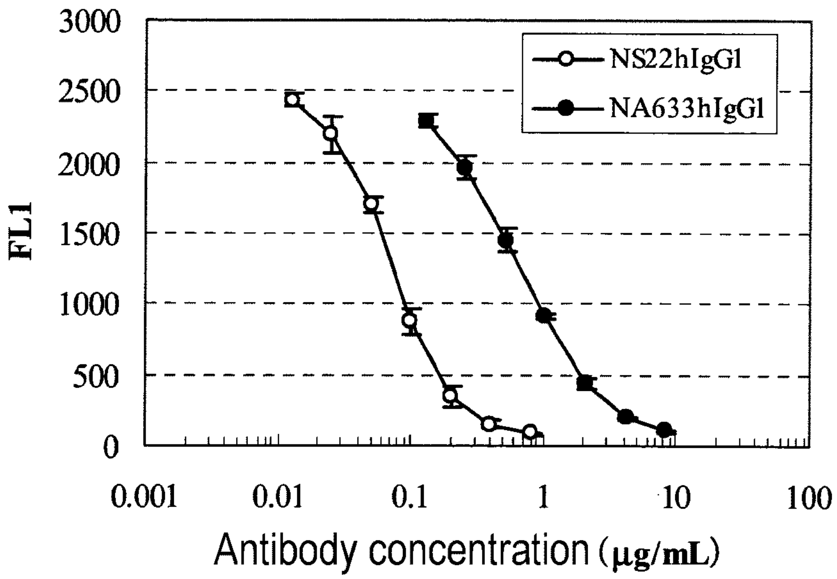
FIG. 7 is a graph showing the assessment of the competition of chimeric NS22 with IL-31.

NS22 and NA633 (the constant region of each is γ1, κ) were diluted at an appropriate concentration using Assay buffer (10 mM HEPES, 140 mM NaCl, 2.5 mM $CaCl_2$, 3 mM $MgCl_2$, 2% FBS, 0.01% $NaN_3$), and then seven serial dilutions were prepared at a common dilution ratio of 2. The dilutions were added at 40 μl/well to plates (96-Well FMAT Plates; Applied Biosystems). Then, FMAT Blue-labeled hIL-31 was diluted 400 times with Assay buffer and added at 20 μl/well. Finally, cell suspensions adjusted to $2.5\times10^5$ cells/ml using Assay buffer were added at 40 μl/well (final $1\times10^4$ cells/well). Two hours after addition of cells, the fluorescence (FL1) was determined using the 8200 Cellular Detection System (Applied Biosystems). The result showed that NS22 inhibited the binding of hIL-31/hNR10 in a dose-dependent manner, and demonstrated that its activity was superior to that of NA633 (FIG. 7).

Example 3

Competition of Anti-NR10 Antibody Against NR10

The antibody NS22 purified from a hybridoma culture supernatant was labeled with FMAT Blue (Applied Biosystems, 4328853). 170 μl of NS22 prepared at 1 mg/ml in PBS was mixed with 17 μl of 1 M $NaHCO_3$ solution and 3.4 μl of FMAT Blue (17 nmoles) dissolved in DMSO. After vortexing, the mixture was allowed to stand at room temperature for 30 minutes. The FMAT Blue conjugating reaction with NS22 was terminated by adding 8 μl of 1 M Tris-HCl (pH 7.4) and 1.9 μl of 1% Tween 20, and then FMAT Blue-labeled NS22 (FMAT Blue-NS22) and unreacted FMAT Blue were separated by gel filtration using Superdex 75 (GE Healthcare, 17-0771-01) column with 0.01% Tween20/PBS developing solution.

Figure 8:
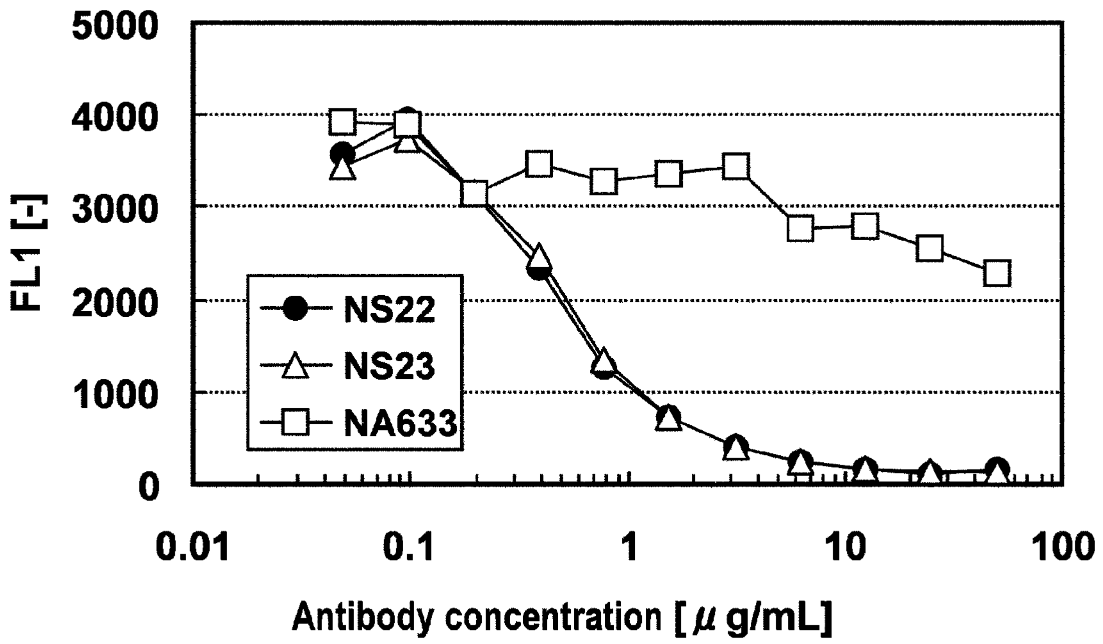
FIG. 8 is a graph showing the NR10 competitive binding activity of anti-NR10 antibodies.

Each antibody was examined for inhibition of the binding of the prepared FMAT Blue-NS22 to hNR10-expressing CHO cells (Referential Example 3) using the 8200 Cellular Detection System (Applied Biosystems, 4342920). The chimeric anti-NR10 antibodies (the constant region of each is γ1, κ) were added at various concentrations to each well containing 7500 cells and $8.8\times10^{-2}$ μg/ml FMAT Blue-NS22. The cells were allowed to stand in the dark for four hours, and then the fluorescent signal from FMAT Blue bound to the cells was measured. The reaction was carried out in 10 mM Hepes-KOH containing 2.5 mM $CaCl_2$, 3 mM $MgCl_2$, 140 mM NaCl, 2% FBS, and 0.01% $NaNO_3$. The result is shown in FIG. 8. The fluorescence value FL1, which represents the binding of FMAT Blue-NS22 to NR10-expressing cells, was reduced with the increase in the concentration of antibody NS22 or NS23. On the other hand, FL1 was hardly reduced with the increase in the concentration of antibody NA633 (Referential Example 6) (FIG. 8).

Example 4

Humanization of NS22 Antibody

Selection of Each Framework Sequence

The variable regions of mouse NS22 antibody were compared with human germline sequences. FR sequences used for humanization are summarized in Table 2. CDRs and FRs were determined based on the Kabat numbering. The humanized variable region sequences of H chain composed of FR1, FR2, FR3__1, and FR4, and composed of FR1, FR2, FR3__2, and FR4, which are listed in Table 2, are designated as H0-VH (SEQ ID NO: 50) and H1-VH (SEQ ID NO: 112), respectively. Meanwhile, the sequence of L chain composed of FR1, FR2, FR3, and FR4 is designated as L0 (SEQ ID NO: 52).

Preparation of Variable Region for Humanized NS22 H0L0

Synthetic oligo DNAs were designed for each of the H and L chains to construct the variable regions of humanized NS22 in which the CDRs of NS22 are grafted onto the FRs used for humanization. The respective synthetic oligo DNAs were mixed, and then subjected to assembly PCR to construct a gene encoding the variable region of humanized NS22. The assembly PCR was carried out using KOD-Plus (TOYOBO) according to the following conditions. A reaction mixture containing 10 pmol synthetic oligo DNAs and the appended PCR Buffer, dNTPs, $MgSO_4$, and KOD-Plus was heated at 94° C. for five minutes. The mixture was then subjected to two PCR cycles of 94° C. for two minutes, 55° C. for two minutes, and 68° C. for two minutes. Then, 10 pmol each of a primer in which a restriction site and Kozak sequence has been added to the 5' end of the variable region, and a primer in which a restriction site has been added to the 3' end of the variable region, was added and subjected to 35 PCR cycles of 94° C. for 30 seconds, 55° C. for 30 seconds, and 68° C. for one minute to yield a amplified fragment. The resulting amplified fragment was cloned into TOPO TA Cloning vector (TOYOBO), and its nucleotide sequence was determined by sequencing. The constructed variable regions were combined with the constant regions to prepare H0-SKSC (SEQ ID NO: 54) and L0 (SEQ ID NO: 56). The resulting construct was inserted into an expression vector capable of expressing the inserted gene in animal cells. The nucleotide sequence of each DNA fragment was determined using BigDye Terminator Cycle Sequencing Kit (Applied Biosystems) with ABI PRISM 3730xL DNA Sequencer or ABI PRISM 3700 DNA Sequencer (Applied Biosystems) according to the method described in the appended instruction manual.

Preparation of Variable Region for Humanized NS22 H1

H1-SKSC (SEQ ID NO: 130) was generated by substituting the glutamine (E) at Kabat-numbering position 73 in FR3 of H0-SKSC (SEQ ID NO: 54) with lysine (K). The mutant was prepared using commercially available QuikChange Site-Directed Mutagenesis Kit (Stratagene) according to the appended instruction manual.

Expression of IgG-Converted Antibody

Antibody expression was performed by the method described below. Human fetal renal cancer cell-derived cell line HEK293H (Invitrogen) was suspended in DMEM (Invitrogen) containing 10% fetal bovine serum (Invitrogen), and 10 ml of cells at a density of $5\text{-}6\times10^5$ cells/ml was seeded onto dishes for adherent cells (10 cm in diameter; CORNING). The cells were incubated in a $CO_2$ incubator (37° C., 5% $CO_2$) for one whole day and night. Then, the medium was removed by aspiration, and 6.9 ml of CHO-S-SFMII medium (Invitrogen) was added to the cells. The prepared plasmid DNA mixture (13.8 μg in total) was mixed with 20.7 μl of 1 μg/ml polyethyleneimine (Polysciences Inc.) and 690 μl of CHO-S-SFMII medium, and allowed to stand at room temperature for 10 minutes. The mixture was added to the cells in each dish, and the cells were incubated in a $CO_2$ incubator (5% $CO_2$, 37° C.) for four to five hours. Then, 6.9 ml of CHO-S-SFMII medium (Invitrogen) was added, and the cells were incubated in a $CO_2$ incubator for three days. The culture supernatant was collected and centrifuged (approx. 2000 g, five minutes, room temperature) to remove the cells. The supernatant was then sterilized by filtration through 0.22-μm filter MILLEX®-GV (Millipore). Each sample was stored at 4° C. until use.

Purification of IgG-Converted Antibody

50 μl of rProtein A Sepharose™ Fast Flow (Amersham Biosciences) suspended in TBS was added to the obtained culture supernatant, and mixed by inversion at 4° C. for four hours or more. The solution was transferred to 0.22-μm filter cup of Ultrafree-MC (Millipore). After three washes with 500 μl of TBS, rProtein A Sepharose™ resin was suspended in 100 μl of aqueous solution of 50 mM sodium acetate (pH 3.3), and allowed to stand for three minutes to elute the antibody. The solution was immediately neutralized by adding 6.7 μl of 1.5 M Tris-HCl (pH 7.8). The elution was performed twice and 200 μl of purified antibody was obtained. 2 μl of the antibody-containing solution was subjected to ND-1000 Spectrophotometer (NanoDrop)(Thermo Scientific NanoDrop™ 1000 Spectrophotometer (Thermo Scientific)) or 50 μl was subjected to Spectrophotometer DU-600 (BECKMAN) to measure absorbance at 280 nm, and the antibody concentration was calculated by the method of Pace et al. (Protein Science (1995) 4: 2411-2423).

Measurement of Competition with IL-31 Using FMAT

Antibodies were assessed for the activity of inhibiting the IL-31/NR10 binding by using hNR10-expressing CHO cells as described below. The chimeric NS22 antibody and NS22_H0L0 (H chain, H0-SKSC/SEQ ID NO: 54; L chain, L0/SEQ ID NO: 56) were diluted at an appropriate concentration using Assay buffer (10 mM HEPES, 140 mM NaCl, 2.5 mM $CaCl_2$, 3 mM $MgCl_2$, 2% FBS, 0.01% $NaN_3$, pH7.4), and further eight serial dilutions were prepared at a common dilution ration of 2. The dilutions were added at 40 μl/well to plates (96-Well FMAT Plates, Applied Biosystems). Then, FMAT Blue-labeled hIL-31 was diluted 400 times with Assay buffer, and added at 20 μl/well. Finally, a cell suspension adjusted to $2.5\times10^5$ cells/ml using Assay buffer was added at 40 μl/well (final $1\times10^4$ cells/well). Two hours after addition of cells, the fluorescence (FL1) was measured using the 8200 Cellular Detection System (Applied Biosystems).

Figure 9:
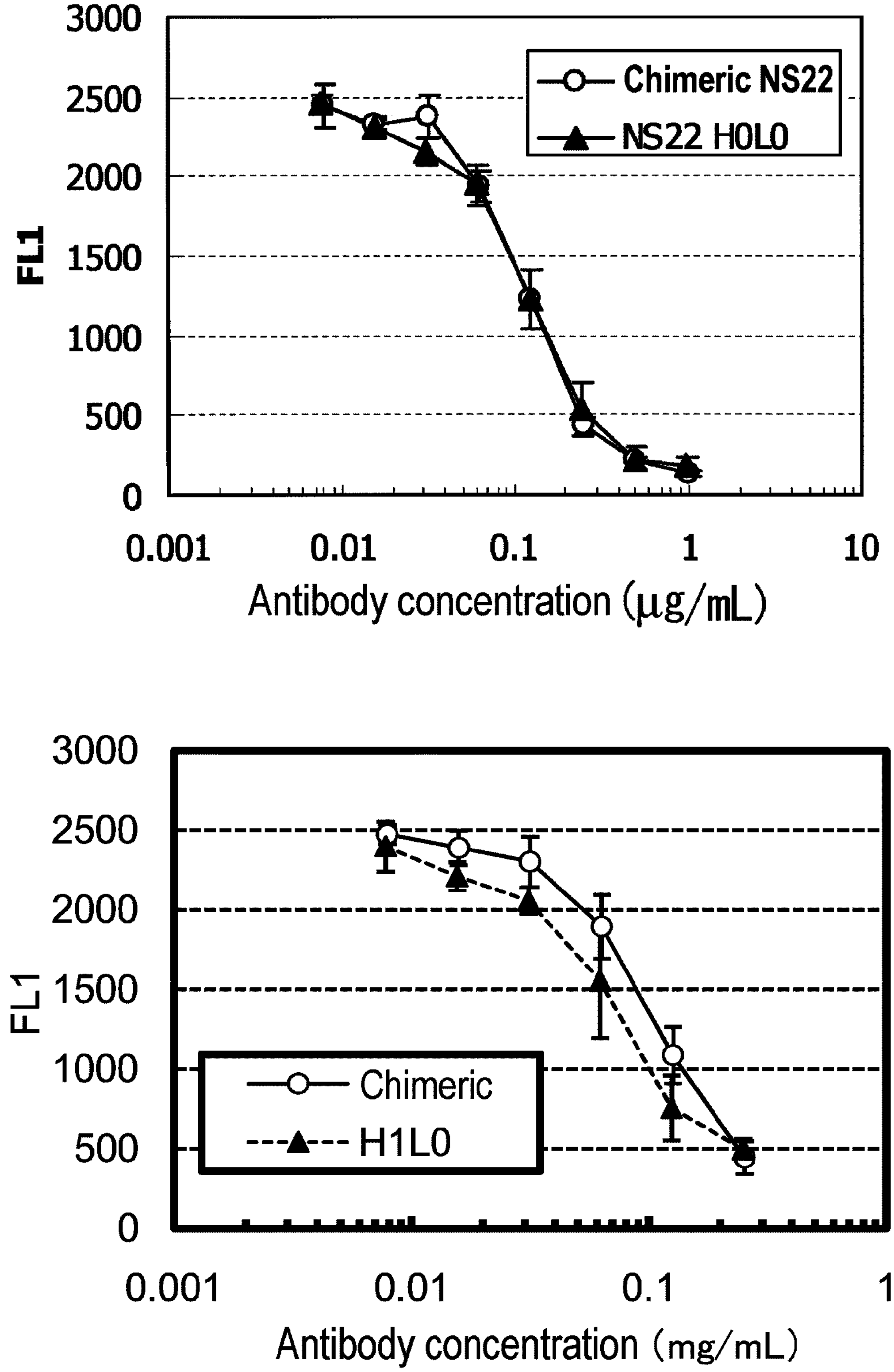
FIG. 9 is a set of graphs showing the assessment of the competition of humanized NS22 (H0L0) with IL-31.

The result showed that, as shown in FIG. 9, humanized NS22 antibodies H0L0 (H chain, H0-SKSC/SEQ ID NO: 54; L chain, L0/SEQ ID NO: 56), and H1L0 (H chain, H1-SKSC/SEQ ID NO: 130; L chain, L0/SEQ ID NO: 56) exhibited a competition activity comparable to that of the chimeric antibody, suggesting that both H0L0 and H1L0 are humanized anti-IL-31 receptor antibodies. In addition, it is considered that the FRs used for H0L0 and H1L0 can be used for humanization.

Accordingly, all of the mutations in CDRs described in the Examples hereinafter can be introduced into both H0 and H1.

TABLE 2

| H0 | Germline | Human FR sequence |
|---|---|---|
| FR1 | Germline: hVH_1_46 (Accession-No. X92343) | QVQLVQSGAEVKKPGASVKVSCK ASGYTFT (SEQ ID NO: 96) |
| FR2 | Germline: hVH_1_46 (Accession-No. X92343) | WVRQAPGQGLEWMG (SEQ ID NO: 97) |
| FR3_1 | Germline: hVH_1_69 (Accession-No. L22582) | RVTITADESTSTAYMELSSLRSED TAVYYCAR (SEQ ID NO: 98) |

TABLE 2-continued

| | | |
|---|---|---|
| FR3_2 | Germline: hVH_1_69 (Accession-No. Z27506) | RVTITADKSTSTAYMELSSLRSED TAVYYCAR (SEQ ID NO: 131) |
| FR4 | Germline: JH1 | WGQGTLVTVSS (SEQ ID NO: 99) |
| L0 | Germline | Human FR sequence |
| FR1 | Germline: hVK_1_39 (Accession-No. X59315) | DIQMTQSPSSLSASVGDRVTITC (SEQ ID NO: 100) |
| FR2 | Germline: hVK_1_39 (Accession-No. X59315) | WYQQKPGKAPKLLIY (SEQ ID NO: 101) |
| FR3 | Germline: hVK_1_39 (Accession-No. X59315) | GVPSRFSGSGSGTDFTLTISSLQP EDFATYYC (SEQ ID NO: 102) |
| FR4 | Germline: JK4 | FGGGTKVEIK (SEQ ID NO: 103) |

Example 5

Heterogeneity-Reducing Effect of Novel Constant Regions M14 and M58 in Humanized Anti-IL31 Receptor Antibody As shown in Referential Examples 7 to 9, it was demonstrated that the conversion of the constant region from IgG2 to M14 or M58 in the huPM1 antibody, a humanized anti-IL-6 receptor antibody, could reduce the heterogeneity derived from the IgG2 hinge region without loss of stability. Thus, humanized anti-IL-31 receptor antibodies were also tested to assess whether the heterogeneity can be reduced by converting their constant regions from the wild-type IgG2 to M14 or M58.

H0-M14, H0-M58, H0-IgG1, and H0-IgG2, which were generated by combining IgG1 (SEQ ID NO: 60), IgG2 (SEQ ID NO: 132), M14 (SEQ ID NO: 129) and M58 (SEQ ID NO: 128) generated in Referential Examples 8 and 9, with H chain variable region H0(H0-VH/SEQ ID NO: 50) of humanized anti-IL-31 receptor antibody generated in Example 4, were used as H chains, and L0 (L0/SEQ ID NO: 56) produced in Example 4 was used as an L chain, to generate H0L0-IgG1 (H chain, H0-IgG1/SEQ ID NO: 133; L chain, L0/SEQ ID NO: 56), H0L0-IgG2 (H chain, H0-IgG2/SEQ ID NO: 134; L chain, L0/SEQ ID NO: 56), H0L0-M14 (H chain, H0-M14/SEQ ID NO: 135; L chain, L0/SEQ ID NO: 56), and H0L0-M58 (H chain, H0-M58/SEQ ID NO: 136; L chain, L0/SEQ ID NO: 56). Each antibody was expressed and purified by the method described in Example 4.

The heterogeneity was assessed by cation exchange chromatography. The prepared antibodies were assessed for heterogeneity using ProPac WCX-10 (Dionex) column, 20 mM sodium acetate (pH 5.0) as mobile phase A, and 20 mM sodium acetate/1M NaCl (pH 5.0) as mobile phase B, with an appropriate flow rate and gradient. The result of assessment by cation exchange chromatography (IEC) is shown in FIG. 10.

Figure 10:
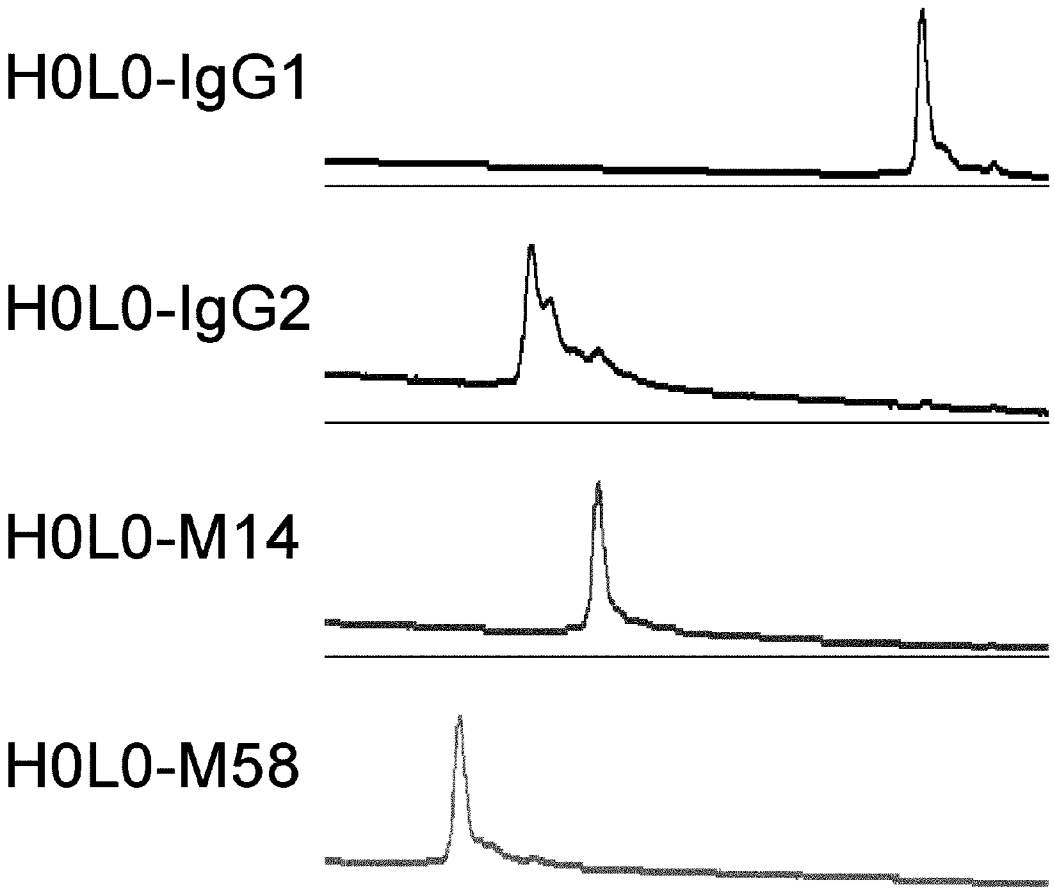
FIG. 10 shows the effect of the constant region of humanized anti-NR10 antibody H0L0 on the heterogeneity assessed by cation exchange chromatography.

As shown in FIG. 10, the heterogeneity was increased by conversion of the constant region from IgG1 to IgG2 in the anti-IL-31 receptor antibody, and the heterogeneity can be reduced by conversion of the constant region to M14 or M58 in any antibody.

Example 6

Pharmacokinetics Improving Effect of Novel Constant Region M58 in anti-IL-31 Receptor Antibodies As shown in Referential Example 9, conversion of the constant region from IgG1 to M58 in anti-IL-6 receptor antibody huPM1 was found to improve its human FcRn-binding activity and the pharmacokinetics in human FcRn transgenic mice. Thus, anti-IL-31 receptor antibodies were also tested to assess whether conversion of the constant region to M58 improves their pharmacokinetics.

H0L0-IgG1 (H chain: H0-IgG1/SEQ ID NO: 133; L chain: L0/SEQ ID NO: 56) and H0L0-M58 (H chain: H0-M58/SEQ ID NO: 136; L chain L0/SEQ ID NO: 56) prepared as described in Examples 4 and 5 were assessed for the human FcRn-binding activity by the method described in Referential Example 9. The result is shown in Table 3.

TABLE 3

| | KD (μM) |
|---|---|
| H0L0-IgG1 | 1.07 |
| H0L0-M58 | 0.91 |

As shown in Table 3, conversion of the constant region from IgG1 to M58 also improved the human FcRn-binding activity of the anti-IL-31 receptor antibody H0L0 as in the anti-IL-6 receptor antibody hPM1. This suggests that conversion of the constant region from IgG1 to M58 may improve the pharmacokinetics of anti-IL-31 receptor antibody in human.

Example 7

Identification of Mutation Sites Reducing the Isoelectric Point

Production of Mutants

Each mutant was produced by the method described in Example 4 or by assembly PCR. In the method using assembly PCR, oligo DNAs are synthesized based on forward and reverse sequences including an altered site. Forward oligo DNA including an altered site and reverse oligo DNA binding to the vector in which the gene to be altered was inserted were combined, and reverse oligo DNA including an altered site and forward oligo DNA binding to the vector in which the gene to be altered was inserted were combined. PCR was carried out using PrimeSTAR (Takara) to produce 5'-end and 3'-end fragments including the altered site. The two fragments were assembled by assembly PCR to produce each mutant. The produced mutant was inserted into an expression vector capable of expressing the insert gene in animal cells. The nucleotide sequence of the resulting expression vector was determined by a method known to those skilled in the art. Antibodies were produced and purified by the method described in Example 4.

Identification of Mutation Sites

To improve the pharmacokinetics of H0L0 (H chain, H0-SKSC/SEQ ID NO: 54; L chain, L0/SEQ ID NO: 56), altered sites capable of reducing the isoelectric point of the variable region were examined. Screening of mutation sites in the variable regions predicted from the three-dimensional structure model revealed mutation sites that would decrease the isoelectric point of the variable regions without significantly reducing its binding to NR10. These are summarized in Table 4 (Hp5-VH/SEQ ID NO: 137, Hp7-VH/SEQ ID NO: 138, Hp8-VH/SEQ ID NO: 139, Hp6-VH/SEQ ID NO: 140, Hp9-VH/SEQ ID NO: 141, Hp1-VH/SEQ ID NO: 142, Hp13-VH/SEQ ID NO: 143, Lp1-VL/SEQ ID NO: 144, Lp2-VL/SEQ ID NO: 145, Lp3-VL/SEQ ID NO: 146, Lp4-VL/SEQ ID NO: 147, Lp7-VL/SEQ ID NO: 148, Lp5-VL/SEQ ID NO: 149, Lp6-VL/SEQ ID NO: 150). Each variant was produced and purified by the method described in Example 4.

Figure 11:
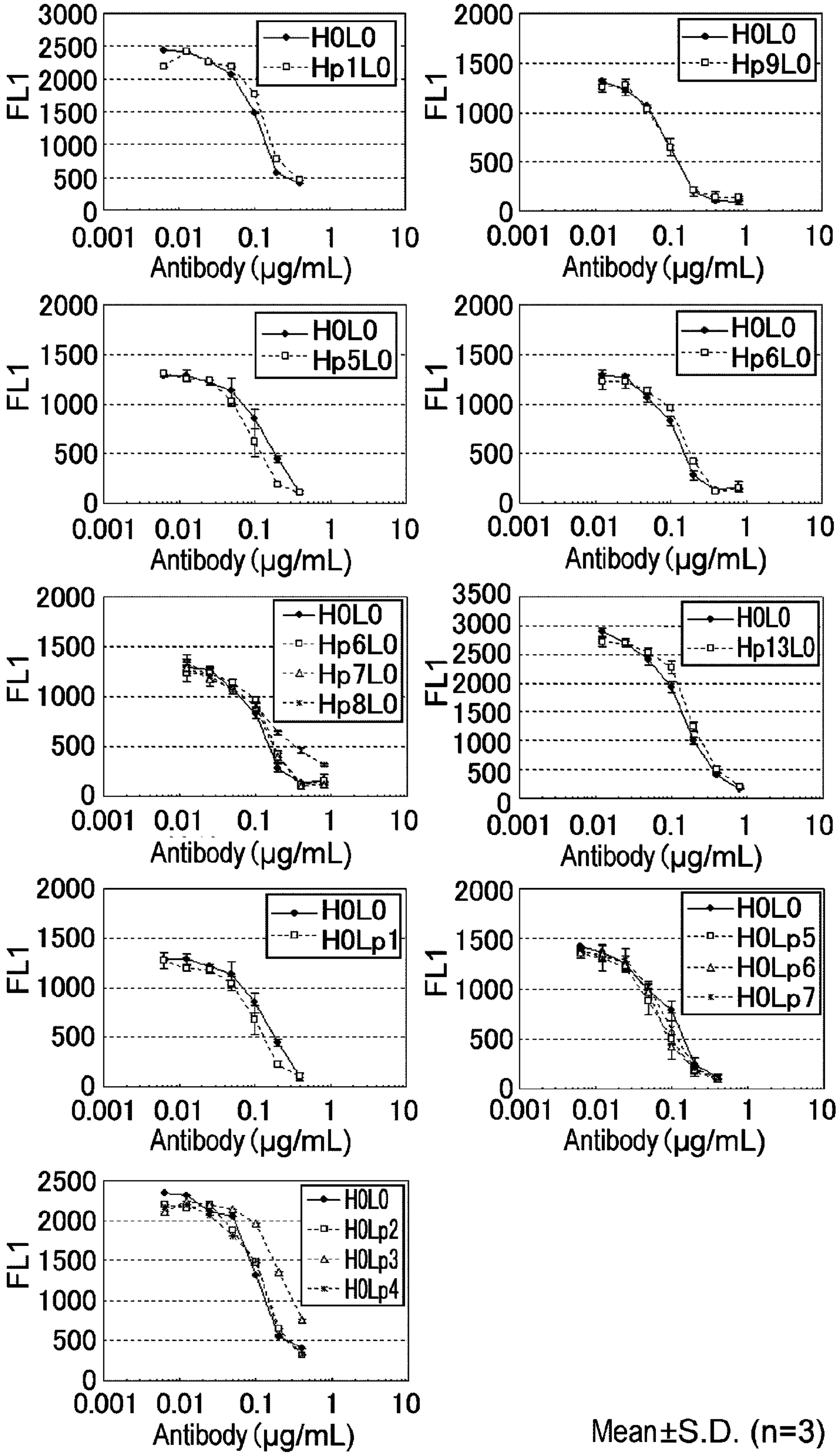
FIG. 11 is a set of graphs showing the assessment of the competition of mutants of the humanized anti-NR10 antibody of which the isoelectric point of the variable regions is lowered without significant loss of the binding to NR10, with IL-31.

Each variant was tested for the activity of inhibiting the hIL-31/hNR10 binding by using FMAT. The test was carried out according to the method as described in Example 4. As shown in FIG. 11, the competition activity of each variant was not greatly reduced as compared to that of H0L0.

Examples of the humanized NS22 antibodies whose isoelectric point has been reduced by combining these alterations include Hp3Lp15 (H chain: Hp3-SKSC/SEQ ID NO: 151; L chain: Lp15/SEQ ID NO: 152). Affinity for NR10, isoelectric point, and plasma retention in mice were compared between Hp3Lp15 and H0L0.

Measurement of Affinity

The affinity of each antibody for NR10 was determined by the method described in Referential Example 10.

The result of affinity measurement is shown in Table 5. The affinity of Hp3Lp15 was shown to be almost the same as that of H0L0.

TABLE 4

| Name | Type | H0 sequence | Mutation site (kabat No) | H0 sequence | Amino acid after mutation | Sequence after mutation |
|---|---|---|---|---|---|---|
| Hp5 | FR2 | WVRQAPGQGLEWMG (SEQ ID NO: 97) | 38<br>40 | R<br>*A | Q<br>S | WVQQSPGQGLEWMG (SEQ ID NO: 120) |
| Hp7 | CDR2 | LINPYNGGTSYNQKFKG (SEQ ID NO: 10) | 50 | L | E | EINPYNGGTSYNQKFKG (SEQ ID NO: 113) |
| Hp8 | CDR2 | LINPYNGGTSYNQKFKG (SEQ ID NO: 10) | 52 | N | D | LIDPYNGGTSYNQKFKG (SEQ ID NO: 114) |
| Hp6 | CDR2 | LINPYNGGTSYNQKFKG (SEQ ID NO: 10) | 61 | Q | D | LINPYNGGTSYNDKFKG (SEQ ID NO: 115) |
| Hp9 | CDR2 | LINPYNGGTSYNQKFKG (SEQ ID NO: 10) | 62 | K | Q | LINPYNGGTSYNQQFKG (SEQ ID NO: 116) |
| Hp1 | CDR2 | LINPYNGGTSYNQKFKG (SEQ ID NO: 10) | 64 | K | Q | LINPYNGGTSYNQKFQG (SEQ ID NO: 117) |
| Hp13 | CDR2 | LINPYNGGTSYNQKFKG (SEQ ID NO: 10) | 64<br>65 | K<br>G | Q<br>D | LINPYNGGTSYNQKFQD (SEQ ID NO: 119) |

| Name | Type | L0 sequence | Mutation site (kabat No) | L0 sequence | Amino acid after mutation | Sequence after mutation |
|---|---|---|---|---|---|---|
| Lp1 | CDR1 | RTSENIYSFLA (SEQ ID NO: 13) | 24 | R | Q | QTSENIYSFLA (SEQ ID NO: 121) |
| Lp2 | CDR1 | RTSENIYSFLA (SEQ ID NO: 13) | 28 | N | D | RTSEDIYSFLA (SEQ ID NO: 122) |
| Lp3 | CDR2 | NAKTLAK (SEQ ID NO: 14) | 50 | N | D | DAKTLAK (SEQ ID NO: 123) |
| Lp4 | CDR2 | NAKTLAK (SEQ ID NO: 14) | 52 | K | Q | NAQTLAK (SEQ ID NO: 124) |
| Lp7 | CDR2 | NAKTLAK (SEQ ID NO: 14) | 54 | L | E | NAKTEAK (SEQ ID NO: 125) |
| Lp5 | CDR2 | NAKTLAK (SEQ ID NO: 14) | 56 | K | Q | NAKTLAQ (SEQ ID NO: 126) |
| Lp6 | CDR2 | NAKTLAK (SEQ ID NO: 14) | 56 | K | D | NAKTLAD (SEQ ID NO: 127) |

Asterisk (*) in Table 4 above indicates a site that was not relevant to the isoelectric point but altered for conversion into a human sequence.

TABLE 5

| | ka (1/Ms) | kd (1/s) | KD (M) |
|---|---|---|---|
| H0L0 | 3.7E+05 | 1.2E−03 | 3.3E−09 |
| Hp3Lp15 | 4.2E+05 | 1.6E−03 | 3.9E−09 |

Measurement of Isoelectric Point

Each antibody was analyzed by isoelectric focusing to assess changes in the isoelectric point of the whole antibody due to the amino acid alterations in its variable region. Isoelectric focusing was performed by the following method.

Phast-Gel Dry IEF gel (Amersham Biosciences) was swollen in Phastsystem Cassette (Amersham Biosciences) for about 30 minutes using the swelling solution shown below.

| | |
|---|---|
| MilliQ water | 1.5 ml |
| Pharmalyte 5-8 for IEF (Amersham Biosciences) | 100 μl |

Electrophoresis was carried out in PhastSystem (Amersham Biosciences) using the swollen gel according to the program indicated below. The samples were loaded onto the gel in Step 2. Calibration Kit for pI (Amersham Biosciences) was used as a pI marker.

| | | | | | |
|---|---|---|---|---|---|
| Step 1: | 2000 V | 2.5 mA | 3.5 W | 15° C. | 75 Vh |
| Step 2: | 200 V | 2.5 mA | 3.5 W | 15° C. | 15 Vh |
| Step 3: | 2000 V | 2.5 mA | 3.5 W | 15° C. | 410 Vh |

After electrophoresis, the gel was fixed with 20% TCA, and then silver-stained using the Silver Staining Kit, Protein (Amersham Biosciences), according to the protocol attached to the kit. After staining, the isoelectric point of the sample (the whole antibody) was calculated from the known isoelectric points of the pI markers.

The result of isoelectric point measurement by isoelectric focusing showed that the isoelectric point of H0L0 was about 7.8, and the isoelectric point of Hp3Lp15 was about 5.5, showing that the isoelectric point of Hp3Lp15 was decreased by about 2.3 as compared to H0L0. When the theoretical isoelectric point of the variable region VH/VL was calculated by GENETYX (GENETYX CORPORATION), the theoretical isoelectric points of the variable regions of H0L0 and Hp3Lp15 were 7.76 and 4.63, respectively. Thus, the theoretical isoelectric point of Hp3Lp15 was decreased by 3.13 as compared to H0L0.

Assessment of Pharmacokinetics of Antibody with Reduced Isoelectric Point Using Mice In order to assess the plasma retention of Hp3Lp15, a modified antibody with reduced isoelectric point, the plasma retention of H0L0 and Hp3Lp15 was compared in normal mice. A single dose of H0L0 or Hp3Lp15 was intravenously administered at 1 mg/kg to mice (C57BL/6J, Charles River Japan, Inc.) to compare the time course of the plasma concentration. The plasma concentrations were determined by ELISA. Appropriate concentrations of a calibration sample and test plasma samples were dispensed into immunoplates (Nunc-Immuno Plate, MaxiSorp (Nalge Nunc International)) coated with anti-human IgG (Fc-specific) antibody (Sigma). The samples were allowed to stand at room temperature for one hour. After reaction with Goat Anti-Human IgG-ALP (Sigma) at room temperature for one hour, color developing reaction was carried out using BluePhos Microwell Phosphatase Substrates System (Kirkegaard & Perry Laboratories) as a substrate. The absorbance at 650 nm was measured with a microplate reader. The plasma concentrations were determined based on the absorbance of the calibration curve using the analytical software SOFTmax PRO (Molecular Devices).

Pharmacokinetic parameters (AUC and systemic clearance (CL)) were calculated from the obtained time-course data of the plasma concentration using the pharmacokinetics analysis software WinNonlin (Pharsight). The parameters are shown in Table 6. AUC and the clearance of Hp3Lp15 after the intravenous administration were increased by about 14% and reduced by about 12%, respectively, as compared to H0L0. Thus, it was demonstrated that Hp3Lp15, in which the isoelectric point of H0L0 has been reduced, had improved pharmacokinetics.

TABLE 6

| | AUC (μg · d/kg) | | CL (ml/d/kg) | |
|---|---|---|---|---|
| | Mean | SD | Mean | SD |
| H0L0 | 281.8 | 13.1 | 3.6 | 0.2 |
| Hp3Lp15 | 321.1 | 26.1 | 3.1 | 0.3 |

Example 8

Effect of Combinations of Variable Region and Constant Region on the Biological Activity In order to assess the effects of different constant regions on the biological activity, the following variants were produced.

SKSC (SEQ ID NO: 62) and M58 (SEQ ID NO: 128), constant regions prepared in Referential Examples 7 and 9, were combined with Hp3 (Hp3-VH/SEQ ID NO: 167), a variable region prepared in Example 7, to produce Hp3-M58 (SEQ ID NO: 240) and Hp3-SKSC (SEQ ID NO: 151) as H chains. The prepared H chains were combined with Lp15 (Lp15/SEQ ID NO: 152), an L chain prepared in Example 7, to produce Hp3Lp15-SKSC(H chain, Hp3-SKSC/SEQ ID NO: 151; L chain, Lp15/SEQ ID NO: 152) and Hp3Lp15-M58 (H chain, Hp3-M58/SEQ ID NO: 240; L chain, Lp15/SEQ ID NO: 152). Each antibody was expressed and purified by the method described in Example 4.

The antibodies produced as described above, H0L0-SKSC(H chain, H0-SKSC/SEQ ID NO: 54; L chain, L0/SEQ ID NO: 56) prepared using the constant region SKSC (SEQ ID NO: 62) described in Referential Example 7, and H0L0-M58 (H chain, H0-M58/SEQ ID NO: 136; L chain, L0/SEQ ID NO: 56) and H0L0-IgG2 (H chain, H0-IgG2/SEQ ID NO: 134; L chain, L0/SEQ ID NO: 56) prepared in Example 5, were assessed for the biological activity by the method described in Example 2 using BaF/NR10. The result is summarized in FIG. 18.

Figure 18:
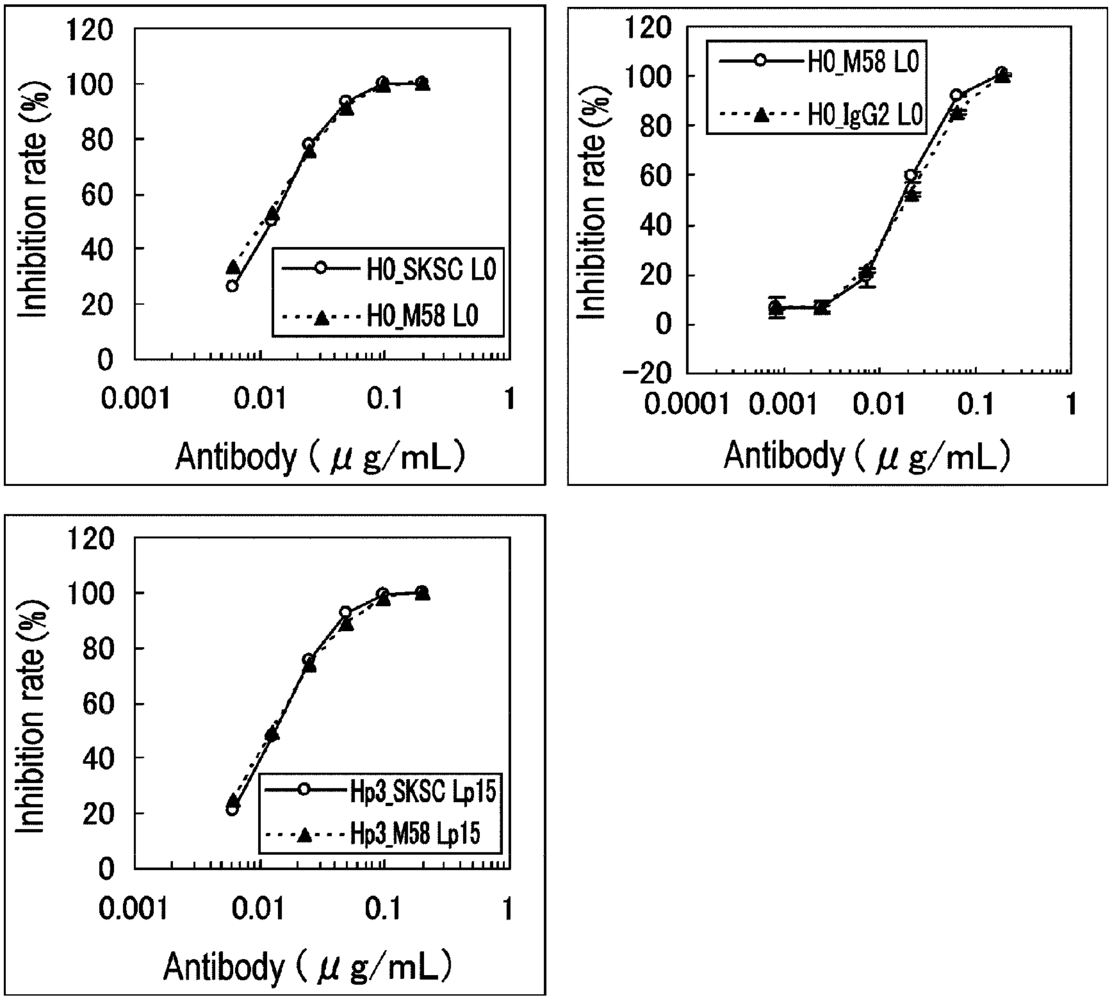
FIG. 18 shows the biological activity of each antibody assessed using BaF/NR10.

As shown in FIG. 18, no significant difference in the biological activity was detected between the constant regions. Since the biological activity was not affected when combining the two variable regions H0 and Hp3 with each constant region, combining variable regions created in future with any constant region would not result in alteration in the biological activity.

Example 9

Identification of Mutation Sites Suppressing Degradation by Thermal Acceleration Study Antibodies used for pharmaceuticals have heterogeneity even though they are monoclonal antibodies obtained from clones derived from single antibody-producing cells. Such antibody heterogeneity is known to result from modification such as oxidation or deamidation, and to be increased during long-term storage or upon exposure to stress conditions, such as heat stress or light stress (see "Heterogeneity of Monoclonal Antibodies", Journal of pharmaceutical sciences, vol. 97, No. 7, 2426-2447). However, when an antibody is developed as a pharmaceutical, physical properties of the protein, particularly homogeneity and stability, are highly important. Thus, it is desired that the heterogeneity of desired/related substances be reduced and the substance be composed of a single substance as much as possible. In this context, the experiment described below was conducted to assess the antibody heterogeneity under stress conditions and to reduce the heterogeneity.

To assess degradation products, an accelerated sample of H0L0 (H chain, H0-SKSC/SEQ ID NO: 54; L chain, L0/SEQ ID NO: 56) was prepared by the method described below. The prepared accelerated sample and non-accelerated sample (initial) were analyzed by cation exchange chromatography using the method described below.

Method for Preparing Accelerated Samples

Buffer: PBS

Antibody concentration: 0.2 to 1.0 mg/ml

Acceleration temperature: 60° C.

Acceleration period: one day

Method for Analysis by Cation Exchange Chromatography

Column: ProPac WCX-10, 4×250 mm (Dionex)

Mobile phase: (A) 25 mmol/l MES/NaOH, pH 6.1

(B) 25 mmol/l MES/NaOH, 250 mmol/l NaCl, pH 6.1

Flow rate: 0.5 ml/min

Column temperature: 40° C.

Gradient: % B 0 to 0 (0-5 min)→0 to 30 (5-80 min)

Detection: 280 nm

Figure 19:
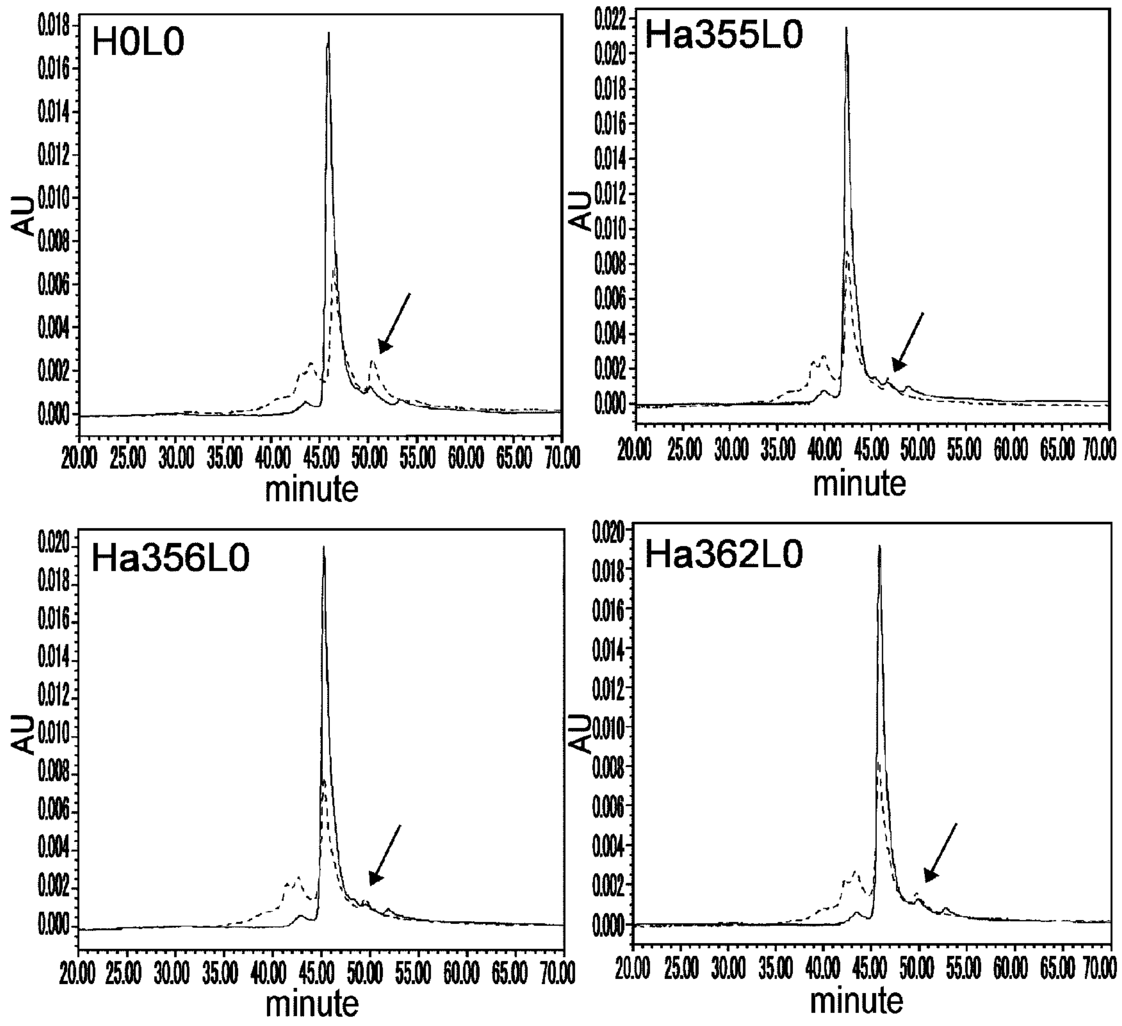
FIG. 19 shows the analysis of thermally-accelerated (dotted line) and non-accelerated (solid line) samples of each modified antibody by cation exchange chromatography to compare the generation of degradation products between before and after thermal acceleration. Arrow indicates the peak position of basic component which was altered.

The resulting chromatograms for H0L0 samples before and after acceleration are shown in FIG. 19. The H0L0 sample after acceleration had a tendency to show an increased basic peak.

Then, screening was carried out to reduce this peak. As a result, Ha355, Ha356, Ha360, and Ha362 were found. These H chain variants were combined with L0 to produce Ha355L0 (H chain, Ha355-SKSC/SEQ ID NO: 242; L chain, L0/SEQ ID NO: 56), Ha356L0 (H chain, Ha356-SKSC/SEQ ID NO: 243; L chain, L0/SEQ ID NO: 56), Ha360L0 (H chain, Ha360-SKSC/SEQ ID NO: 244; L chain, L0/SEQ ID NO: 56), and Ha362L0 (H chain, Ha362-SKSC/SEQ ID NO: 245; L chain, L0/SEQ ID NO: 56). The sequence of each variant is shown in Table 7.

Each of the identified antibodies was expressed and purified by the method described in Example 4. As with H0L0, a accelerated sample of each prepared antibody was prepared, and analyzed by cation exchange chromatography. The result is shown in FIG. 19.

Figure 20:
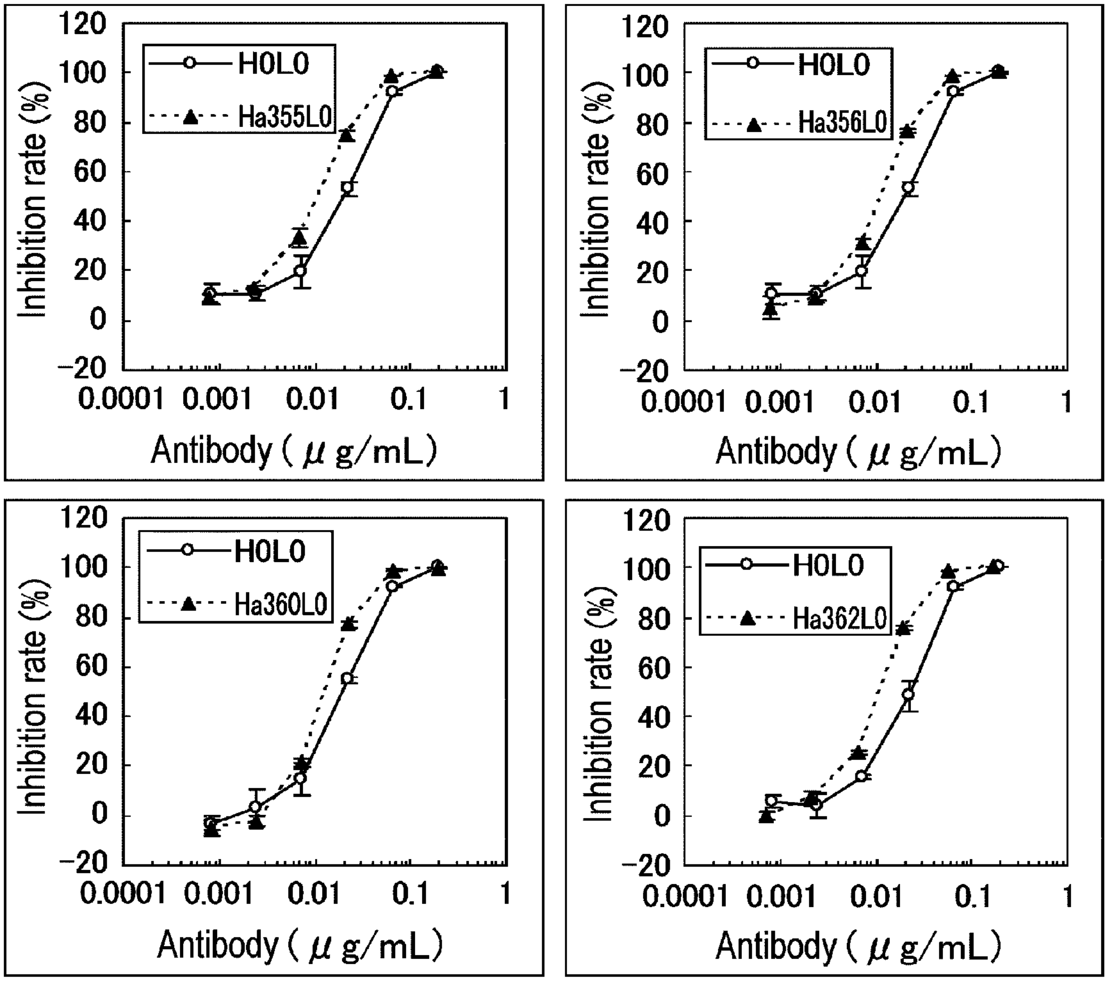
FIG. 20 is a set of graphs showing the assessment (BaF) of the activity of each variant.

The result showed that the generation of the basic peak increased after acceleration was reduced in the modified antibody containing a substitution of aspartic acid with glutamic acid at position 101 in the H chain, as compared to H0L0. The modified antibodies were assessed for the biological activity by the method described in Example 2 using BaF/NR10. The result is shown in FIG. 20. As shown in FIG. 20, the biological activities of the modified antibodies were comparable to or stronger than that of H0L0. These findings demonstrated that the modifications of Ha355, Ha356, Ha360, and Ha362 suppressed the generation of degradation products by acceleration, and therefore are effective in improving the stability of antibody.

Example 10

Identification of Mutation Sites Increasing the Affinity

A library in which mutations were introduced into CDR sequences was constructed and examined to improve the affinity of H0L0 for NR10. As a result of screening of the library in which mutations were introduced into CDRs, mutations that improve the affinity for NR10 were found. The mutations are shown in Table 8. Each of the H chain variants Ha101-SKSC (SEQ ID NO: 246), Ha103-SKSC (SEQ ID NO: 247), Ha111-SKSC (SEQ ID NO: 248), Ha204-SKSC (SEQ ID NO: 249), and Ha219-SKSC (SEQ ID NO: 250) was combined with L0 (L0/SEQ ID NO: 56); and each of the modified L chains La134 (SEQ ID NO: 251), La130 (SEQ ID NO: 252), La303 (SEQ ID NO: 253), and La328 (SEQ ID NO: 254) was combined with H0 (H0-SKSC/SEQ ID NO: 54), to construct an antibody. Each variant was produced and purified by the method described in Example 4.

The affinity of each antibody for NR10 was assessed using Biacore. The result is shown in Table 9. The assay was carried out using the method described in Referential Example 10. As shown in Table 9, the KD value for each variant was found to be improved as compared to that of H0L0 (H chain, H0-SKSC/SEQ ID NO: 54; L chain, L0/SEQ ID NO: 56).

TABLE 7

| Name | Type | H0 sequence | Mutation site (kabat No) | H0 sequence | Amino acid after mutation | Sequence after mutation |
|---|---|---|---|---|---|---|
| Ha355 | CDR3 | DGYDDGPYTMDY (SEQ ID NO: 265) | 100d<br>101<br>102 | M<br>D<br>Y | L<br>E<br>T | DGYDDGPYTLET (SEQ ID NO: 266) |
| Ha356 | CDR3 | DGYDDGPYTMDY (SEQ ID NO: 265) | 101<br>102 | D<br>Y | E<br>T | DGYDDGPYTMET (SEQ ID NO: 267) |
| Ha360 | CDR3 | DGYDDGPYTMDY (SEQ ID NO: 265) | 97<br>101<br>102 | Y<br>D<br>Y | L<br>E<br>T | DGLDDGPYTMET (SEQ ID NO: 268) |
| Ha362 | CDR3 | DGYDDGPYTMDY (SEQ ID NO: 265) | 97<br>101<br>102 | Y<br>D<br>Y | L<br>E<br>S | DGLDDGPYTMES (SEQ ID NO: 269) |

TABLE 8

| Name | Type | H0 sequence | Mutation site (kabat No) | H0 sequence | Amino acid after mutation | Sequence after mutation |
|---|---|---|---|---|---|---|
| Ha101 | CDR1 | GYIMN (SEQ ID NO: 270) | 33 | I | V | GYVMN (SEQ ID NO: 272) |
| Ha103 | CDR1 | GYIMN (SEQ ID NO: 270) | 34 | M | I | GYIIN (SEQ ID NO: 273) |
| Ha111 | CDR1 | GYIMN (SEQ ID NO: 270) | 34 | M | L | GYILN (SEQ ID NO: 274) |
| Ha204 | CDR2 | LINPYNGGTSYNQKFKG (SEQ ID NO: 271) | 58 | S | D | LINPYNGGIDYNQKFKG (SEQ ID NO: 275) |
| Ha219 | CDR2 | LINPYNGGTSYNQKFKG (SEQ ID NO: 271) | 61 | Q | P | LINPYNGGTSYNPKFKG (SEQ ID NO: 276) |
| Name | Type | L0 sequence | Mutation site (kabat No) | L0 sequence | Amino acid after mutation | Sequence after mutation |
| La134 | CDR1 | RISENIYSFLA (SEQ ID NO: 277) | 31 | S | R | RTSENIYRFLA (SEQ ID NO: 279) |
| La130 | CDR1 | RTSENIYSFLA (SEQ ID NO: 277) | 31<br>33 | S<br>L | R<br>V | RISENIYRFVA (SEQ ID NO: 280) |
| Ls303 | CDR3 | QHHYESPLT (SEQ ID NO: 278) | 93 | E | D | QHHYDSPLT (SEQ ID NO: 281) |
| La328 | CDR3 | QHHYESPLT (SEQ ID NO: 278) | 94 | S | D | QHHYEDPLT (SEQ ID NO: 282) |
| La326 | CDR3 | QHHYESPLT (SEQ ID NO: 278) | 97 | T | F | QHHYESPLF (SEQ ID NO: 283) |

TABLE 9

| Name | ka (1/Ms) | kd (1/s) | KD (M) |
|---|---|---|---|
| H0L0 | 1.9E+05 | 6.2E−04 | 3.2E−09 |
| Ha101L0 | 2.0E+05 | 3.1E−04 | 1.5E−09 |
| Ha103L0 | 2.2E+05 | 5.3E−04 | 2.4E−09 |
| Ha111L0 | 2.6E+05 | 5.6E−04 | 2.1E−09 |
| Ha204L0 | 3.7E+05 | 4.8E−04 | 1.3E−09 |
| Ha219L0 | 3.2E+05 | 9.6E−04 | 3.0E−09 |
| H0L0 | 1.5E+05 | 7.4E−04 | 5.1E−09 |
| H0La134 | 2.5E+05 | 4.4E−04 | 1.8E−09 |
| H0La130 | 2.6E+05 | 4.0E−04 | 1.5E−09 |
| HOLa303 | 2.2E+05 | 4.6E−04 | 2.1E−09 |
| H0La328 | 1.8E+05 | 5.2E−04 | 2.9E−09 |
| H0La326 | 1.4E+05 | 5.2E−04 | 3.7E−09 |

Examples of combinations of these affinity-improving mutations with the isoelectric point-lowering mutations generated in Example 7 include, for example, Ha401La402 (H chain, Ha401-SKSC/SEQ ID NO: 255; L chain, La402/SEQ ID NO: 256) and H17L11 (H chain, H17-M58/SEQ ID NO: 222; L chain, L11/SEQ ID NO: 236). Each variant was produced and purified by the method described in Example 4.

Figure 21:
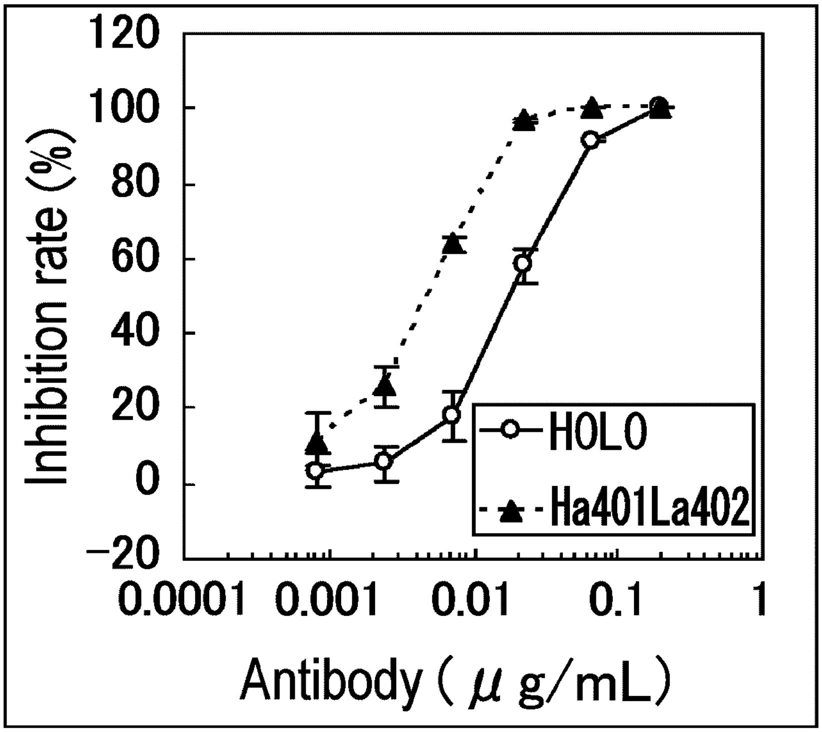
FIG. 21 is a graph showing the assessment (BaF) of the activity of Ha401La402 and H0L0.

Ha401La402 (H chain, Ha401-SKSC/SEQ ID NO: 255; L chain, La402/SEQ ID NO: 256) was assessed for its affinity for NR10 and its biological activity by the method described in Referential Example 10 and the method using BaF/NR10 as described in Example 2, respectively, and they were compared to those of H0L0 (H chain, H0-SKSC/SEQ ID NO: 54; L chain, L0/SEQ ID NO: 56). The result of affinity measurement is shown in Table 10, and the biological activity determined using BaF/NR10 is shown in FIG. 21. Both affinity and biological activity were found to be improved as compared to those of H0L0 (H chain, H0-SKSC/SEQ ID NO: 54; L chain, L0/SEQ ID NO: 56).

TABLE 10

| | ka (1/Ms) | kd (1/s) | KD (M) |
|---|---|---|---|
| H0L0 | 2.9E+05 | 9.1E−04 | 3.2E−09 |
| Ha401La402 | 5.8E+05 | 2.9E−04 | 5.0E−10 |

Figure 22:
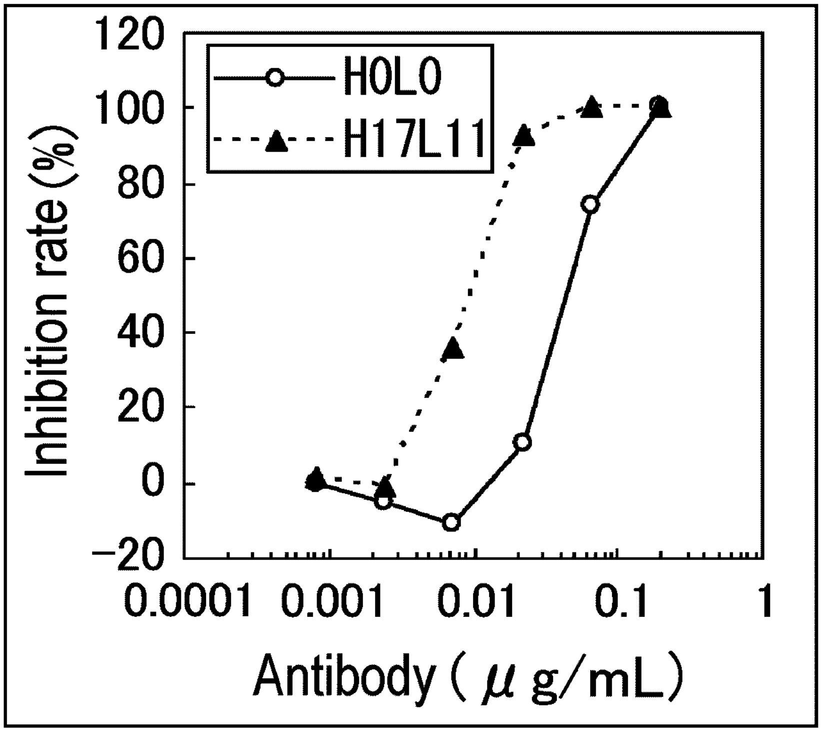
FIG. 22 is a graph showing the assessment (BaF) of the activity of H17L11 and H0L0.

Furthermore, H17L11 (H chain, H17-M58/SEQ ID NO: 222; L chain, L11/SEQ ID NO: 236) was assessed for its affinity for NR10 and its biological activity by the method described in Example 7 and the method using BaF/NR10 as described in Example 2, respectively, and they were compared to those of H0L0 (H chain, H0-M58/SEQ ID NO: 136; L chain, L0/SEQ ID NO: 56). The result of affinity measurement is shown in Table 11, and the biological activity determined using BaF/NR10 is shown in FIG. 22. Both affinity and biological activity were found to be improved as compared to those of H0L0 (H chain, H0-M58/SEQ ID NO: 136; L chain, L0/SEQ ID NO: 56).

TABLE 11

| | ka (1/Ms) | kd (1/s) | KD (M) |
|---|---|---|---|
| H0L0 | 1.4E+05 | 6.9E−04 | 4.8E−09 |
| H17L11 | 4.3E+05 | 2.6E−04 | 6.2E−10 |

Example 11

Identification of Mutation Sites Reducing Immunogenicity Risk

Reduction of Immunogenicity Risk in H Chain CDR1

T-cell epitopes present in the variable region sequence of H0L0 were analyzed using TEPITOPE (Methods 2004 December; 34(4): 468-75). As a result, CDR1 of the H chain was predicted to have many T-cell epitopes that bind to HLA (i.e. have sequences with a high immunogenicity risk). Then, TEPITOPE analysis was carried out to examine substitutions that would reduce the immunogenicity risk of the H chain CDR1. As a result, the immunogenicity risk was found to be greatly reduced by substituting isoleucine at position 33 in kabat numbering with alanine (A) (Table 12). Then, this alteration was added to H17 generated in Example 10 to produce H19 (H19-M58/SEQ ID NO: 223). The generated H19 was combined with L12 to produce H19L12 (H chain, H19-M58/SEQ ID NO: 223; L chain, L12/SEQ ID NO: 237). Each variant was produced and purified by the method described in Example 4.

Figure 23:
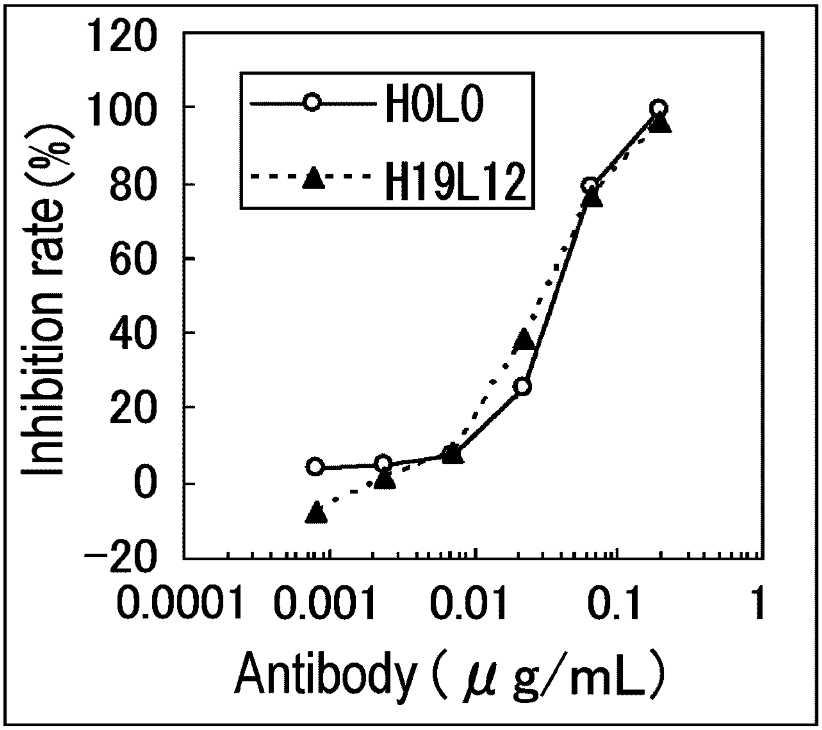
FIG. 23 is a graph showing the assessment (BaF) of the activity of H19L12 and H0L0.

The antibody was assessed for the affinity for NR10 and the biological activity by the method described in Referential Example 10 and the method using BaF/NR10 as described in Example 2, respectively, and they were compared to those of H0L0 (H chain, H0-M58/SEQ ID NO: 136; L chain, L0/SEQ ID NO: 56). The result of affinity measurement is shown in Table 13, and the biological activity determined using BaF/NR10 is shown in FIG. 23. Both affinity and biological activity were shown to be almost equal to those of H0L0.

TABLE 12

| Name | Type | H0 sequence | Mutation site (kabat No) | H0 sequence | Amino acid after mutation | Sequence after mutation |
|---|---|---|---|---|---|---|
| H19 | CDR1 | GYIMN (SEQ ID NO: 270) | 33 | I | A | GYAMN (SEQ ID NO: 284) |

TABLE 13

| | ka (1/Ms) | kd (1/s) | KD (M) |
|---|---|---|---|
| H0L0 | 1.8E+05 | 8.7E−04 | 4.8E−09 |
| H19L12 | 2.3E+05 | 1.2E−03 | 5.1E−09 |

Reduction of Immunogenicity Risk in L Chain CDR1

Threonine (T) present at kabat-numbering position 25 in CDR1 of the L chain corresponds to alanine (A) or serine (S) in the germline sequence. Thus, it is predicted that the immunogenicity risk is reduced by substituting threonine (T) at position 25 with alanine (A) or serine (S) (Table 14). Therefore, the above substitution was added to L12 to produce L17 (SEQ ID NO: 238). The produced L17 was combined with H0 to produce H0L17 (H chain, H0-M58/SEQ ID NO: 136; L chain, L17/SEQ ID NO: 238). Each variant was produced and purified by the method described in Example 4.

Figure 24:
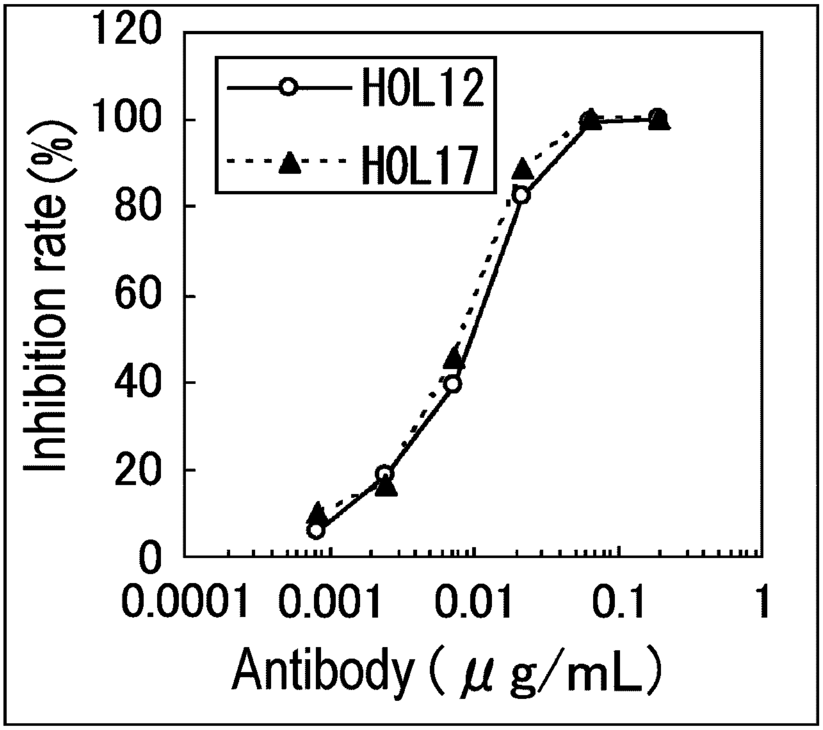
FIG. 24 is a graph showing the biological activity of H0L12 and H0L17 assessed using BaF/NR10.

Each variant was assessed for the affinity for NR10 and the biological activity by the method described in Referential Example 10 and the method using BaF/NR10 as described in Example 2, respectively, and they were compared to those of H0L0 (H chain, H0-M58/SEQ ID NO: 136; L chain, L0/SEQ ID NO: 56) and H0L12 (H chain, H0-M58/SEQ ID NO: 136; L chain, L12/SEQ ID NO: 237). Since L12 contains a sequence that improves the affinity, it exhibits about two times higher affinity than H0L0. The result of affinity measurement is shown in Table 15, and the biological activity determined using BaF/NR10 is shown in FIG. 24. Both affinity and biological activity were shown to be almost equal to those of H0L12.

TABLE 14

| Name | Type | L0 sequence | Mutation site (kabat No) | L0 sequence | Amino acid after mutation | Sequence after mutation |
|---|---|---|---|---|---|---|
| Ld-1 | CDR1 | RTSENIYSFLA (SEQ ID NO: 277) | 25 | T | A | RASENIYSFLA (SEQ ID NO: 285) |
| Ld-2 | CDR1 | RTSENIYSFLA (SEQ ID NO: 277) | 25 | T | S | RSSENIYSFLA (SEQ ID NO: 286) |

TABLE 15

| | ka (1/Ms) | kd (1/s) | KD (M) |
|---|---|---|---|
| H0L0 | 1.6E+05 | 7.8E−04 | 4.8E−09 |
| H0L12 | 3.8E+05 | 7.4E−04 | 2.0E−09 |
| H0L17 | 3.9E+05 | 8.1E−04 | 2.1E−09 |

Example 12

Preparation of Completely Humanized NS22 Antibody

Variable regions of NS22 variants were prepared by combining the multiple mutations that reduce the pI, increase the affinity, suppress the degradation of H chain, and reduce the immunogenicity risk, all of which were found in the above Examples, in H0(H0-M58/SEQ ID NO: 136), H1 (H1-M58/SEQ ID NO: 257), or L0 (L0/SEQ ID NO: 56), and subjected to various screening procedures. As a result, H28L17 (H chain, H28-M58/SEQ ID NO: 224; L chain, L17/SEQ ID NO: 238), H30L17 (H chain, H30-M58/SEQ ID NO: 225; L chain, L17/SEQ ID NO: 238), H34L17 (H chain, H34-M58/SEQ ID NO: 226, L chain, L17/SEQ ID NO: 238), H42L17 (H chain, H42-M58/SEQ ID NO: 227; L chain, L17/SEQ ID NO: 238), H44L17 (H chain, H44-M58/SEQ ID NO: 228; L chain, L17/SEQ ID NO: 238), H46L17 (H chain, H46-M58/SEQ ID NO: 229; L chain, L17/SEQ ID NO: 238), H57L17 (H chain, H57-M58/SEQ ID NO: 230; L chain, L17/SEQ ID NO: 238), H71L17 (H chain, H71-M58/SEQ ID NO: 231; L chain, L17/SEQ ID NO: 238), H78L17 (H chain, H78-M58/SEQ ID NO: 232; L chain, L17/SEQ ID NO: 238), H92L17 (H chain, H92-M58/SEQ ID NO: 233; L chain, L17/SEQ ID NO: 238), H97L50 (H chain, H97-M58/SEQ ID NO: 234; L chain, L50/SEQ ID NO: 239), and H98L50 (H chain, H98-M58/SEQ ID NO: 235; L chain, L50/SEQ ID NO: 239) were found. Each variant was produced and purified by the method described in Example 4.

Figures 1, 25:
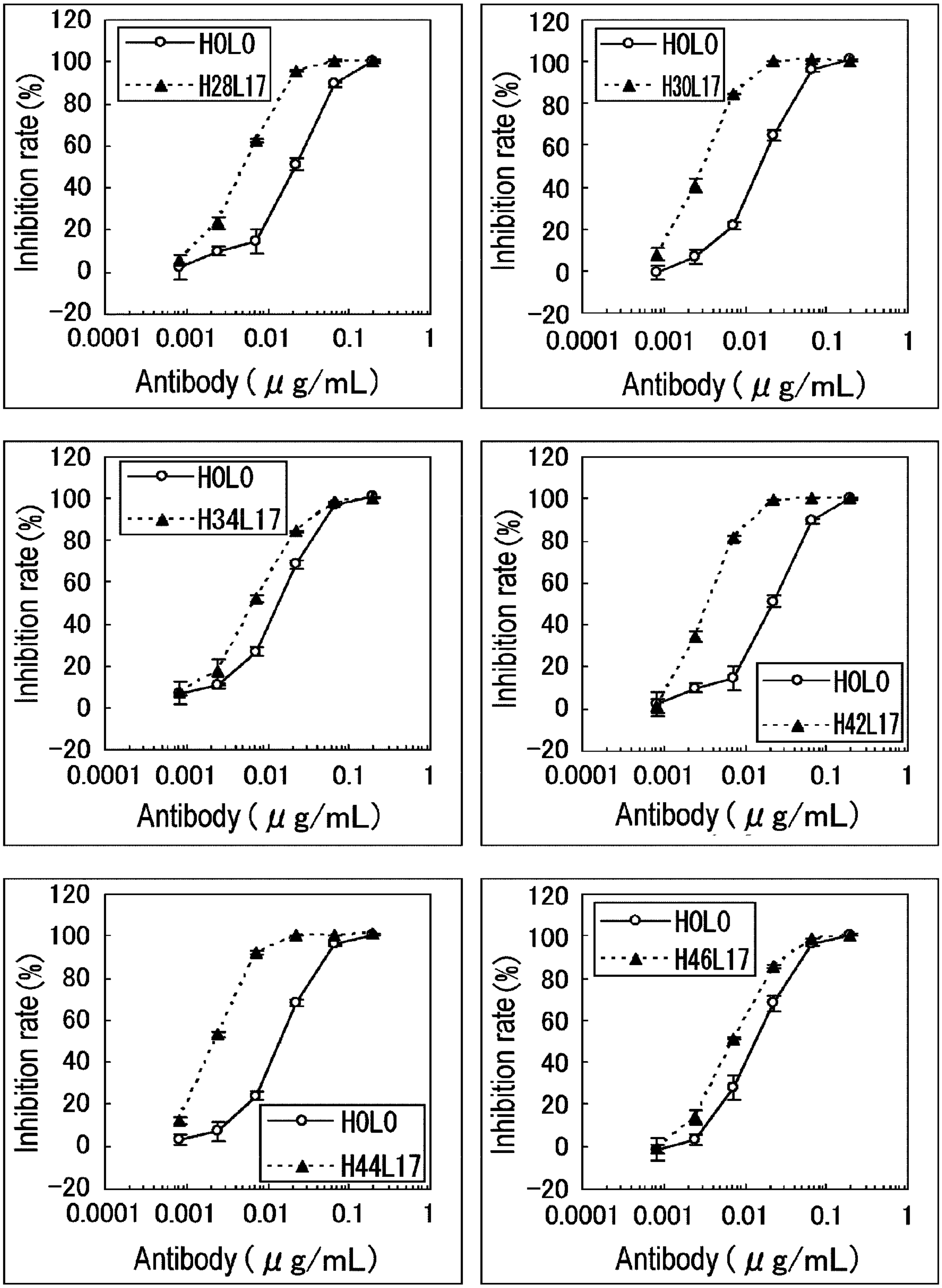
Figures 2, 25:
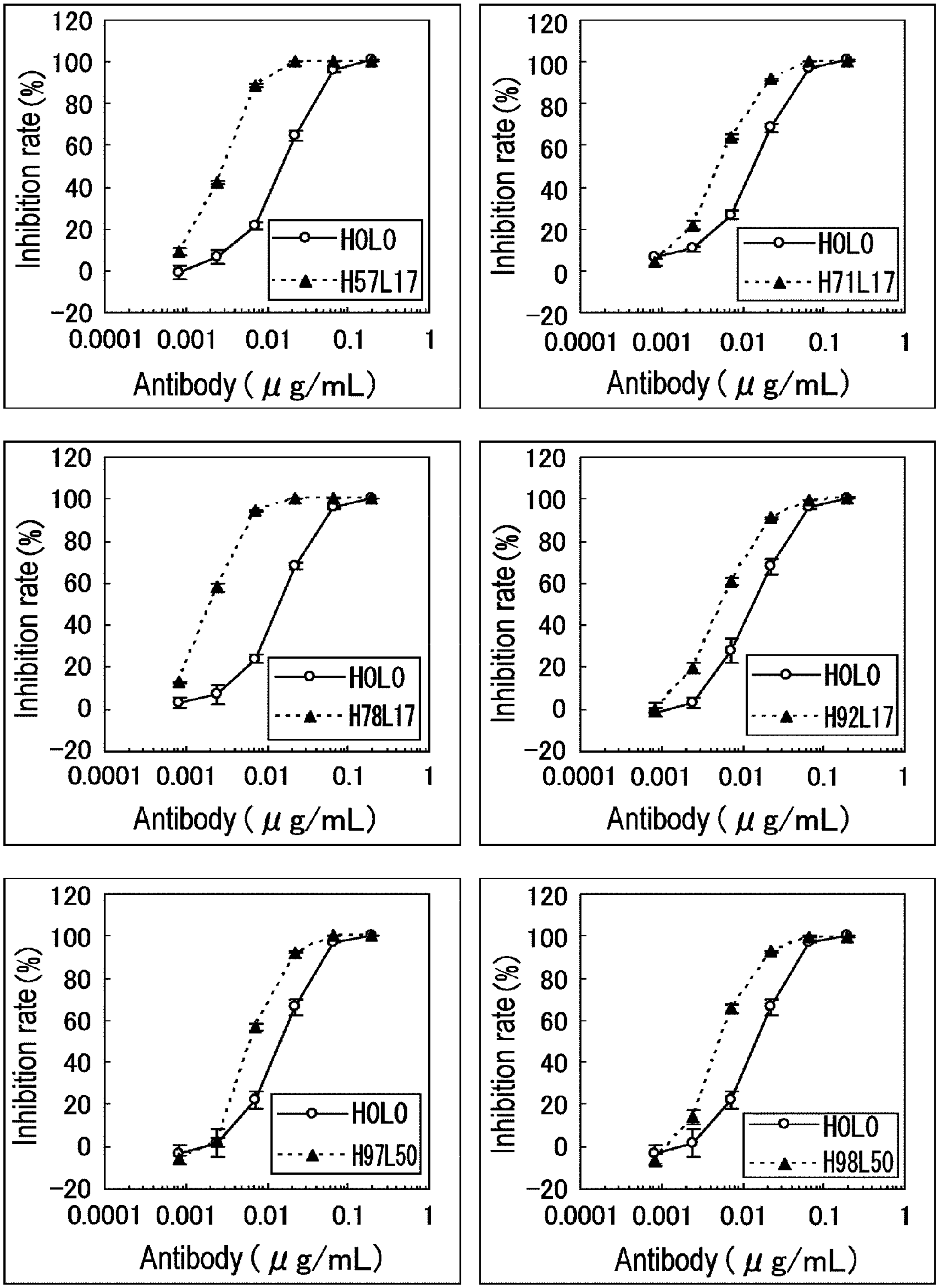

Each variant was assessed for the affinity for NR10 and the biological activity by the method described in Referential Example 10 and the method using BaF/NR10 as described in Example 2, respectively, and they were compared to those of H0L0 (H chain, H0-M58/SEQ ID NO: 136; L chain, L0/SEQ ID NO: 56). The result of affinity measurement is shown in Table 16, and the biological activity determined using BaF/NR10 is shown in FIGS. 25-1 and 25-2. Both affinity and biological activity of each antibody were shown to be almost equal to or greater than those of H0L0.

TABLE 16

| Sample | ka (1/Ms) | kd (1/s) | KD (M) |
|---|---|---|---|
| H0L0 | 2.1E+05 | 8.8E−04 | 4.2E−09 |
| H28L17 | 6.4E+05 | 3.3E−04 | 5.2E−10 |
| H30L17 | 6.8E+05 | 5.7E−04 | 8.3E−10 |
| H34L17 | 3.4E+05 | 1.2E−03 | 3.6E−09 |
| H42L17 | 5.7E+05 | 3.7E−04 | 6.5E−10 |
| H44L17 | 6.1E+05 | 7.2E−04 | 1.2E−09 |
| H46L17 | 2.9E+05 | 1.3E−03 | 4.6E−09 |
| H57L17 | 7.1E+05 | 5.5E−04 | 7.7E−10 |
| H71L17 | 3.7E+05 | 1.2E−03 | 3.3E−09 |
| H78L17 | 6.1E+05 | 7.0E−04 | 1.1E−09 |
| H92L17 | 3.1E+05 | 1.3E−03 | 4.1E−09 |
| H97L50 | 3.6E+05 | 1.3E−03 | 3.5E−09 |
| H98L50 | 2.9E+05 | 1.3E−03 | 4.6E−09 |

Example 13

Figure 26:
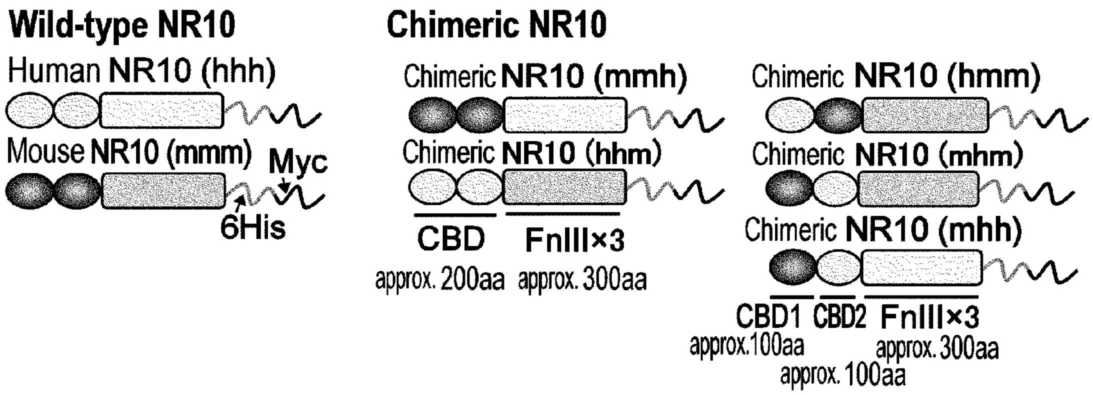
FIG. 26 is a schematic diagram for human/mouse wild-type and chimeric NR10-ECD.

Analysis of the Binding Domain of Anti-NR10 Neutralizing Antibody (1) Preparation of Human/Mouse Wild-Type and Chimeric Antigens The genes encoding human and mouse wild-type extracellular domains and chimeric extracellular domains of NR10 (hhh (SEQ ID NO: 258), mmm (SEQ ID NO: 259), hhm (SEQ ID NO: 260), mmh (SEQ ID NO: 261), hmm (SEQ ID NO: 262), mhm (SEQ ID NO: 263), and mhh (SEQ ID NO: 264)), were fused to His tag and Myc tag (HHHHHHEQKLISEEDL/SEQ ID NO: 287) at their C termini, inserted into an animal expression vector, and transiently expressed using FreeStyle 293 Expression System (Invitrogen™). Schematic diagrams for the human/mouse wild-type and chimeric NR10-ECDs are shown in FIG. 26.

The human/mouse wild-type and chimeric antigens (hhh, mmm, hhm, mmh, hmm, mhm, and mhh) were purified from culture supernatants by Ni-NTA Superflow column chromatography. Specifically, 1 ml of Ni-NTA Superflow (QIAGEN) was loaded onto Poly-Prep Empty Column (BioRad), and 30 ml of each culture supernatant was added thereto. After washing with D-PBS (Dulbecco's phosphate-buffered saline) containing 150 mM sodium chloride and 20 mM imidazole, the column was eluted with D-PBS containing 150 mM sodium chloride and 250 mM imidazole. The eluted fractions were buffer-exchanged with D-PBS and concentrated using Amicon-Ultra (Millipore) with a molecular weight cut-off of 10K.

(2) Detection of Binding Antigen by Western Blotting

Each of the prepared human/mouse wild-type and chimeric antigens was electrophoresed at 0.5 μg/lane on three 4-20% polyacrylamide gels (Daiichi Pure Chemicals Co.). The proteins were electro-transferred onto PVDF membranes (Millipore) in a semi-dry blotting apparatus, and the membranes were blocked with TBS containing 5% skim milk. One membrane was incubated with 5 μg/ml of H44M58L17 (detection system for humanized anti-human NR10 antibody); another with 5 μg/ml of ND41 (detection system for mouse anti-human NR10 antibody); and the other one with anti-Myc antibody (SantaCruz, Cat.#sc-789) 500-times diluted with TBS containing 5% skim milk (detection system for Myc tag) at room temperature for one hour.

Figure 27:
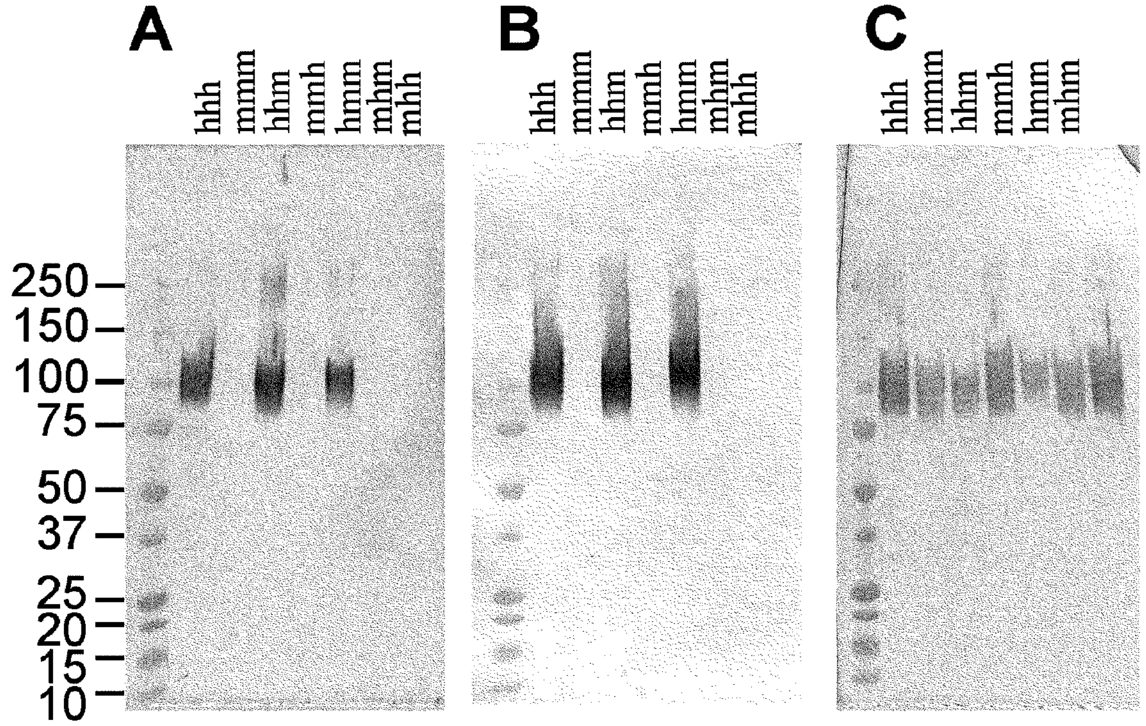
FIG. 27 is a set of photographs showing the detection of the binding domain by Western blotting. A is a photograph showing the result of detection using a humanized anti-human NR10 antibody; B is a photograph showing the result of detection using a mouse anti-human NR10 antibody; and C is a photograph showing the result of detection using an anti-Myc antibody. With the anti-human NR10 antibody a binding antigen was detected only in hhh, hhm, and hmm, but not in mmm, mmh, and mhm.

After washing three times with TBS containing 0.05% Tween™ 20, the secondary antibodies were incubated with the membranes. Alkaline phosphatase-labeled goat anti-human IgGγ (BIOSOURCE, Cat. #AHI0305) was used to detect humanized anti-human NR10 antibody; alkaline phosphatase-labeled goat anti-mouse IgG (SantaCruz, Cat. #sc-2008) was used to detect mouse anti-human NR10 antibody; and alkaline phosphatase-labeled goat anti-rabbit IgG (SantaCruz, Cat. #sc-2057) was used to detect Myc tag. The reaction was carried out at room temperature for one hour. After washing four times with TBS containing 0.05% Tween™ 20 for three minutes, color development was carried out using BCIP/NBT Phosphatase substrate, 1-Component System (KPL). TBS (Tris-buffered saline) used here was prepared by dissolving a pack of TBS (Tris buffered saline) powder (TaKaRa) in 1 L of distilled water. The result is shown in FIG. 27.

When the humanized antibody or mouse antibody was used, the binding was detected only for hhh, hhm, and hmm, which are NR10 extracellular domains.

Referential Example 1

Isolation of Cynomolgus Monkey NR10, OSMR, and IL-31 Genes

Since the cross-reactivity and neutralizing activity in cynomolgus monkeys were considered important for safety assessment at a pre-clinical stage, the cynomolgus monkey NR10 and OSMR genes were isolated. Primers were designed based on published information of Rhesus monkey genome and others, and the NR10 and OSMR genes were successfully amplified by PCR from cynomolgus monkey pancreatic cDNA. The sequences of the isolated cynomolgus monkey NR10, OSMR, and IL-31 genes are shown in SEQ ID NOs: 65, 69, and 67, respectively, and the amino acid sequences of cynomolgus monkey NR10, OSMR, and IL-31 are shown in SEQ ID NOs: 66, 70, and 68, respectively.

Referential Example 2

Establishment of NR10- and OSMR-Expressing Ba/F3 Cell Lines

The full-length human NR10 cDNA (SEQ ID NO: 75) was inserted into the expression vector pCOS1 (Biochem. Biophys. Res. Commun. 228, p838-45, 1996), and the resulting vector was named pCosNR10.3. An oncostatin M receptor cDNA (OSMR, GenBank accession No. NM003999) was isolated by PCR from a human placental library, and the expression vector pCos1-hOSMR was constructed in the same manner. 10 μg each of the vectors were simultaneously introduced into mouse IL-3-dependent pro-B cell-derived cell line Ba/F3 by electroporation (BioRad Gene Pulser, 960 μF, 0.33 kV). After introduction, human IL-31 (R&D Systems) was added, and the cells were cultured to obtain a cell line (hNR10/hOSMR/BaF3 cell) that proliferates in an IL-31-dependent manner. Furthermore, the cynomolgus monkey IL-31 gene (SEQ ID NO: 67) was inserted into a mammalian cell expression vector and introduced into CHO cell line DG44. The resulting culture supernatant was obtained as cynomolgus monkey IL-31. As with hNR10/hOSMR/BaF3, the full-length cynomolgus monkey NR10 and OSMR genes were inserted into the expression vector pCOS1 and expressed in Ba/F3 cells, and a cynomolgus monkey IL-31-dependent cell line (cynNR10/cynOSMR/BaF3 cell) was established using the culture supernatant described above.

Referential Example 3

Establishment of NR10-Expressing CHO Cell Lines

The genes for cytoplasmic domain-lacking human NR10 (SEQ ID NO: 73) and cytoplasmic domain-lacking cynomolgus monkey NR10 (SEQ ID NO: 71) were each inserted to a mammalian cell expression vector. The resulting vectors were linearized with a restriction enzyme, and then introduced into CHO cell line DG44 by electroporation (BioRad Gene Pulser, 25 μF, 1.5 kV). After drug selection, NR10-expressing cells were selected and established by FCM analysis using anti-human NR10 antibody. The amino acid sequence encoded by the nucleotide sequence of cytoplasmic domain-lacking human NR10 gene (SEQ ID NO: 73) is shown in SEQ ID NO: 74, and the amino acid sequence encoded by the nucleotide sequence of cytoplasmic domain-lacking cynomolgus monkey NR10 gene (SEQ ID NO: 71) is shown in SEQ ID NO: 72.

Referential Example 4

Preparation of NR10 Protein (Extracellular Domain)

The human NR10 cDNA was used as a template to amplify only the extracellular domain by PCR. The amplified region was then fused to a FLAG tag sequence at the C terminus and inserted to a mammalian cell expression vector. Ten μg of the linearized vector was introduced into Chinese hamster ovary cell line DG44 by electroporation (BioRad Gene PulserII, 25 μF, 1.5 kV). A cell line showing high level expression was obtained. The supernatant of the cell line cultured on a large scale was purified using anti-FLAG antibody column (Sigma) and gel filtration to obtain soluble NR10. The nucleotide sequence of soluble NR10 is shown in SEQ ID NO: 77, and the amino acid sequence is shown in SEQ ID NO: 78.

Referential Example 5

Preparation of Anti-Human NR10 Antibodies

Mice were immunized with human NR10 protein (extracellular domain) (described in Referential Example 4), and hybridomas were prepared by a conventional method. The culture supernatants of these hybridomas were assessed for the neutralizing activity using the human IL-31-dependent cell line (hNR10/hOSMR/BaF3 cell) described in Referential Example 2, and thereby NA633 which has an NR10-neuralizing activity was obtained.

Furthermore, DNA immunization was carried out by He gas-driven gene gun using a mammalian expression vector carrying the full-length human NR10 gene (SEQ ID NO: 75), and hybridomas were prepared by a conventional method. The culture supernatants of these hybridomas were assessed for the neutralizing activity using the human IL-31-dependent cell line (hNR10/hOSMR/BaF3 cell) described in Referential Example 2, and thereby ND41 which has an NR10-neuralizing activity was obtained.

Referential Example 6

Preparation of Human Chimeric Antibody

The amino acid sequences of heavy chain and light chain variable regions of NA633 are shown in SEQ ID NOs: 104 and 108, respectively. The amino acid sequences of CDR1, CDR2, and CDR3 of the heavy chain variable region of NA633 are shown in SEQ ID NOs: 105, 106, and 107, respectively, while those of CDR1, CDR2, and CDR3 of the light chain variable region are shown in SEQ ID NOs: 109, 110, and 111, respectively. Furthermore, a chimeric antibody between these mouse variable regions and human constant region (H chain, γ1; L chain, κ) was produced by a conventional method.

Referential Example 7

Preparation of huPM1-SKSC in which the Heterogeneity of Wild Type IgG2 is Reduced without Loss of Stability Since the NS22 antibody is an NR10-neutralizing antibody, its binding to Fcγ receptor may be unfavorable in consideration of the immunogenicity and adverse effects. A possible method for reducing the binding to Fcγ receptor is to select IgG2 or IgG4 instead of IgG1 as the isotype of the constant region (Ann Hematol. 1998 June; 76(6): 231-48.). From the viewpoint of Fcγ receptor I and retention in plasma, IgG2 has been considered more desirable than IgG4 (Nat. Biotechnol. 2007 December; 25(12): 1369-72). Meanwhile, when an antibody is developed as a pharmaceutical, properties of the protein, particularly homogeneity and stability, are highly important. The IgG2 isotype has been reported to have very high heterogeneity resulting from the disulfide bonds in the hinge region (J Biol. Chem. 2008 Jun. 6; 283(23): 16206-15.). It is not easy and would be more costly to manufacture it as pharmaceutical in a large scale while maintaining difference in the heterogeneity of desired/related substances among products resulting from the above. Accordingly, it is desired that the substance be composed of a single substance as much as possible. Thus, when antibodies of IgG2 isotype are developed as pharmaceuticals, it is preferred to reduce the heterogeneity resulting from disulfide bonds, without lowering the stability.

In order to reduce the heterogeneity of the wild type IgG2, cysteines in the hinge region and CH1 domain of IgG2 were substituted. As a result of examination of various variants, SKSC (SEQ ID NO: 62), which is a constant region obtained by altering cysteine at position 131 and arginine at position 133 in the EU numbering (Sequences of proteins of immunological interest, NIH Publication No. 91-3242) within the H-chain CH1 domain of the wild type IgG2 constant region sequence to serine and lysine, respectively, and altering cysteine at EU-numbering position 219 in the H-chain upper hinge to serine could reduce the heterogeneity without decreasing the stability. Meanwhile, other possible methods for decreasing heterogeneity are to alter only cysteine at EU-numbering position 219 in the H-chain upper hinge to serine, and to alter only cysteine at EU-numbering position 220 to serine. Thus, constant region SC (SEQ ID NO: 153) in which cysteine at EU-numbering position 219 in IgG2 has been altered to serine, and constant region CS (SEQ ID NO: 154) in which cysteine at EU-numbering position 220 in IgG2 has been altered to serine, were produced.

huPM1-SC (SEQ ID NO: 157), huPM1-CS (SEQ ID NO: 158), huPM1-IgG1 (SEQ ID NO: 159), huPM1-IgG2 (SEQ ID NO: 160), and huPM1-SKSC (SEQ ID NO: 161), which were prepared by combining the constant regions produced as above, IgG1 (SEQ ID NO: 60), and IgG2 (SEQ ID NO: 132) with the variable region of the humanized anti-IL-6 receptor antibody (H chain variable region, huPM1-VH/SEQ ID NO: 155; L chain variable region huPM1-VL/SEQ ID NO: 156) (Cancer Res. 1993 Feb. 15; 53(4): 851-6.), were used as an H chain, and huPM1-L (SEQ ID NO: 162) was used as an L chain, to produce each antibody. Each antibody was expressed and purified by the method described in Example 4.

The antibodies were compared to each other in terms of the heterogeneity. The heterogeneity of huPM1-IgG1, huPM1-IgG2, huPM1-SC, huPM1-CS, and huPM1-SKSC was assessed by cation exchange chromatography. The chromatography was carried out using a ProPac WCX-10 (Dionex) column, 20 mM sodium acetate (pH 5.0) as mobile phase A, and 20 mM sodium acetate/1M NaCl (pH 5.0) as mobile phase B, with an appropriate flow rate and gradient. The result of assessment by cation exchange chromatography is shown in FIG. 12.

Figure 12:
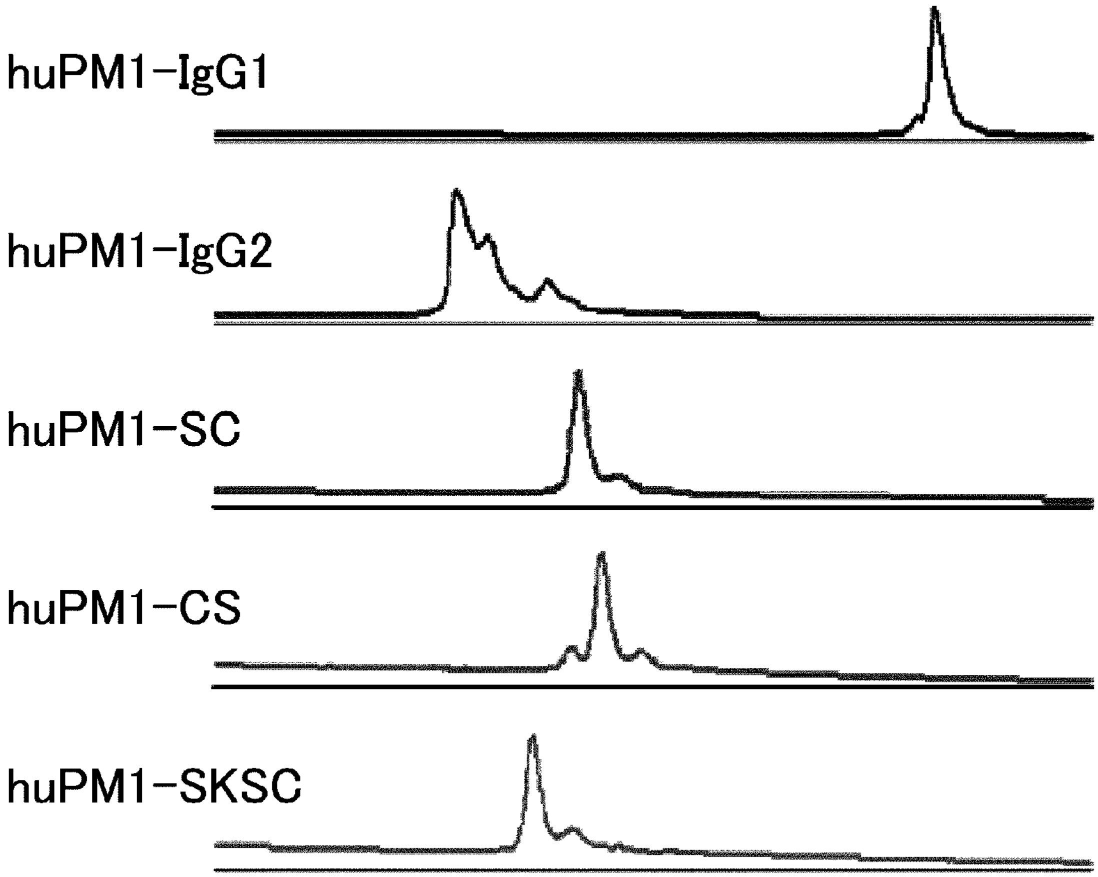
FIG. 12 shows the effect of the constant region of anti-IL-6 receptor antibody on the heterogeneity assessed by cation exchange chromatography.

As shown in FIG. 12, conversion of the constant region from IgG1 into IgG2 increased the heterogeneity. In contrast, the heterogeneity was markedly reduced by converting the constant region into SKSC. While constant region SC resulted in considerable reduction of the heterogeneity as in SKSC, constant region CS did not sufficiently improve the heterogeneity.

Figure 13:
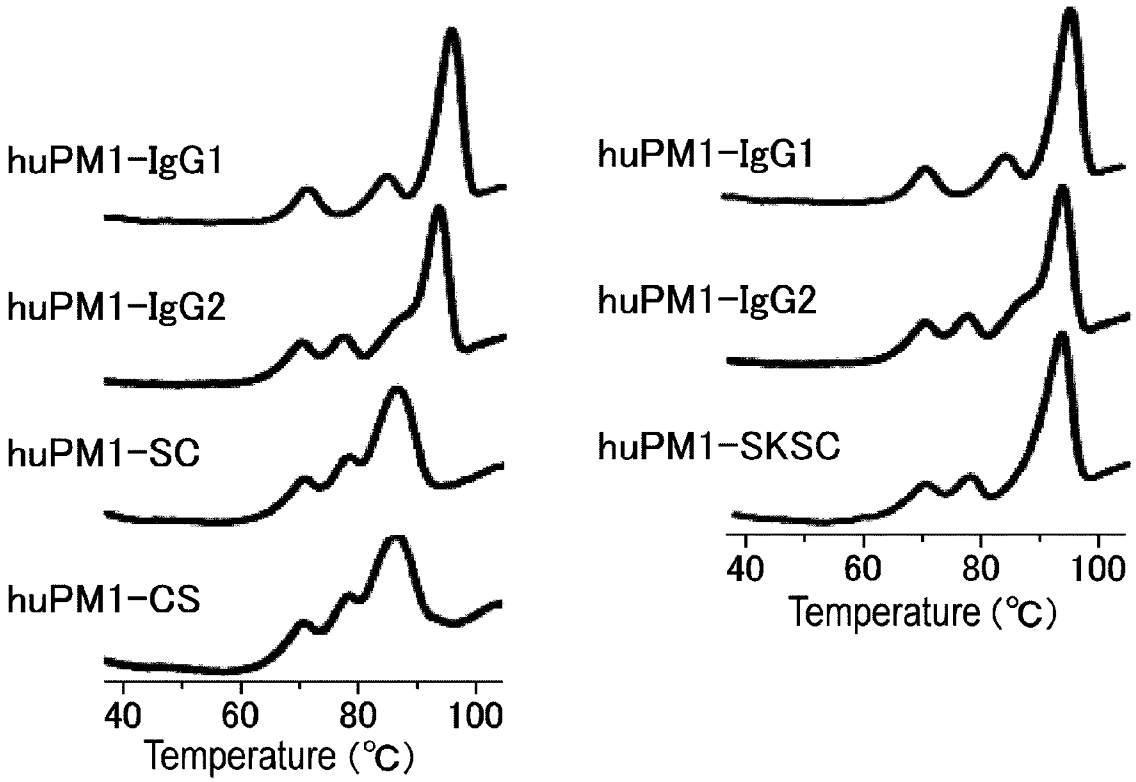
FIG. 13 shows the effect of the constant region of anti-IL-6 receptor antibody on the denaturation peak assessed by DSC.

When an antibody is developed as a pharmaceutical, it is generally desired that the antibody have high stability in addition to low heterogeneity for the production of stable preparations. Thus, to assess the stability, the thermal denaturation midpoint temperature (Tm value) was determined by differential scanning calorimetry (DSC) (VP-DSC; Microcal). The thermal denaturation midpoint temperature (Tm value) serves as an indicator of stability. In order to prepare stable preparations as pharmaceuticals, a higher thermal denaturation midpoint temperature (Tm value) is preferred (J Pharm Sci. 2008 April; 97(4): 1414-26.). Thus, huPM1-IgG1, huPM1-IgG2, huPM1-SC, huPM1-CS, and huPM1-SKSC were dialyzed against a solution of 20 mM sodium acetate/150 mM NaCl (pH 6.0) (EasySEP; TOMY), and DSC measurement was carried out using about 0.1 mg/ml of protein at a heating rate of 1° C./min between 40 and 100° C. The denaturation curves obtained by DSC are shown in FIG. 13. The Tm values of the Fab domains are listed in Table 17 below.

TABLE 17

| Name | Tm/° C. |
|---|---|
| huPM1-IgG1 | 94.8 |
| huPM1-IgG2 | 93.9 |
| huPM1-SC | 86.7 |
| huPM1-CS | 86.4 |
| huPM1-SKSC | 93.7 |

The Tm values of huPM1-IgG1 and huPM1-IgG2 were almost the same, namely, about 94° C. (IgG2 was lower by about 1° C.). Meanwhile, the Tm values of huPM1-SC and huPM1-CS were about 86° C., which was significantly lower than those of huPM1-IgG1 and huPM1-IgG2. On the other hand, the Tm value of huPM1-SKSC was about 94° C., and almost the same as huPM1-IgG1 and huPM1-IgG2. Since the stability of huPM1-SC and huPM1-CS was markedly lower than that of IgG2, huPM1-SKSC in which cysteine in the CH1 domain have also been altered to serine may be more preferred in the development of pharmaceuticals. The significant decrease in Tm value of huPM1-SC and huPM1-CS as compared to IgG2 may be due to the disulfide-bonding pattern of huPM1-SC and huPM1-CS that is different from that of IgG2.

Furthermore, comparison of the DSC denaturation curves showed that the denaturation peak for the Fab domain was sharp in huPM1-IgG1 and huPM1-SKSC, while it was broader in huPM1-SC and huPM1-CS than the above two, and huPM1-IgG2 gave a shoulder peak on the lower temperature side of the Fab domain denaturation peak. The denaturation peak in DSC generally becomes sharp in the case of a single component, but may become broad when two or more components with different Tm values (namely, heterogeneity) are present. Thus, it was suggested that huPM1-IgG2, huPM1-SC, and huPM1-CS contained two or more components, and the heterogeneity of natural IgG2 was not reduced in huPM1-SC and huPM1-CS. This finding suggests that cysteines present in both the hinge region and the CH1 domain are involved in the heterogeneity of natural IgG2, and it is necessary to alter not only cysteine in the hinge region but also that in the CH1 domain to decrease the heterogeneity on DSC. Furthermore, as described above, it is only possible to attain stability equivalent to that of natural IgG2 by altering not only cysteine in the hinge region but also that in the CH1 domain.

As described above, as to the constant regions in which the heterogeneity resulting from the hinge region of IgG2 has been reduced, it was discovered that SC and CS, which are constant regions in which only cysteine in the hinge region has been substituted with serine, may be insufficient from the viewpoint of heterogeneity and stability, and that it is only possible to significantly reduce the heterogeneity while maintaining the stability comparable to IgG2 by additionally substituting cysteine at EU-numbering position 131 in the CH1 domain with serine. Such constant regions include SKSC.

Referential Example 8

Production and Assessment of Optimized, Non-Fcγ Receptor-Binding Constant Region M14

In the Fcγ receptor-binding domain of IgG2 constant region, the residues at EU-numbering positions 233, 234, 235, and 236 are of non-binding type, while the residues at EU-numbering positions 327, 330, and 331 are different from those of IgG4, which are of non-binding type. Thus, it is necessary to alter the amino acids at EU-numbering positions 327, 330, and 331 to the sequence of IgG4 (G2Δa in Eur J.

Immunol. 1999 August; 29(8):2613-24). However, since the amino acid at EU-numbering position 339 is alanine in IgG4 while it is threonine in IgG2, mere alteration of the amino acids at EU-numbering positions 327, 330, and 331 to the sequence of IgG4 will generate a novel non-naturally occurring 9-amino acid peptide sequence that could be a T-cell epitope peptide, thereby causing a risk of immunogenicity. Thus, it was found that the occurrence of the novel peptide sequence could be prevented by altering threonine at EU-numbering position 339 in IgG2 to alanine, in addition to the alterations described above. In addition to the mutations described above, methionine at EU-numbering position 397 was mutated into valine to improve the stability of IgG2 under acidic condition. Furthermore, in SKSC (SEQ ID NO: 62) produced in Referential Example 7, in which the heterogeneity resulting from the disulfide bonds in the hinge region has been improved, introduction of mutations at positions 131 and 133 will generate a novel non-naturally occurring 9-amino acid peptide sequence that could be a T-cell epitope peptide, thereby causing a risk of immunogenicity. Thus, the peptide sequence around positions 131 to 139 was converted into the same as IgG1 by mutating glutamic acid at EU-numbering position 137 into glycine and mutating serine at EU-numbering position 138 into glycine. The constant region sequence M14 (SEQ ID NO: 129) was produced by introducing all the above mutations.

The expression and purification of huPM1-M14, prepared by using huPM1-M14 as an H chain and huPM1-L (SEQ ID NO: 162) as an L chain, was carried out by the method described in Referential Example 7. The prepared huPM1-M14 (SEQ ID NO: 163), huPM1-IgG1, and huPM1-IgG2 were assessed for the heterogeneity using cation exchange chromatography by the method described in Referential Example 7.

Figure 14:
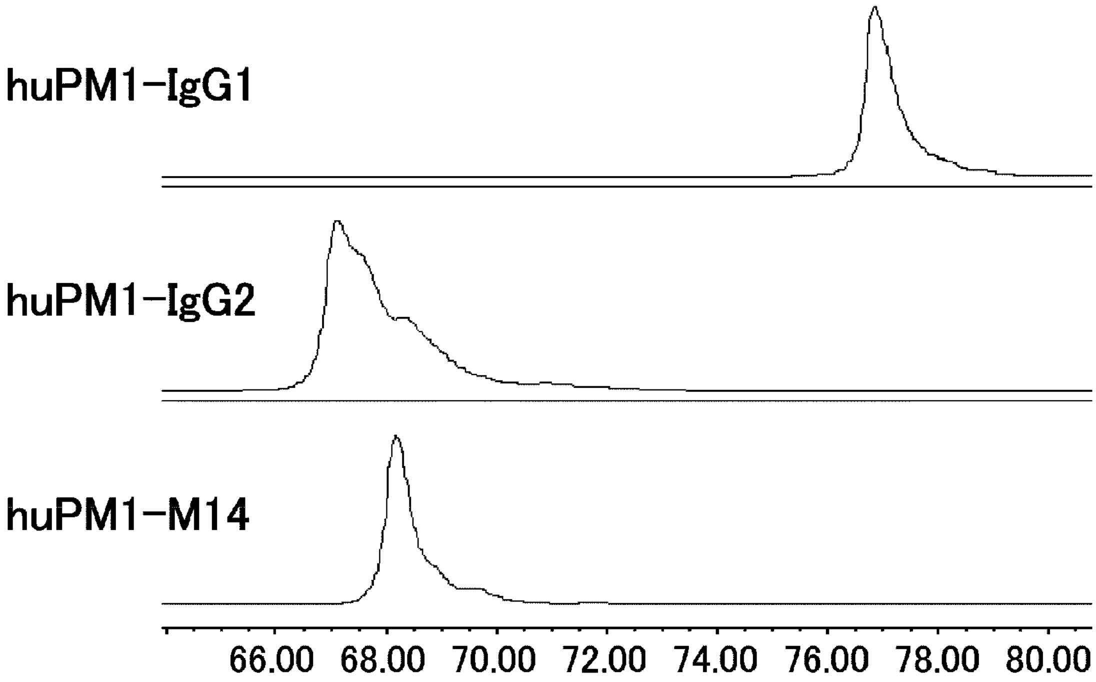
FIG. 14 shows the effect of the novel constant region M14 on the heterogeneity in an anti-IL-6 receptor antibody, assessed by cation exchange chromatography.
Figure 15:
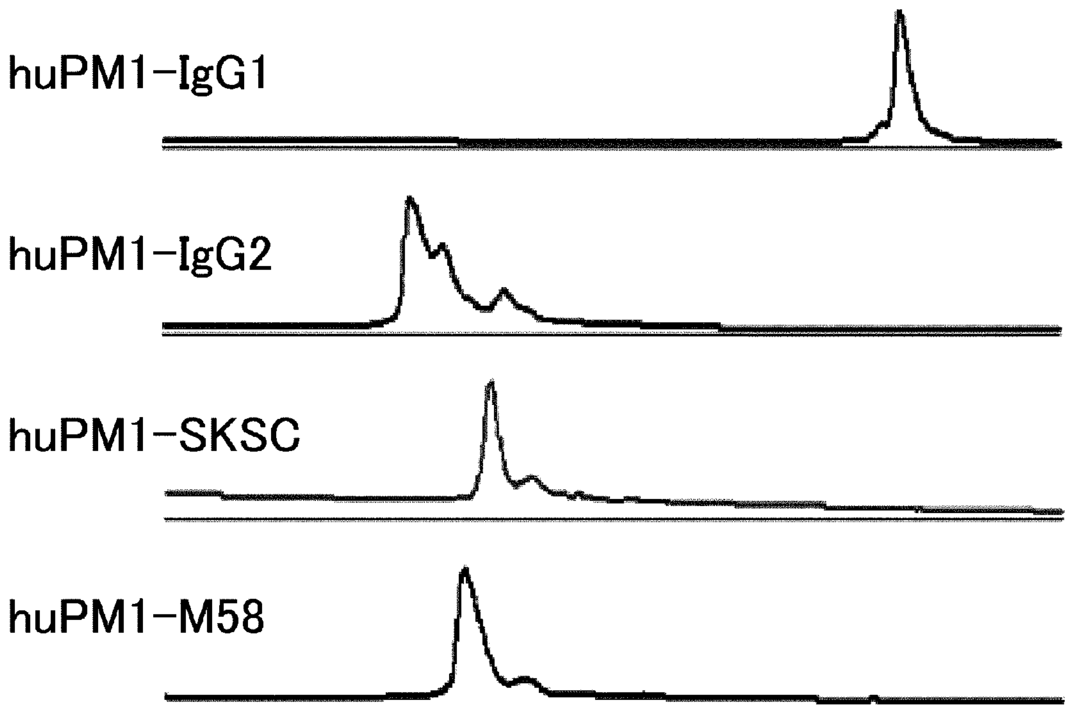
FIG. 15 shows the effect of the novel constant region M58 on the heterogeneity in an anti-IL-6 receptor antibody, assessed by cation exchange chromatography.

As shown in FIG. 14, the heterogeneity was also reduced in huPM1-M14 as in huPM1-SKSC.

Referential Example 9

Preparation of huPM1-M58 with Reduced H-Chain C-Terminal Heterogeneity and Improved Pharmacokinetics Preparation of huPM1-M58 Molecule huPM1 is an IgG1 antibody. For the heterogeneity in the C-terminal sequence of the H chain of IgG antibody, the deletion of the C-terminal lysine residue and the amidation of the C-terminal amino group due to deletion of the two C-terminal amino acids, glycine and lysine, have been reported (Anal Biochem. 2007 Jan. 1; 360(1): 75-83). Also in huPM1, while the major component is a sequence in which the C-terminal lysine encoded by the nucleotide sequence has been deleted by post-translational modification, there are also a minor component in which the lysine remains and a minor component in which the C-terminal amino group is amidated due to deletion of both glycine and lysine, which contribute to heterogeneity. Producing a pharmaceutical in a large scale while maintaining the difference in the heterogeneity of desired/related substances between products is not easy but rather results in increase of cost, and it is thus desired that the substance be composed of a single substance as much as possible. When an antibody is developed as a pharmaceutical, reduction of the heterogeneity is desired. Thus, it is desired that the C-terminal of the H chain has no heterogeneity when developed as pharmaceuticals. It is also desirable to prolong the plasma half-life of the antibody in order to reduce the antibody dose.

Thus, the alterations described below were introduced to prepare a novel constant region in which the heterogeneity at C-terminal of the H chain has been reduced, the pharmacokinetics has been improved as compared to huPM1-IgG1, and the heterogeneity derived from wild-type IgG2 has also been reduced without loss of stability.

Specifically, in huPM1-SKSC, which has high stability and in which the above-mentioned heterogeneity related to antibodies with IgG2-isotype constant regions is reduced, glutamic acid at EU-numbering position 137 was substituted with glycine; serine at position 138 with glycine; histidine at position 268 with glutamine; arginine at position 355 with glutamine; and glutamine at position 419 with glutamic acid. In addition to the above substitutions, glycine and lysine at positions 446 and 447 were deleted to reduce the heterogeneity of the H-chain C terminus, thereby obtaining huPM1-M58 (SEQ ID NO: 164). huPM1-M58 prepared by using huPM1-M58 as an H chain and huPM1-L (SEQ ID NO: 162) as an L chain was expressed and purified by the method described in Example 4.

The huPM1-M58, huPM1-IgG1, and huPM1-IgG2 were assessed for the heterogeneity and stability by the methods described in Example 5 using cation exchange chromatography and DSC, respectively.

Figure 16:
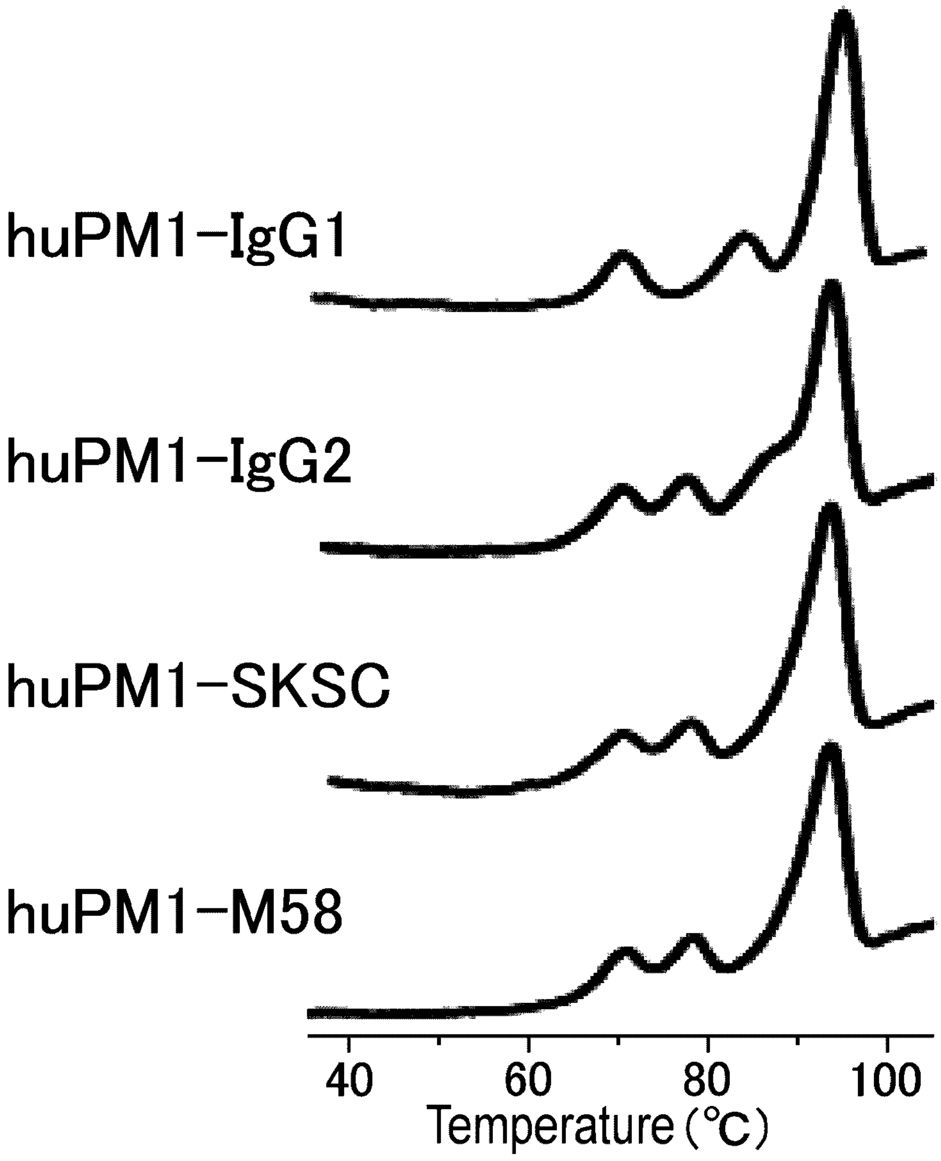
FIG. 16 shows the effect of the novel constant region M58 on the denaturation peak in an anti-IL-6 receptor antibody, assessed by DSC.

The result of DSC is shown in Table 18. As shown in FIGS. 13 and 16, huPM1-M58 was found to show reduced heterogeneity without loss of stability as in huPM1-SKSC.

TABLE 18

| Name | Tm/° C. |
|---|---|
| huPM1-IgG1 | 94.8 |
| huPM1-IgG2 | 93.9 |
| huPM1-SKSC | 93.7 |
| huPM1-M58 | 93.7 |

Assessment of huPM1-M58 for Plasma Retention

The prolonged retention (slow elimination) of IgG molecule in plasma is due to the function of FcRn, which is known as a salvage receptor of IgG molecule (Nat Rev Immunol. 2007 September; 7(9): 715-25). When incorporated into endosomes via pinocytosis, IgG molecules bind to FcRn expressed in endosomes under the acidic conditions within the endosome (approx. pH 6.0). While IgG molecules that are not bound to FcRn are transferred to and degraded in lysosomes, those bound to FcRn are translocated to the cell surface and then released from FcRn into plasma again under the neutral conditions in plasma (approx. pH 7.4).

IgG-type antibodies are known to include IgG1, IgG2, IgG3, and IgG4 isotypes. The plasma half-lives of these isotypes in human are reported to be about 36 days for IgG1 and IgG2; about 29 days for IgG3; and 16 days for IgG4 (Nat. Biotechnol. 2007 December; 25(12): 1369-72). Thus, the retention of IgG1 and IgG2 in plasma is believed to be the longest. In general, the isotypes of antibodies used as pharmaceutical agents are IgG1, IgG2, and IgG4. Reported methods for further improving the pharmacokinetics of these IgG antibodies include methods for improving the above-described binding activity to human FcRn by altering the sequence of IgG constant region (J. Biol. Chem. 2007 Jan. 19; 282(3): 1709-17; J. Immunol. 2006 Jan. 1; 176(1): 346-56).

There are species differences between mouse FcRn and human FcRn (Proc. Natl. Acad. Sci. USA. 2006 Dec. 5; 103(49): 18709-14). Therefore, to predict the retention of IgG antibodies having an altered constant region sequence in human plasma, it may be desirable to assess the binding to human FcRn and the plasma retention in human FcRn transgenic mice (Int. Immunol. 2006 December; 18(12): 1759-69).

Assessment of the Binding to Human FcRn

FcRn is a complex of FcRn and β2-microglobulin. Oligo-DNA primers were prepared based on the published human FcRn gene sequence (J. Exp. Med. (1994) 180 (6), 2377-2381). A DNA fragment encoding the whole gene was prepared by PCR using human cDNA (Human Placenta Marathon-Ready cDNA, Clontech) as a template and the prepared primers. Using the obtained DNA fragment as a template, a DNA fragment encoding the extracellular domain containing the signal region (Met1-Leu290) was amplified by PCR, and inserted into an animal cell expression vector (the amino acid sequence of human FcRn/SEQ ID NO: 165). Likewise, oligo-DNA primers were prepared based on the published human β2-microglobulin gene sequence (Proc. Natl. Acad. Sci. U.S.A. 99 (26), 16899-16903 (2002)). A DNA fragment encoding the whole gene was prepared by PCR using human cDNA (Hu-Placenta Marathon-Ready cDNA, CLONTECH) as a template and the prepared primers. Using the obtained DNA fragment as a template, a DNA fragment encoding the whole β2-microglobulin containing the signal region (Met1-Met119) was amplified by PCR and inserted into an animal cell expression vector (the amino acid sequence of human β2-microglobulin/SEQ ID NO: 166).

Soluble human FcRn was expressed by the following procedure. The prepared plasmids for human FcRn and β2-microglobulin were introduced into the human embryonic kidney cancer-derived cell line HEK293H (Invitrogen) using 10% fetal bovine serum (Invitrogen) by lipofection. The resulting culture supernatant was collected and purified using IgG Sepharose 6 Fast Flow (Amersham Biosciences) by the method described in J. Immunol. 2002 Nov. 1; 169(9):5171-80. Then further purification was carried out using HiTrap Q HP (GE Healthcare).

The binding to human FcRn was assessed using Biacore 3000. An antibody was bound to Protein L or rabbit anti-human IgG Kappa chain antibody immobilized onto a sensor chip, human FcRn was added as an analyte for interaction with the antibody, and the affinity (1(D) was calculated from the amount of bound human FcRn. Specifically, Protein L was immobilized onto sensor chip CM5 (BIACORE) by the amine coupling method using 50 mM Na-phosphate buffer (pH 6.0) containing 150 mM NaCl as the running buffer. Then, an antibody was diluted with the running buffer containing 0.02% Tween20, and injected and allowed to bind to the chip. Human FcRn was then injected to assess the binding activity of the antibody to the human FcRn.

The affinity was calculated using BIAevaluation software. The obtained sensorgram was used to calculate the amount of hFcRn bound to the antibody immediately before the end of human FcRn injection. This was fitted by the steady state affinity method to calculate the affinity of human FcRn for the antibody.

Predictive Assessment of Plasma Retention of huPM1-IgG1 and huPM1-M58 in Human Using Human FcRn The binding activities of huPM1-IgG1 and huPM1-M58 to human FcRn were assessed using BIAcore. As shown in Table 19, the binding activity of huPM1-M58 was greater than that of huPM1-IgG1 by about 1.4 times.

TABLE 19

| | KD (μM) |
|---|---|
| huPM1-IgG1 | 1.62 |
| huPM1-M58 | 1.17 |

Assessment of the Plasma Retention in Human FcRn Transgenic Mice

The pharmacokinetics in human FcRn transgenic mice (B6.mFcRn−/−.hFcRn Tg line 276+/+ mice; Jackson Laboratories) was assessed by the following procedure. An antibody was intravenously administered once at a dose of 1 mg/kg to mice, and blood was collected at appropriate time points. The collected blood was immediately centrifuged at 15,000 rpm for 15 minutes at 4° C. to obtain plasma. The separated plasma was stored in a freezer at −20° C. or below until use. The plasma concentration was determined by ELISA.

Figure 17:
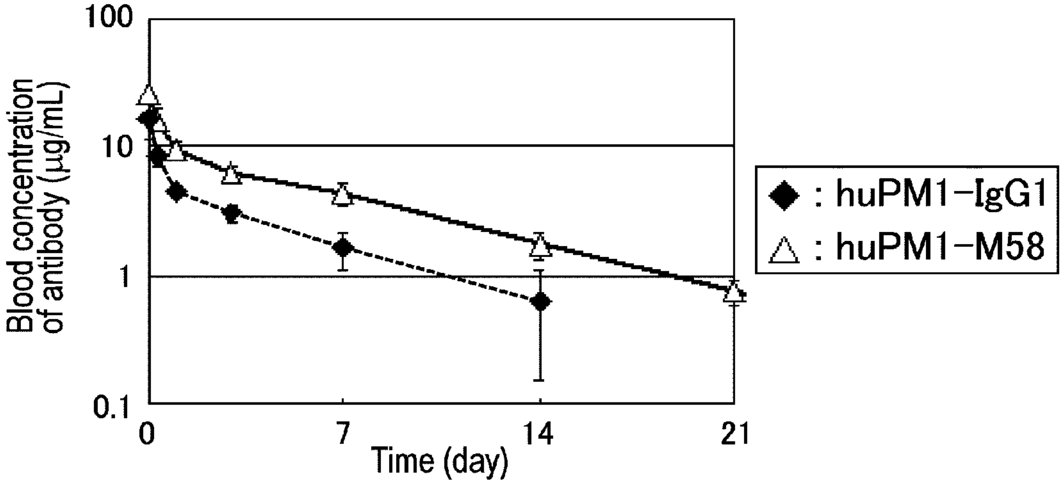
FIG. 17 shows the result of assaying the retention of huPM1-IgG1 and huPM1-M58 in the plasma of human FcRn transgenic mice.

Predictive Assessment of the Plasma Retention of huPM1-IgG1 and huPM1-M58 in Human Using Human FcRn Transgenic Mice The plasma retention of huPM1-IgG1 and huPM1-M58 in human FcRn transgenic mice was assessed. As shown in FIG. 17, the result demonstrated that the pharmacokinetics of huPM1-M58 was improved as compared to huPM1-IgG1. It was suggested that the human FcRn-binding activity was correlated to the plasma retention in human FcRn transgenic mice.

Referential Example 10

Measurement of the Affinity in Antigen-Antibody Reaction Using Biacore

Kinetic analysis of the antigen-antibody reaction was carried out using Biacore T100 (GE Healthcare Biosciences). The antigen-antibody interaction was measured by immobilizing rec-Protein A (hereinafter Protein A) (ZYMED) onto a sensor chip, capturing an antibody on the immobilized Protein A, and then reacting the antigen as an analyte. Various concentrations of rhNR10 were used as the antigen. The kinetic parameters, association rate constant $k_a$ (1/Ms) and dissociation rate constant $k_d$ (1/s), were calculated from the sensorgrams obtained by the measurement. Then, $K_D$ (M) was determined based on the rate constants. Each parameter was determined using Biacore T100 Evaluation Software version 1.1 (GE Healthcare Biosciences).

Immobilization of Protein A onto Sensor Chip

Protein A was immobilized onto all flow cells of sensor chip CM5 (GE Healthcare Biosciences) by the amine coupling method. The experiment was carried out using HBS-EP+(10 mM HEPES, 0.15 M NaCl, 3 mM EDTA, 0.05% v/v Surfactant P20) as a running buffer at a flow rate of 10 μL/min. The carboxyl groups of carboxymethyl dextran on the sensor chip were activated with 100 μL of a 1:1 mixture of 75 mg/ml EDC (N-ethyl-N'-(3-dimethylaminopropyl)carbodiimide hydrochloride) and 11.5 mg/ml NHS (N-hydroxysuccinimide), and Protein A prepared at 50 μg/ml using 10 mM acetate buffer (pH 4.5) was allowed to flow for reaction. Then, 100 μL of 1 M ethanolamine hydrochloride (pH 8.5) was allowed to flow to inactivate the unreacted active groups. Ultimately, about 4000 to 5000 RU were immobilized. The experiment was carried out at 25° C. at all times.

Measurement of Affinity in Antigen-antibody Reaction Between rhNR10 and Antibody Captured on Protein A The running buffer used was HBS-EP+. Each antibody was prepared at 0.25 μg/ml, or prepared so that about 100 RU would bind to Protein A. rhNR10 used as an analyte was prepared at 0, 38.5, 77.0, and 154 nM, or at 0, 19.25, and 77.01 nM using HBS-EP+. In the measurement, first, the antibody solution was captured on Protein A, and an analyte solution was reacted at a flow rate of 20 μL/min for three minutes. Then, the solution was switched to HBS-EP+, and the dissociation phase was measured for five minutes. After measurement of the dissociation phase, the sensor chip was regenerated by washing with 10 mM glycine-HCl (pH 1.5). The obtained sensorgrams were kinetically analyzed using the Biacore-specific data analysis software, Biacore T100 Evaluation Software Version 1.1.

Industrial Applicability

The anti-NR10 antibodies obtained by the present inventors exhibit an effective neutralizing activity against NR10, and are useful as, for example, therapeutic agents for inflammatory diseases.

The invention claimed is:

1. An isolated anti-NR10 antibody selected from the group consisting of:

(1) an antibody comprising a heavy chain variable region comprising the amino acid sequence of SEQ ID NO: 206 and a light chain variable region comprising the amino acid sequence of SEQ ID NO: 220;

(2) an antibody comprising a heavy chain variable region comprising the amino acid sequence of SEQ ID NO: 207 and a light chain variable region comprising the amino acid sequence of SEQ ID NO: 220;

(3) an antibody comprising a heavy chain variable region comprising the amino acid sequence of SEQ ID NO: 208 and a light chain variable region comprising the amino acid sequence of SEQ ID NO: 220;

(4) an antibody comprising a heavy chain variable region comprising the amino acid sequence of SEQ ID NO: 209 and a light chain variable region comprising the amino acid sequence of SEQ ID NO: 220;

(5) an antibody comprising a heavy chain variable region comprising the amino acid sequence of SEQ ID NO: 210 and a light chain variable region comprising the amino acid sequence of SEQ ID NO: 220;

(6) an antibody comprising a heavy chain variable region comprising the amino acid sequence of SEQ ID NO: 211 and a light chain variable region comprising the amino acid sequence of SEQ ID NO: 220;

(7) an antibody comprising a heavy chain variable region comprising the amino acid sequence of SEQ ID NO: 212 and a light chain variable region comprising the amino acid sequence of SEQ ID NO: 220;

(8) an antibody comprising a heavy chain variable region comprising the amino acid sequence of SEQ ID NO: 213 and a light chain variable region comprising the amino acid sequence of SEQ ID NO: 220;

(9) an antibody comprising a heavy chain variable region comprising the amino acid sequence of SEQ ID NO: 214 and a light chain variable region comprising the amino acid sequence of SEQ ID NO: 220;

(10) an antibody comprising a heavy chain variable region comprising the amino acid sequence of SEQ ID NO: 215 and a light chain variable region comprising the amino acid sequence of SEQ ID NO: 220;

(11) an antibody comprising a heavy chain variable region comprising the amino acid sequence of SEQ ID NO: 216 and a light chain variable region comprising the amino acid sequence of SEQ ID NO: 221; and

(12) an antibody comprising a heavy chain variable region comprising the amino acid sequence of SEQ ID NO: 217 and a light chain variable region comprising the amino acid sequence of SEQ ID NO: 221.

2. A pharmaceutical composition comprising the antibody of claim 1.

3. An isolated anti-NR10 antibody selected from the group consisting of:

(1) an antibody comprising a heavy chain comprising the amino acid sequence of SEQ ID NO: 224 and a light chain comprising the amino acid sequence of SEQ ID NO: 238;

(2) an antibody comprising a heavy chain comprising the amino acid sequence of SEQ ID NO: 225 and a light chain comprising the amino acid sequence of SEQ ID NO: 238;

(3) an antibody comprising a heavy chain comprising the amino acid sequence of SEQ ID NO: 226 and a light chain comprising the amino acid sequence of SEQ ID NO: 238;

(4) an antibody comprising a heavy chain comprising the amino acid sequence of SEQ ID NO: 227 and a light chain comprising the amino acid sequence of SEQ ID NO: 238;

(5) an antibody comprising a heavy chain comprising the amino acid sequence of SEQ ID NO: 228 and a light chain comprising the amino acid sequence of SEQ ID NO: 238;

(6) an antibody comprising a heavy chain comprising the amino acid sequence of SEQ ID NO: 229 and a light chain comprising the amino acid sequence of SEQ ID NO: 238;

(7) an antibody comprising a heavy chain comprising the amino acid sequence of SEQ ID NO: 230 and a light chain comprising the amino acid sequence of SEQ ID NO: 238;

(8) an antibody comprising a heavy chain comprising the amino acid sequence of SEQ ID NO: 231 and a light chain comprising the amino acid sequence of SEQ ID NO: 238;

(9) an antibody comprising a heavy chain comprising the amino acid sequence of SEQ ID NO: 232 and a light chain comprising the amino acid sequence of SEQ ID NO: 238;

(10) an antibody comprising a heavy chain comprising the amino acid sequence of SEQ ID NO: 233 and a light chain comprising the amino acid sequence of SEQ ID NO: 238;

(11) an antibody comprising a heavy chain comprising the amino acid sequence of SEQ ID NO: 234 and a light chain comprising the amino acid sequence of SEQ ID NO: 239; and

(12) an antibody comprising a heavy chain comprising the amino acid sequence of SEQ ID NO: 235 and a light chain comprising the amino acid sequence of SEQ ID NO: 239.

4. A pharmaceutical composition comprising the antibody of claim 3.

5. A method of treating atopic dermatitis in a subject in need thereof, the method comprising administering to the subject a therapeutically effective amount of the pharmaceutical composition of claim 2.

6. A method of treating atopic dermatitis in a subject in need thereof, the method comprising administering to the subject a therapeutically effective amount of the pharmaceutical composition of claim 4.

7. A method of treating chronic dermatitis in a subject in need thereof, the method comprising administering to the subject a therapeutically effective amount of the pharmaceutical composition of claim 2.

8. A method of treating chronic dermatitis in a subject in need thereof, the method comprising administering to the subject a therapeutically effective amount of the pharmaceutical composition of claim 4.

9. A method of treating rheumatism in a subject in need thereof, the method comprising administering to the subject a therapeutically effective amount of the pharmaceutical composition of claim 2.

10. A method of treating rheumatism in a subject in need thereof, the method comprising administering to the subject a therapeutically effective amount of the pharmaceutical composition of claim 4.

11. A method of treating osteoarthritis in a subject in need thereof, the method comprising administering to the subject a therapeutically effective amount of the pharmaceutical composition of claim 2.

12. A method of treating osteoarthritis in a subject in need thereof, the method comprising administering to the subject a therapeutically effective amount of the pharmaceutical composition of claim 4.

13. A method of treating rheumatoid arthritis in a subject in need thereof, the method comprising administering to the subject a therapeutically effective amount of the pharmaceutical composition of claim 2.

14. A method of treating rheumatoid arthritis in a subject in need thereof, the method comprising administering to the subject a therapeutically effective amount of the pharmaceutical composition of claim 4.

* * * * *

SEQUENCE LISTING

```
<160> NUMBER OF SEQ ID NOS: 287

<210> SEQ ID NO 1
<211> LENGTH: 5
<212> TYPE: PRT
<213> ORGANISM: Mus musculus

<400> SEQUENCE: 1

Gly Tyr Ile Met Asn
1               5


<210> SEQ ID NO 2
<211> LENGTH: 17
<212> TYPE: PRT
<213> ORGANISM: Mus musculus

<400> SEQUENCE: 2

Leu Ile Asn Pro Tyr Asn Gly Asp Thr Asn Tyr Asn Gln Lys Phe Lys
1               5                   10                  15

Gly


<210> SEQ ID NO 3
<211> LENGTH: 12
<212> TYPE: PRT
<213> ORGANISM: Mus musculus

<400> SEQUENCE: 3

Asp Gly Tyr Asp Asp Gly Pro Tyr Thr Met Asp Tyr
1               5                   10


<210> SEQ ID NO 4
<211> LENGTH: 121
<212> TYPE: PRT
<213> ORGANISM: Mus musculus

<400> SEQUENCE: 4

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Ile Met Asn Trp Val Lys Gln Ser His Gly Lys Asn Leu Glu Trp Ile
        35                  40                  45

Gly Leu Ile Asn Pro Tyr Asn Gly Asp Thr Asn Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Asp Gly Tyr Asp Asp Gly Pro Tyr Thr Met Asp Tyr Trp Gly
```

```
        100                 105                 110

Gln Gly Thr Ser Val Thr Val Ser Ser
        115                 120


<210> SEQ ID NO 5
<211> LENGTH: 11
<212> TYPE: PRT
<213> ORGANISM: Mus musculus

<400> SEQUENCE: 5

Arg Ala Ser Glu Asn Ile Tyr Ser Phe Leu Ala
1               5                   10


<210> SEQ ID NO 6
<211> LENGTH: 7
<212> TYPE: PRT
<213> ORGANISM: Mus musculus

<400> SEQUENCE: 6

Asn Ala Lys Thr Leu Ala Lys
1               5


<210> SEQ ID NO 7
<211> LENGTH: 9
<212> TYPE: PRT
<213> ORGANISM: Mus musculus

<400> SEQUENCE: 7

Gln His His Tyr Glu Ser Pro Leu Thr
1               5


<210> SEQ ID NO 8
<211> LENGTH: 107
<212> TYPE: PRT
<213> ORGANISM: Mus musculus

<400> SEQUENCE: 8

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Phe
            20                  25                  30

Leu Ala Trp Tyr Gln Gln Lys Gln Gly Lys Ser Pro His Leu Leu Val
        35                  40                  45

Tyr Asn Ala Lys Thr Leu Ala Lys Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Glu Ser Pro Leu
                85                  90                  95

Thr Phe Gly Gly Gly Thr Lys Leu Glu Ile Lys
            100                 105


<210> SEQ ID NO 9
<211> LENGTH: 5
<212> TYPE: PRT
<213> ORGANISM: Mus musculus

<400> SEQUENCE: 9

Gly Tyr Ile Met Asn
1               5


<210> SEQ ID NO 10
```

<211> LENGTH: 17
<212> TYPE: PRT
<213> ORGANISM: Mus musculus

<400> SEQUENCE: 10

Leu Ile Asn Pro Tyr Asn Gly Gly Thr Ser Tyr Asn Gln Lys Phe Lys
1 5 10 15

Gly

<210> SEQ ID NO 11
<211> LENGTH: 12
<212> TYPE: PRT
<213> ORGANISM: Mus musculus

<400> SEQUENCE: 11

Asp Gly Tyr Asp Asp Gly Pro Tyr Thr Met Asp Tyr
1 5 10

<210> SEQ ID NO 12
<211> LENGTH: 121
<212> TYPE: PRT
<213> ORGANISM: Mus musculus

<400> SEQUENCE: 12

Glu Val Gln Leu Gln Gln Ser Gly Pro Glu Leu Val Lys Pro Gly Ala
1 5 10 15

Ser Met Lys Ile Ser Cys Lys Ala Ser Gly Tyr Ser Phe Thr Gly Tyr
20 25 30

Ile Met Asn Trp Val Lys Gln Ser His Gly Lys Asn Leu Glu Trp Ile
35 40 45

Gly Leu Ile Asn Pro Tyr Asn Gly Gly Thr Ser Tyr Asn Gln Lys Phe
50 55 60

Lys Gly Lys Ala Thr Leu Thr Val Asp Lys Ser Ser Ser Thr Ala Tyr
65 70 75 80

Met Glu Leu Leu Ser Leu Thr Ser Glu Asp Ser Ala Val Tyr Tyr Cys
85 90 95

Ala Arg Asp Gly Tyr Asp Asp Gly Pro Tyr Thr Met Asp Tyr Trp Gly
100 105 110

Gln Gly Thr Ser Val Thr Val Ser Ser
115 120

<210> SEQ ID NO 13
<211> LENGTH: 11
<212> TYPE: PRT
<213> ORGANISM: Mus musculus

<400> SEQUENCE: 13

Arg Thr Ser Glu Asn Ile Tyr Ser Phe Leu Ala
1 5 10

<210> SEQ ID NO 14
<211> LENGTH: 7
<212> TYPE: PRT
<213> ORGANISM: Mus musculus

<400> SEQUENCE: 14

Asn Ala Lys Thr Leu Ala Lys
1 5

<210> SEQ ID NO 15
<211> LENGTH: 9
<212> TYPE: PRT

<213> ORGANISM: Mus musculus

<400> SEQUENCE: 15

Gln His His Tyr Glu Ser Pro Leu Thr
1 5

<210> SEQ ID NO 16
<211> LENGTH: 107
<212> TYPE: PRT
<213> ORGANISM: Mus musculus

<400> SEQUENCE: 16

Asp Ile Gln Met Thr Gln Ser Pro Ala Ser Leu Ser Ala Ser Val Gly
1 5 10 15

Glu Thr Val Thr Ile Thr Cys Arg Thr Ser Glu Asn Ile Tyr Ser Phe
20 25 30

Leu Ala Trp Tyr Gln Gln Lys Gln Gly Lys Ser Pro His Leu Leu Val
35 40 45

Tyr Asn Ala Lys Thr Leu Ala Lys Gly Val Pro Ser Arg Phe Ser Gly
50 55 60

Ser Gly Ser Gly Thr Gln Phe Ser Leu Lys Ile Asn Ser Leu Gln Pro
65 70 75 80

Glu Asp Phe Gly Ser Tyr Phe Cys Gln His His Tyr Glu Ser Pro Leu
85 90 95

Thr Phe Gly Gly Gly Thr Lys Leu Glu Ile Lys
100 105

<210> SEQ ID NO 17
<211> LENGTH: 5
<212> TYPE: PRT
<213> ORGANISM: Mus musculus

<400> SEQUENCE: 17

Gly Tyr Ile Met Asn
1 5

<210> SEQ ID NO 18
<211> LENGTH: 17
<212> TYPE: PRT
<213> ORGANISM: Mus musculus

<400> SEQUENCE: 18

Leu Ile Asn Pro Tyr Asn Gly Gly Ala Glu Tyr Asn Gln Lys Phe Lys
1 5 10 15

Asp

<210> SEQ ID NO 19
<211> LENGTH: 12
<212> TYPE: PRT
<213> ORGANISM: Mus musculus

<400> SEQUENCE: 19

Asp Gly Tyr Asp Asp Gly Pro Tyr Thr Met Asp Tyr
1 5 10

<210> SEQ ID NO 20
<211> LENGTH: 121
<212> TYPE: PRT
<213> ORGANISM: Mus musculus

<400> SEQUENCE: 20

Glu Val Gln Leu Gln Gln Ser Gly Pro Glu Leu Val Lys Pro Gly Thr

-continued

```
1               5                   10                  15

Ser Met Lys Ile Ser Cys Lys Ala Ser Gly Tyr Ser Phe Thr Gly Tyr
            20                  25                  30

Ile Met Asn Trp Val Lys Gln Ser His Gly Lys Asn Leu Glu Trp Ile
        35                  40                  45

Gly Leu Ile Asn Pro Tyr Asn Gly Gly Ala Glu Tyr Asn Gln Lys Phe
    50                  55                  60

Lys Asp Lys Ala Thr Phe Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Asp Gly Tyr Asp Asp Gly Pro Tyr Thr Met Asp Tyr Trp Gly
            100                 105                 110

Gln Gly Thr Ser Val Thr Val Ser Ser
        115                 120


<210> SEQ ID NO 21
<211> LENGTH: 11
<212> TYPE: PRT
<213> ORGANISM: Mus musculus

<400> SEQUENCE: 21

Arg Ala Asn Glu Asn Ile Tyr Ser Tyr Leu Ala
1               5                   10


<210> SEQ ID NO 22
<211> LENGTH: 7
<212> TYPE: PRT
<213> ORGANISM: Mus musculus

<400> SEQUENCE: 22

Asn Ala Lys Thr Leu Ala Glu
1               5


<210> SEQ ID NO 23
<211> LENGTH: 9
<212> TYPE: PRT
<213> ORGANISM: Mus musculus

<400> SEQUENCE: 23

Gln His His Tyr Gly Thr Pro Pro Thr
1               5


<210> SEQ ID NO 24
<211> LENGTH: 107
<212> TYPE: PRT
<213> ORGANISM: Mus musculus

<400> SEQUENCE: 24

Asp Ile Gln Met Thr Gln Ser Pro Ala Ser Leu Ser Ala Ser Val Gly
1               5                   10                  15

Glu Thr Val Thr Phe Thr Cys Arg Ala Asn Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Pro
```

```
                85                  90                  95

Thr Phe Gly Gly Gly Thr Lys Leu Glu Ile Lys
            100                 105


<210> SEQ ID NO 25
<211> LENGTH: 5
<212> TYPE: PRT
<213> ORGANISM: Mus musculus

<400> SEQUENCE: 25

Asn Tyr Trp Met His
1               5


<210> SEQ ID NO 26
<211> LENGTH: 17
<212> TYPE: PRT
<213> ORGANISM: Mus musculus

<400> SEQUENCE: 26

Ala Ile Tyr Pro Gly Asn Ser Asp Thr Asp Tyr Asn Gln Lys Phe Lys
1               5                   10                  15

Gly


<210> SEQ ID NO 27
<211> LENGTH: 8
<212> TYPE: PRT
<213> ORGANISM: Mus musculus

<400> SEQUENCE: 27

Asp Gly Tyr Asp Asp Phe Asp His
1               5


<210> SEQ ID NO 28
<211> LENGTH: 116
<212> TYPE: PRT
<213> ORGANISM: Mus musculus

<400> SEQUENCE: 28

Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Thr Phe Thr Asn Tyr
            20                  25                  30

Trp Met His Trp Val Lys Gln Arg Pro Gly Gln Gly Leu Glu Trp Ile
        35                  40                  45

Gly Ala Ile Tyr Pro Gly Asn Ser Asp Thr Asp Tyr Asn Gln Lys Phe
    50                  55                  60

Lys Gly Lys Ala Lys Leu Thr Ala Val Thr Ser Ala Ser Thr Ala Tyr
65                  70                  75                  80

Met Glu Leu Ser Ser Leu Thr Asn Glu Asp Ser Ala Val Phe Phe Cys
                85                  90                  95

Thr Thr Gly Tyr Asp Asp Phe Asp His Trp Gly Gln Gly Thr Thr Leu
            100                 105                 110

Thr Val Ser Ser
        115


<210> SEQ ID NO 29
<211> LENGTH: 12
<212> TYPE: PRT
<213> ORGANISM: Mus musculus

<400> SEQUENCE: 29
```

Arg Ala Ser Ser Ser Val Ser Ser Ser Tyr Leu His
1 5 10

<210> SEQ ID NO 30
<211> LENGTH: 7
<212> TYPE: PRT
<213> ORGANISM: Mus musculus

<400> SEQUENCE: 30

Ser Thr Ser Asn Leu Ala Ser
1 5

<210> SEQ ID NO 31
<211> LENGTH: 9
<212> TYPE: PRT
<213> ORGANISM: Mus musculus

<400> SEQUENCE: 31

Gln Gln Tyr Ser Gly Tyr Pro Leu Thr
1 5

<210> SEQ ID NO 32
<211> LENGTH: 108
<212> TYPE: PRT
<213> ORGANISM: Mus musculus

<400> SEQUENCE: 32

Glu Asn Val Leu Thr Gln Ser Pro Ala Ile Met Ser Ala Ser Pro Gly
1 5 10 15

Glu Lys Val Thr Met Thr Cys Arg Ala Ser Ser Ser Val Ser Ser Ser
20 25 30

Tyr Leu His Trp Tyr Gln Gln Lys Ser Gly Ala Ser Pro Lys Leu Trp
35 40 45

Ile Tyr Ser Thr Ser Asn Leu Ala Ser Gly Val Pro Ala Arg Phe Ser
50 55 60

Gly Ser Gly Ser Gly Thr Ser Tyr Tyr Phe Thr Ile Ser Ser Val Glu
65 70 75 80

Ala Glu Asp Ala Ala Thr Tyr Tyr Cys Gln Gln Tyr Ser Gly Tyr Pro
85 90 95

Leu Thr Phe Gly Gly Gly Thr Lys Leu Glu Ile Lys
100 105

<210> SEQ ID NO 33
<211> LENGTH: 1406
<212> TYPE: DNA
<213> ORGANISM: Mus musculus

<400> SEQUENCE: 33
atgggatgga gctggatctt tctcttcctc ctgtcaggaa ctgcaggtgt ccactctgag 60
gtccagctgc aacagtctgg acctgagctg gtgaagcctg gagcttcaat gaagatctcc 120
tgcaaggctt ctggttactc attcactggc tacatcatga actgggtgaa gcagagccat 180
ggaaagaacc ttgagtggat tggacttatt aatccttaca atggtgatac taactacaac 240
cagaagttca agggcaaggc cacattaact gtagacaagt catccagcac agcctacatg 300
gaactcctca gtctgacatc agaggactct gcagtctatt actgtgcaag ggatggttac 360
gacgacggac cctatactat ggactactgg ggtcaaggaa cctcagtcac cgtctcctca 420
gccaaaacga cacccccatc tgtctatcca ctggcccctg gatctgctgc ccaaactaac 480
tccatggtga ccctgggatg cctggtcaag ggctatttcc ctgagccagt gacagtgacc 540

-continued

```
tggaactctg gatccctgtc cagcggtgtg cacaccttcc cagctgtcct gcagtctgac    600

ctctacactc tgagcagctc agtgactgtc ccctccagca cctggcccag cgagaccgtc    660

acctgcaacg ttgcccaccc ggccagcagc accaaggtgg acaagaaaat tgtgcccagg    720

gattgtggtt gtaagccttg catatgtaca gtcccagaag tatcatctgt cttcatcttc    780

cccccaaagc ccaaggatgt gctcaccatt actctgactc ctaaggtcac gtgtgttgtg    840

gtagacatca gcaaggatga tcccgaggtc cagttcagct ggtttgtaga tgatgtggag    900

gtgcacacag ctcagacgca accccgggag gagcagttca acagcacttt ccgctcagtc    960

agtgaacttc ccatcatgca ccaggactgg ctcaatggca aggagttcaa atgcagggtc   1020

aacagtgcag ctttccctgc ccccatcgag aaaaccatct ccaaaaccaa aggcagaccg   1080

aaggctccac aggtgtacac cattccacct cccaaggagc agatggccaa ggataaagtc   1140

agtctgacct gcatgataac agacttcttc cctgaagaca ttactgtgga gtggcagtgg   1200

aatgggcagc cagcggagaa ctacaagaac actcagccca tcatggacac agatggctct   1260

tacttcgtct acagcaagct caatgtgcag aagagcaact gggaggcagg aaatactttc   1320

acctgctctg tgttacatga gggcctgcac aaccaccata ctgagaagag cctctcccac   1380

tctcctggta aataatgagc ggccgc                                        1406
```

<210> SEQ ID NO 34
<211> LENGTH: 445
<212> TYPE: PRT
<213> ORGANISM: Mus musculus

<400> SEQUENCE: 34

```
Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Ile Met Asn Trp Val Lys Gln Ser His Gly Lys Asn Leu Glu Trp Ile
        35                  40                  45

Gly Leu Ile Asn Pro Tyr Asn Gly Asp Thr Asn Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Asp Gly Tyr Asp Asp Gly Pro Tyr Thr Met Asp Tyr Trp Gly
            100                 105                 110

Gln Gly Thr Ser Val Thr Val Ser Ser Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
            180                 185                 190

Ser Ser Thr Trp Pro Ser Glu Thr Val Thr Cys Asn Val Ala His Pro
        195                 200                 205

Ala Ser Ser Thr Lys Val Asp Lys Lys Ile Val Pro Arg Asp Cys Gly
    210                 215                 220
```

```
Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Val Asp Ile Ser Lys Asp Asp Pro Glu Val Gln
            260                 265                 270

Phe Ser Trp Phe Val Asp Asp Val Glu Val His Thr Ala Gln Thr Gln
        275                 280                 285

Pro Arg Glu Glu Gln Phe Asn Ser Thr Phe Arg Ser Val Ser Glu Leu
    290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335

Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
        355                 360                 365

Asp Phe Phe Pro Glu Asp Ile Thr Val Glu Trp Gln Trp Asn Gly Gln
    370                 375                 380

Pro Ala Glu Asn Tyr Lys Asn Thr Gln Pro Ile Met Asp Thr Asp Gly
385                 390                 395                 400

Ser Tyr Phe Val Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly Lys
        435                 440                 445

<210> SEQ ID NO 35
<211> LENGTH: 716
<212> TYPE: DNA
<213> ORGANISM: Mus musculus

<400> SEQUENCE: 35

atgagtgtgc ccactcaggt cctggggttg ctgctgctgt ggcttacagg tgccagatgt      60

gacatccaga tgactcagtc tccagcctcc ctatctgcat ctgtgggaga aactgtcacc     120

atcacatgtc gagcaagtga gaatatttac agttttttag catggtatca gcagaaacag     180

ggaaaatctc ctcacctcct ggtctataat gcaaaaacct tagcaaaagg tgtgccatca     240

aggttcagtg gcagtggatc tggcacacag ttttctctga agatcaacag cctgcagcct     300

gaagattttg ggagttatta ctgtcaacat cattatgaga gtcctctgac gttcggtgga     360

ggcaccaagc tggaaatcaa acgggctgat gctgcaccaa ctgtatccat cttcccacca     420

tccagtgagc agttaacatc tggaggtgcc tcagtcgtgt gcttcttgaa caacttctac     480

cccaaagaca tcaatgtcaa gtggaagatt gatggcagtg aacgacaaaa tggcgtcctg     540

aacagttgga ctgatcagga cagcaaagac agcacctaca gcatgagcag caccctcacg     600

ttgaccaagg acgagtatga acgacataac agctatacct gtgaggccac tcacaagaca     660

tcaacttcac ccattgtcaa gagcttcaac aggaatgagt gttaatgagc ggccgc        716

<210> SEQ ID NO 36
<211> LENGTH: 214
<212> TYPE: PRT
<213> ORGANISM: Mus musculus
```

<400> SEQUENCE: 36

Asp Ile Gln Met Thr Gln Ser Pro Ala Ser Leu Ser Ala Ser Val Gly
1 5 10 15

Glu Thr Val Thr Ile Thr Cys Arg Ala Ser Glu Asn Ile Tyr Ser Phe
20 25 30

Leu Ala Trp Tyr Gln Gln Lys Gln Gly Lys Ser Pro His Leu Leu Val
35 40 45

Tyr Asn Ala Lys Thr Leu Ala Lys Gly Val Pro Ser Arg Phe Ser Gly
50 55 60

Ser Gly Ser Gly Thr Gln Phe Ser Leu Lys Ile Asn Ser Leu Gln Pro
65 70 75 80

Glu Asp Phe Gly Ser Tyr Tyr Cys Gln His His Tyr Glu Ser Pro Leu
85 90 95

Thr Phe Gly Gly Gly Thr Lys Leu Glu Ile Lys Arg Ala Asp Ala Ala
100 105 110

Pro Thr Val Ser Ile Phe Pro Pro Ser Ser Glu Gln Leu Thr Ser Gly
115 120 125

Gly Ala Ser Val Val Cys Phe Leu Asn Asn Phe Tyr Pro Lys Asp Ile
130 135 140

Asn Val Lys Trp Lys Ile Asp Gly Ser Glu Arg Gln Asn Gly Val Leu
145 150 155 160

Asn Ser Trp Thr Asp Gln Asp Ser Lys Asp Ser Thr Tyr Ser Met Ser
165 170 175

Ser Thr Leu Thr Leu Thr Lys Asp Glu Tyr Glu Arg His Asn Ser Tyr
180 185 190

Thr Cys Glu Ala Thr His Lys Thr Ser Thr Ser Pro Ile Val Lys Ser
195 200 205

Phe Asn Arg Asn Glu Cys
210

<210> SEQ ID NO 37
<211> LENGTH: 1406
<212> TYPE: DNA
<213> ORGANISM: Mus musculus

<400> SEQUENCE: 37
atgggatgga gctggatctt tctcttcctc ctgtcaggaa ctgcaggtgt ccactctgag 60
gtccagctgc aacagtctgg acctgagctg gtgaagcctg gagcttcaat gaagatctcc 120
tgcaaggctt ctggttactc attcactggc tacatcatga actgggtgaa gcagagccat 180
ggaaagaacc ttgagtggat tggacttatt aatccttaca atggtggtac tagctacaac 240
cagaagttca agggcaaggc cacattaact gtagacaagt catccagtac agcctacatg 300
gaactcctca gtctgacatc agaggactct gcagtctatt actgtgcaag ggatggttac 360
gacgacggac cctatactat ggactactgg ggtcaaggaa cctcagtcac cgtctcctca 420
gccaaaacga cacccccatc tgtctatcca ctggcccctg gatctgctgc ccaaactaac 480
tccatggtga ccctgggatg cctggtcaag ggctatttcc ctgagccagt gacagtgacc 540
tggaactctg gatccctgtc cagcggtgtg cacaccttcc cagctgtcct gcagtctgac 600
ctctacactc tgagcagctc agtgactgtc ccctccagca cctggcccag cgagaccgtc 660
acctgcaacg ttgcccaccc ggccagcagc accaaggtgg acaagaaaat tgtgcccagg 720
gattgtggtt gtaagccttg catatgtaca gtcccagaag tatcatctgt cttcatcttc 780
cccccaaagc ccaaggatgt gctcaccatt actctgactc ctaaggtcac gtgtgttgtg 840

```
gtagacatca gcaaggatga tcccgaggtc cagttcagct ggtttgtaga tgatgtggag    900

gtgcacacag ctcagacgca accccgggag gagcagttca acagcacttt ccgctcagtc    960

agtgaacttc ccatcatgca ccaggactgg ctcaatggca aggagttcaa atgcagggtc   1020

aacagtgcag ctttccctgc ccccatcgag aaaaccatct ccaaaaccaa aggcagaccg   1080

aaggctccac aggtgtacac cattccacct cccaaggagc agatggccaa ggataaagtc   1140

agtctgacct gcatgataac agacttcttc cctgaagaca ttactgtgga gtggcagtgg   1200

aatgggcagc cagcggagaa ctacaagaac actcagccca tcatggacac agatggctct   1260

tacttcgtct acagcaagct caatgtgcag aagagcaact gggaggcagg aaatactttc   1320

acctgctctg tgttacatga gggcctgcac aaccaccata ctgagaagag cctctcccac   1380

tctcctggta aataatgagc ggccgc                                        1406


<210> SEQ ID NO 38
<211> LENGTH: 445
<212> TYPE: PRT
<213> ORGANISM: Mus musculus

<400> SEQUENCE: 38

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Ile Met Asn Trp Val Lys Gln Ser His Gly Lys Asn Leu Glu Trp Ile
        35                  40                  45

Gly Leu Ile Asn Pro Tyr Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Asp Gly Tyr Asp Asp Gly Pro Tyr Thr Met Asp Tyr Trp Gly
            100                 105                 110

Gln Gly Thr Ser Val Thr Val Ser Ser Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
            180                 185                 190

Ser Ser Thr Trp Pro Ser Glu Thr Val Thr Cys Asn Val Ala His Pro
        195                 200                 205

Ala Ser Ser Thr Lys Val Asp Lys Lys Ile Val Pro Arg Asp Cys Gly
    210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Val Asp Ile Ser Lys Asp Asp Pro Glu Val Gln
            260                 265                 270

Phe Ser Trp Phe Val Asp Asp Val Glu Val His Thr Ala Gln Thr Gln
```

-continued

```
        275                 280                 285

Pro Arg Glu Glu Gln Phe Asn Ser Thr Phe Arg Ser Val Ser Glu Leu
    290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335

Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
        355                 360                 365

Asp Phe Phe Pro Glu Asp Ile Thr Val Glu Trp Gln Trp Asn Gly Gln
    370                 375                 380

Pro Ala Glu Asn Tyr Lys Asn Thr Gln Pro Ile Met Asp Thr Asp Gly
385                 390                 395                 400

Ser Tyr Phe Val Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly Lys
        435                 440                 445
```

<210> SEQ ID NO 39
<211> LENGTH: 716
<212> TYPE: DNA
<213> ORGANISM: Mus musculus

<400> SEQUENCE: 39

```
atgagtgtgc ccactcaggt cctggggttg ctgctgctgt ggcttacagg tgccagatgt     60

gacatccaga tgactcagtc tccagcctcc ctatctgcat ctgtgggaga aactgtcacc    120

atcacatgtc gaacaagtga gaatatttac agttttttag catggtatca gcagaaacag    180

ggaaaatctc ctcacctcct ggtctataat gcaaaaacct tagcaaaagg tgtgccatca    240

aggttcagtg gcagtggatc tggcacacag ttttctctga agatcaacag cctgcagcct    300

gaagattttg ggagttattt ctgtcaacat cattatgaga gtcctctgac gttcggtgga    360

ggcaccaagc tggaaatcaa acgggctgat gctgcaccaa ctgtatccat cttcccacca    420

tccagtgagc agttaacatc tggaggtgcc tcagtcgtgt gcttcttgaa caacttctac    480

cccaaagaca tcaatgtcaa gtggaagatt gatggcagtg aacgacaaaa tggcgtcctg    540

aacagttgga ctgatcagga cagcaaagac agcacctaca gcatgagcag caccctcacg    600

ttgaccaagg acgagtatga acgacataac agctatacct gtgaggccac tcacaagaca    660

tcaacttcac ccattgtcaa gagcttcaac aggaatgagt gttaatgagc ggccgc        716
```

<210> SEQ ID NO 40
<211> LENGTH: 214
<212> TYPE: PRT
<213> ORGANISM: Mus musculus

<400> SEQUENCE: 40

```
Asp Ile Gln Met Thr Gln Ser Pro Ala Ser Leu Ser Ala Ser Val Gly
1               5                   10                  15

Glu Thr Val Thr Ile Thr Cys Arg Thr Ser Glu Asn Ile Tyr Ser Phe
            20                  25                  30

Leu Ala Trp Tyr Gln Gln Lys Gln Gly Lys Ser Pro His Leu Leu Val
        35                  40                  45
```

-continued

```
Tyr Asn Ala Lys Thr Leu Ala Lys Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Phe Cys Gln His His Tyr Glu Ser Pro Leu
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 41
<211> LENGTH: 1406
<212> TYPE: DNA
<213> ORGANISM: Mus musculus

<400> SEQUENCE: 41

```
atgggatgga gctggatctt tctcttcctc ctgtcaggaa ctgcaggtgt ccactctgag      60

gtccagctgc aacagtctgg acctgagctg gtgaagcctg gaacttcaat gaagatatcc     120

tgcaaggctt ctggttactc attcactggc tacatcatga actgggtgaa gcagagccat     180

ggaaagaacc ttgagtggat tggacttatt aatccttaca atggtggtgc tgagtacaac     240

cagaagttca aggacaaggc cacattcact gtagacaagt catccagcac agcctacatg     300

gagctcctca gtctgacatc tgaagactct gcagtctatt actgtgcaag ggatggttac     360

gacgacggac cctatactat ggactactgg ggtcaaggaa cctcagtcac cgtctcctca     420

gccaaaacga cacccccatc tgtctatcca ctggcccctg gatctgctgc ccaaactaac     480

tccatggtga ccctgggatg cctggtcaag ggctatttcc ctgagccagt gacagtgacc     540

tggaactctg gatccctgtc cagcggtgtg cacaccttcc cagctgtcct gcagtctgac     600

ctctacactc tgagcagctc agtgactgtc ccctccagca cctggcccag cgagaccgtc     660

acctgcaacg ttgcccaccc ggccagcagc accaaggtgg acaagaaaat tgtgcccagg     720

gattgtggtt gtaagccttg catatgtaca gtcccagaag tatcatctgt cttcatcttc     780

cccccaaagc ccaaggatgt gctcaccatt actctgactc ctaaggtcac gtgtgttgtg     840

gtagacatca gcaaggatga tcccgaggtc cagttcagct ggtttgtaga tgatgtggag     900

gtgcacacag ctcagacgca accccgggag gagcagttca acagcacttt ccgctcagtc     960

agtgaacttc ccatcatgca ccaggactgg ctcaatggca aggagttcaa atgcagggtc    1020

aacagtgcag ctttccctgc ccccatcgag aaaaccatct ccaaaaccaa aggcagaccg    1080

aaggctccac aggtgtacac cattccacct cccaaggagc agatggccaa ggataaagtc    1140
```

-continued

```
agtctgacct gcatgataac agacttcttc cctgaagaca ttactgtgga gtggcagtgg   1200

aatgggcagc cagcggagaa ctacaagaac actcagccca tcatggacac agatggctct   1260

tacttcgtct acagcaagct caatgtgcag aagagcaact gggaggcagg aaatactttc   1320

acctgctctg tgttacatga gggcctgcac aaccaccata ctgagaagag cctctcccac   1380

tctcctggta aataatgagc ggccgc                                        1406
```

<210> SEQ ID NO 42
<211> LENGTH: 445
<212> TYPE: PRT
<213> ORGANISM: Mus musculus

<400> SEQUENCE: 42

```
Glu Val Gln Leu Gln Gln Ser Gly Pro Glu Leu Val Lys Pro Gly Thr
1               5                   10                  15

Ser Met Lys Ile Ser Cys Lys Ala Ser Gly Tyr Ser Phe Thr Gly Tyr
            20                  25                  30

Ile Met Asn Trp Val Lys Gln Ser His Gly Lys Asn Leu Glu Trp Ile
        35                  40                  45

Gly Leu Ile Asn Pro Tyr Asn Gly Gly Ala Glu Tyr Asn Gln Lys Phe
    50                  55                  60

Lys Asp Lys Ala Thr Phe Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Asp Gly Tyr Asp Asp Gly Pro Tyr Thr Met Asp Tyr Trp Gly
            100                 105                 110

Gln Gly Thr Ser Val Thr Val Ser Ser Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
            180                 185                 190

Ser Ser Thr Trp Pro Ser Glu Thr Val Thr Cys Asn Val Ala His Pro
        195                 200                 205

Ala Ser Ser Thr Lys Val Asp Lys Lys Ile Val Pro Arg Asp Cys Gly
    210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Val Asp Ile Ser Lys Asp Asp Pro Glu Val Gln
            260                 265                 270

Phe Ser Trp Phe Val Asp Asp Val Glu Val His Thr Ala Gln Thr Gln
        275                 280                 285

Pro Arg Glu Glu Gln Phe Asn Ser Thr Phe Arg Ser Val Ser Glu Leu
    290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335
```

```
Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
        355                 360                 365

Asp Phe Phe Pro Glu Asp Ile Thr Val Glu Trp Gln Trp Asn Gly Gln
    370                 375                 380

Pro Ala Glu Asn Tyr Lys Asn Thr Gln Pro Ile Met Asp Thr Asp Gly
385                 390                 395                 400

Ser Tyr Phe Val Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly Lys
        435                 440                 445


<210> SEQ ID NO 43
<211> LENGTH: 716
<212> TYPE: DNA
<213> ORGANISM: Mus musculus

<400> SEQUENCE: 43

atgagtgtgc ccactcaggt cctggggttg ctgctgctgt ggcttacagg tgccagatgt      60

gacatccaga tgactcagtc tccagcctcc ctatctgcat ctgtgggaga aactgtcacc     120

ttcacatgtc gagcaaatga gaatatttac agttatttag catggtatca gcagaaacag     180

ggaaaatctc ctcagctcct ggtctataat gcaaaaacct tagcagaagg tgtgccatca     240

aggttcagtg gcagtggatc aggcacacag ttttctctga agatcaacag cctgcagcct     300

gaagattttg ggagttatta ctgtcaacat cattatggaa ctcctccgac gttcggtgga     360

ggcaccaagc tggaaatcaa acgggctgat gctgcaccaa ctgtatccat cttcccacca     420

tccagtgagc agttaacatc tggaggtgcc tcagtcgtgt gcttcttgaa caacttctac     480

cccaaagaca tcaatgtcaa gtggaagatt gatggcagtg aacgacaaaa tggcgtcctg     540

aacagttgga ctgatcagga cagcaaagac agcacctaca gcatgagcag caccctcacg     600

ttgaccaagg acgagtatga acgacataac agctatacct gtgaggccac tcacaagaca     660

tcaacttcac ccattgtcaa gagcttcaac aggaatgagt gttaatgagc ggccgc         716


<210> SEQ ID NO 44
<211> LENGTH: 214
<212> TYPE: PRT
<213> ORGANISM: Mus musculus

<400> SEQUENCE: 44

Asp Ile Gln Met Thr Gln Ser Pro Ala Ser Leu Ser Ala Ser Val Gly
1               5                   10                  15

Glu Thr Val Thr Phe Thr Cys Arg Ala Asn Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Pro
                85                  90                  95
```

-continued

```
Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210


<210> SEQ ID NO 45
<211> LENGTH: 1391
<212> TYPE: DNA
<213> ORGANISM: Mus musculus

<400> SEQUENCE: 45

atggaatgta actggatact tccttttatt ctgtcggtaa tttcaggggt ctactcagag      60

gttcagctcc agcagtctgg gactgtgctg gcaaggcctg gggcttccgt gaagatgtcc     120

tgcaaggctt ctggctacac ctttaccaac tactggatgc actgggtaaa acagaggcct     180

ggacagggtc tagaatggat tggtgctatt tatcctggaa atagtgatac tgactacaac     240

cagaagttca agggcaaggc caaactgact gcagtcacat ccgccagcac tgcctacatg     300

gaactcagca gcctgacaaa tgaggactct gcggtctttt tctgtaccac tggttacgac     360

gacttcgacc actggggcca aggcaccact ctcacagtct cctcagccaa aacgacaccc     420

ccatctgtct atccactggc ccctggatct gctgcccaaa ctaactccat ggtgaccctg     480

ggatgcctgg tcaagggcta tttccctgag ccagtgacag tgacctggaa ctctggatcc     540

ctgtccagcg gtgtgcacac cttcccagct gtcctgcagt ctgacctcta cactctgagc     600

agctcagtga ctgtcccctc cagcacctgg cccagcgaga ccgtcacctg caacgttgcc     660

cacccggcca gcagcaccaa ggtggacaag aaaattgtgc ccagggattg tggttgtaag     720

ccttgcatat gtacagtccc agaagtatca tctgtcttca tcttcccccc aaagcccaag     780

gatgtgctca ccattactct gactcctaag gtcacgtgtg ttgtggtaga catcagcaag     840

gatgatcccg aggtccagtt cagctggttt gtagatgatg tggaggtgca cacagctcag     900

acgcaacccc gggaggagca gttcaacagc actttccgct cagtcagtga acttcccatc     960

atgcaccagg actggctcaa tggcaaggag ttcaaatgca gggtcaacag tgcagctttc    1020

cctgccccca tcgagaaaac catctccaaa accaaaggca gaccgaaggc tccacaggtg    1080

tacaccattc cacctcccaa ggagcagatg gccaaggata aagtcagtct gacctgcatg    1140

ataacagact tcttccctga agacattact gtggagtggc agtggaatgg gcagccagcg    1200

gagaactaca agaacactca gcccatcatg gacacagatg gctcttactt cgtctacagc    1260

aagctcaatg tgcagaagag caactgggag gcaggaaata ctttcacctg ctctgtgtta    1320

catgagggcc tgcacaacca ccatactgag aagagcctct cccactctcc tggtaaataa    1380

tgagcggccg c                                                         1391
```

<210> SEQ ID NO 46
<211> LENGTH: 440
<212> TYPE: PRT
<213> ORGANISM: Mus musculus

<400> SEQUENCE: 46

Glu Val Gln Leu Gln Gln Ser Gly Thr Val Leu Ala Arg Pro Gly Ala
1 5 10 15

Ser Val Lys Met Ser Cys Lys Ala Ser Gly Tyr Thr Phe Thr Asn Tyr
20 25 30

Trp Met His Trp Val Lys Gln Arg Pro Gly Gln Gly Leu Glu Trp Ile
35 40 45

Gly Ala Ile Tyr Pro Gly Asn Ser Asp Thr Asp Tyr Asn Gln Lys Phe
50 55 60

Lys Gly Lys Ala Lys Leu Thr Ala Val Thr Ser Ala Ser Thr Ala Tyr
65 70 75 80

Met Glu Leu Ser Ser Leu Thr Asn Glu Asp Ser Ala Val Phe Phe Cys
85 90 95

Thr Thr Gly Tyr Asp Asp Phe Asp His Trp Gly Gln Gly Thr Thr Leu
100 105 110

Thr Val Ser Ser Ala Lys Thr Thr Pro Pro Ser Val Tyr Pro Leu Ala
115 120 125

Pro Gly Ser Ala Ala Gln Thr Asn Ser Met Val Thr Leu Gly Cys Leu
130 135 140

Val Lys Gly Tyr Phe Pro Glu Pro Val Thr Val Thr Trp Asn Ser Gly
145 150 155 160

Ser Leu Ser Ser Gly Val His Thr Phe Pro Ala Val Leu Gln Ser Asp
165 170 175

Leu Tyr Thr Leu Ser Ser Ser Val Thr Val Pro Ser Ser Thr Trp Pro
180 185 190

Ser Glu Thr Val Thr Cys Asn Val Ala His Pro Ala Ser Ser Thr Lys
195 200 205

Val Asp Lys Lys Ile Val Pro Arg Asp Cys Gly Cys Lys Pro Cys Ile
210 215 220

Cys Thr Val Pro Glu Val Ser Ser Val Phe Ile Phe Pro Pro Lys Pro
225 230 235 240

Lys Asp Val Leu Thr Ile Thr Leu Thr Pro Lys Val Thr Cys Val Val
245 250 255

Val Asp Ile Ser Lys Asp Asp Pro Glu Val Gln Phe Ser Trp Phe Val
260 265 270

Asp Asp Val Glu Val His Thr Ala Gln Thr Gln Pro Arg Glu Glu Gln
275 280 285

Phe Asn Ser Thr Phe Arg Ser Val Ser Glu Leu Pro Ile Met His Gln
290 295 300

Asp Trp Leu Asn Gly Lys Glu Phe Lys Cys Arg Val Asn Ser Ala Ala
305 310 315 320

Phe Pro Ala Pro Ile Glu Lys Thr Ile Ser Lys Thr Lys Gly Arg Pro
325 330 335

Lys Ala Pro Gln Val Tyr Thr Ile Pro Pro Pro Lys Glu Gln Met Ala
340 345 350

Lys Asp Lys Val Ser Leu Thr Cys Met Ile Thr Asp Phe Phe Pro Glu
355 360 365

Asp Ile Thr Val Glu Trp Gln Trp Asn Gly Gln Pro Ala Glu Asn Tyr
370 375 380

-continued

```
Lys Asn Thr Gln Pro Ile Met Asp Thr Asp Gly Ser Tyr Phe Val Tyr
385                 390                 395                 400

Ser Lys Leu Asn Val Gln Lys Ser Asn Trp Glu Ala Gly Asn Thr Phe
                405                 410                 415

Thr Cys Ser Val Leu His Glu Gly Leu His Asn His His Thr Glu Lys
            420                 425                 430

Ser Leu Ser His Ser Pro Gly Lys
        435                 440


<210> SEQ ID NO 47
<211> LENGTH: 725
<212> TYPE: DNA
<213> ORGANISM: Mus musculus

<400> SEQUENCE: 47

atggattttc tggtgcagat tttcagcttc ttgctaatca gtgcctcagt tgcaatgtcc      60

agaggagaaa atgtgctcac ccagtctcca gcaatcatgt ctgcatctcc aggggaaaag     120

gtcaccatga cctgcagggc cagctcaagt gtaagttcca gttacttgca ctggtaccag     180

cagaagtcag gtgcctcccc caaactctgg atttatagca cttccaactt ggcttctgga     240

gtccctgctc gcttcagtgg cagtgggtct gggacctctt actatttcac aatcagcagt     300

gtggaggctg aagatgctgc cacttattac tgccagcaat acagtggtta cccactcacg     360

ttcggagggg ggaccaagct ggaaataaaa cgggctgatg ctgcaccaac tgtatccatc     420

ttcccaccat ccagtgagca gttaacatct ggaggtgcct cagtcgtgtg cttcttgaac     480

aacttctacc ccaaagacat caatgtcaag tggaagattg atggcagtga acgacaaaat     540

ggcgtcctga acagttggac tgatcaggac agcaaagaca gcacctacag catgagcagc     600

accctcacgt tgaccaagga cgagtatgaa cgacataaca gctatacctg tgaggccact     660

cacaagacat caacttcacc cattgtcaag agcttcaaca ggaatgagtg ttaatgagcg     720

gccgc                                                                 725


<210> SEQ ID NO 48
<211> LENGTH: 215
<212> TYPE: PRT
<213> ORGANISM: Mus musculus

<400> SEQUENCE: 48

Glu Asn Val Leu Thr Gln Ser Pro Ala Ile Met Ser Ala Ser Pro Gly
1               5                   10                  15

Glu Lys Val Thr Met Thr Cys Arg Ala Ser Ser Ser Val Ser Ser Ser
            20                  25                  30

Tyr Leu His Trp Tyr Gln Gln Lys Ser Gly Ala Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Tyr Phe Thr Ile Ser Ser Val Glu
65                  70                  75                  80

Ala Glu Asp Ala Ala Thr Tyr Tyr Cys Gln Gln Tyr Ser Gly Tyr Pro
                85                  90                  95

Leu Thr Phe Gly Gly Gly Thr Lys Leu Glu Ile Lys Arg Ala Asp Ala
            100                 105                 110

Ala Pro Thr Val Ser Ile Phe Pro Pro Ser Ser Glu Gln Leu Thr Ser
        115                 120                 125

Gly Gly Ala Ser Val Val Cys Phe Leu Asn Asn Phe Tyr Pro Lys Asp
    130                 135                 140
```

Ile Asn Val Lys Trp Lys Ile Asp Gly Ser Glu Arg Gln Asn Gly Val
145 150 155 160

Leu Asn Ser Trp Thr Asp Gln Asp Ser Lys Asp Ser Thr Tyr Ser Met
165 170 175

Ser Ser Thr Leu Thr Leu Thr Lys Asp Glu Tyr Glu Arg His Asn Ser
180 185 190

Tyr Thr Cys Glu Ala Thr His Lys Thr Ser Thr Ser Pro Ile Val Lys
195 200 205

Ser Phe Asn Arg Asn Glu Cys
210 215

<210> SEQ ID NO 49
<211> LENGTH: 425
<212> TYPE: DNA
<213> ORGANISM: Artificial
<220> FEATURE:
<223> OTHER INFORMATION: an artificially synthesized sequence

<400> SEQUENCE: 49
ccaccatgga ctggacctgg agggtcttct gcttgctggc tgtagctcca ggtgctcact 60
cccaggtgca gctggtgcag tctggggctg aggtgaagaa gcctggggcc tcagtgaagg 120
tttcctgcaa ggcatctgga tacaccttca ccggctacat catgaactgg gtgcgacagg 180
cccctggaca agggcttgag tggatgggac ttattaatcc ttacaatggt ggtactagct 240
acaaccagaa gttcaagggc agagtcacga ttaccgcgga cgaatccacg agcacagcct 300
acatggagct gagcagcctg agatctgagg acacggccgt gtattactgt gcgagagatg 360
gttacgacga cggaccctat actatggact actggggcca gggcaccctc gtcacagtct 420
cctca 425

<210> SEQ ID NO 50
<211> LENGTH: 121
<212> TYPE: PRT
<213> ORGANISM: Artificial
<220> FEATURE:
<223> OTHER INFORMATION: an artificially synthesized sequence

<400> SEQUENCE: 50

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Ile Met Asn Trp Val Arg Gln Ala Pro Gly Gln Gly Leu Glu Trp Met
35 40 45

Gly Leu Ile Asn Pro Tyr Asn Gly Gly Thr Ser Tyr Asn Gln Lys Phe
50 55 60

Lys Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Asp Gly Tyr Asp Asp Gly Pro Tyr Thr Met Asp Tyr Trp Gly
100 105 110

Gln Gly Thr Leu Val Thr Val Ser Ser
115 120

<210> SEQ ID NO 51
<211> LENGTH: 398
<212> TYPE: DNA

<213> ORGANISM: Artificial
<220> FEATURE:
<223> OTHER INFORMATION: an artificially synthesized sequence

<400> SEQUENCE: 51
ccaccatgga catgagggtc cccgctcagc tcctggggct cctgctactc tggctccgag 60
gtgccagatg tgacatccag atgacccagt ctccatcctc cctgtctgca tctgtaggag 120
acagagtcac catcacttgc cgaacaagtg agaatattta cagtttttta gcatggtatc 180
agcagaaacc agggaaagcc cctaagctcc tgatctataa tgcaaaaacc ttagcaaaag 240
gggtcccatc aaggttcagt ggcagtggat ctgggacaga tttcactctc accatcagca 300
gtctgcaacc tgaagatttt gcaacttact actgtcaaca tcattatgag agtcctctga 360
cgttcggcgg agggaccaag gtggagatca aacgtacg 398

<210> SEQ ID NO 52
<211> LENGTH: 107
<212> TYPE: PRT
<213> ORGANISM: Artificial
<220> FEATURE:
<223> OTHER INFORMATION: an artificially synthesized sequence

<400> SEQUENCE: 52

Asp Ile Gln Met Thr Gln Ser Pro Ser Ser Leu Ser Ala Ser Val Gly
1 5 10 15

Asp Arg Val Thr Ile Thr Cys Arg Thr Ser Glu Asn Ile Tyr Ser Phe
20 25 30

Leu Ala Trp Tyr Gln Gln Lys Pro Gly Lys Ala Pro Lys Leu Leu Ile
35 40 45

Tyr Asn Ala Lys Thr Leu Ala Lys Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln His His Tyr Glu Ser Pro Leu
85 90 95

Thr Phe Gly Gly Gly Thr Lys Val Glu Ile Lys
100 105

<210> SEQ ID NO 53
<211> LENGTH: 1422
<212> TYPE: DNA
<213> ORGANISM: Artificial
<220> FEATURE:
<223> OTHER INFORMATION: an artificially synthesized sequence

<400> SEQUENCE: 53
gaattccacc atggactgga cctggagggt cttctgcttg ctggctgtag ctccaggtgc 60
tcactcccag gtgcagctgg tgcagtctgg ggctgaggtg aagaagcctg gggcctcagt 120
gaaggtttcc tgcaaggcat ctggatacac cttcaccggc tacatcatga actgggtgcg 180
acaggcccct ggacaagggc ttgagtggat gggacttatt aatccttaca atggtggtac 240
tagctacaac cagaagttca agggcagagt cacgattacc gcggacgaat ccacgagcac 300
agcctacatg gagctgagca gcctgagatc tgaggacacg gccgtgtatt actgtgcgag 360
agatggttac gacgacggac cctatactat ggactactgg ggccagggca ccctcgtcac 420
agtctcctca gctagcacca agggcccatc ggtcttcccc ctggcgccct cctccaagag 480
cacctccgag agcacagcgg ccctgggctg cctggtcaag gactacttcc ccgaaccggt 540
gacggtgtcg tggaactcag gcgctctgac cagcggcgtg cacaccttcc cggctgtcct 600

```
acagtcctca ggactctact ccctcagcag cgtggtgacc gtgccctcca gcaacttcgg    660

cacccagacc tacacctgca acgtagatca caagcccagc aacaccaagg tggacaagac    720

agttgagcgc aaatcttgtg tcgagtgccc accgtgccca gcaccacctg tggcaggacc    780

gtcagtcttc ctcttccccc caaaacccaa ggacaccctc atgatctccc ggacccctga    840

ggtcacgtgc gtggtggtgg acgtgagcca cgaagacccc gaggtccagt tcaactggta    900

cgtggacggc gtggaggtgc ataatgccaa gacaaagcca cgggaggagc agttcaacag    960

cacgttccgt gtggtcagcg tcctcaccgt cgtgcaccag gactggctga acggcaagga   1020

gtacaagtgc aaggtctcca acaaaggcct cccagccccc atcgagaaaa ccatctccaa   1080

aaccaaaggg cagccccgag aaccacaggt gtacaccctg cccccatccc gggaggagat   1140

gaccaagaac caggtcagcc tgacctgcct ggtcaaaggc ttctacccca gcgacatcgc   1200

cgtggagtgg gagagcaatg ggcagccgga gaacaactac aagaccacac ctcccatgct   1260

ggactccgac ggctccttct tcctctacag caagctcacc gtggacaaga gcaggtggca   1320

gcaggggaac gtcttctcat gctccgtgat gcatgaggct ctgcacaacc actacacaca   1380

gaagagcctc tccctgtctc cgggtaaatg ataagcggcc gc                      1422
```

```
<210> SEQ ID NO 54
<211> LENGTH: 447
<212> TYPE: PRT
<213> ORGANISM: Artificial
<220> FEATURE:
<223> OTHER INFORMATION: an artificially synthesized sequence

<400> SEQUENCE: 54

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
        35                  40                  45

Gly Leu Ile Asn Pro Tyr Asn Gly Gly Thr Ser Tyr Asn Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Ser Cys
    210                 215                 220
```

-continued

```
Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 55
<211> LENGTH: 719
<212> TYPE: DNA
<213> ORGANISM: Artificial
<220> FEATURE:
<223> OTHER INFORMATION: an artificially synthesized sequence

<400> SEQUENCE: 55

```
ccaccatgga catgagggtc cccgctcagc tcctggggct cctgctactc tggctccgag     60

gtgccagatg tgacatccag atgacccagt ctccatcctc cctgtctgca tctgtaggag    120

acagagtcac catcacttgc cgaacaagtg agaatattta cagtttttta gcatggtatc    180

agcagaaacc agggaaagcc cctaagctcc tgatctataa tgcaaaaacc ttagcaaaag    240

gggtcccatc aaggttcagt ggcagtggat ctgggacaga tttcactctc accatcagca    300

gtctgcaacc tgaagatttt gcaacttact actgtcaaca tcattatgag agtcctctga    360

cgttcggcgg agggaccaag gtggagatca aacgtacggt ggctgcacca tctgtcttca    420

tcttcccgcc atctgatgag cagttgaaat ctggaactgc ctctgttgtg tgcctgctga    480

ataacttcta tcccagagag gccaaagtac agtggaaggt ggataacgcc ctccaatcgg    540

gtaactccca ggagagtgtc acagagcagg acagcaagga cagcacctac agcctcagca    600

gcaccctgac gctgagcaaa gcagactacg agaaacacaa agtctacgcc tgcgaagtca    660

cccatcaggg cctgagctcg cccgtcacaa agagcttcaa caggggagag tgttgataa     719
```

<210> SEQ ID NO 56
<211> LENGTH: 214

<212> TYPE: PRT
<213> ORGANISM: Artificial
<220> FEATURE:
<223> OTHER INFORMATION: an artificially synthesized sequence

<400> SEQUENCE: 56

```
Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Ile Tyr Ser Phe
            20                  25                  30

Leu Ala Trp Tyr Gln Gln Lys Pro Gly Lys Ala Pro Lys Leu Leu Ile
        35                  40                  45

Tyr Asn Ala Lys Thr Leu Ala Lys Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Glu Ser Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 57
<211> LENGTH: 327
<212> TYPE: DNA
<213> ORGANISM: Homo sapiens

<400> SEQUENCE: 57

```
cgtacggtgg ctgcaccatc tgtcttcatc ttcccgccat ctgatgagca gttgaaatct      60

ggaactgcct ctgttgtgtg cctgctgaat aacttctatc ccagagaggc caaagtacag     120

tggaaggtgg ataacgccct ccaatcgggt aactcccagg agagtgtcac agagcaggac     180

agcaaggaca gcacctacag cctcagcagc accctgacgc tgagcaaagc agactacgag     240

aaacacaaag tctacgcctg cgaagtcacc catcagggcc tgagctcgcc cgtcacaaag     300

agcttcaaca ggggagagtg ttgataa                                         327
```

<210> SEQ ID NO 58
<211> LENGTH: 107
<212> TYPE: PRT
<213> ORGANISM: Homo sapiens

<400> SEQUENCE: 58

```
Arg Thr Val Ala Ala Pro Ser Val Phe Ile Phe Pro Pro Ser Asp Glu
1               5                   10                  15
```

```
Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 59
<211> LENGTH: 990
<212> TYPE: DNA
<213> ORGANISM: Homo sapiens

<400> SEQUENCE: 59

gctagcacca agggcccatc ggtcttcccc ctggcaccct cctccaagag cacctctggg      60

ggcacagcgg ccctgggctg cctggtcaag gactacttcc ccgaaccggt gacggtgtcg     120

tggaactcag gcgccctgac cagcggcgtg cacaccttcc cggctgtcct acagtcctca     180

ggactctact ccctcagcag cgtggtgacc gtgccctcca gcagcttggg cacccagacc     240

tacatctgca acgtgaatca caagcccagc aacaccaagg tggacaagaa agttgagccc     300

aaatcttgtg acaaaactca cacatgccca ccgtgcccag cacctgaact cctgggggga     360

ccgtcagtct tcctcttccc cccaaaaccc aaggacaccc tcatgatctc ccggacccct     420

gaggtcacat gcgtggtggt ggacgtgagc cacgaagacc ctgaggtcaa gttcaactgg     480

tacgtggacg gcgtggaggt gcataatgcc aagacaaagc cgcgggagga gcagtacaac     540

agcacgtacc gtgtggtcag cgtcctcacc gtcctgcacc aggactggct gaatggcaag     600

gagtacaagt gcaaggtctc caacaaagcc ctcccagccc ccatcgagaa aaccatctcc     660

aaagccaaag ggcagccccg agaaccacag gtgtacaccc tgcccccatc ccgggatgag     720

ctgaccaaga accaggtcag cctgacctgc ctggtcaaag gcttctatcc cagcgacatc     780

gccgtggagt gggagagcaa tgggcagccg gagaacaact acaagaccac gcctcccgtg     840

ctggactccg acggctcctt cttcctctac agcaagctca ccgtggacaa gagcaggtgg     900

cagcagggga acgtcttctc atgctccgtg atgcatgagg ctctgcacaa ccactacacg     960

cagaagagcc tctccctgtc tccgggtaaa                                      990


<210> SEQ ID NO 60
<211> LENGTH: 330
<212> TYPE: PRT
<213> ORGANISM: Homo sapiens

<400> SEQUENCE: 60

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

```
Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 61
<211> LENGTH: 984
<212> TYPE: DNA
<213> ORGANISM: Homo sapiens

<400> SEQUENCE: 61

gctagcacca agggcccatc ggtcttcccc ctggcgccct cctccaagag cacctccgag     60

agcacagcgg ccctgggctg cctggtcaag gactacttcc ccgaaccggt gacggtgtcg    120

tggaactcag gcgctctgac cagcggcgtg cacaccttcc cggctgtcct acagtcctca    180

ggactctact ccctcagcag cgtggtgacc gtgccctcca gcaacttcgg cacccagacc    240

tacacctgca acgtagatca caagcccagc aacaccaagg tggacaagac agttgagcgc    300

aaatcttgtg tcgagtgccc accgtgccca gcaccacctg tggcaggacc gtcagtcttc    360

ctcttccccc caaaacccaa ggacaccctc atgatctccc ggacccctga ggtcacgtgc    420

gtggtggtgg acgtgagcca cgaagacccc gaggtccagt tcaactggta cgtggacggc    480

gtggaggtgc ataatgccaa gacaaagcca cgggaggagc agttcaacag cacgttccgt    540

gtggtcagcg tcctcaccgt cgtgcaccag gactggctga acggcaagga gtacaagtgc    600

aaggtctcca acaaaggcct cccagccccc atcgagaaaa ccatctccaa aaccaaaggg    660
```

cagccccgag aaccacaggt gtacaccctg cccccatccc gggaggagat gaccaagaac 720
caggtcagcc tgacctgcct ggtcaaaggc ttctacccca gcgacatcgc cgtggagtgg 780
gagagcaatg ggcagccgga gaacaactac aagaccacac ctcccatgct ggactccgac 840
ggctccttct tcctctacag caagctcacc gtggacaaga gcaggtggca gcaggggaac 900
gtcttctcat gctccgtgat gcatgaggct ctgcacaacc actacacaca gaagagcctc 960
tccctgtctc cgggtaaatg ataa 984

<210> SEQ ID NO 62
<211> LENGTH: 326
<212> TYPE: PRT
<213> ORGANISM: Homo sapiens

<400> SEQUENCE: 62

```
Ala Ser Thr Lys Gly Pro Ser Val Phe Pro Leu Ala Pro Ser Ser Lys
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320
```

Ser Leu Ser Pro Gly Lys
325

<210> SEQ ID NO 63
<211> LENGTH: 995
<212> TYPE: DNA
<213> ORGANISM: Homo sapiens

<400> SEQUENCE: 63
gctagcacca agggcccatc cgtcttcccc ctggcgccct gctccaggag cacctccgag 60
agcacagccg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacgaagacc 240
tacacctgca acgtagatca caagcccagc aacaccaagg tggacaagag agttgagtcc 300
aaatatggtc ccccatgccc accatgccca gcacctgagt tcctgggggg accatcagtc 360
ttcctgttcc ccccaaaacc caaggacact ctcatgatct cccggacccc tgaggtcacg 420
tgcgtggtgg tggacgtgag ccaggaagac cccgaggtcc agttcaactg gtacgtggat 480
ggcgtggagg tgcataatgc caagacaaag ccgcgggagg agcagttcaa cagcacgtac 540
cgtgtggtca gcgtcctcac cgtcctgcac caggactggc tgaacggcaa ggagtacaag 600
tgcaaggtct ccaacaaagg cctcccgtcc tccatcgaga aaaccatctc caaagccaaa 660
gggcagcccc gagagccaca ggtgtacacc ctgcccccat cccaggagga gatgaccaag 720
aaccaggtca gcctgacctg cctggtcaaa ggcttctacc ccagcgacat cgccgtggag 780
tgggagagca atgggcagcc ggagaacaac tacaagacca cgcctcccgt gctggactcc 840
gacggctcct tcttcctcta cagcaggcta accgtggaca agagcaggtg gcaggagggg 900
aatgtcttct catgctccgt gatgcatgag gctctgcaca accactacac acagaagagc 960
ctctccctgt ctctgggtta atgataagcg gccgc 995

<210> SEQ ID NO 64
<211> LENGTH: 326
<212> TYPE: PRT
<213> ORGANISM: Homo sapiens

<400> SEQUENCE: 64

Ala Ser Thr Lys Gly Pro Ser Val Phe Pro Leu Ala Pro Cys Ser Arg
1 5 10 15

Ser Thr Ser Glu Ser Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Lys Thr
65 70 75 80

Tyr Thr Cys Asn Val Asp His Lys Pro Ser Asn Thr Lys Val Asp Lys
85 90 95

Arg Val Glu Ser Lys Tyr Gly Pro Pro Cys Pro Pro Cys Pro Ala Pro
100 105 110

Glu Phe Leu Gly Gly Pro Ser Val Phe Leu Phe Pro Pro Lys Pro Lys
115 120 125

Asp Thr Leu Met Ile Ser Arg Thr Pro Glu Val Thr Cys Val Val Val
130 135 140

```
Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325


<210> SEQ ID NO 65
<211> LENGTH: 2208
<212> TYPE: DNA
<213> ORGANISM: Macaca fascicularis

<400> SEQUENCE: 65

atgatgtgga cctgggcact gtggatgttc cctttactct gcaaattcgg cctggcagct      60

ctgccagcta agcctgagaa catttcctgt gtctactact ataggaaaaa tttaacctgc     120

acttggagtc caggaaagga aactagttat acccagtaca cagctaagag aacttacgct     180

tttggaaaaa aacatgataa ttgtacaacc agtagttcta caagtgaaaa tcgtgcttcg     240

tgctcttttt tccttccaag aataacgatc ccagataatt ataccattga ggtggaagct     300

gaaaatggag atggtgtaat taaatctgat atgacatgtt ggagattaga ggacatagcg     360

aaaactgaac cacctgagat tttcagtgtg aaaccagttt tgggcatcaa acgaatgatt     420

cggattgaat ggataaagcc tgagttggca cctgtttcat ctgatttaaa atatgcactt     480

cgattcagga cagtcaatag taccagctgg atggaagtca acttcgctaa gaaccgtaaa     540

gatacaaacc aaacctacaa ccttatgggg ctgcaggctt ttacagagta tgtcgtagct     600

ctgcgatgtg cggtcaagga gtcaaagttc tggagtgact ggagccaaga aaaaatggga     660

atgactgagg aagaagctcc atgtggcctg gaactgtgga gagtcctgaa accaactgag     720

gtggatggaa gaaggccagt gcggttgtta tggaagaagg caagaggagc cccagtccta     780

gagaaaacac ttggctacaa catatggtac tttccagaaa acaacactaa cctcacagag     840

acagtgaaca ccactaacca gcagcttgaa ctgcatctgg gaggcgagag ctattgggtg     900

tctatgattt cttataattc tcttgggaag tctccagtga ccaccctgag gattccagcc     960

attcaggaaa agtcatttcg gtgcattgag gtcatgcagg cctgccttgc tgaggaccag    1020

ctagtggtga agtggcaaag ctctgctcta gacgtgaaca cttggatgat tgaatggttt    1080
```

```
ccggacatgg actcagagca ccccactctt tcctgggaat ctgtgtctca ggccacgaac   1140

tggacaatcc agcaagataa attaaaacct ttctggtgct ataacatctc tgtgtatcca   1200

atgttgcacg acaaagttgg cgagccatat tccatccagg cttatgccaa agaaggcatt   1260

ccatcaaaag gtcctgagac caaggtggag aacattggcg tgaagacggt cacgatcaca   1320

tggaaagaga ttcccaagag tgagagaaag ggtatcatct gcaactacac catcttttac   1380

caagctgaag gtggaaaagg attctccaag acagtcaact ccagcatctt gcagtatggc   1440

ctggagtccc tgaaacgaaa gacctcttac actgttcggg tcatggccag caccagtgct   1500

gggggaatca acgggaccag cataaatttc aagacattgt cattcagtgt ttttgagatt   1560

atccttataa cttctctgat tggtggaggc cttcttattc tcattatcct gacggtggca   1620

tatggtctca aaaaacccaa caaattgact cacctgtgtt ggcccagtgt tcccaaccct   1680

gctgaaagta gtatagccac atggcgtgga gatgatttca aggataagct aaacctgaag   1740

gagtctgatg actctgtgaa cacagaagac aggatcttaa aaccatgttc cacccccagt   1800

gacaagttgg ttattgacaa gtcggtggtg aactttggga atgttctgca agaaatgttc   1860

acagatgaag ccagaacggg tcaggaaaac aatttaggag gggaaaagaa tgagtatgtg   1920

acccacccct tcagggctga ctgtcccctg ggaaaaagtt ttgaggagct cccagtttca   1980

cctgagattc ctcccagaaa atcccaatac ctacgttcga ggatgccaga agggacctgc   2040

ctagaagccg aagagcagct tctcgtttct ggtcaaagtc tagaaagtct agcaccagac   2100

catgtgcggg aggcagcggc cccaaatccg tatttgaaaa attcagtgac aaccagggaa   2160

tttcttgtgt ctcaaaaact tccagagcac accaaaggag aagtctaa               2208
```

<210> SEQ ID NO 66
<211> LENGTH: 735
<212> TYPE: PRT
<213> ORGANISM: Macaca fascicularis

<400> SEQUENCE: 66

```
Met Met Trp Thr Trp Ala Leu Trp Met Phe Pro Leu Leu Cys Lys Phe
1               5                   10                  15

Gly Leu Ala Ala Leu Pro Ala Lys Pro Glu Asn Ile Ser Cys Val Tyr
            20                  25                  30

Tyr Tyr Arg Lys Asn Leu Thr Cys Thr Trp Ser Pro Gly Lys Glu Thr
        35                  40                  45

Ser Tyr Thr Gln Tyr Thr Ala Lys Arg Thr Tyr Ala Phe Gly Lys Lys
    50                  55                  60

His Asp Asn Cys Thr Thr Ser Ser Ser Thr Ser Glu Asn Arg Ala Ser
65                  70                  75                  80

Cys Ser Phe Phe Leu Pro Arg Ile Thr Ile Pro Asp Asn Tyr Thr Ile
                85                  90                  95

Glu Val Glu Ala Glu Asn Gly Asp Gly Val Ile Lys Ser Asp Met Thr
            100                 105                 110

Cys Trp Arg Leu Glu Asp Ile Ala Lys Thr Glu Pro Pro Glu Ile Phe
        115                 120                 125

Ser Val Lys Pro Val Leu Gly Ile Lys Arg Met Ile Arg Ile Glu Trp
    130                 135                 140

Ile Lys Pro Glu Leu Ala Pro Val Ser Ser Asp Leu Lys Tyr Ala Leu
145                 150                 155                 160

Arg Phe Arg Thr Val Asn Ser Thr Ser Trp Met Glu Val Asn Phe Ala
                165                 170                 175
```

```
Lys Asn Arg Lys Asp Thr Asn Gln Thr Tyr Asn Leu Met Gly Leu Gln
            180                 185                 190

Ala Phe Thr Glu Tyr Val Val Ala Leu Arg Cys Ala Val Lys Glu Ser
        195                 200                 205

Lys Phe Trp Ser Asp Trp Ser Gln Glu Lys Met Gly Met Thr Glu Glu
    210                 215                 220

Glu Ala Pro Cys Gly Leu Glu Leu Trp Arg Val Leu Lys Pro Thr Glu
225                 230                 235                 240

Val Asp Gly Arg Arg Pro Val Arg Leu Leu Trp Lys Lys Ala Arg Gly
                245                 250                 255

Ala Pro Val Leu Glu Lys Thr Leu Gly Tyr Asn Ile Trp Tyr Phe Pro
            260                 265                 270

Glu Asn Asn Thr Asn Leu Thr Glu Thr Val Asn Thr Thr Asn Gln Gln
        275                 280                 285

Leu Glu Leu His Leu Gly Gly Glu Ser Tyr Trp Val Ser Met Ile Ser
    290                 295                 300

Tyr Asn Ser Leu Gly Lys Ser Pro Val Thr Thr Leu Arg Ile Pro Ala
305                 310                 315                 320

Ile Gln Glu Lys Ser Phe Arg Cys Ile Glu Val Met Gln Ala Cys Leu
                325                 330                 335

Ala Glu Asp Gln Leu Val Val Lys Trp Gln Ser Ser Ala Leu Asp Val
            340                 345                 350

Asn Thr Trp Met Ile Glu Trp Phe Pro Asp Met Asp Ser Glu His Pro
        355                 360                 365

Thr Leu Ser Trp Glu Ser Val Ser Gln Ala Thr Asn Trp Thr Ile Gln
    370                 375                 380

Gln Asp Lys Leu Lys Pro Phe Trp Cys Tyr Asn Ile Ser Val Tyr Pro
385                 390                 395                 400

Met Leu His Asp Lys Val Gly Glu Pro Tyr Ser Ile Gln Ala Tyr Ala
                405                 410                 415

Lys Glu Gly Ile Pro Ser Lys Gly Pro Glu Thr Lys Val Glu Asn Ile
            420                 425                 430

Gly Val Lys Thr Val Thr Ile Thr Trp Lys Glu Ile Pro Lys Ser Glu
        435                 440                 445

Arg Lys Gly Ile Ile Cys Asn Tyr Thr Ile Phe Tyr Gln Ala Glu Gly
    450                 455                 460

Gly Lys Gly Phe Ser Lys Thr Val Asn Ser Ser Ile Leu Gln Tyr Gly
465                 470                 475                 480

Leu Glu Ser Leu Lys Arg Lys Thr Ser Tyr Thr Val Arg Val Met Ala
                485                 490                 495

Ser Thr Ser Ala Gly Gly Ile Asn Gly Thr Ser Ile Asn Phe Lys Thr
            500                 505                 510

Leu Ser Phe Ser Val Phe Glu Ile Ile Leu Ile Thr Ser Leu Ile Gly
        515                 520                 525

Gly Gly Leu Leu Ile Leu Ile Ile Leu Thr Val Ala Tyr Gly Leu Lys
    530                 535                 540

Lys Pro Asn Lys Leu Thr His Leu Cys Trp Pro Ser Val Pro Asn Pro
545                 550                 555                 560

Ala Glu Ser Ser Ile Ala Thr Trp Arg Gly Asp Asp Phe Lys Asp Lys
                565                 570                 575

Leu Asn Leu Lys Glu Ser Asp Asp Ser Val Asn Thr Glu Asp Arg Ile
            580                 585                 590

Leu Lys Pro Cys Ser Thr Pro Ser Asp Lys Leu Val Ile Asp Lys Ser
        595                 600                 605
```

```
Val Val Asn Phe Gly Asn Val Leu Gln Glu Met Phe Thr Asp Glu Ala
    610                 615                 620

Arg Thr Gly Gln Glu Asn Asn Leu Gly Gly Glu Lys Asn Glu Tyr Val
625                 630                 635                 640

Thr His Pro Phe Arg Ala Asp Cys Pro Leu Gly Lys Ser Phe Glu Glu
                645                 650                 655

Leu Pro Val Ser Pro Glu Ile Pro Pro Arg Lys Ser Gln Tyr Leu Arg
            660                 665                 670

Ser Arg Met Pro Glu Gly Thr Cys Leu Glu Ala Glu Glu Gln Leu Leu
        675                 680                 685

Val Ser Gly Gln Ser Leu Glu Ser Leu Ala Pro Asp His Val Arg Glu
    690                 695                 700

Ala Ala Ala Pro Asn Pro Tyr Leu Lys Asn Ser Val Thr Thr Arg Glu
705                 710                 715                 720

Phe Leu Val Ser Gln Lys Leu Pro Glu His Thr Lys Gly Glu Val
                725                 730                 735


<210> SEQ ID NO 67
<211> LENGTH: 495
<212> TYPE: DNA
<213> ORGANISM: Macaca fascicularis

<400> SEQUENCE: 67

atggcctctc actcagcagg ccccgcgacg tccgtgctgt ttctgctctg ctgcctggga     60

ggctggctga cctcccacac gttgcccgtc catttcctac aaccaagtga tatacagaaa    120

atagtcgagg aattacagtc cctctcgaag atgcttttga aagatgtgaa ggaagacaag    180

ggggtgctcg tgtcccagaa ttacacgctg ccgtgtctca cccctgacgc ccagccgcca    240

aacatcatcc acagcccagc catccgggca tatctcaaga caatcagaca gttagacaac    300

aaatctgtta ttgatgagat catagagcac ctcgacaaac tcatatttca agatgcacca    360

gaaacaaaca tttctgtgcc aacagacacc catgaatgta aacgcttcat cctgactatt    420

tctcaacagt tttcagagtg catggacctt gcattaaaat cgttgacttc tggagcccag    480

caggccacca cttaa                                                     495


<210> SEQ ID NO 68
<211> LENGTH: 164
<212> TYPE: PRT
<213> ORGANISM: Macaca fascicularis

<400> SEQUENCE: 68

Met Ala Ser His Ser Ala Gly Pro Ala Thr Ser Val Leu Phe Leu Leu
1               5                   10                  15

Cys Cys Leu Gly Gly Trp Leu Thr Ser His Thr Leu Pro Val His Phe
            20                  25                  30

Leu Gln Pro Ser Asp Ile Gln Lys Ile Val Glu Glu Leu Gln Ser Leu
        35                  40                  45

Ser Lys Met Leu Leu Lys Asp Val Lys Glu Asp Lys Gly Val Leu Val
    50                  55                  60

Ser Gln Asn Tyr Thr Leu Pro Cys Leu Thr Pro Asp Ala Gln Pro Pro
65                  70                  75                  80

Asn Ile Ile His Ser Pro Ala Ile Arg Ala Tyr Leu Lys Thr Ile Arg
                85                  90                  95

Gln Leu Asp Asn Lys Ser Val Ile Asp Glu Ile Ile Glu His Leu Asp
            100                 105                 110
```

-continued

```
Lys Leu Ile Phe Gln Asp Ala Pro Glu Thr Asn Ile Ser Val Pro Thr
        115                 120                 125

Asp Thr His Glu Cys Lys Arg Phe Ile Leu Thr Ile Ser Gln Gln Phe
    130                 135                 140

Ser Glu Cys Met Asp Leu Ala Leu Lys Ser Leu Thr Ser Gly Ala Gln
145                 150                 155                 160

Gln Ala Thr Thr


<210> SEQ ID NO 69
<211> LENGTH: 2934
<212> TYPE: DNA
<213> ORGANISM: Macaca fascicularis

<400> SEQUENCE: 69

atggctctat ttgtagtctt tcagacaaca ttcttcttaa cattgctgtc cttgaggact      60

taccagagtg aagtcttggc tgaacgttta ccattgactc ctgtgtcact taaagtttcc     120

accaattcta tacatcagag tttgcattta caatggactg tccacaacct tccttatcat     180

caggaattga aaatggtatt tcagatccag atcagtagga ttgaaacatc caatgtcgtc     240

tgggtgggga attacagcac cactgtgaag tggaaccagg ttctgcattg gagctgggaa     300

tcggaactcc ctttggaatg tgccacacac tttgtaagaa tcaagagtgt gatagacgat     360

gccagtttcc ctgagccaaa tttctggagc aactggagtt cctgggagga agtcagtgta     420

caagattatc ttggacgggg cactttgttc gttttcccta aagataagct ggtggaagaa     480

ggctccaatg ttaccatttg ttatgtttct aggaacattc aaaataatgt atcctgttat     540

ttggaaggga aacagattca cggagaacaa cttgatccac atgtaactgc attcaacttg     600

aatagtgtgc ctttcattag gaatagaggg acaaatatct attgtgaggc gagtcaagga     660

aatgtcagta aaggcataga aggcatcgtt ctctttgtct caaaagtact tgaggagccc     720

aaggactttt cttgtgaatc ccaggacttc aacactttgc actgtacttg ggatcctggg     780

acggacactg ccttggggtg gtctaaacaa ccttcccaaa gctacacttt atttgaatca     840

ttttctgggg aaaagaaact ttgtacgcac aaaaactggt gtaattggca aataactcaa     900

gactcacaag aaatgtataa cttcacactc atagctgaaa attacttaag gaagagaagt     960

gtcaatatcc tttttaacct gactcatcga gtttatttaa tgaatccttt tagtgtcaac    1020

tttgaaaatg taaatgccac aaatgccatc atgacctgga aggtgcactc catgaggaat    1080

aatttcacat atttgtgtca gattgaactc catggtgaag gaaaaatgat gcaatacgat    1140

gtttctatca acgtgaacgg tgagtacttc ttaagtgaac tggaacctgc cacagaatat    1200

atggcccgag tacgctgtgc tgatgccagc cacttctgga aatggactga atggagtggt    1260

cagaacttca ccacacttga agctgctccg tcagaggccc ctgatgtctg gagaagtgtg    1320

aactcagagc caggaaatca tactgtgacc ttattctgga agccattatc aaaactgcat    1380

gccaatggaa agatcctgtt ctataatgta gttgtagaaa acctagacaa accgtccagg    1440

tcagagctcc gttccattcc ggcaccagcc aacagcacaa aactaatcct cgacaggtgt    1500

tcctaccaaa tctgcgtcac agctaacaac agtgtgggcg cttctcctgc ttctataata    1560

gtcatctctg cggaccctga aaacaaagag gttgaggaag aaagaattgc aggcacagag    1620

ggtggattct ctctgtcttg gaaaccccag cctggagatg ttataggcta tgttgtggac    1680

tggtgtgacc atccccagga tgtgctccag tggaagaatg taggtcccaa taccacaagc    1740

acagtcatta gcacagatgc ttttaggcca ggagttcgat acgacttcag aatctatggg    1800

ttatctacaa aaaggattgc ttgtttatta gagaaaaaaa caggatactc tcaggaactg    1860
```

-continued

```
gctccttcag acaaccctca cgtgctggta gatatgttga catcccactc cttcactctg   1920

agttggaaag attactctac tgaatctcaa cctggtttta tacaagggta ccatgtctat   1980

ctgaaatcca aggcgaggca gtgccaccca cgatttcaaa aggcagttct ttcagatggt   2040

tcagaatgtt gcaaatacaa aattgacaac ccagaagaaa aggcattgat tgtggacaac   2100

ctaaagccag aatccttcta tgagtttttc gttactccat tcactagtgc tggcgagggc   2160

cccaatgcta cgttcacgaa ggtcacgact ccggatgaac actcctccat gttgattcgt   2220

atcctactgc ccatggtttt ctgcgtcttg ctcatcatga tcgtgtgcta cttgaaaagt   2280

cagtggatca aggagacgtg ttatcctgac atccctgacc cttacaagag cagcatcctg   2340

tcgttaataa aattcaagga gaaccctcac ctaacaataa tgaatgtcag tgactgtatc   2400

ccagatgcta ttgaagttgt cagcaagcca gaagggacaa agatacagct cctaggcact   2460

aggaagtcac tcacagaaac tgagttaact aagcctaact acctttatct ccttccaaca   2520

gaaaagaatc actctggccc tggcccctgc atctgttttg agaactttac ctacaaccag   2580

gcagcttctg acgctggctc ttgtggccat gttccagtac cccccaaagc cccaccaagt   2640

atgctaggac taatgacctc acctgaaaat gtactaaagg cgctagaaaa aaactacatg   2700

aactccctgg gagaagtccc agctggagaa acaagtttga attatgtgtc ccagttggct   2760

tcacccatgt ctggagacaa ggacagtctc ccaacaaacc cagtggagcc accacactgt   2820

tcagagtata aaatgcaaat ggcagtcccc ctgcgtcttg ccctgcctcc cccgaccgag   2880

aatagcagcc tttcctcaat taccctttta gatccaggtg aacactaccg ctaa         2934
```

```
<210> SEQ ID NO 70
<211> LENGTH: 977
<212> TYPE: PRT
<213> ORGANISM: Macaca fascicularis

<400> SEQUENCE: 70

Met Ala Leu Phe Val Val Phe Gln Thr Thr Phe Phe Leu Thr Leu Leu
1               5                   10                  15

Ser Leu Arg Thr Tyr Gln Ser Glu Val Leu Ala Glu Arg Leu Pro Leu
            20                  25                  30

Thr Pro Val Ser Leu Lys Val Ser Thr Asn Ser Ile His Gln Ser Leu
        35                  40                  45

His Leu Gln Trp Thr Val His Asn Leu Pro Tyr His Gln Glu Leu Lys
    50                  55                  60

Met Val Phe Gln Ile Gln Ile Ser Arg Ile Glu Thr Ser Asn Val Val
65                  70                  75                  80

Trp Val Gly Asn Tyr Ser Thr Thr Val Lys Trp Asn Gln Val Leu His
                85                  90                  95

Trp Ser Trp Glu Ser Glu Leu Pro Leu Glu Cys Ala Thr His Phe Val
            100                 105                 110

Arg Ile Lys Ser Val Ile Asp Asp Ala Ser Phe Pro Glu Pro Asn Phe
        115                 120                 125

Trp Ser Asn Trp Ser Ser Trp Glu Glu Val Ser Val Gln Asp Tyr Leu
    130                 135                 140

Gly Arg Gly Thr Leu Phe Val Phe Pro Lys Asp Lys Leu Val Glu Glu
145                 150                 155                 160

Gly Ser Asn Val Thr Ile Cys Tyr Val Ser Arg Asn Ile Gln Asn Asn
                165                 170                 175

Val Ser Cys Tyr Leu Glu Gly Lys Gln Ile His Gly Glu Gln Leu Asp
            180                 185                 190
```

-continued

```
Pro His Val Thr Ala Phe Asn Leu Asn Ser Val Pro Phe Ile Arg Asn
        195                 200                 205

Arg Gly Thr Asn Ile Tyr Cys Glu Ala Ser Gln Gly Asn Val Ser Lys
    210                 215                 220

Gly Ile Glu Gly Ile Val Leu Phe Val Ser Lys Val Leu Glu Glu Pro
225                 230                 235                 240

Lys Asp Phe Ser Cys Glu Ser Gln Asp Phe Asn Thr Leu His Cys Thr
                245                 250                 255

Trp Asp Pro Gly Thr Asp Thr Ala Leu Gly Trp Ser Lys Gln Pro Ser
            260                 265                 270

Gln Ser Tyr Thr Leu Phe Glu Ser Phe Ser Gly Glu Lys Lys Leu Cys
        275                 280                 285

Thr His Lys Asn Trp Cys Asn Trp Gln Ile Thr Gln Asp Ser Gln Glu
    290                 295                 300

Met Tyr Asn Phe Thr Leu Ile Ala Glu Asn Tyr Leu Arg Lys Arg Ser
305                 310                 315                 320

Val Asn Ile Leu Phe Asn Leu Thr His Arg Val Tyr Leu Met Asn Pro
                325                 330                 335

Phe Ser Val Asn Phe Glu Asn Val Asn Ala Thr Asn Ala Ile Met Thr
            340                 345                 350

Trp Lys Val His Ser Met Arg Asn Asn Phe Thr Tyr Leu Cys Gln Ile
        355                 360                 365

Glu Leu His Gly Glu Gly Lys Met Met Gln Tyr Asp Val Ser Ile Asn
    370                 375                 380

Val Asn Gly Glu Tyr Phe Leu Ser Glu Leu Glu Pro Ala Thr Glu Tyr
385                 390                 395                 400

Met Ala Arg Val Arg Cys Ala Asp Ala Ser His Phe Trp Lys Trp Thr
                405                 410                 415

Glu Trp Ser Gly Gln Asn Phe Thr Thr Leu Glu Ala Ala Pro Ser Glu
            420                 425                 430

Ala Pro Asp Val Trp Arg Ser Val Asn Ser Glu Pro Gly Asn His Thr
        435                 440                 445

Val Thr Leu Phe Trp Lys Pro Leu Ser Lys Leu His Ala Asn Gly Lys
    450                 455                 460

Ile Leu Phe Tyr Asn Val Val Val Glu Asn Leu Asp Lys Pro Ser Arg
465                 470                 475                 480

Ser Glu Leu Arg Ser Ile Pro Ala Pro Ala Asn Ser Thr Lys Leu Ile
                485                 490                 495

Leu Asp Arg Cys Ser Tyr Gln Ile Cys Val Thr Ala Asn Asn Ser Val
            500                 505                 510

Gly Ala Ser Pro Ala Ser Ile Ile Val Ile Ser Ala Asp Pro Glu Asn
        515                 520                 525

Lys Glu Val Glu Glu Glu Arg Ile Ala Gly Thr Glu Gly Gly Phe Ser
    530                 535                 540

Leu Ser Trp Lys Pro Gln Pro Gly Asp Val Ile Gly Tyr Val Val Asp
545                 550                 555                 560

Trp Cys Asp His Pro Gln Asp Val Leu Gln Trp Lys Asn Val Gly Pro
                565                 570                 575

Asn Thr Thr Ser Thr Val Ile Ser Thr Asp Ala Phe Arg Pro Gly Val
            580                 585                 590

Arg Tyr Asp Phe Arg Ile Tyr Gly Leu Ser Thr Lys Arg Ile Ala Cys
        595                 600                 605

Leu Leu Glu Lys Lys Thr Gly Tyr Ser Gln Glu Leu Ala Pro Ser Asp
```

```
    610                 615                 620

Asn Pro His Val Leu Val Asp Met Leu Thr Ser His Ser Phe Thr Leu
625                 630                 635                 640

Ser Trp Lys Asp Tyr Ser Thr Glu Ser Gln Pro Gly Phe Ile Gln Gly
                645                 650                 655

Tyr His Val Tyr Leu Lys Ser Lys Ala Arg Gln Cys His Pro Arg Phe
            660                 665                 670

Gln Lys Ala Val Leu Ser Asp Gly Ser Glu Cys Cys Lys Tyr Lys Ile
        675                 680                 685

Asp Asn Pro Glu Glu Lys Ala Leu Ile Val Asp Asn Leu Lys Pro Glu
    690                 695                 700

Ser Phe Tyr Glu Phe Phe Val Thr Pro Phe Thr Ser Ala Gly Glu Gly
705                 710                 715                 720

Pro Asn Ala Thr Phe Thr Lys Val Thr Thr Pro Asp Glu His Ser Ser
                725                 730                 735

Met Leu Ile Arg Ile Leu Leu Pro Met Val Phe Cys Val Leu Leu Ile
            740                 745                 750

Met Ile Val Cys Tyr Leu Lys Ser Gln Trp Ile Lys Glu Thr Cys Tyr
        755                 760                 765

Pro Asp Ile Pro Asp Pro Tyr Lys Ser Ser Ile Leu Ser Leu Ile Lys
    770                 775                 780

Phe Lys Glu Asn Pro His Leu Thr Ile Met Asn Val Ser Asp Cys Ile
785                 790                 795                 800

Pro Asp Ala Ile Glu Val Val Ser Lys Pro Glu Gly Thr Lys Ile Gln
                805                 810                 815

Leu Leu Gly Thr Arg Lys Ser Leu Thr Glu Thr Glu Leu Thr Lys Pro
            820                 825                 830

Asn Tyr Leu Tyr Leu Leu Pro Thr Glu Lys Asn His Ser Gly Pro Gly
        835                 840                 845

Pro Cys Ile Cys Phe Glu Asn Phe Thr Tyr Asn Gln Ala Ala Ser Asp
    850                 855                 860

Ala Gly Ser Cys Gly His Val Pro Val Pro Pro Lys Ala Pro Pro Ser
865                 870                 875                 880

Met Leu Gly Leu Met Thr Ser Pro Glu Asn Val Leu Lys Ala Leu Glu
                885                 890                 895

Lys Asn Tyr Met Asn Ser Leu Gly Glu Val Pro Ala Gly Glu Thr Ser
            900                 905                 910

Leu Asn Tyr Val Ser Gln Leu Ala Ser Pro Met Ser Gly Asp Lys Asp
        915                 920                 925

Ser Leu Pro Thr Asn Pro Val Glu Pro Pro His Cys Ser Glu Tyr Lys
    930                 935                 940

Met Gln Met Ala Val Pro Leu Arg Leu Ala Leu Pro Pro Pro Thr Glu
945                 950                 955                 960

Asn Ser Ser Leu Ser Ser Ile Thr Leu Leu Asp Pro Gly Glu His Tyr
                965                 970                 975

Arg


<210> SEQ ID NO 71
<211> LENGTH: 1665
<212> TYPE: DNA
<213> ORGANISM: Macaca fascicularis

<400> SEQUENCE: 71

atgatgtgga cctgggcact gtggatgttc cctttactct gcaaattcgg cctggcagct      60
```

-continued

```
ctgccagcta agcctgagaa catttcctgt gtctactact ataggaaaaa tttaacctgc    120

acttggagtc caggaaagga aactagttat acccagtaca cagctaagag aacttacgct    180

tttggaaaaa aacatgataa ttgtacaacc agtagttcta caagtgaaaa tcgtgcttcg    240

tgctcttttt tccttccaag aataacgatc ccagataatt ataccattga ggtggaagct    300

gaaaatggag atggtgtaat taaatctgat atgacatgtt ggagattaga ggacatagcg    360

aaaactgaac cacctgagat tttcagtgtg aaaccagttt tgggcatcaa acgaatgatt    420

cggattgaat ggataaagcc tgagttggca cctgtttcat ctgatttaaa atatgcactt    480

cgattcagga cagtcaatag taccagctgg atggaagtca acttcgctaa gaaccgtaaa    540

gatacaaacc aaacctacaa ccttatgggg ctgcaggctt ttacagagta tgtcgtagct    600

ctgcgatgtg cggtcaagga gtcaaagttc tggagtgact ggagccaaga aaaaatggga    660

atgactgagg aagaagctcc atgtggcctg gaactgtgga gagtcctgaa accaactgag    720

gtggatggaa gaaggccagt gcggttgtta tggaagaagg caagaggagc cccagtccta    780

gagaaaacac ttggctacaa catatggtac tttccagaaa acaacactaa cctcacagag    840

acagtgaaca ccactaacca gcagcttgaa ctgcatctgg gaggcgagag ctattgggtg    900

tctatgattt cttataattc tcttgggaag tctccagtga ccaccctgag gattccagcc    960

attcaggaaa agtcatttcg gtgcattgag gtcatgcagg cctgccttgc tgaggaccag   1020

ctagtggtga agtggcaaag ctctgctcta gacgtgaaca cttggatgat tgaatggttt   1080

ccggacatgg actcagagca ccccactctt tcctgggaat ctgtgtctca ggccacgaac   1140

tggacaatcc agcaagataa attaaaacct ttctggtgct ataacatctc tgtgtatcca   1200

atgttgcacg acaaagttgg cgagccatat tccatccagg cttatgccaa agaaggcatt   1260

ccatcaaaag gtcctgagac caaggtggag aacattggcg tgaagacggt cacgatcaca   1320

tggaaagaga ttcccaagag tgagagaaag ggtatcatct gcaactacac catcttttac   1380

caagctgaag gtggaaaagg attctccaag acagtcaact ccagcatctt gcagtatggc   1440

ctggagtccc tgaaacgaaa gacctcttac actgttcggg tcatggccag caccagtgct   1500

gggggaatca acgggaccag cataaatttc aagacattgt cattcagtgt tttgagatt   1560

atccttataa cttctctgat tggtggaggc cttcttattc tcattatcct gacggtggca   1620

tatggtctca aaaaacccaa caaattgact cacctgtgtt aatga                  1665
```

<210> SEQ ID NO 72
<211> LENGTH: 553
<212> TYPE: PRT
<213> ORGANISM: Macaca fascicularis

<400> SEQUENCE: 72

```
Met Met Trp Thr Trp Ala Leu Trp Met Phe Pro Leu Leu Cys Lys Phe
1               5                   10                  15

Gly Leu Ala Ala Leu Pro Ala Lys Pro Glu Asn Ile Ser Cys Val Tyr
            20                  25                  30

Tyr Tyr Arg Lys Asn Leu Thr Cys Thr Trp Ser Pro Gly Lys Glu Thr
        35                  40                  45

Ser Tyr Thr Gln Tyr Thr Ala Lys Arg Thr Tyr Ala Phe Gly Lys Lys
    50                  55                  60

His Asp Asn Cys Thr Thr Ser Ser Ser Thr Ser Glu Asn Arg Ala Ser
65                  70                  75                  80

Cys Ser Phe Phe Leu Pro Arg Ile Thr Ile Pro Asp Asn Tyr Thr Ile
                85                  90                  95
```

-continued

```
Glu Val Glu Ala Glu Asn Gly Asp Gly Val Ile Lys Ser Asp Met Thr
            100                 105                 110

Cys Trp Arg Leu Glu Asp Ile Ala Lys Thr Glu Pro Pro Glu Ile Phe
        115                 120                 125

Ser Val Lys Pro Val Leu Gly Ile Lys Arg Met Ile Arg Ile Glu Trp
    130                 135                 140

Ile Lys Pro Glu Leu Ala Pro Val Ser Ser Asp Leu Lys Tyr Ala Leu
145                 150                 155                 160

Arg Phe Arg Thr Val Asn Ser Thr Ser Trp Met Glu Val Asn Phe Ala
                165                 170                 175

Lys Asn Arg Lys Asp Thr Asn Gln Thr Tyr Asn Leu Met Gly Leu Gln
            180                 185                 190

Ala Phe Thr Glu Tyr Val Val Ala Leu Arg Cys Ala Val Lys Glu Ser
        195                 200                 205

Lys Phe Trp Ser Asp Trp Ser Gln Glu Lys Met Gly Met Thr Glu Glu
    210                 215                 220

Glu Ala Pro Cys Gly Leu Glu Leu Trp Arg Val Leu Lys Pro Thr Glu
225                 230                 235                 240

Val Asp Gly Arg Arg Pro Val Arg Leu Leu Trp Lys Lys Ala Arg Gly
                245                 250                 255

Ala Pro Val Leu Glu Lys Thr Leu Gly Tyr Asn Ile Trp Tyr Phe Pro
            260                 265                 270

Glu Asn Asn Thr Asn Leu Thr Glu Thr Val Asn Thr Thr Asn Gln Gln
        275                 280                 285

Leu Glu Leu His Leu Gly Gly Glu Ser Tyr Trp Val Ser Met Ile Ser
    290                 295                 300

Tyr Asn Ser Leu Gly Lys Ser Pro Val Thr Thr Leu Arg Ile Pro Ala
305                 310                 315                 320

Ile Gln Glu Lys Ser Phe Arg Cys Ile Glu Val Met Gln Ala Cys Leu
                325                 330                 335

Ala Glu Asp Gln Leu Val Val Lys Trp Gln Ser Ser Ala Leu Asp Val
            340                 345                 350

Asn Thr Trp Met Ile Glu Trp Phe Pro Asp Met Asp Ser Glu His Pro
        355                 360                 365

Thr Leu Ser Trp Glu Ser Val Ser Gln Ala Thr Asn Trp Thr Ile Gln
    370                 375                 380

Gln Asp Lys Leu Lys Pro Phe Trp Cys Tyr Asn Ile Ser Val Tyr Pro
385                 390                 395                 400

Met Leu His Asp Lys Val Gly Glu Pro Tyr Ser Ile Gln Ala Tyr Ala
                405                 410                 415

Lys Glu Gly Ile Pro Ser Lys Gly Pro Glu Thr Lys Val Glu Asn Ile
            420                 425                 430

Gly Val Lys Thr Val Thr Ile Thr Trp Lys Glu Ile Pro Lys Ser Glu
        435                 440                 445

Arg Lys Gly Ile Ile Cys Asn Tyr Thr Ile Phe Tyr Gln Ala Glu Gly
    450                 455                 460

Gly Lys Gly Phe Ser Lys Thr Val Asn Ser Ser Ile Leu Gln Tyr Gly
465                 470                 475                 480

Leu Glu Ser Leu Lys Arg Lys Thr Ser Tyr Thr Val Arg Val Met Ala
                485                 490                 495

Ser Thr Ser Ala Gly Gly Ile Asn Gly Thr Ser Ile Asn Phe Lys Thr
            500                 505                 510

Leu Ser Phe Ser Val Phe Glu Ile Ile Leu Ile Thr Ser Leu Ile Gly
        515                 520                 525
```

```
Gly Gly Leu Leu Ile Leu Ile Ile Leu Thr Val Ala Tyr Gly Leu Lys
    530                 535                 540

Lys Pro Asn Lys Leu Thr His Leu Cys
545                 550


<210> SEQ ID NO 73
<211> LENGTH: 1665
<212> TYPE: DNA
<213> ORGANISM: Homo sapiens

<400> SEQUENCE: 73

atgatgtgga cctgggcact gtggatgctc ccctcactct gcaaattcag cctggcagct      60

ctgccagcta agcctgagaa catttcctgt gtctactact ataggaaaaa tttaacctgc     120

acttggagtc caggaaagga aaccagttat acccagtaca cagttaagag aacttacgct     180

tttggagaaa aacatgataa ttgtacaacc aatagttcta caagtgaaaa tcgtgcttcg     240

tgctcttttt tccttccaag aataacgatc ccagataatt ataccattga ggtggaagct     300

gaaaatggag atggtgtaat taaatctcat atgacatact ggagattaga gaacatagcg     360

aaaactgaac cacctaagat tttccgtgtg aaaccagttt tgggcatcaa acgaatgatt     420

caaattgaat ggataaagcc tgagttggcg cctgtttcat ctgatttaaa atacacactt     480

cgattcagga cagtcaacag taccagctgg atggaagtca acttcgctaa gaaccgtaag     540

gataaaaacc aaacgtacaa cctcacgggg ctgcagcctt ttacagaata tgtcatagct     600

ctgcgatgtg cggtcaagga gtcaaagttc tggagtgact ggagccaaga aaaaatggga     660

atgactgagg aagaagctcc atgtggcctg gaactgtgga gagtcctgaa accagctgag     720

gcggatggaa gaaggccagt gcggttgtta tggaagaagg caagaggagc cccagtccta     780

gagaaaacac ttggctacaa catatggtac tatccagaaa gcaacactaa cctcacagaa     840

acaatgaaca ctactaacca gcagcttgaa ctgcatctgg gaggcgagag cttttgggtg     900

tctatgattt cttataattc tcttgggaag tctccagtgg ccaccctgag gattccagct     960

attcaagaaa aatcgtttca gtgcattgag gtcatgcagg cctgcgttgc tgaggaccag    1020

ctagtggtga agtggcaaag ctctgctcta gacgtgaaca cttggatgat tgaatggttt    1080

ccggatgtgg actcagagcc caccaccctt tcctgggaat ctgtgtctca ggccacgaac    1140

tggacgatcc agcaagataa attaaaacct ttctggtgct ataacatctc tgtgtatcca    1200

atgttgcatg acaaagttgg cgagccatat tccatccagg cttatgccaa agaaggcgtt    1260

ccatcagaag gtcctgagac caaggtggag aacattggcg tgaagacggt cacgatcaca    1320

tggaaagaga ttcccaagag tgagagaaag ggtatcatct gcaactacac catcttttac    1380

caagctgaag gtggaaaagg attctccaag acagtcaatt ccagcatctt gcagtacggc    1440

ctggagtccc tgaaacgaaa gacctcttac attgttcagg tcatggccag caccagtgct    1500

gggggaacca acgggaccag cataaatttc aagacattgt cattcagtgt ctttgagatt    1560

atcctcataa cttctctgat tggtggaggc cttcttattc tcattatcct gacagtggca    1620

tatggtctca aaaaacccaa caaattgact catctgtgtt aatga                    1665


<210> SEQ ID NO 74
<211> LENGTH: 553
<212> TYPE: PRT
<213> ORGANISM: Homo sapiens

<400> SEQUENCE: 74

Met Met Trp Thr Trp Ala Leu Trp Met Leu Pro Ser Leu Cys Lys Phe
```

-continued

```
1               5                   10                  15

Ser Leu Ala Ala Leu Pro Ala Lys Pro Glu Asn Ile Ser Cys Val Tyr
            20                  25                  30

Tyr Tyr Arg Lys Asn Leu Thr Cys Thr Trp Ser Pro Gly Lys Glu Thr
        35                  40                  45

Ser Tyr Thr Gln Tyr Thr Val Lys Arg Thr Tyr Ala Phe Gly Glu Lys
    50                  55                  60

His Asp Asn Cys Thr Thr Asn Ser Ser Thr Ser Glu Asn Arg Ala Ser
65                  70                  75                  80

Cys Ser Phe Phe Leu Pro Arg Ile Thr Ile Pro Asp Asn Tyr Thr Ile
                85                  90                  95

Glu Val Glu Ala Glu Asn Gly Asp Gly Val Ile Lys Ser His Met Thr
            100                 105                 110

Tyr Trp Arg Leu Glu Asn Ile Ala Lys Thr Glu Pro Pro Lys Ile Phe
        115                 120                 125

Arg Val Lys Pro Val Leu Gly Ile Lys Arg Met Ile Gln Ile Glu Trp
    130                 135                 140

Ile Lys Pro Glu Leu Ala Pro Val Ser Ser Asp Leu Lys Tyr Thr Leu
145                 150                 155                 160

Arg Phe Arg Thr Val Asn Ser Thr Ser Trp Met Glu Val Asn Phe Ala
                165                 170                 175

Lys Asn Arg Lys Asp Lys Asn Gln Thr Tyr Asn Leu Thr Gly Leu Gln
            180                 185                 190

Pro Phe Thr Glu Tyr Val Ile Ala Leu Arg Cys Ala Val Lys Glu Ser
        195                 200                 205

Lys Phe Trp Ser Asp Trp Ser Gln Glu Lys Met Gly Met Thr Glu Glu
    210                 215                 220

Glu Ala Pro Cys Gly Leu Glu Leu Trp Arg Val Leu Lys Pro Ala Glu
225                 230                 235                 240

Ala Asp Gly Arg Arg Pro Val Arg Leu Leu Trp Lys Lys Ala Arg Gly
                245                 250                 255

Ala Pro Val Leu Glu Lys Thr Leu Gly Tyr Asn Ile Trp Tyr Tyr Pro
            260                 265                 270

Glu Ser Asn Thr Asn Leu Thr Glu Thr Met Asn Thr Thr Asn Gln Gln
        275                 280                 285

Leu Glu Leu His Leu Gly Gly Glu Ser Phe Trp Val Ser Met Ile Ser
    290                 295                 300

Tyr Asn Ser Leu Gly Lys Ser Pro Val Ala Thr Leu Arg Ile Pro Ala
305                 310                 315                 320

Ile Gln Glu Lys Ser Phe Gln Cys Ile Glu Val Met Gln Ala Cys Val
                325                 330                 335

Ala Glu Asp Gln Leu Val Val Lys Trp Gln Ser Ser Ala Leu Asp Val
            340                 345                 350

Asn Thr Trp Met Ile Glu Trp Phe Pro Asp Val Asp Ser Glu Pro Thr
        355                 360                 365

Thr Leu Ser Trp Glu Ser Val Ser Gln Ala Thr Asn Trp Thr Ile Gln
    370                 375                 380

Gln Asp Lys Leu Lys Pro Phe Trp Cys Tyr Asn Ile Ser Val Tyr Pro
385                 390                 395                 400

Met Leu His Asp Lys Val Gly Glu Pro Tyr Ser Ile Gln Ala Tyr Ala
                405                 410                 415

Lys Glu Gly Val Pro Ser Glu Gly Pro Glu Thr Lys Val Glu Asn Ile
            420                 425                 430
```

```
Gly Val Lys Thr Val Thr Ile Thr Trp Lys Glu Ile Pro Lys Ser Glu
        435                 440                 445

Arg Lys Gly Ile Ile Cys Asn Tyr Thr Ile Phe Tyr Gln Ala Glu Gly
    450                 455                 460

Gly Lys Gly Phe Ser Lys Thr Val Asn Ser Ser Ile Leu Gln Tyr Gly
465                 470                 475                 480

Leu Glu Ser Leu Lys Arg Lys Thr Ser Tyr Ile Val Gln Val Met Ala
                485                 490                 495

Ser Thr Ser Ala Gly Gly Thr Asn Gly Thr Ser Ile Asn Phe Lys Thr
            500                 505                 510

Leu Ser Phe Ser Val Phe Glu Ile Ile Leu Ile Thr Ser Leu Ile Gly
        515                 520                 525

Gly Gly Leu Leu Ile Leu Ile Ile Leu Thr Val Ala Tyr Gly Leu Lys
    530                 535                 540

Lys Pro Asn Lys Leu Thr His Leu Cys
545                 550


<210> SEQ ID NO 75
<211> LENGTH: 2199
<212> TYPE: DNA
<213> ORGANISM: Homo sapiens

<400> SEQUENCE: 75

atgatgtgga cctgggcact gtggatgctc ccctcactct gcaaattcag cctggcagct     60

ctgccagcta agcctgagaa catttcctgt gtctactact ataggaaaaa tttaacctgc    120

acttggagtc caggaaagga aaccagttat acccagtaca cagttaagag aacttacgct    180

tttggagaaa aacatgataa ttgtacaacc aatagttcta caagtgaaaa tcgtgcttcg    240

tgctcttttt tccttccaag aataacgatc ccagataatt ataccattga ggtggaagct    300

gaaaatggag atggtgtaat taaatctcat atgacatact ggagattaga gaacatagcg    360

aaaactgaac cacctaagat tttccgtgtg aaaccagttt tgggcatcaa acgaatgatt    420

caaattgaat ggataaagcc tgagttggcg cctgtttcat ctgatttaaa atacacactt    480

cgattcagga cagtcaacag taccagctgg atggaagtca acttcgctaa gaaccgtaag    540

gataaaaacc aaacgtacaa cctcacgggg ctgcagcctt ttacagaata tgtcatagct    600

ctgcgatgtg cggtcaagga gtcaaagttc tggagtgact ggagccaaga aaaaatggga    660

atgactgagg aagaagctcc atgtggcctg gaactgtgga gagtcctgaa accagctgag    720

gcggatggaa gaaggccagt gcggttgtta tggaagaagg caagaggagc cccagtccta    780

gagaaaacac ttggctacaa catatggtac tatccagaaa gcaacactaa cctcacagaa    840

acaatgaaca ctactaacca gcagcttgaa ctgcatctgg gaggcgagag cttttgggtg    900

tctatgattt cttataattc tcttgggaag tctccagtgg ccaccctgag gattccagct    960

attcaagaaa aatcgtttca gtgcattgag gtcatgcagg cctgcgttgc tgaggaccag   1020

ctagtggtga agtggcaaag ctctgctcta gacgtgaaca cttggatgat tgaatggttt   1080

ccggatgtgg actcagagcc caccaccctt tcctgggaat ctgtgtctca ggccacgaac   1140

tggacgatcc agcaagataa attaaaacct ttctggtgct ataacatctc tgtgtatcca   1200

atgttgcatg acaaagttgg cgagccatat tccatccagg cttatgccaa agaaggcgtt   1260

ccatcagaag gtcctgagac caaggtggag aacattggcg tgaagacggt cacgatcaca   1320

tggaaagaga ttcccaagag tgagagaaag ggtatcatct gcaactacac catcttttac   1380

caagctgaag gtggaaaagg attctccaag acagtcaatt ccagcatctt gcagtacggc   1440
```

-continued

```
ctggagtccc tgaaacgaaa gacctcttac attgttcagg tcatggccag caccagtgct   1500

gggggaacca acgggaccag cataaatttc aagacattgt cattcagtgt ctttgagatt   1560

atcctcataa cttctctgat tggtggaggc cttcttattc tcattatcct gacagtggca   1620

tatggtctca aaaaacccaa caaattgact catctgtgtt ggcccaccgt tcccaaccct   1680

gctgaaagta gtatagccac atggcatgga gatgatttca aggataagct aaacctgaag   1740

gagtctgatg actctgtgaa cacagaagac aggatcttaa aaccatgttc cacccccagt   1800

gacaagttgg tgattgacaa gttggtggtg aactttggga atgttctgca agaaattttc   1860

acagatgaag ccagaacggg tcaggaaaac aatttaggag gggaaaagaa tgggtatgtg   1920

acctgcccct tcaggcctga ttgtcccctg ggaaaagtt ttgaggagct cccagtttca   1980

cctgagattc cgcccagaaa atcccaatac ctacgttcga ggatgccaga ggggacccgc   2040

ccagaagcca aagagcagct tctcttttct ggtcaaagtt tagtaccaga tcatctgtgt   2100

gaggaaggag ccccaaatcc atatttgaaa aattcagtga cagccaggga atttcttgtg   2160

tctgaaaaac ttccagagca caccaaggga gaagtctaa                          2199
```

```
<210> SEQ ID NO 76
<211> LENGTH: 732
<212> TYPE: PRT
<213> ORGANISM: Homo sapiens

<400> SEQUENCE: 76

Met Met Trp Thr Trp Ala Leu Trp Met Leu Pro Ser Leu Cys Lys Phe
1               5                   10                  15

Ser Leu Ala Ala Leu Pro Ala Lys Pro Glu Asn Ile Ser Cys Val Tyr
            20                  25                  30

Tyr Tyr Arg Lys Asn Leu Thr Cys Thr Trp Ser Pro Gly Lys Glu Thr
        35                  40                  45

Ser Tyr Thr Gln Tyr Thr Val Lys Arg Thr Tyr Ala Phe Gly Glu Lys
    50                  55                  60

His Asp Asn Cys Thr Thr Asn Ser Ser Thr Ser Glu Asn Arg Ala Ser
65                  70                  75                  80

Cys Ser Phe Phe Leu Pro Arg Ile Thr Ile Pro Asp Asn Tyr Thr Ile
                85                  90                  95

Glu Val Glu Ala Glu Asn Gly Asp Gly Val Ile Lys Ser His Met Thr
            100                 105                 110

Tyr Trp Arg Leu Glu Asn Ile Ala Lys Thr Glu Pro Pro Lys Ile Phe
        115                 120                 125

Arg Val Lys Pro Val Leu Gly Ile Lys Arg Met Ile Gln Ile Glu Trp
    130                 135                 140

Ile Lys Pro Glu Leu Ala Pro Val Ser Ser Asp Leu Lys Tyr Thr Leu
145                 150                 155                 160

Arg Phe Arg Thr Val Asn Ser Thr Ser Trp Met Glu Val Asn Phe Ala
                165                 170                 175

Lys Asn Arg Lys Asp Lys Asn Gln Thr Tyr Asn Leu Thr Gly Leu Gln
            180                 185                 190

Pro Phe Thr Glu Tyr Val Ile Ala Leu Arg Cys Ala Val Lys Glu Ser
        195                 200                 205

Lys Phe Trp Ser Asp Trp Ser Gln Glu Lys Met Gly Met Thr Glu Glu
    210                 215                 220

Glu Ala Pro Cys Gly Leu Glu Leu Trp Arg Val Leu Lys Pro Ala Glu
225                 230                 235                 240

Ala Asp Gly Arg Arg Pro Val Arg Leu Leu Trp Lys Lys Ala Arg Gly
```

-continued

```
                245                 250                 255

Ala Pro Val Leu Glu Lys Thr Leu Gly Tyr Asn Ile Trp Tyr Tyr Pro
            260                 265                 270

Glu Ser Asn Thr Asn Leu Thr Glu Thr Met Asn Thr Thr Asn Gln Gln
        275                 280                 285

Leu Glu Leu His Leu Gly Gly Glu Ser Phe Trp Val Ser Met Ile Ser
    290                 295                 300

Tyr Asn Ser Leu Gly Lys Ser Pro Val Ala Thr Leu Arg Ile Pro Ala
305                 310                 315                 320

Ile Gln Glu Lys Ser Phe Gln Cys Ile Glu Val Met Gln Ala Cys Val
                325                 330                 335

Ala Glu Asp Gln Leu Val Val Lys Trp Gln Ser Ser Ala Leu Asp Val
            340                 345                 350

Asn Thr Trp Met Ile Glu Trp Phe Pro Asp Val Asp Ser Glu Pro Thr
        355                 360                 365

Thr Leu Ser Trp Glu Ser Val Ser Gln Ala Thr Asn Trp Thr Ile Gln
    370                 375                 380

Gln Asp Lys Leu Lys Pro Phe Trp Cys Tyr Asn Ile Ser Val Tyr Pro
385                 390                 395                 400

Met Leu His Asp Lys Val Gly Glu Pro Tyr Ser Ile Gln Ala Tyr Ala
                405                 410                 415

Lys Glu Gly Val Pro Ser Glu Gly Pro Glu Thr Lys Val Glu Asn Ile
            420                 425                 430

Gly Val Lys Thr Val Thr Ile Thr Trp Lys Glu Ile Pro Lys Ser Glu
        435                 440                 445

Arg Lys Gly Ile Ile Cys Asn Tyr Thr Ile Phe Tyr Gln Ala Glu Gly
    450                 455                 460

Gly Lys Gly Phe Ser Lys Thr Val Asn Ser Ser Ile Leu Gln Tyr Gly
465                 470                 475                 480

Leu Glu Ser Leu Lys Arg Lys Thr Ser Tyr Ile Val Gln Val Met Ala
                485                 490                 495

Ser Thr Ser Ala Gly Gly Thr Asn Gly Thr Ser Ile Asn Phe Lys Thr
            500                 505                 510

Leu Ser Phe Ser Val Phe Glu Ile Ile Leu Ile Thr Ser Leu Ile Gly
        515                 520                 525

Gly Gly Leu Leu Ile Leu Ile Ile Leu Thr Val Ala Tyr Gly Leu Lys
    530                 535                 540

Lys Pro Asn Lys Leu Thr His Leu Cys Trp Pro Thr Val Pro Asn Pro
545                 550                 555                 560

Ala Glu Ser Ser Ile Ala Thr Trp His Gly Asp Asp Phe Lys Asp Lys
                565                 570                 575

Leu Asn Leu Lys Glu Ser Asp Asp Ser Val Asn Thr Glu Asp Arg Ile
            580                 585                 590

Leu Lys Pro Cys Ser Thr Pro Ser Asp Lys Leu Val Ile Asp Lys Leu
        595                 600                 605

Val Val Asn Phe Gly Asn Val Leu Gln Glu Ile Phe Thr Asp Glu Ala
    610                 615                 620

Arg Thr Gly Gln Glu Asn Asn Leu Gly Gly Glu Lys Asn Gly Tyr Val
625                 630                 635                 640

Thr Cys Pro Phe Arg Pro Asp Cys Pro Leu Gly Lys Ser Phe Glu Glu
                645                 650                 655

Leu Pro Val Ser Pro Glu Ile Pro Pro Arg Lys Ser Gln Tyr Leu Arg
            660                 665                 670
```

```
Ser Arg Met Pro Glu Gly Thr Arg Pro Glu Ala Lys Glu Gln Leu Leu
        675                 680                 685

Phe Ser Gly Gln Ser Leu Val Pro Asp His Leu Cys Glu Glu Gly Ala
    690                 695                 700

Pro Asn Pro Tyr Leu Lys Asn Ser Val Thr Ala Arg Glu Phe Leu Val
705                 710                 715                 720

Ser Glu Lys Leu Pro Glu His Thr Lys Gly Glu Val
                725                 730


<210> SEQ ID NO 77
<211> LENGTH: 1542
<212> TYPE: DNA
<213> ORGANISM: Homo sapiens

<400> SEQUENCE: 77

atgatgtgga cctgggcact gtggatgctc ccttcactct gcaaattcag cctggcagct      60

ctgccagcta agcctgagaa catttcctgt gtctactact ataggaaaaa tttaacctgc     120

acttggagtc caggaaagga aaccagttat acccagtaca cagttaagag aacttacgct     180

tttggagaaa aacatgataa ttgtacaacc aatagttcta caagtgaaaa tcgtgcttcg     240

tgctcttttt tccttccaag aataacgatc ccagataatt ataccattga ggtggaagct     300

gaaaatggag atggtgtaat taaatctcat atgacatact ggagattaga gaacatagcg     360

aaaactgaac cacctaagat tttccgtgtg aaaccagttt tgggcatcaa acgaatgatt     420

caaattgaat ggataaagcc tgagttggcg cctgtttcat ctgatttaaa atacacactt     480

cgattcagga cagtcaacag taccagctgg atggaagtca acttcgctaa gaaccgtaag     540

gataaaaacc aaacgtacaa cctcacgggg ctgcagcctt ttacagaata tgtcatagct     600

ctgcgatgtg cggtcaagga gtcaaagttc tggagtgact ggagccaaga aaaaatggga     660

atgactgagg aagaagctcc atgtggcctg gaactgtgga gagtcctgaa accagctgag     720

gcggatggaa gaaggccagt gcggttgtta tggaagaagg caagaggagc cccagtccta     780

gagaaaacac ttggctacaa catatggtac tatccagaaa gcaacactaa cctcacagaa     840

acaatgaaca ctactaacca gcagcttgaa ctgcatctgg gaggcgagag cttttgggtg     900

tctatgattt cttataattc tcttgggaag tctccagtgg ccaccctgag gattccagct     960

attcaagaaa aatcgtttca gtgcattgag gtcatgcagg cctgcgttgc tgaggaccag    1020

ctagtggtga agtggcaaag ctctgctcta gacgtgaaca cttggatgat tgaatggttt    1080

ccggatgtgg actcagagcc caccaccctt tcctgggaat ctgtgtctca ggccacgaac    1140

tggacgatcc agcaagataa attaaaacct ttctggtgct ataacatctc tgtgtatcca    1200

atgttgcatg acaaagttgg cgagccatat tccatccagg cttatgccaa agaaggcgtt    1260

ccatcagaag gtcctgagac caaggtggag aacattggcg tgaagacggt cacgatcaca    1320

tggaaagaga ttcccaagag tgagagaaag ggtatcatct gcaactacac catcttttac    1380

caagctgaag gtggaaaagg attctccaag acagtcaatt ccagcatctt gcagtacggc    1440

ctggagtccc tgaaacgaaa gacctcttac attgttcagg tcatggccag caccagtgct    1500

gggggaacca acgggaccag cataaatttc aagacattgt ca                       1542


<210> SEQ ID NO 78
<211> LENGTH: 514
<212> TYPE: PRT
<213> ORGANISM: Homo sapiens

<400> SEQUENCE: 78
```

-continued

```
Met Met Trp Thr Trp Ala Leu Trp Met Leu Pro Ser Leu Cys Lys Phe
1               5                   10                  15

Ser Leu Ala Ala Leu Pro Ala Lys Pro Glu Asn Ile Ser Cys Val Tyr
            20                  25                  30

Tyr Tyr Arg Lys Asn Leu Thr Cys Thr Trp Ser Pro Gly Lys Glu Thr
        35                  40                  45

Ser Tyr Thr Gln Tyr Thr Val Lys Arg Thr Tyr Ala Phe Gly Glu Lys
    50                  55                  60

His Asp Asn Cys Thr Thr Asn Ser Ser Thr Ser Glu Asn Arg Ala Ser
65                  70                  75                  80

Cys Ser Phe Phe Leu Pro Arg Ile Thr Ile Pro Asp Asn Tyr Thr Ile
                85                  90                  95

Glu Val Glu Ala Glu Asn Gly Asp Gly Val Ile Lys Ser His Met Thr
            100                 105                 110

Tyr Trp Arg Leu Glu Asn Ile Ala Lys Thr Glu Pro Pro Lys Ile Phe
        115                 120                 125

Arg Val Lys Pro Val Leu Gly Ile Lys Arg Met Ile Gln Ile Glu Trp
    130                 135                 140

Ile Lys Pro Glu Leu Ala Pro Val Ser Ser Asp Leu Lys Tyr Thr Leu
145                 150                 155                 160

Arg Phe Arg Thr Val Asn Ser Thr Ser Trp Met Glu Val Asn Phe Ala
                165                 170                 175

Lys Asn Arg Lys Asp Lys Asn Gln Thr Tyr Asn Leu Thr Gly Leu Gln
            180                 185                 190

Pro Phe Thr Glu Tyr Val Ile Ala Leu Arg Cys Ala Val Lys Glu Ser
        195                 200                 205

Lys Phe Trp Ser Asp Trp Ser Gln Glu Lys Met Gly Met Thr Glu Glu
    210                 215                 220

Glu Ala Pro Cys Gly Leu Glu Leu Trp Arg Val Leu Lys Pro Ala Glu
225                 230                 235                 240

Ala Asp Gly Arg Arg Pro Val Arg Leu Leu Trp Lys Lys Ala Arg Gly
                245                 250                 255

Ala Pro Val Leu Glu Lys Thr Leu Gly Tyr Asn Ile Trp Tyr Tyr Pro
            260                 265                 270

Glu Ser Asn Thr Asn Leu Thr Glu Thr Met Asn Thr Thr Asn Gln Gln
        275                 280                 285

Leu Glu Leu His Leu Gly Gly Glu Ser Phe Trp Val Ser Met Ile Ser
    290                 295                 300

Tyr Asn Ser Leu Gly Lys Ser Pro Val Ala Thr Leu Arg Ile Pro Ala
305                 310                 315                 320

Ile Gln Glu Lys Ser Phe Gln Cys Ile Glu Val Met Gln Ala Cys Val
                325                 330                 335

Ala Glu Asp Gln Leu Val Val Lys Trp Gln Ser Ser Ala Leu Asp Val
            340                 345                 350

Asn Thr Trp Met Ile Glu Trp Phe Pro Asp Val Asp Ser Glu Pro Thr
        355                 360                 365

Thr Leu Ser Trp Glu Ser Val Ser Gln Ala Thr Asn Trp Thr Ile Gln
    370                 375                 380

Gln Asp Lys Leu Lys Pro Phe Trp Cys Tyr Asn Ile Ser Val Tyr Pro
385                 390                 395                 400

Met Leu His Asp Lys Val Gly Glu Pro Tyr Ser Ile Gln Ala Tyr Ala
                405                 410                 415

Lys Glu Gly Val Pro Ser Glu Gly Pro Glu Thr Lys Val Glu Asn Ile
            420                 425                 430
```

```
Gly Val Lys Thr Val Thr Ile Thr Trp Lys Glu Ile Pro Lys Ser Glu
        435                 440                 445

Arg Lys Gly Ile Ile Cys Asn Tyr Thr Ile Phe Tyr Gln Ala Glu Gly
    450                 455                 460

Gly Lys Gly Phe Ser Lys Thr Val Asn Ser Ser Ile Leu Gln Tyr Gly
465                 470                 475                 480

Leu Glu Ser Leu Lys Arg Lys Thr Ser Tyr Ile Val Gln Val Met Ala
                485                 490                 495

Ser Thr Ser Ala Gly Gly Thr Asn Gly Thr Ser Ile Asn Phe Lys Thr
            500                 505                 510

Leu Ser


<210> SEQ ID NO 79
<211> LENGTH: 662
<212> TYPE: PRT
<213> ORGANISM: Homo sapiens

<400> SEQUENCE: 79

Met Lys Leu Ser Pro Gln Pro Ser Cys Val Asn Leu Gly Met Met Trp
1               5                   10                  15

Thr Trp Ala Leu Trp Met Leu Pro Ser Leu Cys Lys Phe Ser Leu Ala
            20                  25                  30

Ala Leu Pro Ala Lys Pro Glu Asn Ile Ser Cys Val Tyr Tyr Tyr Arg
        35                  40                  45

Lys Asn Leu Thr Cys Thr Trp Ser Pro Gly Lys Glu Thr Ser Tyr Thr
    50                  55                  60

Gln Tyr Thr Val Lys Arg Thr Tyr Ala Phe Gly Glu Lys His Asp Asn
65                  70                  75                  80

Cys Thr Thr Asn Ser Ser Thr Ser Glu Asn Arg Ala Ser Cys Ser Phe
                85                  90                  95

Phe Leu Pro Arg Ile Thr Ile Pro Asp Asn Tyr Thr Ile Glu Val Glu
            100                 105                 110

Ala Glu Asn Gly Asp Gly Val Ile Lys Ser His Met Thr Tyr Trp Arg
        115                 120                 125

Leu Glu Asn Ile Ala Lys Thr Glu Pro Pro Lys Ile Phe Arg Val Lys
    130                 135                 140

Pro Val Leu Gly Ile Lys Arg Met Ile Gln Ile Glu Trp Ile Lys Pro
145                 150                 155                 160

Glu Leu Ala Pro Val Ser Ser Asp Leu Lys Tyr Thr Leu Arg Phe Arg
                165                 170                 175

Thr Val Asn Ser Thr Ser Trp Met Glu Val Asn Phe Ala Lys Asn Arg
            180                 185                 190

Lys Asp Lys Asn Gln Thr Tyr Asn Leu Thr Gly Leu Gln Pro Phe Thr
        195                 200                 205

Glu Tyr Val Ile Ala Leu Arg Cys Ala Val Lys Glu Ser Lys Phe Trp
    210                 215                 220

Ser Asp Trp Ser Gln Glu Lys Met Gly Met Thr Glu Glu Glu Ala Pro
225                 230                 235                 240

Cys Gly Leu Glu Leu Trp Arg Val Leu Lys Pro Ala Glu Ala Asp Gly
                245                 250                 255

Arg Arg Pro Val Arg Leu Leu Trp Lys Lys Ala Arg Gly Ala Pro Val
            260                 265                 270

Leu Glu Lys Thr Leu Gly Tyr Asn Ile Trp Tyr Tyr Pro Glu Ser Asn
        275                 280                 285
```

```
Thr Asn Leu Thr Glu Thr Met Asn Thr Thr Asn Gln Gln Leu Glu Leu
    290                 295                 300

His Leu Gly Gly Glu Ser Phe Trp Val Ser Met Ile Ser Tyr Asn Ser
305                 310                 315                 320

Leu Gly Lys Ser Pro Val Ala Thr Leu Arg Ile Pro Ala Ile Gln Glu
                325                 330                 335

Lys Ser Phe Gln Cys Ile Glu Val Met Gln Ala Cys Val Ala Glu Asp
            340                 345                 350

Gln Leu Val Val Lys Trp Gln Ser Ser Ala Leu Asp Val Asn Thr Trp
        355                 360                 365

Met Ile Glu Trp Phe Pro Asp Val Asp Ser Glu Pro Thr Thr Leu Ser
    370                 375                 380

Trp Glu Ser Val Ser Gln Ala Thr Asn Trp Thr Ile Gln Gln Asp Lys
385                 390                 395                 400

Leu Lys Pro Phe Trp Cys Tyr Asn Ile Ser Val Tyr Pro Met Leu His
                405                 410                 415

Asp Lys Val Gly Glu Pro Tyr Ser Ile Gln Ala Tyr Ala Lys Glu Gly
            420                 425                 430

Val Pro Ser Glu Gly Pro Glu Thr Lys Val Glu Asn Ile Gly Val Lys
        435                 440                 445

Thr Val Thr Ile Thr Trp Lys Glu Ile Pro Lys Ser Glu Arg Lys Gly
    450                 455                 460

Ile Ile Cys Asn Tyr Thr Ile Phe Tyr Gln Ala Glu Gly Gly Lys Gly
465                 470                 475                 480

Phe Ser Lys Thr Val Asn Ser Ser Ile Leu Gln Tyr Gly Leu Glu Ser
                485                 490                 495

Leu Lys Arg Lys Thr Ser Tyr Ile Val Gln Val Met Ala Ser Thr Ser
            500                 505                 510

Ala Gly Gly Thr Asn Gly Thr Ser Ile Asn Phe Lys Thr Leu Ser Phe
        515                 520                 525

Ser Val Phe Glu Ile Ile Leu Ile Thr Ser Leu Ile Gly Gly Gly Leu
    530                 535                 540

Leu Ile Leu Ile Ile Leu Thr Val Ala Tyr Gly Leu Lys Lys Pro Asn
545                 550                 555                 560

Lys Leu Thr His Leu Cys Trp Pro Thr Val Pro Asn Pro Ala Glu Ser
                565                 570                 575

Ser Ile Ala Thr Trp His Gly Asp Asp Phe Lys Asp Lys Leu Asn Leu
            580                 585                 590

Lys Glu Ser Asp Asp Ser Val Asn Thr Glu Asp Arg Ile Leu Lys Pro
        595                 600                 605

Cys Ser Thr Pro Ser Asp Lys Leu Val Ile Asp Lys Leu Val Val Asn
    610                 615                 620

Phe Gly Asn Val Leu Gln Glu Ile Phe Thr Asp Glu Ala Arg Thr Gly
625                 630                 635                 640

Gln Glu Asn Asn Leu Gly Gly Glu Lys Asn Gly Thr Arg Ile Leu Ser
                645                 650                 655

Ser Cys Pro Thr Ser Ile
            660
```

<210> SEQ ID NO 80
<211> LENGTH: 732
<212> TYPE: PRT
<213> ORGANISM: Homo sapiens
<220> FEATURE:
<221> NAME/KEY: SIGNAL
<222> LOCATION: (1)..(20)

<220> FEATURE:
<221> NAME/KEY: TRANSMEM
<222> LOCATION: (520)..(543)

<400> SEQUENCE: 80

```
Met Met Trp Thr Trp Ala Leu Trp Met Leu Pro Ser Leu Cys Lys Phe
1               5                   10                  15

Ser Leu Ala Ala Leu Pro Ala Lys Pro Glu Asn Ile Ser Cys Val Tyr
            20                  25                  30

Tyr Tyr Arg Lys Asn Leu Thr Cys Thr Trp Ser Pro Gly Lys Glu Thr
        35                  40                  45

Ser Tyr Thr Gln Tyr Thr Val Lys Arg Thr Tyr Ala Phe Gly Glu Lys
    50                  55                  60

His Asp Asn Cys Thr Thr Asn Ser Ser Thr Ser Glu Asn Arg Ala Ser
65                  70                  75                  80

Cys Ser Phe Phe Leu Pro Arg Ile Thr Ile Pro Asp Asn Tyr Thr Ile
                85                  90                  95

Glu Val Glu Ala Glu Asn Gly Asp Gly Val Ile Lys Ser His Met Thr
            100                 105                 110

Tyr Trp Arg Leu Glu Asn Ile Ala Lys Thr Glu Pro Pro Lys Ile Phe
        115                 120                 125

Arg Val Lys Pro Val Leu Gly Ile Lys Arg Met Ile Gln Ile Glu Trp
    130                 135                 140

Ile Lys Pro Glu Leu Ala Pro Val Ser Ser Asp Leu Lys Tyr Thr Leu
145                 150                 155                 160

Arg Phe Arg Thr Val Asn Ser Thr Ser Trp Met Glu Val Asn Phe Ala
                165                 170                 175

Lys Asn Arg Lys Asp Lys Asn Gln Thr Tyr Asn Leu Thr Gly Leu Gln
            180                 185                 190

Pro Phe Thr Glu Tyr Val Ile Ala Leu Arg Cys Ala Val Lys Glu Ser
        195                 200                 205

Lys Phe Trp Ser Asp Trp Ser Gln Glu Lys Met Gly Met Thr Glu Glu
    210                 215                 220

Glu Ala Pro Cys Gly Leu Glu Leu Trp Arg Val Leu Lys Pro Ala Glu
225                 230                 235                 240

Ala Asp Gly Arg Arg Pro Val Arg Leu Leu Trp Lys Lys Ala Arg Gly
                245                 250                 255

Ala Pro Val Leu Glu Lys Thr Leu Gly Tyr Asn Ile Trp Tyr Tyr Pro
            260                 265                 270

Glu Ser Asn Thr Asn Leu Thr Glu Thr Met Asn Thr Thr Asn Gln Gln
        275                 280                 285

Leu Glu Leu His Leu Gly Gly Glu Ser Phe Trp Val Ser Met Ile Ser
    290                 295                 300

Tyr Asn Ser Leu Gly Lys Ser Pro Val Ala Thr Leu Arg Ile Pro Ala
305                 310                 315                 320

Ile Gln Glu Lys Ser Phe Gln Cys Ile Glu Val Met Gln Ala Cys Val
                325                 330                 335

Ala Glu Asp Gln Leu Val Val Lys Trp Gln Ser Ser Ala Leu Asp Val
            340                 345                 350

Asn Thr Trp Met Ile Glu Trp Phe Pro Asp Val Asp Ser Glu Pro Thr
        355                 360                 365

Thr Leu Ser Trp Glu Ser Val Ser Gln Ala Thr Asn Trp Thr Ile Gln
    370                 375                 380

Gln Asp Lys Leu Lys Pro Phe Trp Cys Tyr Asn Ile Ser Val Tyr Pro
385                 390                 395                 400
```

```
Met Leu His Asp Lys Val Gly Glu Pro Tyr Ser Ile Gln Ala Tyr Ala
                405                 410                 415

Lys Glu Gly Val Pro Ser Glu Gly Pro Glu Thr Lys Val Glu Asn Ile
            420                 425                 430

Gly Val Lys Thr Val Thr Ile Thr Trp Lys Glu Ile Pro Lys Ser Glu
        435                 440                 445

Arg Lys Gly Ile Ile Cys Asn Tyr Thr Ile Phe Tyr Gln Ala Glu Gly
    450                 455                 460

Gly Lys Gly Phe Ser Lys Thr Val Asn Ser Ser Ile Leu Gln Tyr Gly
465                 470                 475                 480

Leu Glu Ser Leu Lys Arg Lys Thr Ser Tyr Ile Val Gln Val Met Ala
                485                 490                 495

Ser Thr Ser Ala Gly Gly Thr Asn Gly Thr Ser Ile Asn Phe Lys Thr
            500                 505                 510

Leu Ser Phe Ser Val Phe Glu Ile Ile Leu Ile Thr Ser Leu Ile Gly
        515                 520                 525

Gly Gly Leu Leu Ile Leu Ile Ile Leu Thr Val Ala Tyr Gly Leu Lys
    530                 535                 540

Lys Pro Asn Lys Leu Thr His Leu Cys Trp Pro Thr Val Pro Asn Pro
545                 550                 555                 560

Ala Glu Ser Ser Ile Ala Thr Trp His Gly Asp Asp Phe Lys Asp Lys
                565                 570                 575

Leu Asn Leu Lys Glu Ser Asp Asp Ser Val Asn Thr Glu Asp Arg Ile
            580                 585                 590

Leu Lys Pro Cys Ser Thr Pro Ser Asp Lys Leu Val Ile Asp Lys Leu
        595                 600                 605

Val Val Asn Phe Gly Asn Val Leu Gln Glu Ile Phe Thr Asp Glu Ala
    610                 615                 620

Arg Thr Gly Gln Glu Asn Asn Leu Gly Gly Glu Lys Asn Gly Tyr Val
625                 630                 635                 640

Thr Cys Pro Phe Arg Pro Asp Cys Pro Leu Gly Lys Ser Phe Glu Glu
                645                 650                 655

Leu Pro Val Ser Pro Glu Ile Pro Pro Arg Lys Ser Gln Tyr Leu Arg
            660                 665                 670

Ser Arg Met Pro Glu Gly Thr Arg Pro Glu Ala Lys Glu Gln Leu Leu
        675                 680                 685

Phe Ser Gly Gln Ser Leu Val Pro Asp His Leu Cys Glu Glu Gly Ala
    690                 695                 700

Pro Asn Pro Tyr Leu Lys Asn Ser Val Thr Ala Arg Glu Phe Leu Val
705                 710                 715                 720

Ser Glu Lys Leu Pro Glu His Thr Lys Gly Glu Val
                725                 730
```

<210> SEQ ID NO 81
<211> LENGTH: 716
<212> TYPE: PRT
<213> ORGANISM: Mus musculus

<400> SEQUENCE: 81

```
Met Trp Thr Leu Ala Leu Trp Ala Phe Ser Phe Leu Cys Lys Phe Ser
1               5                   10                  15

Leu Ala Val Leu Pro Thr Lys Pro Glu Asn Ile Ser Cys Val Phe Tyr
            20                  25                  30

Phe Asp Arg Asn Leu Thr Cys Thr Trp Arg Pro Glu Lys Glu Thr Asn
        35                  40                  45
```

-continued

```
Asp Thr Ser Tyr Ile Val Thr Leu Thr Tyr Ser Tyr Gly Lys Ser Asn
    50                  55                  60

Tyr Ser Asp Asn Ala Thr Glu Ala Ser Tyr Ser Phe Pro Arg Ser Cys
65                  70                  75                  80

Ala Met Pro Pro Asp Ile Cys Ser Val Glu Val Gln Ala Gln Asn Gly
                85                  90                  95

Asp Gly Lys Val Lys Ser Asp Ile Thr Tyr Trp His Leu Ile Ser Ile
            100                 105                 110

Ala Lys Thr Glu Pro Pro Ile Ile Leu Ser Val Asn Pro Ile Cys Asn
        115                 120                 125

Arg Met Phe Gln Ile Gln Trp Lys Pro Arg Glu Lys Thr Arg Gly Phe
    130                 135                 140

Pro Leu Val Cys Met Leu Arg Phe Arg Thr Val Asn Ser Ser Arg Trp
145                 150                 155                 160

Thr Glu Val Asn Phe Glu Asn Cys Lys Gln Val Cys Asn Leu Thr Gly
                165                 170                 175

Leu Gln Ala Phe Thr Glu Tyr Val Leu Ala Leu Arg Phe Arg Phe Asn
            180                 185                 190

Asp Ser Arg Tyr Trp Ser Lys Trp Ser Lys Glu Glu Thr Arg Val Thr
        195                 200                 205

Met Glu Glu Val Pro His Val Leu Asp Leu Trp Arg Ile Leu Glu Pro
    210                 215                 220

Ala Asp Met Asn Gly Asp Arg Lys Val Arg Leu Leu Trp Lys Lys Ala
225                 230                 235                 240

Arg Gly Ala Pro Val Leu Glu Lys Thr Phe Gly Tyr His Ile Gln Tyr
                245                 250                 255

Phe Ala Glu Asn Ser Thr Asn Leu Thr Glu Ile Asn Asn Ile Thr Thr
            260                 265                 270

Gln Gln Tyr Glu Leu Leu Leu Met Ser Gln Ala His Ser Val Ser Val
        275                 280                 285

Thr Ser Phe Asn Ser Leu Gly Lys Ser Gln Glu Ala Ile Leu Arg Ile
    290                 295                 300

Pro Asp Val His Glu Lys Thr Phe Gln Tyr Ile Lys Ser Met Lys Ala
305                 310                 315                 320

Tyr Ile Ala Glu Pro Leu Leu Val Val Asn Trp Gln Ser Ser Ile Pro
                325                 330                 335

Ala Val Asp Thr Trp Ile Val Glu Trp Leu Pro Glu Ala Ala Met Ser
            340                 345                 350

Lys Phe Pro Ala Leu Ser Trp Glu Ser Val Ser Gln Val Thr Asn Trp
        355                 360                 365

Thr Ile Glu Gln Asp Lys Leu Lys Pro Phe Thr Cys Tyr Asn Ile Ser
    370                 375                 380

Val Tyr Pro Val Leu Gly His Arg Val Gly Glu Pro Tyr Ser Ile Gln
385                 390                 395                 400

Ala Tyr Ala Lys Glu Gly Thr Pro Leu Lys Gly Pro Glu Thr Arg Val
                405                 410                 415

Glu Asn Ile Gly Leu Arg Thr Ala Thr Ile Thr Trp Lys Glu Ile Pro
            420                 425                 430

Lys Ser Ala Arg Asn Gly Phe Ile Asn Asn Tyr Thr Val Phe Tyr Gln
        435                 440                 445

Ala Glu Gly Gly Lys Glu Leu Ser Lys Thr Val Asn Ser His Ala Leu
    450                 455                 460

Gln Cys Asp Leu Glu Ser Leu Thr Arg Arg Thr Ser Tyr Thr Val Trp
```

465 470 475 480

Val Met Ala Ser Thr Arg Ala Gly Gly Thr Asn Gly Val Arg Ile Asn
485 490 495

Phe Lys Thr Leu Ser Ile Ser Val Phe Glu Ile Val Leu Leu Thr Ser
500 505 510

Leu Val Gly Gly Gly Leu Leu Leu Leu Ser Ile Lys Thr Val Thr Phe
515 520 525

Gly Leu Arg Lys Pro Asn Arg Leu Thr Pro Leu Cys Cys Pro Asp Val
530 535 540

Pro Asn Pro Ala Glu Ser Ser Leu Ala Thr Trp Leu Gly Asp Gly Phe
545 550 555 560

Lys Lys Ser Asn Met Lys Glu Thr Gly Asn Ser Gly Asp Thr Glu Asp
565 570 575

Val Val Leu Lys Pro Cys Pro Val Pro Ala Asp Leu Ile Asp Lys Leu
580 585 590

Val Val Asn Phe Glu Asn Phe Leu Glu Val Val Leu Thr Glu Glu Ala
595 600 605

Gly Lys Gly Gln Ala Ser Ile Leu Gly Gly Glu Ala Asn Glu Tyr Val
610 615 620

Thr Ser Pro Ser Arg Pro Asp Gly Pro Pro Gly Lys Ser Phe Lys Glu
625 630 635 640

Pro Ser Val Leu Thr Glu Val Ala Ser Glu Asp Ser His Ser Thr Cys
645 650 655

Ser Arg Met Ala Asp Glu Ala Tyr Ser Glu Leu Ala Arg Gln Pro Ser
660 665 670

Ser Ser Cys Gln Ser Pro Gly Leu Ser Pro Pro Arg Glu Asp Gln Ala
675 680 685

Gln Asn Pro Tyr Leu Lys Asn Ser Val Thr Thr Arg Glu Phe Leu Val
690 695 700

His Glu Asn Ile Pro Glu His Ser Lys Gly Glu Val
705 710 715

<210> SEQ ID NO 82
<211> LENGTH: 4
<212> TYPE: PRT
<213> ORGANISM: Artificial
<220> FEATURE:
<223> OTHER INFORMATION: an artificially synthesized peptide sequence

<400> SEQUENCE: 82

Gly Gly Gly Ser
1

<210> SEQ ID NO 83
<211> LENGTH: 4
<212> TYPE: PRT
<213> ORGANISM: Artificial
<220> FEATURE:
<223> OTHER INFORMATION: an artificially synthesized peptide sequence

<400> SEQUENCE: 83

Ser Gly Gly Gly
1

<210> SEQ ID NO 84
<211> LENGTH: 5
<212> TYPE: PRT
<213> ORGANISM: Artificial
<220> FEATURE:
<223> OTHER INFORMATION: an artificially synthesized peptide sequence

<400> SEQUENCE: 84

Gly Gly Gly Gly Ser
1 5

<210> SEQ ID NO 85
<211> LENGTH: 5
<212> TYPE: PRT
<213> ORGANISM: Artificial
<220> FEATURE:
<223> OTHER INFORMATION: an artificially synthesized peptide sequence

<400> SEQUENCE: 85

Ser Gly Gly Gly Gly
1 5

<210> SEQ ID NO 86
<211> LENGTH: 6
<212> TYPE: PRT
<213> ORGANISM: Artificial
<220> FEATURE:
<223> OTHER INFORMATION: an artificially synthesized peptide sequence

<400> SEQUENCE: 86

Gly Gly Gly Gly Gly Ser
1 5

<210> SEQ ID NO 87
<211> LENGTH: 6
<212> TYPE: PRT
<213> ORGANISM: Artificial
<220> FEATURE:
<223> OTHER INFORMATION: an artificially synthesized peptide sequence

<400> SEQUENCE: 87

Ser Gly Gly Gly Gly Gly
1 5

<210> SEQ ID NO 88
<211> LENGTH: 7
<212> TYPE: PRT
<213> ORGANISM: Artificial
<220> FEATURE:
<223> OTHER INFORMATION: an artificially synthesized peptide sequence

<400> SEQUENCE: 88

Gly Gly Gly Gly Gly Gly Ser
1 5

<210> SEQ ID NO 89
<211> LENGTH: 7
<212> TYPE: PRT
<213> ORGANISM: Artificial
<220> FEATURE:
<223> OTHER INFORMATION: an artificially synthesized peptide sequence

<400> SEQUENCE: 89

Ser Gly Gly Gly Gly Gly Gly
1 5

<210> SEQ ID NO 90
<211> LENGTH: 40
<212> TYPE: DNA
<213> ORGANISM: Artificial
<220> FEATURE:
<223> OTHER INFORMATION: an artificially synthesized primer sequence

<400> SEQUENCE: 90
taatagcggc cgctcattat ttaccaggag agtgggagag 40

<210> SEQ ID NO 91
<211> LENGTH: 40
<212> TYPE: DNA
<213> ORGANISM: Artificial
<220> FEATURE:
<223> OTHER INFORMATION: an artificially synthesized primer sequence

<400> SEQUENCE: 91
taatagcggc cgctcattaa cactcattcc tgttgaagct 40

<210> SEQ ID NO 92
<211> LENGTH: 33
<212> TYPE: DNA
<213> ORGANISM: Artificial
<220> FEATURE:
<223> OTHER INFORMATION: an artificially synthesized primer sequence

<400> SEQUENCE: 92
gacgaattcc accatgggat ggagctggat ctt 33

<210> SEQ ID NO 93
<211> LENGTH: 33
<212> TYPE: DNA
<213> ORGANISM: Artificial
<220> FEATURE:
<223> OTHER INFORMATION: an artificially synthesized primer sequence

<400> SEQUENCE: 93
gacgaattcc accatgagtg tgcccactca ggt 33

<210> SEQ ID NO 94
<211> LENGTH: 33
<212> TYPE: DNA
<213> ORGANISM: Artificial
<220> FEATURE:
<223> OTHER INFORMATION: an artificially synthesized primer sequence

<400> SEQUENCE: 94
gacgaattcc accatggaat gtaactggat act 33

<210> SEQ ID NO 95
<211> LENGTH: 33
<212> TYPE: DNA
<213> ORGANISM: Artificial
<220> FEATURE:
<223> OTHER INFORMATION: an artificially synthesized primer sequence

<400> SEQUENCE: 95
gacgaattcc accatggatt ttctggtgca gat 33

<210> SEQ ID NO 96
<211> LENGTH: 30
<212> TYPE: PRT
<213> ORGANISM: Homo sapiens

<400> SEQUENCE: 96

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30
```

<210> SEQ ID NO 97
<211> LENGTH: 14

<212> TYPE: PRT
<213> ORGANISM: Homo sapiens

<400> SEQUENCE: 97

Trp Val Arg Gln Ala Pro Gly Gln Gly Leu Glu Trp Met Gly
1               5                   10

<210> SEQ ID NO 98
<211> LENGTH: 32
<212> TYPE: PRT
<213> ORGANISM: Homo sapiens

<400> SEQUENCE: 98

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 99
<211> LENGTH: 11
<212> TYPE: PRT
<213> ORGANISM: Homo sapiens

<400> SEQUENCE: 99

Trp Gly Gln Gly Thr Leu Val Thr Val Ser Ser
1               5                   10

<210> SEQ ID NO 100
<211> LENGTH: 23
<212> TYPE: PRT
<213> ORGANISM: Homo sapiens

<400> SEQUENCE: 100

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 101
<211> LENGTH: 15
<212> TYPE: PRT
<213> ORGANISM: Homo sapiens

<400> SEQUENCE: 101

Trp Tyr Gln Gln Lys Pro Gly Lys Ala Pro Lys Leu Leu Ile Tyr
1               5                   10                  15

<210> SEQ ID NO 102
<211> LENGTH: 32
<212> TYPE: PRT
<213> ORGANISM: Homo sapiens

<400> SEQUENCE: 102

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 103
<211> LENGTH: 10
<212> TYPE: PRT
<213> ORGANISM: Homo sapiens

<400> SEQUENCE: 103

Phe Gly Gly Gly Thr Lys Val Glu Ile Lys
1 5 10

<210> SEQ ID NO 104
<211> LENGTH: 119
<212> TYPE: PRT
<213> ORGANISM: Mus musculus

<400> SEQUENCE: 104

Asp Val Gln Leu Arg Glu Ser Gly Pro Gly Leu Val Lys Pro Ser Gln
1 5 10 15

Ser Leu Ser Leu Thr Cys Thr Val Thr Gly Tyr Ser Ile Thr Ser Asp
20 25 30

Tyr Ala Trp Asn Trp Ile Arg Gln Phe Pro Gly Asn Lys Leu Glu Trp
35 40 45

Met Gly Tyr Ile Ser Tyr Ser Gly Ser Thr Ser Tyr Asn Pro Ser Leu
50 55 60

Lys Ser Arg Val Ser Ile Thr Arg Asp Thr Ser Lys Asn Gln Phe Phe
65 70 75 80

Leu Gln Leu Asn Ser Val Thr Thr Glu Asp Thr Ala Thr Tyr Tyr Cys
85 90 95

Ala Pro Met Ile Thr Thr Asp Trp Phe Phe Asp Val Trp Gly Ala Gly
100 105 110

Thr Thr Val Thr Val Ser Ser
115

<210> SEQ ID NO 105
<211> LENGTH: 6
<212> TYPE: PRT
<213> ORGANISM: Mus musculus

<400> SEQUENCE: 105

Ser Asp Tyr Ala Trp Asn
1 5

<210> SEQ ID NO 106
<211> LENGTH: 15
<212> TYPE: PRT
<213> ORGANISM: Mus musculus

<400> SEQUENCE: 106

Tyr Ile Ser Tyr Ser Gly Ser Thr Ser Tyr Asn Pro Ser Leu Lys
1 5 10 15

<210> SEQ ID NO 107
<211> LENGTH: 10
<212> TYPE: PRT
<213> ORGANISM: Mus musculus

<400> SEQUENCE: 107

Met Ile Thr Thr Asp Trp Phe Phe Asp Val
1 5 10

<210> SEQ ID NO 108
<211> LENGTH: 107
<212> TYPE: PRT
<213> ORGANISM: Mus musculus

<400> SEQUENCE: 108

Asp Ile Val Met Thr Gln Ser Pro Ala Thr Leu Ser Val Thr Pro Gly
1 5 10 15

Asp Arg Val Ser Leu Ser Cys Arg Ala Ser His Asp Ile Ser Asp Phe

```
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Trp
                85                  90                  95

Thr Phe Gly Gly Gly Thr Lys Leu Glu Ile Lys
            100                 105


<210> SEQ ID NO 109
<211> LENGTH: 11
<212> TYPE: PRT
<213> ORGANISM: Mus musculus

<400> SEQUENCE: 109

Arg Ala Ser His Asp Ile Ser Asp Phe Leu His
1               5                   10


<210> SEQ ID NO 110
<211> LENGTH: 7
<212> TYPE: PRT
<213> ORGANISM: Mus musculus

<400> SEQUENCE: 110

Tyr Ala Ser Gln Ser Ile Ser
1               5


<210> SEQ ID NO 111
<211> LENGTH: 9
<212> TYPE: PRT
<213> ORGANISM: Mus musculus

<400> SEQUENCE: 111

Gln Asn Gly His Ser Phe Pro Trp Thr
1               5


<210> SEQ ID NO 112
<211> LENGTH: 121
<212> TYPE: PRT
<213> ORGANISM: Artificial
<220> FEATURE:
<223> OTHER INFORMATION: An artificially synthesized peptide sequence

<400> SEQUENCE: 112

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
        35                  40                  45

Gly Leu Ile Asn Pro Tyr Asn Gly Gly Thr Ser Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Met Asp Tyr Trp Gly
            100                 105                 110
```

Gln Gly Thr Leu Val Thr Val Ser Ser
115 120

<210> SEQ ID NO 113
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 113

Glu Ile Asn Pro Tyr Asn Gly Gly Thr Ser Tyr Asn Gln Lys Phe Lys
1 5 10 15

Gly

<210> SEQ ID NO 114
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 114

Leu Ile Asp Pro Tyr Asn Gly Gly Thr Ser Tyr Asn Gln Lys Phe Lys
1 5 10 15

Gly

<210> SEQ ID NO 115
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 115

Leu Ile Asn Pro Tyr Asn Gly Gly Thr Ser Tyr Asn Asp Lys Phe Lys
1 5 10 15

Gly

<210> SEQ ID NO 116
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 116

Leu Ile Asn Pro Tyr Asn Gly Gly Thr Ser Tyr Asn Gln Gln Phe Lys
1 5 10 15

Gly

<210> SEQ ID NO 117
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 117

Leu Ile Asn Pro Tyr Asn Gly Gly Thr Ser Tyr Asn Gln Lys Phe Gln
1 5 10 15

Gly

<210> SEQ ID NO 118
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 118

Leu Ile Asn Pro Tyr Asn Gly Gly Thr Ser Tyr Asn Gln Lys Phe Lys
1 5 10 15

Asp

<210> SEQ ID NO 119
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 119

Leu Ile Asn Pro Tyr Asn Gly Gly Thr Ser Tyr Asn Gln Lys Phe Gln
1 5 10 15

Asp

<210> SEQ ID NO 120
<211> LENGTH: 14
<212> TYPE: PRT
<213> ORGANISM: Artificial
<220> FEATURE:
<223> OTHER INFORMATION: An artificially synthesized peptide sequence

<400> SEQUENCE: 120

Trp Val Gln Gln Ser Pro Gly Gln Gly Leu Glu Trp Met Gly
1 5 10

<210> SEQ ID NO 121
<211> LENGTH: 11
<212> TYPE: PRT
<213> ORGANISM: Artificial
<220> FEATURE:
<223> OTHER INFORMATION: An artificially synthesized peptide sequence

<400> SEQUENCE: 121

Gln Thr Ser Glu Asn Ile Tyr Ser Phe Leu Ala
1 5 10

<210> SEQ ID NO 122
<211> LENGTH: 11
<212> TYPE: PRT
<213> ORGANISM: Artificial
<220> FEATURE:
<223> OTHER INFORMATION: An artificially synthesized peptide sequence

<400> SEQUENCE: 122

Arg Thr Ser Glu Asp Ile Tyr Ser Phe Leu Ala
1 5 10

<210> SEQ ID NO 123
<211> LENGTH: 7
<212> TYPE: PRT
<213> ORGANISM: Artificial
<220> FEATURE:
<223> OTHER INFORMATION: An artificially synthesized peptide sequence

<400> SEQUENCE: 123

Asp Ala Lys Thr Leu Ala Lys
1 5

<210> SEQ ID NO 124
<211> LENGTH: 7
<212> TYPE: PRT
<213> ORGANISM: Artificial
<220> FEATURE:
<223> OTHER INFORMATION: An artificially synthesized peptide sequence

<400> SEQUENCE: 124

Asn Ala Gln Thr Leu Ala Lys
1 5

<210> SEQ ID NO 125
<211> LENGTH: 7
<212> TYPE: PRT
<213> ORGANISM: Artificial
<220> FEATURE:
<223> OTHER INFORMATION: An artificially synthesized peptide sequence

<400> SEQUENCE: 125

Asn Ala Lys Thr Glu Ala Lys
1 5

<210> SEQ ID NO 126
<211> LENGTH: 7
<212> TYPE: PRT
<213> ORGANISM: Artificial
<220> FEATURE:
<223> OTHER INFORMATION: An artificially synthesized peptide sequence

<400> SEQUENCE: 126

Asn Ala Lys Thr Leu Ala Gln
1 5

<210> SEQ ID NO 127
<211> LENGTH: 7
<212> TYPE: PRT
<213> ORGANISM: Artificial
<220> FEATURE:
<223> OTHER INFORMATION: An artificially synthesized peptide sequence

<400> SEQUENCE: 127

Asn Ala Lys Thr Leu Ala Asp
1 5

<210> SEQ ID NO 128
<211> LENGTH: 324
<212> TYPE: PRT
<213> ORGANISM: Artificial
<220> FEATURE:
<223> OTHER INFORMATION: An artificially synthesized peptide sequence

<400> SEQUENCE: 128

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Asn Phe Gly Thr Gln Thr
65 70 75 80

Tyr Thr Cys Asn Val Asp His Lys Pro Ser Asn Thr Lys Val Asp Lys
85 90 95

```
Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Glu Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro


<210> SEQ ID NO 129
<211> LENGTH: 326
<212> TYPE: PRT
<213> ORGANISM: Artificial
<220> FEATURE:
<223> OTHER INFORMATION: An artificially synthesized peptide sequence

<400> SEQUENCE: 129

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
```

```
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 130
<211> LENGTH: 447
<212> TYPE: PRT
<213> ORGANISM: Artificial
<220> FEATURE:
<223> OTHER INFORMATION: An artificially synthesized peptide sequence

<400> SEQUENCE: 130

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
        35                  40                  45

Gly Leu Ile Asn Pro Tyr Asn Gly Gly Thr Ser Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175
```

```
Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Ser Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 131
<211> LENGTH: 32
<212> TYPE: PRT
<213> ORGANISM: Artificial
<220> FEATURE:
<223> OTHER INFORMATION: An artificially synthesized peptide sequence

<400> SEQUENCE: 131

Arg Val Thr Ile Thr Ala Asp Lys Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30


<210> SEQ ID NO 132
<211> LENGTH: 326
<212> TYPE: PRT
<213> ORGANISM: Artificial
<220> FEATURE:
<223> OTHER INFORMATION: An artificially synthesized peptide sequence

<400> SEQUENCE: 132

Ala Ser Thr Lys Gly Pro Ser Val Phe Pro Leu Ala Pro Cys Ser Arg
1               5                   10                  15
```

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 133
<211> LENGTH: 451
<212> TYPE: PRT
<213> ORGANISM: Artificial
<220> FEATURE:
<223> OTHER INFORMATION: An artificially synthesized peptide sequence

<400> SEQUENCE: 133

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
        35                  40                  45
```

-continued

```
Gly Leu Ile Asn Pro Tyr Asn Gly Gly Thr Ser Tyr Asn Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 134

<211> LENGTH: 447
<212> TYPE: PRT
<213> ORGANISM: Artificial
<220> FEATURE:
<223> OTHER INFORMATION: An artificially synthesized peptide sequence

<400> SEQUENCE: 134

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
        35                  40                  45

Gly Leu Ile Asn Pro Tyr Asn Gly Gly Thr Ser Tyr Asn Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380
```

Gly Gln Pro Glu Asn Asn Tyr Lys Thr Thr Pro Pro Met Leu Asp Ser
385 390 395 400

Asp Gly Ser Phe Phe Leu Tyr Ser Lys Leu Thr Val Asp Lys Ser Arg
405 410 415

Trp Gln Gln Gly Asn Val Phe Ser Cys Ser Val Met His Glu Ala Leu
420 425 430

His Asn His Tyr Thr Gln Lys Ser Leu Ser Leu Ser Pro Gly Lys
435 440 445

<210> SEQ ID NO 135
<211> LENGTH: 447
<212> TYPE: PRT
<213> ORGANISM: Artificial
<220> FEATURE:
<223> OTHER INFORMATION: An artificially synthesized peptide sequence

<400> SEQUENCE: 135

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Ile Met Asn Trp Val Arg Gln Ala Pro Gly Gln Gly Leu Glu Trp Met
35 40 45

Gly Leu Ile Asn Pro Tyr Asn Gly Gly Thr Ser Tyr Asn Gln Lys Phe
50 55 60

Lys Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Asp Gly Tyr Asp Asp Gly Pro Tyr Thr Met Asp Tyr Trp Gly
100 105 110

Gln Gly Thr Leu Val Thr Val Ser Ser Ala Ser Thr Lys Gly Pro Ser
115 120 125

Val Phe Pro Leu Ala Pro Ser Ser Lys Ser Thr Ser Gly Gly Thr Ala
130 135 140

Ala Leu Gly Cys Leu Val Lys Asp Tyr Phe Pro Glu Pro Val Thr Val
145 150 155 160

Ser Trp Asn Ser Gly Ala Leu Thr Ser Gly Val His Thr Phe Pro Ala
165 170 175

Val Leu Gln Ser Ser Gly Leu Tyr Ser Leu Ser Ser Val Val Thr Val
180 185 190

Pro Ser Ser Asn Phe Gly Thr Gln Thr Tyr Thr Cys Asn Val Asp His
195 200 205

Lys Pro Ser Asn Thr Lys Val Asp Lys Thr Val Glu Arg Lys Ser Cys
210 215 220

Val Glu Cys Pro Pro Cys Pro Ala Pro Pro Val Ala Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser His Glu Asp Pro Glu
260 265 270

Val Gln Phe Asn Trp Tyr Val Asp Gly Val Glu Val His Asn Ala Lys
275 280 285

Thr Lys Pro Arg Glu Glu Gln Phe Asn Ser Thr Phe Arg Val Val Ser
290 295 300

Val Leu Thr Val Val His Gln Asp Trp Leu Asn Gly Lys Glu Tyr Lys

```
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 136
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 136

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
        35                  40                  45

Gly Leu Ile Asn Pro Tyr Asn Gly Gly Thr Ser Tyr Asn Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Ser Cys
    210                 215                 220

Val Glu Cys Pro Pro Cys Pro Ala Pro Pro Val Ala Gly Pro Ser Val
225                 230                 235                 240
```

```
Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro
        435                 440                 445


<210> SEQ ID NO 137
<211> LENGTH: 121
<212> TYPE: PRT
<213> ORGANISM: Artificial
<220> FEATURE:
<223> OTHER INFORMATION: An artificially synthesized peptide sequence

<400> SEQUENCE: 137

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Gln Gln Ser Pro Gly Gln Gly Leu Glu Trp Met
        35                  40                  45

Gly Leu Ile Asn Pro Tyr Asn Gly Gly Thr Ser Tyr Asn Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Met Asp Tyr Trp Gly
            100                 105                 110

Gln Gly Thr Leu Val Thr Val Ser Ser
        115                 120


<210> SEQ ID NO 138
<211> LENGTH: 121
<212> TYPE: PRT
<213> ORGANISM: Artificial
<220> FEATURE:
```

<223> OTHER INFORMATION: An artificially synthesized peptide sequence

<400> SEQUENCE: 138

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
        35                  40                  45

Gly Glu Ile Asn Pro Tyr Asn Gly Gly Thr Ser Tyr Asn Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Met Asp Tyr Trp Gly
            100                 105                 110

Gln Gly Thr Leu Val Thr Val Ser Ser
        115                 120
```

<210> SEQ ID NO 139
<211> LENGTH: 121
<212> TYPE: PRT
<213> ORGANISM: Artificial
<220> FEATURE:
<223> OTHER INFORMATION: An artificially synthesized peptide sequence

<400> SEQUENCE: 139

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
        35                  40                  45

Gly Leu Ile Asp Pro Tyr Asn Gly Gly Thr Ser Tyr Asn Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Met Asp Tyr Trp Gly
            100                 105                 110

Gln Gly Thr Leu Val Thr Val Ser Ser
        115                 120
```

<210> SEQ ID NO 140
<211> LENGTH: 121
<212> TYPE: PRT
<213> ORGANISM: Artificial
<220> FEATURE:
<223> OTHER INFORMATION: An artificially synthesized peptide sequence

<400> SEQUENCE: 140

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
        35                  40                  45
```

Gly Leu Ile Asn Pro Tyr Asn Gly Gly Thr Ser Tyr Asn Asp Lys Phe
50 55 60

Lys Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Asp Gly Tyr Asp Asp Gly Pro Tyr Thr Met Asp Tyr Trp Gly
100 105 110

Gln Gly Thr Leu Val Thr Val Ser Ser
115 120

<210> SEQ ID NO 141
<211> LENGTH: 121
<212> TYPE: PRT
<213> ORGANISM: Artificial
<220> FEATURE:
<223> OTHER INFORMATION: An artificially synthesized peptide sequence

<400> SEQUENCE: 141

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Ile Met Asn Trp Val Arg Gln Ala Pro Gly Gln Gly Leu Glu Trp Met
35 40 45

Gly Leu Ile Asn Pro Tyr Asn Gly Gly Thr Ser Tyr Asn Gln Gln Phe
50 55 60

Lys Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Asp Gly Tyr Asp Asp Gly Pro Tyr Thr Met Asp Tyr Trp Gly
100 105 110

Gln Gly Thr Leu Val Thr Val Ser Ser
115 120

<210> SEQ ID NO 142
<211> LENGTH: 121
<212> TYPE: PRT
<213> ORGANISM: Artificial
<220> FEATURE:
<223> OTHER INFORMATION: An artificially synthesized peptide sequence

<400> SEQUENCE: 142

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Ile Met Asn Trp Val Arg Gln Ala Pro Gly Gln Gly Leu Glu Trp Met
35 40 45

Gly Leu Ile Asn Pro Tyr Asn Gly Gly Thr Ser Tyr Asn Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Asp Gly Tyr Asp Asp Gly Pro Tyr Thr Met Asp Tyr Trp Gly
100 105 110

```
Gln Gly Thr Leu Val Thr Val Ser Ser
        115                 120


<210> SEQ ID NO 143
<211> LENGTH: 121
<212> TYPE: PRT
<213> ORGANISM: Artificial
<220> FEATURE:
<223> OTHER INFORMATION: An artificially synthesized peptide sequence

<400> SEQUENCE: 143

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
        35                  40                  45

Gly Leu Ile Asn Pro Tyr Asn Gly Gly Thr Ser Tyr Asn Gln Lys Phe
    50                  55                  60

Gln Asp Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Met Asp Tyr Trp Gly
            100                 105                 110

Gln Gly Thr Leu Val Thr Val Ser Ser
        115                 120


<210> SEQ ID NO 144
<211> LENGTH: 107
<212> TYPE: PRT
<213> ORGANISM: Artificial
<220> FEATURE:
<223> OTHER INFORMATION: An artificially synthesized peptide sequence

<400> SEQUENCE: 144

Asp Ile Gln Met Thr Gln Ser Pro Ser Ser Leu Ser Ala Ser Val Gly
1               5                   10                  15

Asp Arg Val Thr Ile Thr Cys Gln Thr Ser Glu Asn Ile Tyr Ser Phe
            20                  25                  30

Leu Ala Trp Tyr Gln Gln Lys Pro Gly Lys Ala Pro Lys Leu Leu Ile
        35                  40                  45

Tyr Asn Ala Lys Thr Leu Ala Lys Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Glu Ser Pro Leu
                85                  90                  95

Thr Phe Gly Gly Gly Thr Lys Val Glu Ile Lys
            100                 105


<210> SEQ ID NO 145
<211> LENGTH: 107
<212> TYPE: PRT
<213> ORGANISM: Artificial
<220> FEATURE:
<223> OTHER INFORMATION: An artificially synthesized peptide sequence

<400> SEQUENCE: 145

Asp Ile Gln Met Thr Gln Ser Pro Ser Ser Leu Ser Ala Ser Val Gly
```

1 5 10 15

Asp Arg Val Thr Ile Thr Cys Arg Thr Ser Glu Asp Ile Tyr Ser Phe
20 25 30

Leu Ala Trp Tyr Gln Gln Lys Pro Gly Lys Ala Pro Lys Leu Leu Ile
35 40 45

Tyr Asn Ala Lys Thr Leu Ala Lys Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln His His Tyr Glu Ser Pro Leu
85 90 95

Thr Phe Gly Gly Gly Thr Lys Val Glu Ile Lys
100 105

<210> SEQ ID NO 146
<211> LENGTH: 107
<212> TYPE: PRT
<213> ORGANISM: Artificial
<220> FEATURE:
<223> OTHER INFORMATION: An artificially synthesized peptide sequence

<400> SEQUENCE: 146

Asp Ile Gln Met Thr Gln Ser Pro Ser Ser Leu Ser Ala Ser Val Gly
1 5 10 15

Asp Arg Val Thr Ile Thr Cys Arg Thr Ser Glu Asn Ile Tyr Ser Phe
20 25 30

Leu Ala Trp Tyr Gln Gln Lys Pro Gly Lys Ala Pro Lys Leu Leu Ile
35 40 45

Tyr Asp Ala Lys Thr Leu Ala Lys Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln His His Tyr Glu Ser Pro Leu
85 90 95

Thr Phe Gly Gly Gly Thr Lys Val Glu Ile Lys
100 105

<210> SEQ ID NO 147
<211> LENGTH: 107
<212> TYPE: PRT
<213> ORGANISM: Artificial
<220> FEATURE:
<223> OTHER INFORMATION: An artificially synthesized peptide sequence

<400> SEQUENCE: 147

Asp Ile Gln Met Thr Gln Ser Pro Ser Ser Leu Ser Ala Ser Val Gly
1 5 10 15

Asp Arg Val Thr Ile Thr Cys Arg Thr Ser Glu Asn Ile Tyr Ser Phe
20 25 30

Leu Ala Trp Tyr Gln Gln Lys Pro Gly Lys Ala Pro Lys Leu Leu Ile
35 40 45

Tyr Asn Ala Gln Thr Leu Ala Lys Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln His His Tyr Glu Ser Pro Leu
85 90 95

Thr Phe Gly Gly Gly Thr Lys Val Glu Ile Lys 100 105

<210> SEQ ID NO 148
<211> LENGTH: 107
<212> TYPE: PRT
<213> ORGANISM: Artificial
<220> FEATURE:
<223> OTHER INFORMATION: An artificially synthesized peptide sequence

<400> SEQUENCE: 148

Asp Ile Gln Met Thr Gln Ser Pro Ser Ser Leu Ser Ala Ser Val Gly
1 5 10 15

Asp Arg Val Thr Ile Thr Cys Arg Thr Ser Glu Asn Ile Tyr Ser Phe
20 25 30

Leu Ala Trp Tyr Gln Gln Lys Pro Gly Lys Ala Pro Lys Leu Leu Ile
35 40 45

Tyr Asn Ala Lys Thr Glu Ala Lys Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln His His Tyr Glu Ser Pro Leu
85 90 95

Thr Phe Gly Gly Gly Thr Lys Val Glu Ile Lys
100 105

<210> SEQ ID NO 149
<211> LENGTH: 107
<212> TYPE: PRT
<213> ORGANISM: Artificial
<220> FEATURE:
<223> OTHER INFORMATION: An artificially synthesized peptide sequence

<400> SEQUENCE: 149

Asp Ile Gln Met Thr Gln Ser Pro Ser Ser Leu Ser Ala Ser Val Gly
1 5 10 15

Asp Arg Val Thr Ile Thr Cys Arg Thr Ser Glu Asn Ile Tyr Ser Phe
20 25 30

Leu Ala Trp Tyr Gln Gln Lys Pro Gly Lys Ala Pro Lys Leu Leu Ile
35 40 45

Tyr Asn Ala Lys Thr Leu Ala Gln Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln His His Tyr Glu Ser Pro Leu
85 90 95

Thr Phe Gly Gly Gly Thr Lys Val Glu Ile Lys
100 105

<210> SEQ ID NO 150
<211> LENGTH: 107
<212> TYPE: PRT
<213> ORGANISM: Artificial
<220> FEATURE:
<223> OTHER INFORMATION: An artificially synthesized peptide sequence

<400> SEQUENCE: 150

Asp Ile Gln Met Thr Gln Ser Pro Ser Ser Leu Ser Ala Ser Val Gly
1 5 10 15

Asp Arg Val Thr Ile Thr Cys Arg Thr Ser Glu Asn Ile Tyr Ser Phe
20 25 30

```
Leu Ala Trp Tyr Gln Gln Lys Pro Gly Lys Ala Pro Lys Leu Leu Ile
        35                  40                  45

Tyr Asn Ala Lys Thr Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Glu Ser Pro Leu
                85                  90                  95

Thr Phe Gly Gly Gly Thr Lys Val Glu Ile Lys
            100                 105


<210> SEQ ID NO 151
<211> LENGTH: 447
<212> TYPE: PRT
<213> ORGANISM: Artificial
<220> FEATURE:
<223> OTHER INFORMATION: An artificially synthesized peptide sequence

<400> SEQUENCE: 151

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
        35                  40                  45

Gly Leu Ile Asn Pro Tyr Asn Gly Gly Thr Ser Tyr Asn Gln Gln Phe
    50                  55                  60

Gln Asp Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Ser Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
```

-continued

```
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 152
<211> LENGTH: 214
<212> TYPE: PRT
<213> ORGANISM: Artificial
<220> FEATURE:
<223> OTHER INFORMATION: An artificially synthesized peptide sequence

<400> SEQUENCE: 152

Asp Ile Gln Met Thr Gln Ser Pro Ser Ser Leu Ser Ala Ser Val Gly
1               5                   10                  15

Asp Arg Val Thr Ile Thr Cys Gln Thr Ser Glu Asp Ile Tyr Ser Phe
            20                  25                  30

Leu Ala Trp Tyr Gln Gln Lys Pro Gly Lys Ala Pro Lys Leu Leu Ile
        35                  40                  45

Tyr Asn Ala Gln Thr Glu Ala Gln Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Glu Ser Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 153
<211> LENGTH: 326
<212> TYPE: PRT
<213> ORGANISM: Artificial
<220> FEATURE:
<223> OTHER INFORMATION: An artificially synthesized peptide sequence

<400> SEQUENCE: 153

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 154
<211> LENGTH: 326
<212> TYPE: PRT
<213> ORGANISM: Artificial
<220> FEATURE:

<223> OTHER INFORMATION: An artificially synthesized peptide sequence

<400> SEQUENCE: 154

Ala Ser Thr Lys Gly Pro Ser Val Phe Pro Leu Ala Pro Cys Ser Arg
1 5 10 15

Ser Thr Ser Glu Ser Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Asn Phe Gly Thr Gln Thr
65 70 75 80

Tyr Thr Cys Asn Val Asp His Lys Pro Ser Asn Thr Lys Val Asp Lys
85 90 95

Thr Val Glu Arg Lys Cys Ser Val Glu Cys Pro Pro Cys Pro Ala Pro
100 105 110

Pro Val Ala Gly Pro Ser Val Phe Leu Phe Pro Pro Lys Pro Lys Asp
115 120 125

Thr Leu Met Ile Ser Arg Thr Pro Glu Val Thr Cys Val Val Val Asp
130 135 140

Val Ser His Glu Asp Pro Glu Val Gln Phe Asn Trp Tyr Val Asp Gly
145 150 155 160

Val Glu Val His Asn Ala Lys Thr Lys Pro Arg Glu Glu Gln Phe Asn
165 170 175

Ser Thr Phe Arg Val Val Ser Val Leu Thr Val Val His Gln Asp Trp
180 185 190

Leu Asn Gly Lys Glu Tyr Lys Cys Lys Val Ser Asn Lys Gly Leu Pro
195 200 205

Ala Pro Ile Glu Lys Thr Ile Ser Lys Thr Lys Gly Gln Pro Arg Glu
210 215 220

Pro Gln Val Tyr Thr Leu Pro Pro Ser Arg Glu Glu Met Thr Lys Asn
225 230 235 240

Gln Val Ser Leu Thr Cys Leu Val Lys Gly Phe Tyr Pro Ser Asp Ile
245 250 255

Ala Val Glu Trp Glu Ser Asn Gly Gln Pro Glu Asn Asn Tyr Lys Thr
260 265 270

Thr Pro Pro Met Leu Asp Ser Asp Gly Ser Phe Phe Leu Tyr Ser Lys
275 280 285

Leu Thr Val Asp Lys Ser Arg Trp Gln Gln Gly Asn Val Phe Ser Cys
290 295 300

Ser Val Met His Glu Ala Leu His Asn His Tyr Thr Gln Lys Ser Leu
305 310 315 320

Ser Leu Ser Pro Gly Lys
325

<210> SEQ ID NO 155
<211> LENGTH: 119
<212> TYPE: PRT
<213> ORGANISM: Artificial
<220> FEATURE:
<223> OTHER INFORMATION: An artificially synthesized peptide sequence

<400> SEQUENCE: 155

Gln Val Gln Leu Gln Glu Ser Gly Pro Gly Leu Val Arg Pro Ser Gln
1 5 10 15

```
Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser
        115
```

<210> SEQ ID NO 156
<211> LENGTH: 107
<212> TYPE: PRT
<213> ORGANISM: Artificial
<220> FEATURE:
<223> OTHER INFORMATION: An artificially synthesized peptide sequence

<400> SEQUENCE: 156

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys
            100                 105
```

<210> SEQ ID NO 157
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 157

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95
```

```
Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Ser Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445
```

<210> SEQ ID NO 158
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 158

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
```

-continued

```
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Ser Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445
```

<210> SEQ ID NO 159
<211> LENGTH: 449
<212> TYPE: PRT
<213> ORGANISM: Artificial
<220> FEATURE:
<223> OTHER INFORMATION: An artificially synthesized peptide sequence

<400> SEQUENCE: 159

Gln Val Gln Leu Gln Glu Ser Gly Pro Gly Leu Val Arg Pro Ser Gln
1 5 10 15

Thr Leu Ser Leu Thr Cys Thr Val Ser Gly Tyr Ser Ile Thr Ser Asp
20 25 30

His Ala Trp Ser Trp Val Arg Gln Pro Pro Gly Arg Gly Leu Glu Trp
35 40 45

Ile Gly Tyr Ile Ser Tyr Ser Gly Ile Thr Thr Tyr Asn Pro Ser Leu
50 55 60

Lys Ser Arg Val Thr Met Leu Arg Asp Thr Ser Lys Asn Gln Phe Ser
65 70 75 80

Leu Arg Leu Ser Ser Val Thr Ala Ala Asp Thr Ala Val Tyr Tyr Cys
85 90 95

Ala Arg Ser Leu Ala Arg Thr Thr Ala Met Asp Tyr Trp Gly Gln Gly
100 105 110

Ser Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Asp Glu Leu Thr Lys Asn Gln Val Ser Leu Thr
355 360 365

Cys Leu Val Lys Gly Phe Tyr Pro Ser Asp Ile Ala Val Glu Trp Glu 370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 160
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 160

Gln Val Gln Leu Gln Glu Ser Gly Pro Gly Leu Val Arg Pro Ser Gln
1 5 10 15

Thr Leu Ser Leu Thr Cys Thr Val Ser Gly Tyr Ser Ile Thr Ser Asp
20 25 30

His Ala Trp Ser Trp Val Arg Gln Pro Pro Gly Arg Gly Leu Glu Trp
35 40 45

Ile Gly Tyr Ile Ser Tyr Ser Gly Ile Thr Thr Tyr Asn Pro Ser Leu
50 55 60

Lys Ser Arg Val Thr Met Leu Arg Asp Thr Ser Lys Asn Gln Phe Ser
65 70 75 80

Leu Arg Leu Ser Ser Val Thr Ala Ala Asp Thr Ala Val Tyr Tyr Cys
85 90 95

Ala Arg Ser Leu Ala Arg Thr Thr Ala Met Asp Tyr Trp Gly Gln Gly
100 105 110

Ser Leu Val Thr Val Ser Ser Ala Ser Thr Lys Gly Pro Ser Val Phe
115 120 125

Pro Leu Ala Pro Cys Ser Arg Ser Thr Ser Glu Ser Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Asn Phe Gly Thr Gln Thr Tyr Thr Cys Asn Val Asp His Lys Pro
195 200 205

Ser Asn Thr Lys Val Asp Lys Thr Val Glu Arg Lys Cys Cys Val Glu
210 215 220

Cys Pro Pro Cys Pro Ala Pro Pro Val Ala Gly Pro Ser Val Phe Leu
225 230 235 240

Phe Pro Pro Lys Pro Lys Asp Thr Leu Met Ile Ser Arg Thr Pro Glu
245 250 255

Val Thr Cys Val Val Val Asp Val Ser His Glu Asp Pro Glu Val Gln
260 265 270

Phe Asn Trp Tyr Val Asp Gly Val Glu Val His Asn Ala Lys Thr Lys
275 280 285

Pro Arg Glu Glu Gln Phe Asn Ser Thr Phe Arg Val Val Ser Val Leu
290 295 300

Thr Val Val His Gln Asp Trp Leu Asn Gly Lys Glu Tyr Lys Cys Lys
305 310 315 320

Val Ser Asn Lys Gly Leu Pro Ala Pro Ile Glu Lys Thr Ile Ser Lys
325 330 335

Thr Lys Gly Gln Pro Arg Glu Pro Gln Val Tyr Thr Leu Pro Pro Ser
340 345 350

Arg Glu Glu Met Thr Lys Asn Gln Val Ser Leu Thr Cys Leu Val Lys
355 360 365

Gly Phe Tyr Pro Ser Asp Ile Ala Val Glu Trp Glu Ser Asn Gly Gln
370 375 380

Pro Glu Asn Asn Tyr Lys Thr Thr Pro Pro Met Leu Asp Ser Asp Gly
385 390 395 400

Ser Phe Phe Leu Tyr Ser Lys Leu Thr Val Asp Lys Ser Arg Trp Gln
405 410 415

Gln Gly Asn Val Phe Ser Cys Ser Val Met His Glu Ala Leu His Asn
420 425 430

His Tyr Thr Gln Lys Ser Leu Ser Leu Ser Pro Gly Lys
435 440 445

<210> SEQ ID NO 161
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 161

Gln Val Gln Leu Gln Glu Ser Gly Pro Gly Leu Val Arg Pro Ser Gln
1 5 10 15

Thr Leu Ser Leu Thr Cys Thr Val Ser Gly Tyr Ser Ile Thr Ser Asp
20 25 30

His Ala Trp Ser Trp Val Arg Gln Pro Pro Gly Arg Gly Leu Glu Trp
35 40 45

Ile Gly Tyr Ile Ser Tyr Ser Gly Ile Thr Thr Tyr Asn Pro Ser Leu
50 55 60

Lys Ser Arg Val Thr Met Leu Arg Asp Thr Ser Lys Asn Gln Phe Ser
65 70 75 80

Leu Arg Leu Ser Ser Val Thr Ala Ala Asp Thr Ala Val Tyr Tyr Cys
85 90 95

Ala Arg Ser Leu Ala Arg Thr Thr Ala Met Asp Tyr Trp Gly Gln Gly
100 105 110

Ser Leu Val Thr Val Ser Ser Ala Ser Thr Lys Gly Pro Ser Val Phe
115 120 125

Pro Leu Ala Pro Ser Ser Lys Ser Thr Ser Glu Ser Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Asn Phe Gly Thr Gln Thr Tyr Thr Cys Asn Val Asp His Lys Pro
195 200 205

Ser Asn Thr Lys Val Asp Lys Thr Val Glu Arg Lys Ser Cys Val Glu 210 215 220

Cys Pro Pro Cys Pro Ala Pro Pro Val Ala Gly Pro Ser Val Phe Leu
225 230 235 240

Phe Pro Pro Lys Pro Lys Asp Thr Leu Met Ile Ser Arg Thr Pro Glu
245 250 255

Val Thr Cys Val Val Val Asp Val Ser His Glu Asp Pro Glu Val Gln
260 265 270

Phe Asn Trp Tyr Val Asp Gly Val Glu Val His Asn Ala Lys Thr Lys
275 280 285

Pro Arg Glu Glu Gln Phe Asn Ser Thr Phe Arg Val Val Ser Val Leu
290 295 300

Thr Val Val His Gln Asp Trp Leu Asn Gly Lys Glu Tyr Lys Cys Lys
305 310 315 320

Val Ser Asn Lys Gly Leu Pro Ala Pro Ile Glu Lys Thr Ile Ser Lys
325 330 335

Thr Lys Gly Gln Pro Arg Glu Pro Gln Val Tyr Thr Leu Pro Pro Ser
340 345 350

Arg Glu Glu Met Thr Lys Asn Gln Val Ser Leu Thr Cys Leu Val Lys
355 360 365

Gly Phe Tyr Pro Ser Asp Ile Ala Val Glu Trp Glu Ser Asn Gly Gln
370 375 380

Pro Glu Asn Asn Tyr Lys Thr Thr Pro Pro Met Leu Asp Ser Asp Gly
385 390 395 400

Ser Phe Phe Leu Tyr Ser Lys Leu Thr Val Asp Lys Ser Arg Trp Gln
405 410 415

Gln Gly Asn Val Phe Ser Cys Ser Val Met His Glu Ala Leu His Asn
420 425 430

His Tyr Thr Gln Lys Ser Leu Ser Leu Ser Pro Gly Lys
435 440 445

<210> SEQ ID NO 162
<211> LENGTH: 214
<212> TYPE: PRT
<213> ORGANISM: Artificial
<220> FEATURE:
<223> OTHER INFORMATION: An artificially synthesized peptide sequence

<400> SEQUENCE: 162

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Ile Ser Ser Tyr
20 25 30

Leu Asn Trp Tyr Gln Gln Lys Pro Gly Lys Ala Pro Lys Leu Leu Ile
35 40 45

Tyr Tyr Thr Ser Arg Leu His Ser Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys Gln Gln Gly Asn Thr Leu Pro Tyr
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 163
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 163

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Ser Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285
```

Pro Arg Glu Glu Gln Phe Asn Ser Thr Phe Arg Val Val Ser Val Leu
290 295 300

Thr Val Val His Gln Asp Trp Leu Asn Gly Lys Glu Tyr Lys Cys Lys
305 310 315 320

Val Ser Asn Lys Gly Leu Pro Ser Ser Ile Glu Lys Thr Ile Ser Lys
325 330 335

Ala Lys Gly Gln Pro Arg Glu Pro Gln Val Tyr Thr Leu Pro Pro Ser
340 345 350

Arg Glu Glu Met Thr Lys Asn Gln Val Ser Leu Thr Cys Leu Val Lys
355 360 365

Gly Phe Tyr Pro Ser Asp Ile Ala Val Glu Trp Glu Ser Asn Gly Gln
370 375 380

Pro Glu Asn Asn Tyr Lys Thr Thr Pro Pro Val Leu Asp Ser Asp Gly
385 390 395 400

Ser Phe Phe Leu Tyr Ser Lys Leu Thr Val Asp Lys Ser Arg Trp Gln
405 410 415

Gln Gly Asn Val Phe Ser Cys Ser Val Met His Glu Ala Leu His Asn
420 425 430

His Tyr Thr Gln Lys Ser Leu Ser Leu Ser Pro Gly Lys
435 440 445

<210> SEQ ID NO 164
<211> LENGTH: 443
<212> TYPE: PRT
<213> ORGANISM: Artificial
<220> FEATURE:
<223> OTHER INFORMATION: An artificially synthesized peptide sequence

<400> SEQUENCE: 164

Gln Val Gln Leu Gln Glu Ser Gly Pro Gly Leu Val Arg Pro Ser Gln
1 5 10 15

Thr Leu Ser Leu Thr Cys Thr Val Ser Gly Tyr Ser Ile Thr Ser Asp
20 25 30

His Ala Trp Ser Trp Val Arg Gln Pro Pro Gly Arg Gly Leu Glu Trp
35 40 45

Ile Gly Tyr Ile Ser Tyr Ser Gly Ile Thr Thr Tyr Asn Pro Ser Leu
50 55 60

Lys Ser Arg Val Thr Met Leu Arg Asp Thr Ser Lys Asn Gln Phe Ser
65 70 75 80

Leu Arg Leu Ser Ser Val Thr Ala Ala Asp Thr Ala Val Tyr Tyr Cys
85 90 95

Ala Arg Ser Leu Ala Arg Thr Thr Ala Met Asp Tyr Trp Gly Gln Gly
100 105 110

Ser Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Asn Phe Gly Thr Gln Thr Tyr Thr Cys Asn Val Asp His Lys Pro
195 200 205

Ser Asn Thr Lys Val Asp Lys Thr Val Glu Arg Lys Ser Cys Val Glu

```
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Pro
        435                 440


<210> SEQ ID NO 165
<211> LENGTH: 267
<212> TYPE: PRT
<213> ORGANISM: Artificial
<220> FEATURE:
<223> OTHER INFORMATION: An artificially synthesized peptide sequence

<400> SEQUENCE: 165

Ala Glu Ser His Leu Ser Leu Leu Tyr His Leu Thr Ala Val Ser Ser
1               5                   10                  15

Pro Ala Pro Gly Thr Pro Ala Phe Trp Val Ser Gly Trp Leu Gly Pro
            20                  25                  30

Gln Gln Tyr Leu Ser Tyr Asn Ser Leu Arg Gly Glu Ala Glu Pro Cys
        35                  40                  45

Gly Ala Trp Val Trp Glu Asn Gln Val Ser Trp Tyr Trp Glu Lys Glu
    50                  55                  60

Thr Thr Asp Leu Arg Ile Lys Glu Lys Leu Phe Leu Glu Ala Phe Lys
65                  70                  75                  80

Ala Leu Gly Gly Lys Gly Pro Tyr Thr Leu Gln Gly Leu Leu Gly Cys
                85                  90                  95

Glu Leu Gly Pro Asp Asn Thr Ser Val Pro Thr Ala Lys Phe Ala Leu
            100                 105                 110

Asn Gly Glu Glu Phe Met Asn Phe Asp Leu Lys Gln Gly Thr Trp Gly
        115                 120                 125

Gly Asp Trp Pro Glu Ala Leu Ala Ile Ser Gln Arg Trp Gln Gln Gln
    130                 135                 140
```

```
Asp Lys Ala Ala Asn Lys Glu Leu Thr Phe Leu Leu Phe Ser Cys Pro
145                 150                 155                 160

His Arg Leu Arg Glu His Leu Glu Arg Gly Arg Gly Asn Leu Glu Trp
                165                 170                 175

Lys Glu Pro Pro Ser Met Arg Leu Lys Ala Arg Pro Ser Ser Pro Gly
            180                 185                 190

Phe Ser Val Leu Thr Cys Ser Ala Phe Ser Phe Tyr Pro Pro Glu Leu
        195                 200                 205

Gln Leu Arg Phe Leu Arg Asn Gly Leu Ala Ala Gly Thr Gly Gln Gly
    210                 215                 220

Asp Phe Gly Pro Asn Ser Asp Gly Ser Phe His Ala Ser Ser Ser Leu
225                 230                 235                 240

Thr Val Lys Ser Gly Asp Glu His His Tyr Cys Cys Ile Val Gln His
                245                 250                 255

Ala Gly Leu Ala Gln Pro Leu Arg Val Glu Leu
            260                 265


<210> SEQ ID NO 166
<211> LENGTH: 99
<212> TYPE: PRT
<213> ORGANISM: Artificial
<220> FEATURE:
<223> OTHER INFORMATION: An artificially synthesized peptide sequence

<400> SEQUENCE: 166

Ile Gln Arg Thr Pro Lys Ile Gln Val Tyr Ser Arg His Pro Ala Glu
1               5                   10                  15

Asn Gly Lys Ser Asn Phe Leu Asn Cys Tyr Val Ser Gly Phe His Pro
            20                  25                  30

Ser Asp Ile Glu Val Asp Leu Leu Lys Asn Gly Glu Arg Ile Glu Lys
        35                  40                  45

Val Glu His Ser Asp Leu Ser Phe Ser Lys Asp Trp Ser Phe Tyr Leu
    50                  55                  60

Leu Tyr Tyr Thr Glu Phe Thr Pro Thr Glu Lys Asp Glu Tyr Ala Cys
65                  70                  75                  80

Arg Val Asn His Val Thr Leu Ser Gln Pro Lys Ile Val Lys Trp Asp
                85                  90                  95

Arg Asp Met


<210> SEQ ID NO 167
<211> LENGTH: 121
<212> TYPE: PRT
<213> ORGANISM: Artificial
<220> FEATURE:
<223> OTHER INFORMATION: An artificially synthesized peptide sequence

<400> SEQUENCE: 167

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
        35                  40                  45

Gly Leu Ile Asn Pro Tyr Asn Gly Gly Thr Ser Tyr Asn Gln Gln Phe
    50                  55                  60

Gln Asp Arg Val Thr Ile Thr Ala Asp Glu Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Met Asp Tyr Trp Gly
            100                 105                 110

Gln Gly Thr Leu Val Thr Val Ser Ser
        115                 120
```

<210> SEQ ID NO 168
<211> LENGTH: 107
<212> TYPE: PRT
<213> ORGANISM: Artificial
<220> FEATURE:
<223> OTHER INFORMATION: An artificially synthesized peptide sequence

<400> SEQUENCE: 168

```
Asp Ile Gln Met Thr Gln Ser Pro Ser Ser Leu Ser Ala Ser Val Gly
1               5                   10                  15

Asp Arg Val Thr Ile Thr Cys Gln Thr Ser Glu Asp Ile Tyr Ser Phe
            20                  25                  30

Leu Ala Trp Tyr Gln Gln Lys Pro Gly Lys Ala Pro Lys Leu Leu Ile
        35                  40                  45

Tyr Asn Ala Gln Thr Glu Ala Gln Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Glu Ser Pro Leu
                85                  90                  95

Thr Phe Gly Gly Gly Thr Lys Val Glu Ile Lys
            100                 105
```

<210> SEQ ID NO 169
<211> LENGTH: 11
<212> TYPE: PRT
<213> ORGANISM: Artificial
<220> FEATURE:
<223> OTHER INFORMATION: An artificially synthesized peptide sequence

<400> SEQUENCE: 169

```
Gln Thr Ser Glu Asp Ile Tyr Ser Phe Leu Ala
1               5                   10
```

<210> SEQ ID NO 170
<211> LENGTH: 7
<212> TYPE: PRT
<213> ORGANISM: Artificial
<220> FEATURE:
<223> OTHER INFORMATION: An artificially synthesized peptide sequence

<400> SEQUENCE: 170

```
Asn Ala Gln Thr Glu Ala Gln
1               5
```

<210> SEQ ID NO 171
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 171

```
Leu Ile Asn Pro Tyr Asn Gly Gly Thr Ser Tyr Asn Gln Gln Phe Gln
1               5                   10                  15

Asp
```

<210> SEQ ID NO 172
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 172

Leu Ile Asn Pro Tyr Asn Gly Gly Thr Ser Tyr Asn Asp Gln Phe Gln
1 5 10 15

Asp

<210> SEQ ID NO 173
<211> LENGTH: 5
<212> TYPE: PRT
<213> ORGANISM: Artificial
<220> FEATURE:
<223> OTHER INFORMATION: An artificially synthesized peptide sequence

<400> SEQUENCE: 173

Gly Tyr Val Met Asn
1 5

<210> SEQ ID NO 174
<211> LENGTH: 5
<212> TYPE: PRT
<213> ORGANISM: Artificial
<220> FEATURE:
<223> OTHER INFORMATION: An artificially synthesized peptide sequence

<400> SEQUENCE: 174

Gly Tyr Ile Ile Asn
1 5

<210> SEQ ID NO 175
<211> LENGTH: 5
<212> TYPE: PRT
<213> ORGANISM: Artificial
<220> FEATURE:
<223> OTHER INFORMATION: An artificially synthesized peptide sequence

<400> SEQUENCE: 175

Gly Tyr Ile Leu Asn
1 5

<210> SEQ ID NO 176
<211> LENGTH: 5
<212> TYPE: PRT
<213> ORGANISM: Artificial
<220> FEATURE:
<223> OTHER INFORMATION: An artificially synthesized peptide sequence

<400> SEQUENCE: 176

Gly Tyr Ala Met Asn
1 5

<210> SEQ ID NO 177
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 177

Leu Ile Asn Pro Tyr Asn Gly Gly Thr Asp Tyr Asn Gln Lys Phe Lys
1 5 10 15

Gly

<210> SEQ ID NO 178
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 178

Leu Ile Asn Pro Tyr Asn Gly Gly Thr Ser Tyr Asn Pro Lys Phe Lys
1               5                   10                  15

Gly

<210> SEQ ID NO 179
<211> LENGTH: 12
<212> TYPE: PRT
<213> ORGANISM: Artificial
<220> FEATURE:
<223> OTHER INFORMATION: An artificially synthesized peptide sequence

<400> SEQUENCE: 179

Asp Gly Leu Asp Asp Gly Pro Tyr Thr Met Asp Tyr
1               5                   10

<210> SEQ ID NO 180
<211> LENGTH: 12
<212> TYPE: PRT
<213> ORGANISM: Artificial
<220> FEATURE:
<223> OTHER INFORMATION: An artificially synthesized peptide sequence

<400> SEQUENCE: 180

Asp Gly Tyr Asp Asp Gly Pro Tyr Thr Leu Asp Tyr
1               5                   10

<210> SEQ ID NO 181
<211> LENGTH: 12
<212> TYPE: PRT
<213> ORGANISM: Artificial
<220> FEATURE:
<223> OTHER INFORMATION: An artificially synthesized peptide sequence

<400> SEQUENCE: 181

Asp Gly Tyr Asp Asp Gly Pro Tyr Thr Met Glu Tyr
1               5                   10

<210> SEQ ID NO 182
<211> LENGTH: 12
<212> TYPE: PRT
<213> ORGANISM: Artificial
<220> FEATURE:
<223> OTHER INFORMATION: An artificially synthesized peptide sequence

<400> SEQUENCE: 182

Asp Gly Tyr Asp Asp Gly Pro Tyr Thr Met Asp Thr
1               5                   10

<210> SEQ ID NO 183
<211> LENGTH: 12
<212> TYPE: PRT
<213> ORGANISM: Artificial
<220> FEATURE:
<223> OTHER INFORMATION: An artificially synthesized peptide sequence

<400> SEQUENCE: 183

Asp Gly Tyr Asp Asp Gly Pro Tyr Thr Met Asp Ser
1 5 10

<210> SEQ ID NO 184
<211> LENGTH: 12
<212> TYPE: PRT
<213> ORGANISM: Artificial
<220> FEATURE:
<223> OTHER INFORMATION: An artificially synthesized peptide sequence

<400> SEQUENCE: 184

Asp Gly Tyr Asp Asp Gly Pro Tyr Thr Leu Glu Thr
1 5 10

<210> SEQ ID NO 185
<211> LENGTH: 12
<212> TYPE: PRT
<213> ORGANISM: Artificial
<220> FEATURE:
<223> OTHER INFORMATION: An artificially synthesized peptide sequence

<400> SEQUENCE: 185

Asp Gly Tyr Asp Asp Gly Pro Tyr Thr Met Glu Thr
1 5 10

<210> SEQ ID NO 186
<211> LENGTH: 12
<212> TYPE: PRT
<213> ORGANISM: Artificial
<220> FEATURE:
<223> OTHER INFORMATION: An artificially synthesized peptide sequence

<400> SEQUENCE: 186

Asp Gly Leu Asp Asp Gly Pro Tyr Thr Met Glu Thr
1 5 10

<210> SEQ ID NO 187
<211> LENGTH: 12
<212> TYPE: PRT
<213> ORGANISM: Artificial
<220> FEATURE:
<223> OTHER INFORMATION: An artificially synthesized peptide sequence

<400> SEQUENCE: 187

Asp Gly Leu Asp Asp Gly Pro Tyr Thr Met Glu Ser
1 5 10

<210> SEQ ID NO 188
<211> LENGTH: 11
<212> TYPE: PRT
<213> ORGANISM: Artificial
<220> FEATURE:
<223> OTHER INFORMATION: An artificially synthesized peptide sequence

<400> SEQUENCE: 188

Arg Thr Ser Glu Asn Ile Tyr Arg Phe Leu Ala
1 5 10

<210> SEQ ID NO 189
<211> LENGTH: 11
<212> TYPE: PRT
<213> ORGANISM: Artificial
<220> FEATURE:
<223> OTHER INFORMATION: An artificially synthesized peptide sequence

<400> SEQUENCE: 189

Arg Thr Ser Glu Asn Ile Tyr Ser Phe Val Ala
1 5 10

<210> SEQ ID NO 190
<211> LENGTH: 11
<212> TYPE: PRT
<213> ORGANISM: Artificial
<220> FEATURE:
<223> OTHER INFORMATION: An artificially synthesized peptide sequence

<400> SEQUENCE: 190

Arg Thr Ser Glu Asn Ile Tyr Arg Phe Val Ala
1               5                   10

<210> SEQ ID NO 191
<211> LENGTH: 11
<212> TYPE: PRT
<213> ORGANISM: Artificial
<220> FEATURE:
<223> OTHER INFORMATION: An artificially synthesized peptide sequence

<400> SEQUENCE: 191

Arg Ala Ser Glu Asn Ile Tyr Ser Phe Leu Ala
1               5                   10

<210> SEQ ID NO 192
<211> LENGTH: 11
<212> TYPE: PRT
<213> ORGANISM: Artificial
<220> FEATURE:
<223> OTHER INFORMATION: An artificially synthesized peptide sequence

<400> SEQUENCE: 192

Arg Ser Ser Glu Asn Ile Tyr Ser Phe Leu Ala
1               5                   10

<210> SEQ ID NO 193
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 193

Gln His His Tyr Asp Ser Pro Leu Thr
1               5

<210> SEQ ID NO 194
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 194

Gln His His Tyr Glu Asp Pro Leu Thr
1               5

<210> SEQ ID NO 195
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 195

Gln His His Tyr Glu Ser Pro Leu Phe
1               5

<210> SEQ ID NO 196
<211> LENGTH: 5
<212> TYPE: PRT
<213> ORGANISM: Artificial
<220> FEATURE:
<223> OTHER INFORMATION: An artificially synthesized peptide sequence

<400> SEQUENCE: 196

Gly Tyr Val Leu Asn
1 5

<210> SEQ ID NO 197
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 197

Leu Ile Asn Pro Tyr Asn Gly Gly Thr Asp Tyr Asn Pro Gln Phe Gln
1 5 10 15

Asp

<210> SEQ ID NO 198
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 198

Leu Ile Asn Pro Tyr Asn Gly Gly Thr Asp Tyr Asn Pro Gln Phe Gln
1 5 10 15

Gly

<210> SEQ ID NO 199
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 199

Leu Ile Asn Pro Tyr Asn Gly Gly Thr Ser Tyr Asn Gln Gln Phe Gln
1 5 10 15

Asp

<210> SEQ ID NO 200
<211> LENGTH: 11
<212> TYPE: PRT
<213> ORGANISM: Artificial
<220> FEATURE:
<223> OTHER INFORMATION: An artificially synthesized peptide sequence

<400> SEQUENCE: 200

Gln Thr Ser Glu Asp Ile Tyr Arg Phe Val Ala
1 5 10

<210> SEQ ID NO 201
<211> LENGTH: 11
<212> TYPE: PRT
<213> ORGANISM: Artificial
<220> FEATURE:
<223> OTHER INFORMATION: An artificially synthesized peptide sequence

<400> SEQUENCE: 201

```
Gln Thr Ser Glu Asp Ile Tyr Ser Phe Val Ala
1               5                   10


<210> SEQ ID NO 202
<211> LENGTH: 11
<212> TYPE: PRT
<213> ORGANISM: Artificial
<220> FEATURE:
<223> OTHER INFORMATION: An artificially synthesized peptide sequence

<400> SEQUENCE: 202

Gln Ala Ser Glu Asp Ile Tyr Ser Phe Val Ala
1               5                   10


<210> SEQ ID NO 203
<211> LENGTH: 11
<212> TYPE: PRT
<213> ORGANISM: Artificial
<220> FEATURE:
<223> OTHER INFORMATION: An artificially synthesized peptide sequence

<400> SEQUENCE: 203

Gln Ala Ser Glu Asp Ile Tyr Ser Phe Leu Ala
1               5                   10


<210> SEQ ID NO 204
<211> LENGTH: 121
<212> TYPE: PRT
<213> ORGANISM: Artificial
<220> FEATURE:
<223> OTHER INFORMATION: An artificially synthesized peptide sequence

<400> SEQUENCE: 204

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Val Leu Asn Trp Val Arg Gln Ala Pro Gly Gln Gly Leu Glu Trp Met
        35                  40                  45

Gly Leu Ile Asn Pro Tyr Asn Gly Gly Thr Asp Tyr Asn Pro Gln Phe
    50                  55                  60

Gln Asp Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Met Asp Tyr Trp Gly
            100                 105                 110

Gln Gly Thr Leu Val Thr Val Ser Ser
        115                 120


<210> SEQ ID NO 205
<211> LENGTH: 121
<212> TYPE: PRT
<213> ORGANISM: Artificial
<220> FEATURE:
<223> OTHER INFORMATION: An artificially synthesized peptide sequence

<400> SEQUENCE: 205

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ala Met Asn Trp Val Arg Gln Ala Pro Gly Gln Gly Leu Glu Trp Met
```

35 40 45

Gly Leu Ile Asn Pro Tyr Asn Gly Gly Thr Asp Tyr Asn Pro Gln Phe
50 55 60

Gln Asp Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Asp Gly Tyr Asp Asp Gly Pro Tyr Thr Met Asp Tyr Trp Gly
100 105 110

Gln Gly Thr Leu Val Thr Val Ser Ser
115 120

<210> SEQ ID NO 206
<211> LENGTH: 121
<212> TYPE: PRT
<213> ORGANISM: Artificial
<220> FEATURE:
<223> OTHER INFORMATION: An artificially synthesized peptide sequence

<400> SEQUENCE: 206

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Val Leu Asn Trp Val Arg Gln Ala Pro Gly Gln Gly Leu Glu Trp Met
35 40 45

Gly Leu Ile Asn Pro Tyr Asn Gly Gly Thr Asp Tyr Asn Pro Gln Phe
50 55 60

Gln Asp Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Asp Gly Tyr Asp Asp Gly Pro Tyr Thr Leu Glu Thr Trp Gly
100 105 110

Gln Gly Thr Leu Val Thr Val Ser Ser
115 120

<210> SEQ ID NO 207
<211> LENGTH: 121
<212> TYPE: PRT
<213> ORGANISM: Artificial
<220> FEATURE:
<223> OTHER INFORMATION: An artificially synthesized peptide sequence

<400> SEQUENCE: 207

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Ile Met Asn Trp Val Arg Gln Ala Pro Gly Gln Gly Leu Glu Trp Met
35 40 45

Gly Leu Ile Asn Pro Tyr Asn Gly Gly Thr Asp Tyr Asn Pro Gln Phe
50 55 60

Gln Asp Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Asp Gly Tyr Asp Asp Gly Pro Tyr Thr Leu Glu Thr Trp Gly

```
            100                 105                 110

Gln Gly Thr Leu Val Thr Val Ser Ser
        115                 120


<210> SEQ ID NO 208
<211> LENGTH: 121
<212> TYPE: PRT
<213> ORGANISM: Artificial
<220> FEATURE:
<223> OTHER INFORMATION: An artificially synthesized peptide sequence

<400> SEQUENCE: 208

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ala Met Asn Trp Val Arg Gln Ala Pro Gly Gln Gly Leu Glu Trp Met
        35                  40                  45

Gly Leu Ile Asn Pro Tyr Asn Gly Gly Thr Asp Tyr Asn Pro Gln Phe
    50                  55                  60

Gln Asp Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Leu Glu Thr Trp Gly
            100                 105                 110

Gln Gly Thr Leu Val Thr Val Ser Ser
        115                 120


<210> SEQ ID NO 209
<211> LENGTH: 121
<212> TYPE: PRT
<213> ORGANISM: Artificial
<220> FEATURE:
<223> OTHER INFORMATION: An artificially synthesized peptide sequence

<400> SEQUENCE: 209

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Val Leu Asn Trp Val Arg Gln Ala Pro Gly Gln Gly Leu Glu Trp Met
        35                  40                  45

Gly Leu Ile Asn Pro Tyr Asn Gly Gly Thr Asp Tyr Asn Pro Gln Phe
    50                  55                  60

Gln Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Leu Glu Thr Trp Gly
            100                 105                 110

Gln Gly Thr Leu Val Thr Val Ser Ser
        115                 120


<210> SEQ ID NO 210
<211> LENGTH: 121
<212> TYPE: PRT
<213> ORGANISM: Artificial
<220> FEATURE:
<223> OTHER INFORMATION: An artificially synthesized peptide sequence
```

<400> SEQUENCE: 210

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Ile Met Asn Trp Val Arg Gln Ala Pro Gly Gln Gly Leu Glu Trp Met
35 40 45

Gly Leu Ile Asn Pro Tyr Asn Gly Gly Thr Asp Tyr Asn Pro Gln Phe
50 55 60

Gln Asp Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Asp Gly Tyr Asp Asp Gly Pro Tyr Thr Leu Glu Thr Trp Gly
100 105 110

Gln Gly Thr Leu Val Thr Val Ser Ser
115 120

<210> SEQ ID NO 211
<211> LENGTH: 121
<212> TYPE: PRT
<213> ORGANISM: Artificial
<220> FEATURE:
<223> OTHER INFORMATION: An artificially synthesized peptide sequence

<400> SEQUENCE: 211

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Ala Met Asn Trp Val Arg Gln Ala Pro Gly Gln Gly Leu Glu Trp Met
35 40 45

Gly Leu Ile Asn Pro Tyr Asn Gly Gly Thr Asp Tyr Asn Pro Gln Phe
50 55 60

Gln Asp Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Asp Gly Tyr Asp Asp Gly Pro Tyr Thr Leu Glu Thr Trp Gly
100 105 110

Gln Gly Thr Leu Val Thr Val Ser Ser
115 120

<210> SEQ ID NO 212
<211> LENGTH: 121
<212> TYPE: PRT
<213> ORGANISM: Artificial
<220> FEATURE:
<223> OTHER INFORMATION: An artificially synthesized peptide sequence

<400> SEQUENCE: 212

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Ile Met Asn Trp Val Arg Gln Ala Pro Gly Gln Gly Leu Glu Trp Met
35 40 45

Gly Leu Ile Asn Pro Tyr Asn Gly Gly Thr Asp Tyr Asn Pro Gln Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Asp Gly Tyr Asp Asp Gly Pro Tyr Thr Leu Glu Thr Trp Gly
100 105 110

Gln Gly Thr Leu Val Thr Val Ser Ser
115 120

<210> SEQ ID NO 213
<211> LENGTH: 121
<212> TYPE: PRT
<213> ORGANISM: Artificial
<220> FEATURE:
<223> OTHER INFORMATION: An artificially synthesized peptide sequence

<400> SEQUENCE: 213

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Ala Met Asn Trp Val Arg Gln Ala Pro Gly Gln Gly Leu Glu Trp Met
35 40 45

Gly Leu Ile Asn Pro Tyr Asn Gly Gly Thr Asp Tyr Asn Pro Gln Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Asp Gly Tyr Asp Asp Gly Pro Tyr Thr Leu Glu Thr Trp Gly
100 105 110

Gln Gly Thr Leu Val Thr Val Ser Ser
115 120

<210> SEQ ID NO 214
<211> LENGTH: 121
<212> TYPE: PRT
<213> ORGANISM: Artificial
<220> FEATURE:
<223> OTHER INFORMATION: An artificially synthesized peptide sequence

<400> SEQUENCE: 214

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Ile Met Asn Trp Val Arg Gln Ala Pro Gly Gln Gly Leu Glu Trp Met
35 40 45

Gly Leu Ile Asn Pro Tyr Asn Gly Gly Thr Asp Tyr Asn Pro Gln Phe
50 55 60

Gln Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Asp Gly Tyr Asp Asp Gly Pro Tyr Thr Leu Glu Thr Trp Gly
100 105 110

Gln Gly Thr Leu Val Thr Val Ser Ser
115 120

<210> SEQ ID NO 215
<211> LENGTH: 121
<212> TYPE: PRT
<213> ORGANISM: Artificial
<220> FEATURE:
<223> OTHER INFORMATION: An artificially synthesized peptide sequence

<400> SEQUENCE: 215

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Ala Met Asn Trp Val Arg Gln Ala Pro Gly Gln Gly Leu Glu Trp Met
35 40 45

Gly Leu Ile Asn Pro Tyr Asn Gly Gly Thr Asp Tyr Asn Pro Gln Phe
50 55 60

Gln Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Asp Gly Tyr Asp Asp Gly Pro Tyr Thr Leu Glu Thr Trp Gly
100 105 110

Gln Gly Thr Leu Val Thr Val Ser Ser
115 120

<210> SEQ ID NO 216
<211> LENGTH: 121
<212> TYPE: PRT
<213> ORGANISM: Artificial
<220> FEATURE:
<223> OTHER INFORMATION: An artificially synthesized peptide sequence

<400> SEQUENCE: 216

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Ile Met Asn Trp Val Arg Gln Ala Pro Gly Gln Gly Leu Glu Trp Met
35 40 45

Gly Leu Ile Asn Pro Tyr Asn Gly Gly Thr Ser Tyr Asn Gln Gln Phe
50 55 60

Gln Asp Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Asp Gly Tyr Asp Asp Gly Pro Tyr Thr Leu Glu Thr Trp Gly
100 105 110

Gln Gly Thr Leu Val Thr Val Ser Ser
115 120

<210> SEQ ID NO 217
<211> LENGTH: 121
<212> TYPE: PRT
<213> ORGANISM: Artificial
<220> FEATURE:
<223> OTHER INFORMATION: An artificially synthesized peptide sequence

<400> SEQUENCE: 217

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
        35                  40                  45

Gly Leu Ile Asn Pro Tyr Asn Gly Gly Thr Ser Tyr Asn Gln Gln Phe
    50                  55                  60

Gln Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Leu Glu Thr Trp Gly
            100                 105                 110

Gln Gly Thr Leu Val Thr Val Ser Ser
        115                 120


<210> SEQ ID NO 218
<211> LENGTH: 107
<212> TYPE: PRT
<213> ORGANISM: Artificial
<220> FEATURE:
<223> OTHER INFORMATION: An artificially synthesized peptide sequence

<400> SEQUENCE: 218

Asp Ile Gln Met Thr Gln Ser Pro Ser Ser Leu Ser Ala Ser Val Gly
1               5                   10                  15

Asp Arg Val Thr Ile Thr Cys Gln Thr Ser Glu Asp Ile Tyr Arg Phe
            20                  25                  30

Val Ala Trp Tyr Gln Gln Lys Pro Gly Lys Ala Pro Lys Leu Leu Ile
        35                  40                  45

Tyr Asn Ala Gln Thr Glu Ala Gln Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Asp Ser Pro Leu
                85                  90                  95

Thr Phe Gly Gly Gly Thr Lys Val Glu Ile Lys
            100                 105


<210> SEQ ID NO 219
<211> LENGTH: 107
<212> TYPE: PRT
<213> ORGANISM: Artificial
<220> FEATURE:
<223> OTHER INFORMATION: An artificially synthesized peptide sequence

<400> SEQUENCE: 219

Asp Ile Gln Met Thr Gln Ser Pro Ser Ser Leu Ser Ala Ser Val Gly
1               5                   10                  15

Asp Arg Val Thr Ile Thr Cys Gln Thr Ser Glu Asp Ile Tyr Ser Phe
            20                  25                  30

Val Ala Trp Tyr Gln Gln Lys Pro Gly Lys Ala Pro Lys Leu Leu Ile
        35                  40                  45

Tyr Asn Ala Gln Thr Glu Ala Gln Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln His His Tyr Asp Ser Pro Leu
                85                  90                  95

Thr Phe Gly Gly Gly Thr Lys Val Glu Ile Lys
            100                 105
```

<210> SEQ ID NO 220
<211> LENGTH: 107
<212> TYPE: PRT
<213> ORGANISM: Artificial
<220> FEATURE:
<223> OTHER INFORMATION: An artificially synthesized peptide sequence

<400> SEQUENCE: 220

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asp Ile Tyr Ser Phe
            20                  25                  30

Val Ala Trp Tyr Gln Gln Lys Pro Gly Lys Ala Pro Lys Leu Leu Ile
        35                  40                  45

Tyr Asn Ala Gln Thr Glu Ala Gln Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Asp Ser Pro Leu
                85                  90                  95

Thr Phe Gly Gly Gly Thr Lys Val Glu Ile Lys
            100                 105
```

<210> SEQ ID NO 221
<211> LENGTH: 107
<212> TYPE: PRT
<213> ORGANISM: Artificial
<220> FEATURE:
<223> OTHER INFORMATION: An artificially synthesized peptide sequence

<400> SEQUENCE: 221

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asp Ile Tyr Ser Phe
            20                  25                  30

Leu Ala Trp Tyr Gln Gln Lys Pro Gly Lys Ala Pro Lys Leu Leu Ile
        35                  40                  45

Tyr Asn Ala Gln Thr Glu Ala Gln Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Asp Ser Pro Leu
                85                  90                  95

Thr Phe Gly Gly Gly Thr Lys Val Glu Ile Lys
            100                 105
```

<210> SEQ ID NO 222
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 222

```
Gln Val Gln Leu Val Gln Ser Gly Ala Glu Val Lys Lys Pro Gly Ala
```

-continued

```
1               5                   10                  15

Ser Val Lys Val Ser Cys Lys Ala Ser Gly Tyr Thr Phe Thr Gly Tyr
            20                  25                  30

Val Leu Asn Trp Val Arg Gln Ala Pro Gly Gln Gly Leu Glu Trp Met
        35                  40                  45

Gly Leu Ile Asn Pro Tyr Asn Gly Gly Thr Asp Tyr Asn Pro Gln Phe
    50                  55                  60

Gln Asp Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Ser Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Glu Gly Asn Val Phe Ser Cys Ser Val Met His Glu Ala Leu
            420                 425                 430
```

His Asn His Tyr Thr Gln Lys Ser Leu Ser Leu Ser Pro
435 440 445

<210> SEQ ID NO 223
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 223

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Ala Met Asn Trp Val Arg Gln Ala Pro Gly Gln Gly Leu Glu Trp Met
35 40 45

Gly Leu Ile Asn Pro Tyr Asn Gly Gly Thr Asp Tyr Asn Pro Gln Phe
50 55 60

Gln Asp Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Asp Gly Tyr Asp Asp Gly Pro Tyr Thr Met Asp Tyr Trp Gly
100 105 110

Gln Gly Thr Leu Val Thr Val Ser Ser Ala Ser Thr Lys Gly Pro Ser
115 120 125

Val Phe Pro Leu Ala Pro Ser Ser Lys Ser Thr Ser Gly Gly Thr Ala
130 135 140

Ala Leu Gly Cys Leu Val Lys Asp Tyr Phe Pro Glu Pro Val Thr Val
145 150 155 160

Ser Trp Asn Ser Gly Ala Leu Thr Ser Gly Val His Thr Phe Pro Ala
165 170 175

Val Leu Gln Ser Ser Gly Leu Tyr Ser Leu Ser Ser Val Val Thr Val
180 185 190

Pro Ser Ser Asn Phe Gly Thr Gln Thr Tyr Thr Cys Asn Val Asp His
195 200 205

Lys Pro Ser Asn Thr Lys Val Asp Lys Thr Val Glu Arg Lys Ser Cys
210 215 220

Val Glu Cys Pro Pro Cys Pro Ala Pro Pro Val Ala Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser Gln Glu Asp Pro Glu
260 265 270

Val Gln Phe Asn Trp Tyr Val Asp Gly Val Glu Val His Asn Ala Lys
275 280 285

Thr Lys Pro Arg Glu Glu Gln Phe Asn Ser Thr Phe Arg Val Val Ser
290 295 300

Val Leu Thr Val Val His Gln Asp Trp Leu Asn Gly Lys Glu Tyr Lys
305 310 315 320

Cys Lys Val Ser Asn Lys Gly Leu Pro Ala Pro Ile Glu Lys Thr Ile
325 330 335

Ser Lys Thr Lys Gly Gln Pro Arg Glu Pro Gln Val Tyr Thr Leu Pro
340 345 350

Pro Ser Gln Glu Glu Met Thr Lys Asn Gln Val Ser Leu Thr Cys Leu

```
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro
        435                 440                 445


<210> SEQ ID NO 224
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 224

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Val Leu Asn Trp Val Arg Gln Ala Pro Gly Gln Gly Leu Glu Trp Met
        35                  40                  45

Gly Leu Ile Asn Pro Tyr Asn Gly Gly Thr Asp Tyr Asn Pro Gln Phe
    50                  55                  60

Gln Asp Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Leu Glu Thr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Ser Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285
```

Thr Lys Pro Arg Glu Glu Gln Phe Asn Ser Thr Phe Arg Val Val Ser
290 295 300

Val Leu Thr Val Val His Gln Asp Trp Leu Asn Gly Lys Glu Tyr Lys
305 310 315 320

Cys Lys Val Ser Asn Lys Gly Leu Pro Ala Pro Ile Glu Lys Thr Ile
325 330 335

Ser Lys Thr Lys Gly Gln Pro Arg Glu Pro Gln Val Tyr Thr Leu Pro
340 345 350

Pro Ser Gln Glu Glu Met Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Met Leu Asp Ser
385 390 395 400

Asp Gly Ser Phe Phe Leu Tyr Ser Lys Leu Thr Val Asp Lys Ser Arg
405 410 415

Trp Gln Glu Gly Asn Val Phe Ser Cys Ser Val Met His Glu Ala Leu
420 425 430

His Asn His Tyr Thr Gln Lys Ser Leu Ser Leu Ser Pro
435 440 445

<210> SEQ ID NO 225
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 225

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Ile Met Asn Trp Val Arg Gln Ala Pro Gly Gln Gly Leu Glu Trp Met
35 40 45

Gly Leu Ile Asn Pro Tyr Asn Gly Gly Thr Asp Tyr Asn Pro Gln Phe
50 55 60

Gln Asp Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Asp Gly Tyr Asp Asp Gly Pro Tyr Thr Leu Glu Thr Trp Gly
100 105 110

Gln Gly Thr Leu Val Thr Val Ser Ser Ala Ser Thr Lys Gly Pro Ser
115 120 125

Val Phe Pro Leu Ala Pro Ser Ser Lys Ser Thr Ser Gly Gly Thr Ala
130 135 140

Ala Leu Gly Cys Leu Val Lys Asp Tyr Phe Pro Glu Pro Val Thr Val
145 150 155 160

Ser Trp Asn Ser Gly Ala Leu Thr Ser Gly Val His Thr Phe Pro Ala
165 170 175

Val Leu Gln Ser Ser Gly Leu Tyr Ser Leu Ser Ser Val Val Thr Val
180 185 190

Pro Ser Ser Asn Phe Gly Thr Gln Thr Tyr Thr Cys Asn Val Asp His
195 200 205

```
Lys Pro Ser Asn Thr Lys Val Asp Lys Thr Val Glu Arg Lys Ser Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro
        435                 440                 445
```

```
<210> SEQ ID NO 226
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 226

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ala Met Asn Trp Val Arg Gln Ala Pro Gly Gln Gly Leu Glu Trp Met
        35                  40                  45

Gly Leu Ile Asn Pro Tyr Asn Gly Gly Thr Asp Tyr Asn Pro Gln Phe
    50                  55                  60

Gln Asp Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Leu Glu Thr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
```

```
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Ser Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro
        435                 440                 445


<210> SEQ ID NO 227
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 227

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Val Leu Asn Trp Val Arg Gln Ala Pro Gly Gln Gly Leu Glu Trp Met
        35                  40                  45

Gly Leu Ile Asn Pro Tyr Asn Gly Gly Thr Asp Tyr Asn Pro Gln Phe
    50                  55                  60
```

```
Gln Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Leu Glu Thr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Ser Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro
        435                 440                 445
```

<210> SEQ ID NO 228
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 228

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
        35                  40                  45

Gly Leu Ile Asn Pro Tyr Asn Gly Gly Thr Asp Tyr Asn Pro Gln Phe
    50                  55                  60

Gln Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Leu Glu Thr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Ser Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

```
Trp Gln Glu Gly Asn Val Phe Ser Cys Ser Val Met His Glu Ala Leu
            420                 425                 430

His Asn His Tyr Thr Gln Lys Ser Leu Ser Leu Ser Pro
        435                 440                 445


<210> SEQ ID NO 229
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 229

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ala Met Asn Trp Val Arg Gln Ala Pro Gly Gln Gly Leu Glu Trp Met
        35                  40                  45

Gly Leu Ile Asn Pro Tyr Asn Gly Gly Thr Asp Tyr Asn Pro Gln Phe
    50                  55                  60

Gln Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Leu Glu Thr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Ser Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335
```

```
Ser Lys Thr Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro
        435                 440                 445


<210> SEQ ID NO 230
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 230

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
        35                  40                  45

Gly Leu Ile Asn Pro Tyr Asn Gly Gly Thr Asp Tyr Asn Pro Gln Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Leu Glu Thr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Ser Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
```

```
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro
        435                 440                 445


<210> SEQ ID NO 231
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 231

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ala Met Asn Trp Val Arg Gln Ala Pro Gly Gln Gly Leu Glu Trp Met
        35                  40                  45

Gly Leu Ile Asn Pro Tyr Asn Gly Gly Thr Asp Tyr Asn Pro Gln Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Leu Glu Thr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190
```

Pro Ser Ser Asn Phe Gly Thr Gln Thr Tyr Thr Cys Asn Val Asp His
195 200 205

Lys Pro Ser Asn Thr Lys Val Asp Lys Thr Val Glu Arg Lys Ser Cys
210 215 220

Val Glu Cys Pro Pro Cys Pro Ala Pro Pro Val Ala Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser Gln Glu Asp Pro Glu
260 265 270

Val Gln Phe Asn Trp Tyr Val Asp Gly Val Glu Val His Asn Ala Lys
275 280 285

Thr Lys Pro Arg Glu Glu Gln Phe Asn Ser Thr Phe Arg Val Val Ser
290 295 300

Val Leu Thr Val Val His Gln Asp Trp Leu Asn Gly Lys Glu Tyr Lys
305 310 315 320

Cys Lys Val Ser Asn Lys Gly Leu Pro Ala Pro Ile Glu Lys Thr Ile
325 330 335

Ser Lys Thr Lys Gly Gln Pro Arg Glu Pro Gln Val Tyr Thr Leu Pro
340 345 350

Pro Ser Gln Glu Glu Met Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Met Leu Asp Ser
385 390 395 400

Asp Gly Ser Phe Phe Leu Tyr Ser Lys Leu Thr Val Asp Lys Ser Arg
405 410 415

Trp Gln Glu Gly Asn Val Phe Ser Cys Ser Val Met His Glu Ala Leu
420 425 430

His Asn His Tyr Thr Gln Lys Ser Leu Ser Leu Ser Pro
435 440 445

<210> SEQ ID NO 232
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 232

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Ile Met Asn Trp Val Arg Gln Ala Pro Gly Gln Gly Leu Glu Trp Met
35 40 45

Gly Leu Ile Asn Pro Tyr Asn Gly Gly Thr Asp Tyr Asn Pro Gln Phe
50 55 60

Gln Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Asp Gly Tyr Asp Asp Gly Pro Tyr Thr Leu Glu Thr Trp Gly
100 105 110

```
Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Ser Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro
        435                 440                 445


<210> SEQ ID NO 233
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 233

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ala Met Asn Trp Val Arg Gln Ala Pro Gly Gln Gly Leu Glu Trp Met
```

```
        35                  40                  45

Gly Leu Ile Asn Pro Tyr Asn Gly Gly Thr Asp Tyr Asn Pro Gln Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Leu Glu Thr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Ser Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro
        435                 440                 445
```

<210> SEQ ID NO 234
<211> LENGTH: 445

<212> TYPE: PRT
<213> ORGANISM: Artificial
<220> FEATURE:
<223> OTHER INFORMATION: An artificially synthesized peptide sequence

<400> SEQUENCE: 234

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Ile Met Asn Trp Val Arg Gln Ala Pro Gly Gln Gly Leu Glu Trp Met
35 40 45

Gly Leu Ile Asn Pro Tyr Asn Gly Gly Thr Ser Tyr Asn Gln Gln Phe
50 55 60

Gln Asp Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Asp Gly Tyr Asp Asp Gly Pro Tyr Thr Leu Glu Thr Trp Gly
100 105 110

Gln Gly Thr Leu Val Thr Val Ser Ser Ala Ser Thr Lys Gly Pro Ser
115 120 125

Val Phe Pro Leu Ala Pro Ser Ser Lys Ser Thr Ser Gly Gly Thr Ala
130 135 140

Ala Leu Gly Cys Leu Val Lys Asp Tyr Phe Pro Glu Pro Val Thr Val
145 150 155 160

Ser Trp Asn Ser Gly Ala Leu Thr Ser Gly Val His Thr Phe Pro Ala
165 170 175

Val Leu Gln Ser Ser Gly Leu Tyr Ser Leu Ser Ser Val Val Thr Val
180 185 190

Pro Ser Ser Asn Phe Gly Thr Gln Thr Tyr Thr Cys Asn Val Asp His
195 200 205

Lys Pro Ser Asn Thr Lys Val Asp Lys Thr Val Glu Arg Lys Ser Cys
210 215 220

Val Glu Cys Pro Pro Cys Pro Ala Pro Pro Val Ala Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser Gln Glu Asp Pro Glu
260 265 270

Val Gln Phe Asn Trp Tyr Val Asp Gly Val Glu Val His Asn Ala Lys
275 280 285

Thr Lys Pro Arg Glu Glu Gln Phe Asn Ser Thr Phe Arg Val Val Ser
290 295 300

Val Leu Thr Val Val His Gln Asp Trp Leu Asn Gly Lys Glu Tyr Lys
305 310 315 320

Cys Lys Val Ser Asn Lys Gly Leu Pro Ala Pro Ile Glu Lys Thr Ile
325 330 335

Ser Lys Thr Lys Gly Gln Pro Arg Glu Pro Gln Val Tyr Thr Leu Pro
340 345 350

Pro Ser Gln Glu Glu Met Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Met Leu Asp Ser

```
385                 390                 395                 400

Asp Gly Ser Phe Phe Leu Tyr Ser Lys Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro
        435                 440                 445


<210> SEQ ID NO 235
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 235

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
        35                  40                  45

Gly Leu Ile Asn Pro Tyr Asn Gly Gly Thr Ser Tyr Asn Gln Gln Phe
    50                  55                  60

Gln Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Leu Glu Thr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Ser Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320
```

```
Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro
        435                 440                 445
```

<210> SEQ ID NO 236
<211> LENGTH: 214
<212> TYPE: PRT
<213> ORGANISM: Artificial
<220> FEATURE:
<223> OTHER INFORMATION: An artificially synthesized peptide sequence

<400> SEQUENCE: 236

```
Asp Ile Gln Met Thr Gln Ser Pro Ser Ser Leu Ser Ala Ser Val Gly
1               5                   10                  15

Asp Arg Val Thr Ile Thr Cys Gln Thr Ser Glu Asp Ile Tyr Arg Phe
            20                  25                  30

Val Ala Trp Tyr Gln Gln Lys Pro Gly Lys Ala Pro Lys Leu Leu Ile
        35                  40                  45

Tyr Asn Ala Gln Thr Glu Ala Gln Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Asp Ser Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 237
<211> LENGTH: 214

<212> TYPE: PRT
<213> ORGANISM: Artificial
<220> FEATURE:
<223> OTHER INFORMATION: An artificially synthesized peptide sequence

<400> SEQUENCE: 237

```
Asp Ile Gln Met Thr Gln Ser Pro Ser Ser Leu Ser Ala Ser Val Gly
1               5                   10                  15

Asp Arg Val Thr Ile Thr Cys Gln Thr Ser Glu Asp Ile Tyr Ser Phe
            20                  25                  30

Val Ala Trp Tyr Gln Gln Lys Pro Gly Lys Ala Pro Lys Leu Leu Ile
        35                  40                  45

Tyr Asn Ala Gln Thr Glu Ala Gln Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Asp Ser Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 238
<211> LENGTH: 214
<212> TYPE: PRT
<213> ORGANISM: Artificial
<220> FEATURE:
<223> OTHER INFORMATION: An artificially synthesized peptide sequence

<400> SEQUENCE: 238

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asp Ile Tyr Ser Phe
            20                  25                  30

Val Ala Trp Tyr Gln Gln Lys Pro Gly Lys Ala Pro Lys Leu Leu Ile
        35                  40                  45

Tyr Asn Ala Gln Thr Glu Ala Gln Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Asp Ser Pro Leu
                85                  90                  95

Thr Phe Gly Gly Gly Thr Lys Val Glu Ile Lys Arg Thr Val Ala Ala
            100                 105                 110
```

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 239
<211> LENGTH: 214
<212> TYPE: PRT
<213> ORGANISM: Artificial
<220> FEATURE:
<223> OTHER INFORMATION: An artificially synthesized peptide sequence

<400> SEQUENCE: 239

Asp Ile Gln Met Thr Gln Ser Pro Ser Ser Leu Ser Ala Ser Val Gly
1 5 10 15

Asp Arg Val Thr Ile Thr Cys Gln Ala Ser Glu Asp Ile Tyr Ser Phe
20 25 30

Leu Ala Trp Tyr Gln Gln Lys Pro Gly Lys Ala Pro Lys Leu Leu Ile
35 40 45

Tyr Asn Ala Gln Thr Glu Ala Gln Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln His His Tyr Asp Ser Pro Leu
85 90 95

Thr Phe Gly Gly Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 240
<211> LENGTH: 445
<212> TYPE: PRT
<213> ORGANISM: Artificial
<220> FEATURE:
<223> OTHER INFORMATION: An artificially synthesized peptide sequence -continued

<400> SEQUENCE: 240

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
        35                  40                  45

Gly Leu Ile Asn Pro Tyr Asn Gly Gly Thr Ser Tyr Asn Gln Gln Phe
    50                  55                  60

Gln Asp Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Ser Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415
```

Trp Gln Glu Gly Asn Val Phe Ser Cys Ser Val Met His Glu Ala Leu
420 425 430

His Asn His Tyr Thr Gln Lys Ser Leu Ser Leu Ser Pro
435 440 445

<210> SEQ ID NO 241
<211> LENGTH: 447
<212> TYPE: PRT
<213> ORGANISM: Artificial
<220> FEATURE:
<223> OTHER INFORMATION: An artificially synthesized peptide sequence

<400> SEQUENCE: 241

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Ile Met Asn Trp Val Arg Gln Ala Pro Gly Gln Gly Leu Glu Trp Met
35 40 45

Gly Leu Ile Asn Pro Tyr Asn Gly Gly Thr Ser Tyr Asn Gln Gln Phe
50 55 60

Gln Asp Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Asp Gly Tyr Asp Asp Gly Pro Tyr Thr Met Asp Tyr Trp Gly
100 105 110

Gln Gly Thr Leu Val Thr Val Ser Ser Ala Ser Thr Lys Gly Pro Ser
115 120 125

Val Phe Pro Leu Ala Pro Cys Ser Arg Ser Thr Ser Glu Ser Thr Ala
130 135 140

Ala Leu Gly Cys Leu Val Lys Asp Tyr Phe Pro Glu Pro Val Thr Val
145 150 155 160

Ser Trp Asn Ser Gly Ala Leu Thr Ser Gly Val His Thr Phe Pro Ala
165 170 175

Val Leu Gln Ser Ser Gly Leu Tyr Ser Leu Ser Ser Val Val Thr Val
180 185 190

Pro Ser Ser Asn Phe Gly Thr Gln Thr Tyr Thr Cys Asn Val Asp His
195 200 205

Lys Pro Ser Asn Thr Lys Val Asp Lys Thr Val Glu Arg Lys Cys Cys
210 215 220

Val Glu Cys Pro Pro Cys Pro Ala Pro Pro Val Ala Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser His Glu Asp Pro Glu
260 265 270

Val Gln Phe Asn Trp Tyr Val Asp Gly Val Glu Val His Asn Ala Lys
275 280 285

Thr Lys Pro Arg Glu Glu Gln Phe Asn Ser Thr Phe Arg Val Val Ser
290 295 300

Val Leu Thr Val Val His Gln Asp Trp Leu Asn Gly Lys Glu Tyr Lys
305 310 315 320

Cys Lys Val Ser Asn Lys Gly Leu Pro Ala Pro Ile Glu Lys Thr Ile
325 330 335

```
Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 242
<211> LENGTH: 447
<212> TYPE: PRT
<213> ORGANISM: Artificial
<220> FEATURE:
<223> OTHER INFORMATION: An artificially synthesized peptide sequence

<400> SEQUENCE: 242

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
        35                  40                  45

Gly Leu Ile Asn Pro Tyr Asn Gly Gly Thr Ser Tyr Asn Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Leu Glu Thr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Ser Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
```

-continued

```
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 243
<211> LENGTH: 447
<212> TYPE: PRT
<213> ORGANISM: Artificial
<220> FEATURE:
<223> OTHER INFORMATION: An artificially synthesized peptide sequence

<400> SEQUENCE: 243

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
        35                  40                  45

Gly Leu Ile Asn Pro Tyr Asn Gly Gly Thr Ser Tyr Asn Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Met Glu Thr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190
```

```
Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Ser Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 244
<211> LENGTH: 447
<212> TYPE: PRT
<213> ORGANISM: Artificial
<220> FEATURE:
<223> OTHER INFORMATION: An artificially synthesized peptide sequence

<400> SEQUENCE: 244

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
        35                  40                  45

Gly Leu Ile Asn Pro Tyr Asn Gly Gly Thr Ser Tyr Asn Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Leu Asp Asp Gly Pro Tyr Thr Met Glu Thr Trp Gly
            100                 105                 110
```

```
Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Ser Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 245
<211> LENGTH: 447
<212> TYPE: PRT
<213> ORGANISM: Artificial
<220> FEATURE:
<223> OTHER INFORMATION: An artificially synthesized peptide sequence

<400> SEQUENCE: 245

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
```

```
        35                  40                  45

Gly Leu Ile Asn Pro Tyr Asn Gly Gly Thr Ser Tyr Asn Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Leu Asp Asp Gly Pro Tyr Thr Met Glu Ser Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Ser Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 246
<211> LENGTH: 447

<212> TYPE: PRT
<213> ORGANISM: Artificial
<220> FEATURE:
<223> OTHER INFORMATION: An artificially synthesized peptide sequence

<400> SEQUENCE: 246

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Val Met Asn Trp Val Arg Gln Ala Pro Gly Gln Gly Leu Glu Trp Met
        35                  40                  45

Gly Leu Ile Asn Pro Tyr Asn Gly Gly Thr Ser Tyr Asn Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Ser Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
```

-continued

```
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 247
<211> LENGTH: 447
<212> TYPE: PRT
<213> ORGANISM: Artificial
<220> FEATURE:
<223> OTHER INFORMATION: An artificially synthesized peptide sequence

<400> SEQUENCE: 247

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Ile Asn Trp Val Arg Gln Ala Pro Gly Gln Gly Leu Glu Trp Met
        35                  40                  45

Gly Leu Ile Asn Pro Tyr Asn Gly Gly Thr Ser Tyr Asn Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Ser Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320
```

Cys Lys Val Ser Asn Lys Gly Leu Pro Ala Pro Ile Glu Lys Thr Ile
325 330 335

Ser Lys Thr Lys Gly Gln Pro Arg Glu Pro Gln Val Tyr Thr Leu Pro
340 345 350

Pro Ser Arg Glu Glu Met Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Met Leu Asp Ser
385 390 395 400

Asp Gly Ser Phe Phe Leu Tyr Ser Lys Leu Thr Val Asp Lys Ser Arg
405 410 415

Trp Gln Gln Gly Asn Val Phe Ser Cys Ser Val Met His Glu Ala Leu
420 425 430

His Asn His Tyr Thr Gln Lys Ser Leu Ser Leu Ser Pro Gly Lys
435 440 445

<210> SEQ ID NO 248
<211> LENGTH: 447
<212> TYPE: PRT
<213> ORGANISM: Artificial
<220> FEATURE:
<223> OTHER INFORMATION: An artificially synthesized peptide sequence

<400> SEQUENCE: 248

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Ile Leu Asn Trp Val Arg Gln Ala Pro Gly Gln Gly Leu Glu Trp Met
35 40 45

Gly Leu Ile Asn Pro Tyr Asn Gly Gly Thr Ser Tyr Asn Gln Lys Phe
50 55 60

Lys Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Asp Gly Tyr Asp Asp Gly Pro Tyr Thr Met Asp Tyr Trp Gly
100 105 110

Gln Gly Thr Leu Val Thr Val Ser Ser Ala Ser Thr Lys Gly Pro Ser
115 120 125

Val Phe Pro Leu Ala Pro Ser Ser Lys Ser Thr Ser Glu Ser Thr Ala
130 135 140

Ala Leu Gly Cys Leu Val Lys Asp Tyr Phe Pro Glu Pro Val Thr Val
145 150 155 160

Ser Trp Asn Ser Gly Ala Leu Thr Ser Gly Val His Thr Phe Pro Ala
165 170 175

Val Leu Gln Ser Ser Gly Leu Tyr Ser Leu Ser Ser Val Val Thr Val
180 185 190

Pro Ser Ser Asn Phe Gly Thr Gln Thr Tyr Thr Cys Asn Val Asp His
195 200 205

Lys Pro Ser Asn Thr Lys Val Asp Lys Thr Val Glu Arg Lys Ser Cys
210 215 220

Val Glu Cys Pro Pro Cys Pro Ala Pro Pro Val Ala Gly Pro Ser Val
225 230 235 240

```
Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 249
<211> LENGTH: 447
<212> TYPE: PRT
<213> ORGANISM: Artificial
<220> FEATURE:
<223> OTHER INFORMATION: An artificially synthesized peptide sequence

<400> SEQUENCE: 249

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
        35                  40                  45

Gly Leu Ile Asn Pro Tyr Asn Gly Gly Thr Asp Tyr Asn Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
```

-continued

```
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Ser Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 250
<211> LENGTH: 447
<212> TYPE: PRT
<213> ORGANISM: Artificial
<220> FEATURE:
<223> OTHER INFORMATION: An artificially synthesized peptide sequence

<400> SEQUENCE: 250

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
        35                  40                  45

Gly Leu Ile Asn Pro Tyr Asn Gly Gly Thr Ser Tyr Asn Pro Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

```
Ala Arg Asp Gly Tyr Asp Asp Gly Pro Tyr Thr Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Ser Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 251
<211> LENGTH: 214
<212> TYPE: PRT
<213> ORGANISM: Artificial
<220> FEATURE:
<223> OTHER INFORMATION: An artificially synthesized peptide sequence

<400> SEQUENCE: 251

```
Asp Ile Gln Met Thr Gln Ser Pro Ser Ser Leu Ser Ala Ser Val Gly
1               5                   10                  15
```

```
Asp Arg Val Thr Ile Thr Cys Arg Thr Ser Glu Asn Ile Tyr Arg Phe
            20                  25                  30

Leu Ala Trp Tyr Gln Gln Lys Pro Gly Lys Ala Pro Lys Leu Leu Ile
        35                  40                  45

Tyr Asn Ala Lys Thr Leu Ala Lys Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Glu Ser Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 252
<211> LENGTH: 214
<212> TYPE: PRT
<213> ORGANISM: Artificial
<220> FEATURE:
<223> OTHER INFORMATION: An artificially synthesized peptide sequence

<400> SEQUENCE: 252

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Ile Tyr Arg Phe
            20                  25                  30

Val Ala Trp Tyr Gln Gln Lys Pro Gly Lys Ala Pro Lys Leu Leu Ile
        35                  40                  45

Tyr Asn Ala Lys Thr Leu Ala Lys Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Glu Ser Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

```
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 253
<211> LENGTH: 214
<212> TYPE: PRT
<213> ORGANISM: Artificial
<220> FEATURE:
<223> OTHER INFORMATION: An artificially synthesized peptide sequence

<400> SEQUENCE: 253

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Ile Tyr Ser Phe
            20                  25                  30

Leu Ala Trp Tyr Gln Gln Lys Pro Gly Lys Ala Pro Lys Leu Leu Ile
        35                  40                  45

Tyr Asn Ala Lys Thr Leu Ala Lys Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Asp Ser Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 254
<211> LENGTH: 214
<212> TYPE: PRT
<213> ORGANISM: Artificial
<220> FEATURE:
<223> OTHER INFORMATION: An artificially synthesized peptide sequence

<400> SEQUENCE: 254

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Ile Tyr Ser Phe
            20                  25                  30

Leu Ala Trp Tyr Gln Gln Lys Pro Gly Lys Ala Pro Lys Leu Leu Ile
```

```
        35                  40                  45

Tyr Asn Ala Lys Thr Leu Ala Lys Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Glu Asp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 255
<211> LENGTH: 447
<212> TYPE: PRT
<213> ORGANISM: Artificial
<220> FEATURE:
<223> OTHER INFORMATION: An artificially synthesized peptide sequence

<400> SEQUENCE: 255

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Val Ile Asn Trp Val Arg Gln Ala Pro Gly Gln Gly Leu Glu Trp Met
        35                  40                  45

Gly Leu Ile Asn Pro Tyr Asn Gly Gly Thr Asp Tyr Asn Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190
```

```
Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Ser Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 256
<211> LENGTH: 214
<212> TYPE: PRT
<213> ORGANISM: Artificial
<220> FEATURE:
<223> OTHER INFORMATION: An artificially synthesized peptide sequence

<400> SEQUENCE: 256

Asp Ile Gln Met Thr Gln Ser Pro Ser Ser Leu Ser Ala Ser Val Gly
1               5                   10                  15

Asp Arg Val Thr Ile Thr Cys Gln Thr Ser Glu Asn Ile Tyr Arg Phe
            20                  25                  30

Val Ala Trp Tyr Gln Gln Lys Pro Gly Lys Ala Pro Lys Leu Leu Ile
        35                  40                  45

Tyr Asn Ala Lys Thr Leu Ala Lys Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Asp Ser Pro Leu
                85                  90                  95

Thr Phe Gly Gly Gly Thr Lys Val Glu Ile Lys Arg Thr Val Ala Ala
            100                 105                 110
```

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 257
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 257

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
        35                  40                  45

Gly Leu Ile Asn Pro Tyr Asn Gly Gly Thr Ser Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Ser Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
```

```
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro
        435                 440                 445


<210> SEQ ID NO 258
<211> LENGTH: 530
<212> TYPE: PRT
<213> ORGANISM: Homo sapiens

<400> SEQUENCE: 258

Met Met Trp Thr Trp Ala Leu Trp Met Leu Pro Ser Leu Cys Lys Phe
1               5                   10                  15

Ser Leu Ala Ala Leu Pro Ala Lys Pro Glu Asn Ile Ser Cys Val Tyr
            20                  25                  30

Tyr Tyr Arg Lys Asn Leu Thr Cys Thr Trp Ser Pro Gly Lys Glu Thr
        35                  40                  45

Ser Tyr Thr Gln Tyr Thr Val Lys Arg Thr Tyr Ala Phe Gly Glu Lys
    50                  55                  60

His Asp Asn Cys Thr Thr Asn Ser Ser Thr Ser Glu Asn Arg Ala Ser
65                  70                  75                  80

Cys Ser Phe Phe Leu Pro Arg Ile Thr Ile Pro Asp Asn Tyr Thr Ile
                85                  90                  95

Glu Val Glu Ala Glu Asn Gly Asp Gly Val Ile Lys Ser His Met Thr
            100                 105                 110

Tyr Trp Arg Leu Glu Asn Ile Ala Lys Thr Glu Pro Pro Lys Ile Phe
        115                 120                 125

Arg Val Lys Pro Val Leu Gly Ile Lys Arg Met Ile Gln Ile Glu Trp
    130                 135                 140

Ile Lys Pro Glu Leu Ala Pro Val Ser Ser Asp Leu Lys Tyr Thr Leu
145                 150                 155                 160

Arg Phe Arg Thr Val Asn Ser Thr Ser Trp Met Glu Val Asn Phe Ala
                165                 170                 175

Lys Asn Arg Lys Asp Lys Asn Gln Thr Tyr Asn Leu Thr Gly Leu Gln
            180                 185                 190

Pro Phe Thr Glu Tyr Val Ile Ala Leu Arg Cys Ala Val Lys Glu Ser
```

```
        195                 200                 205

Lys Phe Trp Ser Asp Trp Ser Gln Glu Lys Met Gly Met Thr Glu Glu
    210                 215                 220

Glu Ala Pro Cys Gly Leu Glu Leu Trp Arg Val Leu Lys Pro Ala Glu
225                 230                 235                 240

Ala Asp Gly Arg Arg Pro Val Arg Leu Leu Trp Lys Lys Ala Arg Gly
                245                 250                 255

Ala Pro Val Leu Glu Lys Thr Leu Gly Tyr Asn Ile Trp Tyr Tyr Pro
            260                 265                 270

Glu Ser Asn Thr Asn Leu Thr Glu Thr Met Asn Thr Thr Asn Gln Gln
        275                 280                 285

Leu Glu Leu His Leu Gly Gly Glu Ser Phe Trp Val Ser Met Ile Ser
    290                 295                 300

Tyr Asn Ser Leu Gly Lys Ser Pro Val Ala Thr Leu Arg Ile Pro Ala
305                 310                 315                 320

Ile Gln Glu Lys Ser Phe Gln Cys Ile Glu Val Met Gln Ala Cys Val
                325                 330                 335

Ala Glu Asp Gln Leu Val Val Lys Trp Gln Ser Ser Ala Leu Asp Val
            340                 345                 350

Asn Thr Trp Met Ile Glu Trp Phe Pro Asp Val Asp Ser Glu Pro Thr
        355                 360                 365

Thr Leu Ser Trp Glu Ser Val Ser Gln Ala Thr Asn Trp Thr Ile Gln
    370                 375                 380

Gln Asp Lys Leu Lys Pro Phe Trp Cys Tyr Asn Ile Ser Val Tyr Pro
385                 390                 395                 400

Met Leu His Asp Lys Val Gly Glu Pro Tyr Ser Ile Gln Ala Tyr Ala
                405                 410                 415

Lys Glu Gly Val Pro Ser Glu Gly Pro Glu Thr Lys Val Glu Asn Ile
            420                 425                 430

Gly Val Lys Thr Val Thr Ile Thr Trp Lys Glu Ile Pro Lys Ser Glu
        435                 440                 445

Arg Lys Gly Ile Ile Cys Asn Tyr Thr Ile Phe Tyr Gln Ala Glu Gly
    450                 455                 460

Gly Lys Gly Phe Ser Lys Thr Val Asn Ser Ser Ile Leu Gln Tyr Gly
465                 470                 475                 480

Leu Glu Ser Leu Lys Arg Lys Thr Ser Tyr Ile Val Gln Val Met Ala
                485                 490                 495

Ser Thr Ser Ala Gly Gly Thr Asn Gly Thr Ser Ile Asn Phe Lys Thr
            500                 505                 510

Leu Ser His His His His His His Glu Gln Lys Leu Ile Ser Glu Glu
        515                 520                 525

Asp Leu
    530


<210> SEQ ID NO 259
<211> LENGTH: 517
<212> TYPE: PRT
<213> ORGANISM: Mus musculus

<400> SEQUENCE: 259

Met Trp Thr Leu Ala Leu Trp Ala Phe Ser Phe Leu Cys Lys Phe Ser
1               5                   10                  15

Leu Ala Val Leu Pro Thr Lys Pro Glu Asn Ile Ser Cys Val Phe Tyr
            20                  25                  30

Phe Asp Arg Asn Leu Thr Cys Thr Trp Arg Pro Glu Lys Glu Thr Asn
```

```
        35                  40                  45

Asp Thr Ser Tyr Ile Val Thr Leu Thr Tyr Ser Tyr Gly Lys Ser Asn
    50                  55                  60

Tyr Ser Asp Asn Ala Thr Glu Ala Ser Tyr Ser Phe Pro Arg Ser Cys
65                  70                  75                  80

Ala Met Pro Pro Asp Ile Cys Ser Val Glu Val Gln Ala Gln Asn Gly
                85                  90                  95

Asp Gly Lys Val Lys Ser Asp Ile Thr Tyr Trp His Leu Ile Ser Ile
            100                 105                 110

Ala Lys Thr Glu Pro Pro Ile Ile Leu Ser Val Asn Pro Ile Cys Asn
        115                 120                 125

Arg Met Phe Gln Ile Gln Trp Lys Pro Arg Glu Lys Thr Arg Gly Phe
    130                 135                 140

Pro Leu Val Cys Met Leu Arg Phe Arg Thr Val Asn Ser Ser Arg Trp
145                 150                 155                 160

Thr Glu Val Asn Phe Glu Asn Cys Lys Gln Val Cys Asn Leu Thr Gly
                165                 170                 175

Leu Gln Ala Phe Thr Glu Tyr Val Leu Ala Leu Arg Phe Arg Phe Asn
            180                 185                 190

Asp Ser Arg Tyr Trp Ser Lys Trp Ser Lys Glu Glu Thr Arg Val Thr
        195                 200                 205

Met Glu Glu Val Pro His Val Leu Asp Leu Trp Arg Ile Leu Glu Pro
    210                 215                 220

Ala Asp Met Asn Gly Asp Arg Lys Val Arg Leu Leu Trp Lys Lys Ala
225                 230                 235                 240

Arg Gly Ala Pro Val Leu Glu Lys Thr Phe Gly Tyr His Ile Gln Tyr
                245                 250                 255

Phe Ala Glu Asn Ser Thr Asn Leu Thr Glu Ile Asn Asn Ile Thr Thr
            260                 265                 270

Gln Gln Tyr Glu Leu Leu Leu Met Ser Gln Ala His Ser Val Ser Val
        275                 280                 285

Thr Ser Phe Asn Ser Leu Gly Lys Ser Gln Glu Thr Ile Leu Arg Ile
    290                 295                 300

Pro Asp Val His Glu Lys Thr Phe Gln Tyr Ile Lys Ser Met Gln Ala
305                 310                 315                 320

Tyr Ile Ala Glu Pro Leu Leu Val Val Asn Trp Gln Ser Ser Ile Pro
                325                 330                 335

Ala Val Asp Thr Trp Ile Val Glu Trp Leu Pro Glu Ala Ala Met Ser
            340                 345                 350

Lys Phe Pro Ala Leu Ser Trp Glu Ser Val Ser Gln Val Thr Asn Trp
        355                 360                 365

Thr Ile Glu Gln Asp Lys Leu Lys Pro Phe Thr Cys Tyr Asn Ile Ser
    370                 375                 380

Val Tyr Pro Val Leu Gly His Arg Val Gly Glu Pro Tyr Ser Ile Gln
385                 390                 395                 400

Ala Tyr Ala Lys Glu Gly Thr Pro Leu Lys Gly Pro Glu Thr Arg Val
                405                 410                 415

Glu Asn Ile Gly Leu Arg Thr Ala Thr Ile Thr Trp Lys Glu Ile Pro
            420                 425                 430

Lys Ser Ala Arg Asn Gly Phe Ile Asn Asn Tyr Thr Val Phe Tyr Gln
        435                 440                 445

Ala Glu Gly Gly Lys Glu Leu Ser Lys Thr Val Asn Ser His Ala Leu
    450                 455                 460
```

```
Gln Cys Asp Leu Glu Ser Leu Thr Arg Arg Thr Ser Tyr Thr Val Trp
465                 470                 475                 480

Val Met Ala Ser Thr Arg Ala Gly Gly Thr Asn Gly Val Arg Ile Asn
                485                 490                 495

Phe Lys Thr Leu Ser His His His His His His Glu Gln Lys Leu Ile
            500                 505                 510

Ser Glu Glu Asp Leu
        515


<210> SEQ ID NO 260
<211> LENGTH: 531
<212> TYPE: PRT
<213> ORGANISM: Artificial
<220> FEATURE:
<223> OTHER INFORMATION: An artificially synthesized peptide sequence

<400> SEQUENCE: 260

Met Met Trp Thr Trp Ala Leu Trp Met Leu Pro Ser Leu Cys Lys Phe
1               5                   10                  15

Ser Leu Ala Ala Leu Pro Ala Lys Pro Glu Asn Ile Ser Cys Val Tyr
            20                  25                  30

Tyr Tyr Arg Lys Asn Leu Thr Cys Thr Trp Ser Pro Gly Lys Glu Thr
        35                  40                  45

Ser Tyr Thr Gln Tyr Thr Val Lys Arg Thr Tyr Ala Phe Gly Glu Lys
    50                  55                  60

His Asp Asn Cys Thr Thr Asn Ser Ser Thr Ser Glu Asn Arg Ala Ser
65                  70                  75                  80

Cys Ser Phe Phe Leu Pro Arg Ile Thr Ile Pro Asp Asn Tyr Thr Ile
                85                  90                  95

Glu Val Glu Ala Glu Asn Gly Asp Gly Val Ile Lys Ser His Met Thr
            100                 105                 110

Tyr Trp Arg Leu Glu Asn Ile Ala Lys Thr Glu Pro Pro Lys Ile Phe
        115                 120                 125

Arg Val Lys Pro Val Leu Gly Ile Lys Arg Met Ile Gln Ile Glu Trp
    130                 135                 140

Ile Lys Pro Glu Leu Ala Pro Val Ser Ser Asp Leu Lys Tyr Thr Leu
145                 150                 155                 160

Arg Phe Arg Thr Val Asn Ser Thr Ser Trp Met Glu Val Asn Phe Ala
                165                 170                 175

Lys Asn Arg Lys Asp Lys Asn Gln Thr Tyr Asn Leu Thr Gly Leu Gln
            180                 185                 190

Pro Phe Thr Glu Tyr Val Ile Ala Leu Arg Cys Ala Val Lys Glu Ser
        195                 200                 205

Lys Phe Trp Ser Asp Trp Ser Gln Glu Lys Met Gly Met Thr Glu Glu
    210                 215                 220

Glu Ala Pro His Val Leu Asp Leu Trp Arg Ile Leu Glu Pro Ala Asp
225                 230                 235                 240

Met Asn Gly Asp Arg Lys Val Arg Leu Leu Trp Lys Lys Ala Arg Gly
                245                 250                 255

Ala Pro Val Leu Glu Lys Thr Phe Gly Tyr His Ile Gln Tyr Phe Ala
            260                 265                 270

Glu Asn Ser Thr Asn Leu Thr Glu Ile Asn Asn Ile Thr Thr Gln Gln
        275                 280                 285

Tyr Glu Leu Leu Leu Met Ser Gln Ala His Ser Val Ser Val Thr Ser
    290                 295                 300

Phe Asn Ser Leu Gly Lys Ser Gln Glu Thr Ile Leu Arg Ile Pro Asp
```

305 310 315 320

Val His Glu Lys Thr Phe Gln Tyr Ile Lys Ser Met Gln Ala Tyr Ile
325 330 335

Ala Glu Pro Leu Leu Val Val Asn Trp Gln Ser Ser Ile Pro Ala Val
340 345 350

Asp Thr Trp Ile Val Glu Trp Leu Pro Glu Ala Ala Met Ser Lys Phe
355 360 365

Pro Ala Leu Ser Trp Glu Ser Val Ser Gln Val Thr Asn Trp Thr Ile
370 375 380

Glu Gln Asp Lys Leu Lys Pro Phe Thr Cys Tyr Asn Ile Ser Val Tyr
385 390 395 400

Pro Val Leu Gly His Arg Val Gly Glu Pro Tyr Ser Ile Gln Ala Tyr
405 410 415

Ala Lys Glu Gly Thr Pro Leu Lys Gly Pro Glu Thr Arg Val Glu Asn
420 425 430

Ile Gly Leu Arg Thr Ala Thr Ile Thr Trp Lys Glu Ile Pro Lys Ser
435 440 445

Ala Arg Asn Gly Phe Ile Asn Asn Tyr Thr Val Phe Tyr Gln Ala Glu
450 455 460

Gly Gly Lys Glu Leu Ser Lys Thr Val Asn Ser His Ala Leu Gln Cys
465 470 475 480

Asp Leu Glu Ser Leu Thr Arg Arg Thr Ser Tyr Thr Val Trp Val Met
485 490 495

Ala Ser Thr Arg Ala Gly Gly Thr Asn Gly Val Arg Ile Asn Phe Lys
500 505 510

Thr Leu Ser His His His His His His Glu Gln Lys Leu Ile Ser Glu
515 520 525

Glu Asp Leu
530

<210> SEQ ID NO 261
<211> LENGTH: 516
<212> TYPE: PRT
<213> ORGANISM: Artificial
<220> FEATURE:
<223> OTHER INFORMATION: An artificially synthesized peptide sequence

<400> SEQUENCE: 261

Met Trp Thr Leu Ala Leu Trp Ala Phe Ser Phe Leu Cys Lys Phe Ser
1 5 10 15

Leu Ala Val Leu Pro Thr Lys Pro Glu Asn Ile Ser Cys Val Phe Tyr
20 25 30

Phe Asp Arg Asn Leu Thr Cys Thr Trp Arg Pro Glu Lys Glu Thr Asn
35 40 45

Asp Thr Ser Tyr Ile Val Thr Leu Thr Tyr Ser Tyr Gly Lys Ser Asn
50 55 60

Tyr Ser Asp Asn Ala Thr Glu Ala Ser Tyr Ser Phe Pro Arg Ser Cys
65 70 75 80

Ala Met Pro Pro Asp Ile Cys Ser Val Glu Val Gln Ala Gln Asn Gly
85 90 95

Asp Gly Lys Val Lys Ser Asp Ile Thr Tyr Trp His Leu Ile Ser Ile
100 105 110

Ala Lys Thr Glu Pro Pro Ile Ile Leu Ser Val Asn Pro Ile Cys Asn
115 120 125

Arg Met Phe Gln Ile Gln Trp Lys Pro Arg Glu Lys Thr Arg Gly Phe
130 135 140

```
Pro Leu Val Cys Met Leu Arg Phe Arg Thr Val Asn Ser Ser Arg Trp
145                 150                 155                 160

Thr Glu Val Asn Phe Glu Asn Cys Lys Gln Val Cys Asn Leu Thr Gly
                165                 170                 175

Leu Gln Ala Phe Thr Glu Tyr Val Leu Ala Leu Arg Phe Arg Phe Asn
            180                 185                 190

Asp Ser Arg Tyr Trp Ser Lys Trp Ser Lys Glu Glu Thr Arg Val Thr
        195                 200                 205

Met Glu Glu Val Pro Cys Gly Leu Glu Leu Trp Arg Val Leu Lys Pro
    210                 215                 220

Ala Glu Ala Asp Gly Arg Arg Pro Val Arg Leu Leu Trp Lys Lys Ala
225                 230                 235                 240

Arg Gly Ala Pro Val Leu Glu Lys Thr Leu Gly Tyr Asn Ile Trp Tyr
                245                 250                 255

Tyr Pro Glu Ser Asn Thr Asn Leu Thr Glu Thr Met Asn Thr Thr Asn
            260                 265                 270

Gln Gln Leu Glu Leu His Leu Gly Gly Glu Ser Phe Trp Val Ser Met
        275                 280                 285

Ile Ser Tyr Asn Ser Leu Gly Lys Ser Pro Val Ala Thr Leu Arg Ile
    290                 295                 300

Pro Ala Ile Gln Glu Lys Ser Phe Gln Cys Ile Glu Val Met Gln Ala
305                 310                 315                 320

Cys Val Ala Glu Asp Gln Leu Val Val Lys Trp Gln Ser Ser Ala Leu
                325                 330                 335

Asp Val Asn Thr Trp Met Ile Glu Trp Phe Pro Asp Val Asp Ser Glu
            340                 345                 350

Pro Thr Thr Leu Ser Trp Glu Ser Val Ser Gln Ala Thr Asn Trp Thr
        355                 360                 365

Ile Gln Gln Asp Lys Leu Lys Pro Phe Trp Cys Tyr Asn Ile Ser Val
    370                 375                 380

Tyr Pro Met Leu His Asp Lys Val Gly Glu Pro Tyr Ser Ile Gln Ala
385                 390                 395                 400

Tyr Ala Lys Glu Gly Val Pro Ser Glu Gly Pro Glu Thr Lys Val Glu
                405                 410                 415

Asn Ile Gly Val Lys Thr Val Thr Ile Thr Trp Lys Glu Ile Pro Lys
            420                 425                 430

Ser Glu Arg Lys Gly Ile Ile Cys Asn Tyr Thr Ile Phe Tyr Gln Ala
        435                 440                 445

Glu Gly Gly Lys Gly Phe Ser Lys Thr Val Asn Ser Ser Ile Leu Gln
    450                 455                 460

Tyr Gly Leu Glu Ser Leu Lys Arg Lys Thr Ser Tyr Ile Val Gln Val
465                 470                 475                 480

Met Ala Ser Thr Ser Ala Gly Gly Thr Asn Gly Thr Ser Ile Asn Phe
                485                 490                 495

Lys Thr Leu Ser His His His His His His Glu Gln Lys Leu Ile Ser
            500                 505                 510

Glu Glu Asp Leu
        515
```

<210> SEQ ID NO 262
<211> LENGTH: 524
<212> TYPE: PRT
<213> ORGANISM: Artificial
<220> FEATURE:
<223> OTHER INFORMATION: An artificially synthesized peptide sequence

<400> SEQUENCE: 262

Met Met Trp Thr Trp Ala Leu Trp Met Leu Pro Ser Leu Cys Lys Phe
1               5                   10                  15

Ser Leu Ala Ala Leu Pro Ala Lys Pro Glu Asn Ile Ser Cys Val Tyr
            20                  25                  30

Tyr Tyr Arg Lys Asn Leu Thr Cys Thr Trp Ser Pro Gly Lys Glu Thr
        35                  40                  45

Ser Tyr Thr Gln Tyr Thr Val Lys Arg Thr Tyr Ala Phe Gly Glu Lys
    50                  55                  60

His Asp Asn Cys Thr Thr Asn Ser Ser Thr Ser Glu Asn Arg Ala Ser
65                  70                  75                  80

Cys Ser Phe Phe Leu Pro Arg Ile Thr Ile Pro Asp Asn Tyr Thr Ile
                85                  90                  95

Glu Val Glu Ala Glu Asn Gly Asp Gly Val Ile Lys Ser His Met Thr
            100                 105                 110

Tyr Trp Arg Leu Glu Asn Ile Ala Lys Thr Glu Pro Pro Ile Ile Leu
        115                 120                 125

Ser Val Asn Pro Ile Cys Asn Arg Met Phe Gln Ile Gln Trp Lys Pro
    130                 135                 140

Arg Glu Lys Thr Arg Gly Phe Pro Leu Val Cys Met Leu Arg Phe Arg
145                 150                 155                 160

Thr Val Asn Ser Ser Arg Trp Thr Glu Val Asn Phe Glu Asn Cys Lys
                165                 170                 175

Gln Val Cys Asn Leu Thr Gly Leu Gln Ala Phe Thr Glu Tyr Val Leu
            180                 185                 190

Ala Leu Arg Phe Arg Phe Asn Asp Ser Arg Tyr Trp Ser Lys Trp Ser
        195                 200                 205

Lys Glu Glu Thr Arg Val Thr Met Glu Glu Val Pro His Val Leu Asp
    210                 215                 220

Leu Trp Arg Ile Leu Glu Pro Ala Asp Met Asn Gly Asp Arg Lys Val
225                 230                 235                 240

Arg Leu Leu Trp Lys Lys Ala Arg Gly Ala Pro Val Leu Glu Lys Thr
                245                 250                 255

Phe Gly Tyr His Ile Gln Tyr Phe Ala Glu Asn Ser Thr Asn Leu Thr
            260                 265                 270

Glu Ile Asn Asn Ile Thr Thr Gln Gln Tyr Glu Leu Leu Leu Met Ser
        275                 280                 285

Gln Ala His Ser Val Ser Val Thr Ser Phe Asn Ser Leu Gly Lys Ser
    290                 295                 300

Gln Glu Thr Ile Leu Arg Ile Pro Asp Val His Glu Lys Thr Phe Gln
305                 310                 315                 320

Tyr Ile Lys Ser Met Gln Ala Tyr Ile Ala Glu Pro Leu Leu Val Val
                325                 330                 335

Asn Trp Gln Ser Ser Ile Pro Ala Val Asp Thr Trp Ile Val Glu Trp
            340                 345                 350

Leu Pro Glu Ala Ala Met Ser Lys Phe Pro Ala Leu Ser Trp Glu Ser
        355                 360                 365

Val Ser Gln Val Thr Asn Trp Thr Ile Glu Gln Asp Lys Leu Lys Pro
    370                 375                 380

Phe Thr Cys Tyr Asn Ile Ser Val Tyr Pro Val Leu Gly His Arg Val
385                 390                 395                 400

Gly Glu Pro Tyr Ser Ile Gln Ala Tyr Ala Lys Glu Gly Thr Pro Leu
                405                 410                 415

```
Lys Gly Pro Glu Thr Arg Val Glu Asn Ile Gly Leu Arg Thr Ala Thr
            420                 425                 430

Ile Thr Trp Lys Glu Ile Pro Lys Ser Ala Arg Asn Gly Phe Ile Asn
        435                 440                 445

Asn Tyr Thr Val Phe Tyr Gln Ala Glu Gly Gly Lys Glu Leu Ser Lys
    450                 455                 460

Thr Val Asn Ser His Ala Leu Gln Cys Asp Leu Glu Ser Leu Thr Arg
465                 470                 475                 480

Arg Thr Ser Tyr Thr Val Trp Val Met Ala Ser Thr Arg Ala Gly Gly
                485                 490                 495

Thr Asn Gly Val Arg Ile Asn Phe Lys Thr Leu Ser His His His His
            500                 505                 510

His His Glu Gln Lys Leu Ile Ser Glu Glu Asp Leu
        515                 520


<210> SEQ ID NO 263
<211> LENGTH: 524
<212> TYPE: PRT
<213> ORGANISM: Artificial
<220> FEATURE:
<223> OTHER INFORMATION: An artificially synthesized peptide sequence

<400> SEQUENCE: 263

Met Trp Thr Leu Ala Leu Trp Ala Phe Ser Phe Leu Cys Lys Phe Ser
1               5                   10                  15

Leu Ala Val Leu Pro Thr Lys Pro Glu Asn Ile Ser Cys Val Phe Tyr
            20                  25                  30

Phe Asp Arg Asn Leu Thr Cys Thr Trp Arg Pro Glu Lys Glu Thr Asn
        35                  40                  45

Asp Thr Ser Tyr Ile Val Thr Leu Thr Tyr Ser Tyr Gly Lys Ser Asn
    50                  55                  60

Tyr Ser Asp Asn Ala Thr Glu Ala Ser Tyr Ser Phe Pro Arg Ser Cys
65                  70                  75                  80

Ala Met Pro Pro Asp Ile Cys Ser Val Glu Val Gln Ala Gln Asn Gly
                85                  90                  95

Asp Gly Lys Val Lys Ser Asp Ile Thr Tyr Trp His Leu Ile Ser Ile
            100                 105                 110

Ala Lys Thr Glu Pro Pro Lys Ile Phe Arg Val Lys Pro Val Leu Gly
        115                 120                 125

Ile Lys Arg Met Ile Gln Ile Glu Trp Ile Lys Pro Glu Leu Ala Pro
    130                 135                 140

Val Ser Ser Asp Leu Lys Tyr Thr Leu Arg Phe Arg Thr Val Asn Ser
145                 150                 155                 160

Thr Ser Trp Met Glu Val Asn Phe Ala Lys Asn Arg Lys Asp Lys Asn
                165                 170                 175

Gln Thr Tyr Asn Leu Thr Gly Leu Gln Pro Phe Thr Glu Tyr Val Ile
            180                 185                 190

Ala Leu Arg Cys Ala Val Lys Glu Ser Lys Phe Trp Ser Asp Trp Ser
        195                 200                 205

Gln Glu Lys Met Gly Met Thr Glu Glu Glu Ala Pro His Val Leu Asp
    210                 215                 220

Leu Trp Arg Ile Leu Glu Pro Ala Asp Met Asn Gly Asp Arg Lys Val
225                 230                 235                 240

Arg Leu Leu Trp Lys Lys Ala Arg Gly Ala Pro Val Leu Glu Lys Thr
                245                 250                 255
```

```
Phe Gly Tyr His Ile Gln Tyr Phe Ala Glu Asn Ser Thr Asn Leu Thr
            260                 265                 270

Glu Ile Asn Asn Ile Thr Thr Gln Gln Tyr Glu Leu Leu Leu Met Ser
        275                 280                 285

Gln Ala His Ser Val Ser Val Thr Ser Phe Asn Ser Leu Gly Lys Ser
    290                 295                 300

Gln Glu Thr Ile Leu Arg Ile Pro Asp Val His Glu Lys Thr Phe Gln
305                 310                 315                 320

Tyr Ile Lys Ser Met Gln Ala Tyr Ile Ala Glu Pro Leu Leu Val Val
                325                 330                 335

Asn Trp Gln Ser Ser Ile Pro Ala Val Asp Thr Trp Ile Val Glu Trp
            340                 345                 350

Leu Pro Glu Ala Ala Met Ser Lys Phe Pro Ala Leu Ser Trp Glu Ser
        355                 360                 365

Val Ser Gln Val Thr Asn Trp Thr Ile Glu Gln Asp Lys Leu Lys Pro
    370                 375                 380

Phe Thr Cys Tyr Asn Ile Ser Val Tyr Pro Val Leu Gly His Arg Val
385                 390                 395                 400

Gly Glu Pro Tyr Ser Ile Gln Ala Tyr Ala Lys Glu Gly Thr Pro Leu
                405                 410                 415

Lys Gly Pro Glu Thr Arg Val Glu Asn Ile Gly Leu Arg Thr Ala Thr
            420                 425                 430

Ile Thr Trp Lys Glu Ile Pro Lys Ser Ala Arg Asn Gly Phe Ile Asn
        435                 440                 445

Asn Tyr Thr Val Phe Tyr Gln Ala Glu Gly Gly Lys Glu Leu Ser Lys
    450                 455                 460

Thr Val Asn Ser His Ala Leu Gln Cys Asp Leu Glu Ser Leu Thr Arg
465                 470                 475                 480

Arg Thr Ser Tyr Thr Val Trp Val Met Ala Ser Thr Arg Ala Gly Gly
                485                 490                 495

Thr Asn Gly Val Arg Ile Asn Phe Lys Thr Leu Ser His His His His
            500                 505                 510

His His Glu Gln Lys Leu Ile Ser Glu Glu Asp Leu
        515                 520


<210> SEQ ID NO 264
<211> LENGTH: 523
<212> TYPE: PRT
<213> ORGANISM: Artificial
<220> FEATURE:
<223> OTHER INFORMATION: An artificially synthesized peptide sequence

<400> SEQUENCE: 264

Met Trp Thr Leu Ala Leu Trp Ala Phe Ser Phe Leu Cys Lys Phe Ser
1               5                   10                  15

Leu Ala Val Leu Pro Thr Lys Pro Glu Asn Ile Ser Cys Val Phe Tyr
            20                  25                  30

Phe Asp Arg Asn Leu Thr Cys Thr Trp Arg Pro Glu Lys Glu Thr Asn
        35                  40                  45

Asp Thr Ser Tyr Ile Val Thr Leu Thr Tyr Ser Tyr Gly Lys Ser Asn
    50                  55                  60

Tyr Ser Asp Asn Ala Thr Glu Ala Ser Tyr Ser Phe Pro Arg Ser Cys
65                  70                  75                  80

Ala Met Pro Pro Asp Ile Cys Ser Val Glu Val Gln Ala Gln Asn Gly
                85                  90                  95

Asp Gly Lys Val Lys Ser Asp Ile Thr Tyr Trp His Leu Ile Ser Ile
```

```
            100                 105                 110

Ala Lys Thr Glu Pro Pro Lys Ile Phe Arg Val Lys Pro Val Leu Gly
        115                 120                 125

Ile Lys Arg Met Ile Gln Ile Glu Trp Ile Lys Pro Glu Leu Ala Pro
    130                 135                 140

Val Ser Ser Asp Leu Lys Tyr Thr Leu Arg Phe Arg Thr Val Asn Ser
145                 150                 155                 160

Thr Ser Trp Met Glu Val Asn Phe Ala Lys Asn Arg Lys Asp Lys Asn
                165                 170                 175

Gln Thr Tyr Asn Leu Thr Gly Leu Gln Pro Phe Thr Glu Tyr Val Ile
            180                 185                 190

Ala Leu Arg Cys Ala Val Lys Glu Ser Lys Phe Trp Ser Asp Trp Ser
        195                 200                 205

Gln Glu Lys Met Gly Met Thr Glu Glu Glu Ala Pro Cys Gly Leu Glu
    210                 215                 220

Leu Trp Arg Val Leu Lys Pro Ala Glu Ala Asp Gly Arg Arg Pro Val
225                 230                 235                 240

Arg Leu Leu Trp Lys Lys Ala Arg Gly Ala Pro Val Leu Glu Lys Thr
                245                 250                 255

Leu Gly Tyr Asn Ile Trp Tyr Tyr Pro Glu Ser Asn Thr Asn Leu Thr
            260                 265                 270

Glu Thr Met Asn Thr Thr Asn Gln Gln Leu Glu Leu His Leu Gly Gly
        275                 280                 285

Glu Ser Phe Trp Val Ser Met Ile Ser Tyr Asn Ser Leu Gly Lys Ser
    290                 295                 300

Pro Val Ala Thr Leu Arg Ile Pro Ala Ile Gln Glu Lys Ser Phe Gln
305                 310                 315                 320

Cys Ile Glu Val Met Gln Ala Cys Val Ala Glu Asp Gln Leu Val Val
                325                 330                 335

Lys Trp Gln Ser Ser Ala Leu Asp Val Asn Thr Trp Met Ile Glu Trp
            340                 345                 350

Phe Pro Asp Val Asp Ser Glu Pro Thr Thr Leu Ser Trp Glu Ser Val
        355                 360                 365

Ser Gln Ala Thr Asn Trp Thr Ile Gln Gln Asp Lys Leu Lys Pro Phe
    370                 375                 380

Trp Cys Tyr Asn Ile Ser Val Tyr Pro Met Leu His Asp Lys Val Gly
385                 390                 395                 400

Glu Pro Tyr Ser Ile Gln Ala Tyr Ala Lys Glu Gly Val Pro Ser Glu
                405                 410                 415

Gly Pro Glu Thr Lys Val Glu Asn Ile Gly Val Lys Thr Val Thr Ile
            420                 425                 430

Thr Trp Lys Glu Ile Pro Lys Ser Glu Arg Lys Gly Ile Ile Cys Asn
        435                 440                 445

Tyr Thr Ile Phe Tyr Gln Ala Glu Gly Gly Lys Gly Phe Ser Lys Thr
    450                 455                 460

Val Asn Ser Ser Ile Leu Gln Tyr Gly Leu Glu Ser Leu Lys Arg Lys
465                 470                 475                 480

Thr Ser Tyr Ile Val Gln Val Met Ala Ser Thr Ser Ala Gly Gly Thr
                485                 490                 495

Asn Gly Thr Ser Ile Asn Phe Lys Thr Leu Ser His His His His His
            500                 505                 510

His Glu Gln Lys Leu Ile Ser Glu Glu Asp Leu
        515                 520
```

<210> SEQ ID NO 265
<211> LENGTH: 12
<212> TYPE: PRT
<213> ORGANISM: Artificial
<220> FEATURE:
<223> OTHER INFORMATION: An artificially synthesized peptide sequence

<400> SEQUENCE: 265

Asp Gly Tyr Asp Asp Gly Pro Tyr Thr Met Asp Tyr
1 5 10

<210> SEQ ID NO 266
<211> LENGTH: 12
<212> TYPE: PRT
<213> ORGANISM: Artificial
<220> FEATURE:
<223> OTHER INFORMATION: An artificially synthesized peptide sequence

<400> SEQUENCE: 266

Asp Gly Tyr Asp Asp Gly Pro Tyr Thr Leu Glu Thr
1 5 10

<210> SEQ ID NO 267
<211> LENGTH: 12
<212> TYPE: PRT
<213> ORGANISM: Artificial
<220> FEATURE:
<223> OTHER INFORMATION: An artificially synthesized peptide sequence

<400> SEQUENCE: 267

Asp Gly Tyr Asp Asp Gly Pro Tyr Thr Met Glu Thr
1 5 10

<210> SEQ ID NO 268
<211> LENGTH: 12
<212> TYPE: PRT
<213> ORGANISM: Artificial
<220> FEATURE:
<223> OTHER INFORMATION: An artificially synthesized peptide sequence

<400> SEQUENCE: 268

Asp Gly Leu Asp Asp Gly Pro Tyr Thr Met Glu Thr
1 5 10

<210> SEQ ID NO 269
<211> LENGTH: 12
<212> TYPE: PRT
<213> ORGANISM: Artificial
<220> FEATURE:
<223> OTHER INFORMATION: An artificially synthesized peptide sequence

<400> SEQUENCE: 269

Asp Gly Leu Asp Asp Gly Pro Tyr Thr Met Glu Ser
1 5 10

<210> SEQ ID NO 270
<211> LENGTH: 5
<212> TYPE: PRT
<213> ORGANISM: Artificial
<220> FEATURE:
<223> OTHER INFORMATION: An artificially synthesized peptide sequence

<400> SEQUENCE: 270

Gly Tyr Ile Met Asn
1 5

<210> SEQ ID NO 271

-continued

<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 271

Leu Ile Asn Pro Tyr Asn Gly Gly Thr Ser Tyr Asn Gln Lys Phe Lys
1 5 10 15

Gly

<210> SEQ ID NO 272
<211> LENGTH: 5
<212> TYPE: PRT
<213> ORGANISM: Artificial
<220> FEATURE:
<223> OTHER INFORMATION: An artificially synthesized peptide sequence

<400> SEQUENCE: 272

Gly Tyr Val Met Asn
1 5

<210> SEQ ID NO 273
<211> LENGTH: 5
<212> TYPE: PRT
<213> ORGANISM: Artificial
<220> FEATURE:
<223> OTHER INFORMATION: An artificially synthesized peptide sequence

<400> SEQUENCE: 273

Gly Tyr Ile Ile Asn
1 5

<210> SEQ ID NO 274
<211> LENGTH: 5
<212> TYPE: PRT
<213> ORGANISM: Artificial
<220> FEATURE:
<223> OTHER INFORMATION: An artificially synthesized peptide sequence

<400> SEQUENCE: 274

Gly Tyr Ile Leu Asn
1 5

<210> SEQ ID NO 275
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 275

Leu Ile Asn Pro Tyr Asn Gly Gly Thr Asp Tyr Asn Gln Lys Phe Lys
1 5 10 15

Gly

<210> SEQ ID NO 276
<211> LENGTH: 17
<212> TYPE: PRT
<213> ORGANISM: Artificial
<220> FEATURE:
<223> OTHER INFORMATION: An artificially synthesized peptide sequence

<400> SEQUENCE: 276

Leu Ile Asn Pro Tyr Asn Gly Gly Thr Ser Tyr Asn Pro Lys Phe Lys
1 5 10 15

Gly

<210> SEQ ID NO 277
<211> LENGTH: 11
<212> TYPE: PRT
<213> ORGANISM: Artificial
<220> FEATURE:
<223> OTHER INFORMATION: An artificially synthesized peptide sequence

<400> SEQUENCE: 277

Arg Thr Ser Glu Asn Ile Tyr Ser Phe Leu Ala
1 5 10

<210> SEQ ID NO 278
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 278

Gln His His Tyr Glu Ser Pro Leu Thr
1 5

<210> SEQ ID NO 279
<211> LENGTH: 11
<212> TYPE: PRT
<213> ORGANISM: Artificial
<220> FEATURE:
<223> OTHER INFORMATION: An artificially synthesized peptide sequence

<400> SEQUENCE: 279

Arg Thr Ser Glu Asn Ile Tyr Arg Phe Leu Ala
1 5 10

<210> SEQ ID NO 280
<211> LENGTH: 11
<212> TYPE: PRT
<213> ORGANISM: Artificial
<220> FEATURE:
<223> OTHER INFORMATION: An artificially synthesized peptide sequence

<400> SEQUENCE: 280

Arg Thr Ser Glu Asn Ile Tyr Arg Phe Val Ala
1 5 10

<210> SEQ ID NO 281
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 281

Gln His His Tyr Asp Ser Pro Leu Thr
1 5

<210> SEQ ID NO 282
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 282

Gln His His Tyr Glu Asp Pro Leu Thr
1 5

-continued

<210> SEQ ID NO 283
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 283

Gln His His Thr Glu Ser Pro Leu Phe
1               5

<210> SEQ ID NO 284
<211> LENGTH: 5
<212> TYPE: PRT
<213> ORGANISM: Artificial
<220> FEATURE:
<223> OTHER INFORMATION: An artificially synthesized peptide sequence

<400> SEQUENCE: 284

Gly Tyr Ala Met Asn
1               5

<210> SEQ ID NO 285
<211> LENGTH: 11
<212> TYPE: PRT
<213> ORGANISM: Artificial
<220> FEATURE:
<223> OTHER INFORMATION: An artificially synthesized peptide sequence

<400> SEQUENCE: 285

Arg Ala Ser Glu Asn Ile Tyr Ser Phe Leu Ala
1               5                   10

<210> SEQ ID NO 286
<211> LENGTH: 11
<212> TYPE: PRT
<213> ORGANISM: Artificial
<220> FEATURE:
<223> OTHER INFORMATION: An artificially synthesized peptide sequence

<400> SEQUENCE: 286

Arg Ser Ser Glu Asn Ile Tyr Ser Phe Leu Ala
1               5                   10

<210> SEQ ID NO 287
<211> LENGTH: 16
<212> TYPE: PRT
<213> ORGANISM: Artificial
<220> FEATURE:
<223> OTHER INFORMATION: An artificially synthesized sequence

<400> SEQUENCE: 287

His His His His His His Glu Gln Lys Leu Ile Ser Glu Glu Asp Leu
1               5                   10                  15